United States Patent
Sinha et al.

(10) Patent No.: US 9,072,731 B2
(45) Date of Patent: Jul. 7, 2015

(54) HETEROARYL DERIVATIVES AS ALPHA7 NACHR MODULATORS

(75) Inventors: Neelima Sinha, Maharashtra (IN); Gourhari Jana, Maharashtra (IN); Sachchidanand Sachchidanand, Maharashtra (IN); Sanjay Pralhad Kurhade, Maharashtra (IN); Navnath Popat Karche, Maharashtra (IN); Anil Kashiram Hajare, Maharashtra (IN); Ajay Ramchandra Tilekar, Maharashtra (IN); Venkata P. Palle, Maharashtra (IN); Rajender Kumar Kamboj, Maharashtra (IN)

(73) Assignee: Lupin Limited, Mumbai (IN)

( * ) Notice: Subject to any disclaimer, the term of this patent is extended or adjusted under 35 U.S.C. 154(b) by 30 days.

(21) Appl. No.: 14/000,829

(22) PCT Filed: Feb. 22, 2012

(86) PCT No.: PCT/IB2012/050806
§ 371 (c)(1),
(2), (4) Date: Aug. 21, 2013

(87) PCT Pub. No.: WO2012/114285
PCT Pub. Date: Aug. 30, 2012

(65) Prior Publication Data
US 2013/0331387 A1    Dec. 12, 2013

(30) Foreign Application Priority Data

Feb. 23, 2011 (IN) .............. 242/KOL/2011
Sep. 9, 2011 (IN) .............. 1184/KOL/2011

(51) Int. Cl.

| | |
|---|---|
| C07D 333/22 | (2006.01) |
| C07D 207/32 | (2006.01) |
| A61K 31/4436 | (2006.01) |
| C07D 207/333 | (2006.01) |
| C07D 207/337 | (2006.01) |
| C07D 333/36 | (2006.01) |
| C07D 333/38 | (2006.01) |
| C07D 409/04 | (2006.01) |
| A61K 45/06 | (2006.01) |
| A61K 31/381 | (2006.01) |
| A61K 31/341 | (2006.01) |
| A61K 31/40 | (2006.01) |

(Continued)

(52) U.S. Cl.
CPC .......... *A61K 31/4436* (2013.01); *C07D 207/32* (2013.01); *C07D 207/333* (2013.01); *C07D 207/337* (2013.01); *C07D 333/22* (2013.01); *C07D 333/36* (2013.01); *C07D 333/38* (2013.01); *C07D 409/04* (2013.01); *A61K 45/06* (2013.01); *A61K 31/381* (2013.01); *A61K 31/341* (2013.01); *A61K 31/40* (2013.01); *A61K 31/404* (2013.01); *A61K 31/4535* (2013.01); *A61K 31/496* (2013.01); *A61K 31/5377* (2013.01); *C07D 307/68* (2013.01); *C07D 333/26* (2013.01)

(58) Field of Classification Search
CPC ............................. C07D 333/22; C07D 207/32
USPC ............................................. 549/72; 548/561
See application file for complete search history.

(56) References Cited

U.S. PATENT DOCUMENTS

| | | |
|---|---|---|
| 3,953,596 A | 4/1976 | Miller |
| 4,235,871 A | 11/1980 | Papahadjopoulos et al. |

(Continued)

FOREIGN PATENT DOCUMENTS

| | | |
|---|---|---|
| EP | 1012142 B1 | 8/1998 |
| EP | 1489077 A1 | 12/2004 |

(Continued)

OTHER PUBLICATIONS

Haydar et al. (Bioorg. Med. Chem. 17 (2009) 5247-5258).*
Kubinyi (3D QSAR in Drug Design: Ligand-Protein Interactions and Molecular Similarity, vol. 2-3, Springer, 1998, 800 pages). p. 243-44 provided.*
Wermuth, The Practice of Medicinal Chemsitry, 2d ed. (2003), 768 pages. Chapters 9-10.*
Pfefferkorn et al. (Bioorg. Med. Chem. Lett. 17 (2007) 4538-4544).*
Mai et al. (The International Journal of Biochemistry & Cell Biology 41 (2009) 235-247).*

(Continued)

*Primary Examiner* — Robert Havlin
(74) *Attorney, Agent, or Firm* — Leydig, Voit & Mayer, Ltd.

(57) ABSTRACT

Disclosed is a compound of formula (I), wherein Z, m and $R^1$-$R^6$ are as described herein, as a modulator of nicotinic acetylcholine receptors particularly the α7 subtype, in a subject in need thereof, as well as analogs, prodrugs, isotopically substituted analogs, metabolites, pharmaceutically acceptable salts, polymorphs, solvates, isomers, clathrates, and co-crystal thereof, for use either alone or in combinations with suitable other medicaments, and pharmaceutical compositions containing such compounds and analogs. Also disclosed are a process of preparation of the compounds and the intended uses thereof in therapy, particularly in the prophylaxis and therapy of disorders such as Alzheimer's disease, mild cognitive impairment, senile dementia, and the like.

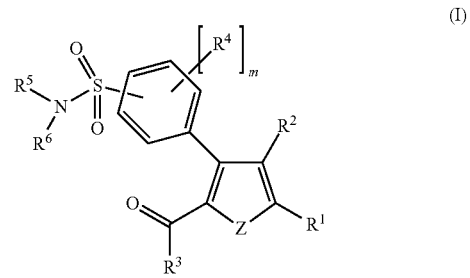

39 Claims, No Drawings

(51) Int. Cl.

| | |
|---|---|
| A61K 31/404 | (2006.01) |
| A61K 31/4535 | (2006.01) |
| A61K 31/496 | (2006.01) |
| A61K 31/5377 | (2006.01) |
| C07D 307/68 | (2006.01) |
| C07D 333/26 | (2006.01) |

(56) References Cited

U.S. PATENT DOCUMENTS

| | | |
|---|---|---|
| 4,501,728 A | 2/1985 | Geho et al. |
| 4,837,028 A | 6/1989 | Allen |
| 5,019,369 A | 5/1991 | Presant et al. |
| 5,608,082 A | 3/1997 | Varney et al. |
| 7,683,084 B2 | 3/2010 | Faghih et al. |
| 7,741,364 B2 | 6/2010 | Faghih et al. |
| 2003/0236413 A1 | 12/2003 | Cellier et al. |
| 2005/0080095 A1 | 4/2005 | Zheng et al. |
| 2006/0142349 A1 | 6/2006 | Hurst et al. |
| 2006/0258670 A1 | 11/2006 | Desos et al. |
| 2007/0032531 A1 | 2/2007 | Smith et al. |
| 2007/0142450 A1 | 6/2007 | Dahl et al. |
| 2009/0253691 A1 | 10/2009 | Thuring et al. |
| 2010/0190819 A1 | 7/2010 | Kanner |
| 2010/0222398 A1 | 9/2010 | Nardi et al. |
| 2010/0227869 A1 | 9/2010 | Peters et al. |
| 2010/0240707 A1 | 9/2010 | Thuring et al. |
| 2010/0298388 A1 | 11/2010 | Haydon et al. |

FOREIGN PATENT DOCUMENTS

| | | |
|---|---|---|
| EP | 1790640 A1 | 5/2007 |
| EP | 1866314 B1 | 9/2010 |
| WO | WO 04/000792 A1 | 12/2003 |
| WO | WO 2004/031186 A1 | 4/2004 |
| WO | WO 2005/030715 A1 | 4/2005 |
| WO | WO 2005/077932 A2 | 8/2005 |
| WO | WO 2005/105789 A2 | 11/2005 |
| WO | WO 2007/031440 A2 | 3/2007 |
| WO | WO 2007/092751 A2 | 8/2007 |
| WO | WO 2008/002974 A1 | 1/2008 |
| WO | WO 2008/057336 A2 | 5/2008 |
| WO | WO 2008/084300 A1 | 7/2008 |
| WO | WO 2009/043780 A1 | 4/2009 |
| WO | WO 2009/043784 A1 | 4/2009 |
| WO | WO 2009/115547 A1 | 9/2009 |
| WO | WO 2009/127678 A1 | 10/2009 |
| WO | WO 2009/127679 A1 | 10/2009 |
| WO | WO 2009/135944 A1 | 11/2009 |
| WO | WO 2009/145996 A2 | 12/2009 |
| WO | WO 2010/120854 A1 | 10/2010 |
| WO | WO 2010/130768 A1 | 11/2010 |
| WO | WO 2011/036167 A1 | 3/2011 |
| WO | WO 2011/064288 A1 | 6/2011 |
| WO | WO 2012/104782 A1 | 8/2012 |
| WO | WO 2012/131576 A1 | 10/2012 |
| WO | WO 2013/005153 A1 | 1/2013 |

OTHER PUBLICATIONS

Wermuth, The Practice of Medicinal Chemsitry, 2d ed. (2003), 768 pages. Chapters 13-14.*
International Search Report in corresponding International Application No. PCT/IB2012/050806, mailed May 25, 2012.
Albuquerque, E.X., et al., "Modulation of Nicotinic Receptor Activity in the Central Nervous System: A Novel Approach to the Treatment of Alzheimer Disease," *Alzheimer Disease and Associated Disorders*, vol. 15, Suppl. 1, pp. S19-S25 (2001).
Alkondon, Manickavasagom, et al., "α7 Nicotinic acetylcholine receptors and modulation of gabaergic synaptic transmission in the hippocampus," *European Journal of Pharmacology*, vol. 393, pp. 59-67 (2000).
Arias, Hugo R., et al., "Role of non-neuronal nicotinic acetylcholine receptors in angiogenesis," *The International Journal of Biochemistry & Cell Biology*, vol. 41, pp. 1441-1451 (2009).
Avis, Kenneth E., "Parenteral Preparations," *Remington's Pharmaceutical Sciences*, 17th Edition, Chapter 85, Mack Publishing Company, Easton, PA, pp. 1518-1541 (1985).
Bennouna, M., et al., "Cholinergic hypothesis in psychosis following traumatic brain injury and cholinergic hypothesis in schizophrenia: a link?," *L'Encéphale*, vol. 33, pp. 616-620 (Sep. 2007).
Berge, Stephen M., et al., "Pharmaceutical Salts," Review Article from *Journal of Pharmaceutical Sciences*, vol. 66, No. 1, pp. 1-19 (Jan. 1977).
Bitner, Robert S., et al., "Broad-Spectrum Efficacy across Cognitive Domains by α7 Nicotinic Acetylcholine Receptor Agonism Correlates with Activation of ERK1/2 and CREB Phosphorylation Pathways," *The Journal of Neuroscience*, vol. 27, No. 39, pp. 10578-10587 (Sep. 26, 2007).
Boess, Frank G., et al., "The Novel α7 Nicotinic Acetylcholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents," *The Journal of Pharmacology and Experimental Therapeutics*, vol. 321, No. 2, pp. 716-725 (2007).
Bruchfeld, A., et al., "Whole blood cytokine attenuation by cholinergic agonists ex vivo and relationship to vagus nerve activity in rheumatoid arthritis," *Journal of Internal Medicine*, vol. 268, No. 1, pp. 94-101 (Jul. 2010).
Calleja-Macias, Itzel E., "Cholinergic signaling through nicotinic acetylcholine receptors stimulates the proliferation of cervical cancer cells: An explanation for the molecular role of tobacco smoking in cervical carcinogenesis?," *International Journal of Cancer*, vol. 124, pp. 1090-1096 (2009).
Cannon, Tyrone D., "The inheritance of intermediate phenotypes for schizophrenia," *Current Opinion in Psychiatry*, vol. 18, pp. 135-140 (2005).
Carson, Robyn, et al., "Genetic Variation in the α7 Nicotinic Acetylcholine Receptor is Associated with Delusional Symptoms in Alzheimers's Disease," *NeuroMolecular Medicine*, vol. 10, pp. 377-384 (2008).
Chadwick, Derek J., et al., "Esters of Furan-, Thiophen-, and N-Methylpyrrole-2-carboxylic Acids. Brornination of Methyl Furan-2-carboxylate, Furan-2-carbaldehyde, and Thiopen-2-carbaldehyde in the Presence of Aluminum Chloride," *Journal of the Chemical Society, Perkin Transactions 1*, pp. 1765-1773 (1973).
Chan, Wai Kit, et al., "Frontal cortical α7 and α4β2 nicotinic acetylcholine receptors in working and reference memory," *Neuropharmacology*, vol. 52, pp. 1641-1649 (2007).
Chen, Zheng-Bo, et al., "A Cascade Approach to Pyridines from 2-Azido-2,4-dienoates and α-Diazocarbonyl Compounds," *The Journal of Organic Chemistry*, vol. 74, pp. 903-905 (2009).
Cui, Xinjiang, et al., "Fe(II)-catalyzed N-alkyiation of sulfonamides with benzylic alcohols," *Tetrahedron Letters*, vol. 51, pp. 2048-2051 (2010).
Curzon, Peter, et al., "Antisense knockdown of the rat α7 nicotinic acetylcholine receptor produces spatial memory impairment," *Neuroscience Letters*, vol. 410, pp. 15-19 (2006).
Dajas-Bailador, Federico, et al., "Nicotinic acetylcholine receptors and the regulation of neuronal signalling," *TRENDS in Pharmacological Sciences*, vol. 25, No. 6, pp. 317-324 (Jun. 2004).
Damaj, M. Imad, et al., "The antinociceptive effects of α7 nicotinic agonists in an acute pain model," *Neuropharmacology*, vol. 39, pp. 2785-2791 (2000).
Decker, Michael W., et al., "The therapeutic potential of nicotinic acetylcholine receptor agonists for pain control," *Expert Opinion on Investigational Drugs*, vol. 10, No. 10, pp. 1819-1830 (2001).
Deng, Wei, et al., "Copper-catalyzed cross-coupling of sulfonamides with aryl iodides and bromides facilitated by amino acid ligands," *Tetrahedron Letters*, vol. 46, pp. 7295-7298 (2005).
Deutsch, Stephen I., et al., "Progressive Worsening of Adaptive Functions in Down Syndrome May Be Mediated by Complexing of Soluble Aβ Peptides With the α7 Nicotinic Acetylcholine Receptor: Therapeutic Implications," *Clinical Neuropharmacology*, vol. 26, No. 5, pp. 277-283 (2003).
Dong, Huijun, et al., "Transition Metal-Catalyzed Synthesis of Pyrroles from Dienyl Azides," *Organic Letters*, vol. 9, No. 25, pp. 5191-5194 (2007).

(56) References Cited

OTHER PUBLICATIONS

Donnelly-Roberts, Diana L., et al., "ABT-594 [(R)-5-(2-Azetidinylmethoxy)-2-Chloropyridine]: A Novel, Orally Effective Analgesic Acting via Neuronal Nicotinic Acetylcholine Receptors: 1. In Vitro Characterization," *The Journal of Pharmacology and Experimental Therapeutics*, vol. 285, No. 2, pp. 777-736 (1998).

Dunlop, John, et al., "Old and New Pharmacology: Positive Allosteric Modulation of the α7 Nicotinic Acetylcholine Receptor by the 5-Hydroxytryptamine$_{2B/C}$ Receptor Antagonist SB-206553 (3,5-Dihydro-5-methyl-N-3-pyridinylbenzo[1,2-b:4,5-b'] di pyrrole-1-(2H)-carboxamide)," *The Journal of Pharmacology and Experimental Therapeutics*, vol. 328, No. 3, pp. 766-776 (2009).

Duris, Karnil, et al., "α7 Nicotinic Acetylcholine Receptor Agonist PNU-282987 Attenuates Early Brain Injury in a Perforation Model of Subarachnoid Hemorrhage in Rats," *Stroke*, vol. 42, pp. 3530-3536 (2011).

Dvornikova, Elena, et al., "Synthesis of 2- and 3-Substituted N-Methylpyrroles" *Synlett*, vol. 7, pp. 1153-1153 (2002).

Ebbert, Jon O., et al., "Varenicline for smoking cessation: efficacy, safety, and treatment recommendations," *Patient Preference and Adherence*, vol. 4, pp. 355-362 (2010).

EnVivo Pharmaceuticals, "EnVivo Reports Positive Results of its EVP-6124 Clinical Bio-Marker Study in Schizophrenia Patients," Press Release (Jan. 12, 2009).

Faghih, Ramin, et al., "Discovery of 4-(5-(4-Chlorophenyl)-2-methyl-3-propionyl-1H-pyrrol-1-yl)benzenesulfonamide (A-867744) as a Novel Positive Allosteric Modulator of the α7 Nicotinic Acetylcholine Receptor," *Journal of Medicinal Chemistry*, vol. 52, pp. 3377-3384 (2009).

Fehér, Ágnes, et al., "Association between a Genetic Variant of the Alpha-7 Nicotinic Acetylcholine Receptor Subunit and Four Types of Dementia," *Dementia and Geriatric Cognitive Disorders*, vol. 28, pp. 56-62 (2009).

Freedman, Robert, et al., "Evidence in Postmortem Brain Tissue for Decreased Numbers of Hippocampal Nicotinic Receptors in Schizophrenia," *Biological Psychiatry*, vol. 38, pp. 22-33 (1995).

Freedman, Robert, et al., "The Genetics of Sensory Gating Deficits in Schizophrenia," *Current Psychiatry Reports*, vol. 5, pp. 155-161 (2003).

Gallowitsch-Puerta, Margot, et al., "Neuro-immune interactions via the cholinergic anti-inflammatory pathway," *Life Sciences*, vol. 80, No. 24-25, pp. 2325-2329 (May 30, 2007).

Giebelen, Ida A., et al., "Stimulation of α7 Cholinergic Receptors Inhibits Lipopolysaccharide-Induced Neutrophil Recruitment by a Tumor Necrosis Factor α-Independent Mechanism," *Shock*, vol. 27, No. 4, pp. 443-447 (2007).

Goldstein, Richard, et al., "Cholinergic Agonists Inhibit LPS Induced Whole Blood TNF Release Ex Vivo in Patients With Severe Sepsis: A Pilot Study," *Academic Emergency Medicine*, vol. 14, No. 5, Suppl. 1, pp. S185-S186, Abstract 474 (May 2007).

Gupton, John T., et al., "The application of vinylogous iminium salt derivatives to an efficient synthesis of the pyrrole containing alkaloids Rigidin and Rigidin E," *Tetrahedron*, vol. 62, pp. 8243-8255 (2006).

Harrington, C.R, et al., "Senile Dementia of Lewy Body Type and Alzheimer Type Are Biochemically Distinct in Terms of Paired Helical Filaments and Hyperphosphorylated Tau Protein," *Dementia*, vol. 5, pp. 215-228 (1994).

Hashimoto, Kenji, et al., "Phencyclidine-Induced Cognitive Deficits in Mice Are Improved by Subsequent Subchronic Administration of the Novel Selective α7 Nicotinic Receptor Agonist SSR180711," *Biological Psychiatry*, vol. 63, pp. 92-97 (2008).

Hauser, T.A., et al., "TC-5619: An alpha7 neuronal nicotinic receptor-selective agonist that demonstrates efficacy in animal models of the positive and negative symptoms and cognitive dysfunction of schizophrenia," *Biochemical Pharmacology*, vol. 78, No. 7, pp. 803-812 (Oct. 1, 2009).

Haydar, Simon N., et al., "SAR and biological evaluation of SEN12333/WAY-317538: Novel alpha 7 nicotinic acetylcholine receptor agonist," *Bioorganic & Medicinal Chemistry*, vol. 17, pp. 5247-5258 (2009).

He, Huan, et al., "Copper-catalyzed N-arylation of sulfonamides with aryl bromides and iodides using microwave heating," *Tetrahedron Letters*, vol. 44, pp. 3385-3386 (2003).

Heeschen, Christopher, et al., "A novel angiogenic pathway mediated by non-neuronal nicotinic acetylcholine receptors," *The Journal of Clinical Investigation*, vol. 110, No. 4, pp. 527-536 (Aug. 2002).

Imamura, Yorishige, et al., "Catalytic Properties of Carbonyl Reductase from Rabbit Kidney for Acetohexamide and Its Analogs," *Bioorganic Chemistry*, vol. 22, pp. 387-394 (1994).

Jeyarasasingam, G., et al., "Stimulation of Non-α7 Nicotinic: Receptors Partially Protects Dopaminergic Neurons From 1-Methyl-4-Phenylpyridinium-Induced Toxicity in Culture," *Neuroscience*, vol. 109, No. 2, pp. 275-285 (2002).

Jin, Y., et al., "Genomic polymorphisms within alpha 7 nicotinic acetylcholine receptor and severe sepsis in Chinese Han population," *International Journal of Immunogenetics*, vol. 37, pp. 361-365 (2010).

Karshtedt, Dmitry, et al., "Platinum-Based Catalysts for the Hydroamination of Olefins with Sulfonamides and Weakiy Basic Anilines," *Journal of the American Chemical Society*, vol. 127, pp, 12640-12646 (2005).

Kawamorita, Soichiro, et al., "Ester-Directed Regioselective Borylation of Heteroarenes Catalyzed by a Silica-Supported Iridium Complex," *The Journal of Organic Chemistry*, vol. 75, pp. 3855-3858 (2010).

Kuzmin, Alexander, et al., "Effects of subunit selective nACh receptors on operant ethanol self-administration and relapse-like ethanol-drinking behavior," *Psychopharmacology*, vol. 203, pp. 99-108 (2009).

Lee, Sang-Hyuep, et al., "The direct conversion of carbamates to ureas using aluminum amides," *Tetrahedron*, vol. 60, pp. 3439-3443 (2004).

Leiser, Steven C., et al., "A cog in cognition: How the α7 nicotinic acetylcholine receptor is geared towards improving cognitive defects," *Pharmacology & Therapeutics*, vol. 122, No. 3, pp. 302-311 (Jun. 2009).

Leonard, S., et al., "Smoking and mental illness," *Pharmacology, Biochemistry and Behavior*, vol. 70, pp. 561-570 (2001).

Letellier, Marie-Anne, et al., "Synthesis of potential Rho-kinase inhibitors based on the chemistry of an original heterocycle: 4,4-Dimethyl-3,4-dihydro-1H-quinolin-2-one," *European Journal of Medicinal Chemistry*, vol. 43, pp. 1730-1736 (2008).

Liu, Chong, et al., "Antishock effect of anisodamine involves a novel pathway for activating α7 nicotinic acetylcholine receptor," *Critical Care Medicine*, vol. 37, No. 2, pp. 634-641 (2009).

Luo, Fan, et al., "Highly enantioselective bioreduction of 2-fluorocinnamyl alcohols mediated by Saccharomyces cerevisiae," *Tetrahedron Letters*, vol. 51, pp. 1693-1695 (2010).

Mansvelder, Huibert D., et al., "Nicotinic modulation of neuronal networks: from receptors to cognition," *Psychopharmacology*, vol. 184, pp. 292-305 (2006).

Marrero, Mario B., et al., "Convergence of alpha 7 nicotinic acetylcholine receptor-activated pathways for anti-apoptosis and anti-inflammation: Central role for JAK2 activation of STAT3 and NF-κB," *Brain Research*, vol. 1256, pp. 1-7 (2009).

Martin, Laura F., et al., "Sensory Gating and Alpha-7 Nicotinic Receptor Gene Allelic Variants in Schizoaffective Disorder, Bipolar Type," *American Journal of Medical Genetics Part B: Neuropsychiatric Genetics*, vol. 144B, No. 5, pp. 611-614 (Jul. 5, 2007).

Martin, Laura F., et al., "Alpha-7 nicotinic receptor agonists: potential new candidates for the treatment of schizophrenia," *Psychopharmacology*, vol. 174, pp. 54-64 (2004).

McKay, Bruce E., et al., "Regulation of synaptic transmission of plasticity by neuronal nicotinic acetylcholine receptors," *Biochemical Pharmacology*, vol. 74, pp. 1120-1133 (2007).

Miyaura, Norio, et al., "Paliadium-Catalyzed Cross-Coupling Reactions of Organoboron Compounds," *Chemical Reviews*, vol. 95, pp. 2457-2483 (1995).

(56) References Cited

OTHER PUBLICATIONS

Nagele, R.G., et al., "intracellular Accumulation of β-Amyloid$_{1-42}$ in Neurons is Facilitated by the α7 Nicotinic Acetylcholine Receptor in Alzheimer's Disease," *Neuroscience*, vol. 110, No. 2, pp. 199-211 (2002).
Nakano, Jun, et al., "Studies on Ketene and its Derivatives. CX.[1]) Synthesis of 1,3-Dimethoxyfluoren-9-ones," *Chemical and Pharmaceutical Bulletin*, vol. 30, No. 7, pp. 2590-2594 (1982).
Iiiing, Herman J., at al., "Nootropic α7 nicotinic receptor allosteric modulator derived from GABA$_A$ receptor modulators," *Proceedings of the National Academy of Sciences*, vol. 104, No. 19, pp. 8059-8064 (May 8, 2007).
Nishio, Takehiko, "Sulfur-Containing Heterocycles Derived by Reaction of ω-Keto Amides with *Lawesson's* Reagent," *Helvetica Chimica Acta*, vol. 81, pp. 1207-1214 (1998).
Nizri. Eran, et al., "The Role of Cholinergic Balance Perturbation in Neurological Diseases," *Drug News & Perspectives*, vol. 20, No. 7, pp. 421-429 (Sep. 2007).
Nordberg, Agneta, et al., "Neuroprotection in Alzheimer's Disease—New Strategies for Treatment," *Neurotoxicity Research*, vol. 2, pp. 157-165 (2000).
O'Donnell, Christopher J., et al., "Discovery of 4-(5-Methyloxazolo[4,5-*b*]pyridine-2-yl)-1,4-diazabicyclo[3.2.2]nonane (CP-810123), a Novel α7 Nicotinic Acetylcholine Receptor Agonist for the Treatment of Cognitive Disorders in Schizophrenia: Synthesis, SAR Development, and in Vivo Efficacy in Cognition Models," *Journal of Medicinal Chemistry*, vol. 53, pp. 1222-1237 (2010).
Olincy, Ann, et al., "Proof-of-Concept Trial of an α7 Nicotinic Agonist in Schizophrenia," *Archives of General Psychiatry*, vol. 63, pp. 630-638 (Jun. 2006).
Olincy, Ann, "Nicotine Receptor Dysfunction in Schizophrenia and Therapeutic Effects of Nicotine Agonist DMXBA," *Biological Psychiatry*, vol. 57, p. 13S, Abstract No. 44 (2005).
Pan, Changduo et al. "Cu(OAc)$_2$-Catalyzed *N*-Arylation of Sulfonamides with Arylboronic Acids or Trimethoxy(phenyl)silane," *Synthetic Communications*, pp. 2082-2092 (2009).
Paterson, David, et al., "Neuronal nicotinic receptors in the human brain," *Progress in Neurobiology*, vol. 61, p. 75-111 (2000).
Pena, Geber, et al., "Unphosphorylated STAT3 modulates alpha7 nicotinic receptor signaling and cytokine production in sepsis," *European Journal of Immunology*, vol. 40, No. 9, pp. 2580-2589 (Sep. 2010).
Peng, ZZ, et al., "The transmission of disequilibrium analysis between neuronal nicotinic acetylcholine receptor alpha 7 subunit gene polymorphisms and schizophrenia," *Zhonghua Yi Xue Yi Chuan Xue Za Zhi*, vol. 25, No. 2, pp. 154-158 (Apr. 2008).
Perry, Elaine, et al., "Nicotinic receptor subtypes in human brain ageing, Alzheimer and Lewy body diseases," *European Journal of Pharmacology*, vol. 393, pp. 215-222 (2000).
Pichat, Philippe, et al., "SSR180711, a Novel Selective α7 Nicotinic Receptor Partial Agonist: (II) Efficacy in Experimental Models Predictive of Activity Against Cognitive Symptoms of Schizophrenia," *Neuropsychopharmacology*, vol. 32, pp. 17-34 (2007).
"Product identification Guide," *Physicians' Desk Reference*, 58th Edition, Thomson PDR, Montvale, NJ, pp. 303-340 (2004).
"Product Information—Eisai," *Physicians' Desk Reference*, 58th Edition, Thomson PDR, Montvale, NJ, pp. 1221-1223 (2004).
"Product Information—Janssen," *Physicians' Desk Reference*, 58th Edition, Thomson PDR, Montvale, NJ, pp. 1759-1764 (2004).
"Product information—Novartis Pharmaceuticals," *Physicians' Desk Reference*, 58th Edition, Thomson PDR, Montvale, NJ, pp. 2252-2259 (2004).
"Product information—Pfizer," *Physicians' Desk Reference*, 58th Edition, Thomson PDR, Montvale, NJ, pp. 2570-2573 (2004).
Redrobe, John P., et al., "α7 nicotinic acetylcholine receptor activation ameliorates scopolamine-induced behavioural changes in a modified continuous Y-maze task in mice," *European Journal of Pharmacology*, vol. 602, pp. 58-65 (2009).
Remingtons' Pharmaceutical Sciences, 18th Edition, p. 1445 (1990).
Roncarati, Renza, et al., "Procognitive and Neuroprotective Activity of a Novel α7 Nicotinic Acetylcholine Receptor Agonist for Treatment of Neruodegenerative and Cognitive Diseases," *The Journal of Pharmacology and Experimental Therapeutics*, vol. 329, No. 2, pp. 459-468 (2009).
Rosas-Ballina, M., et al., "Cholinergic control of inflammation," *Journal of Internal Medicine*, vol. 265, pp. 663-679 (2009).
Rosas-Ballina, Mauricio, et al., "The Selective α7 Agonist GTS-21 Attenuates Cytokine Production in Human Whole Blood and Human Monocytes Activated by Ligands for TLR2, TLR3, TLR4, TLR9, and RAGE," *Molecular Medicine*, vol. 15, No. 7-8, pp. 195-202 (Jul.-Aug. 2009).
Rowbotham, Michael C., et al., "A randomized, double-blind, placebo-controlled trial evaluating the efficacy and safety of ABT-594 in patients with diabetic peripheral neuropathic pain," *Pain*, vol. 146, pp. 245-252 (2009).
Rowley, T.J., et al., "Antinociceptive and anti-inflammatory effects of choline in a mouse model of postoperative pain," *British Journal of Anaesthesia*, vol. 105, No. 2, pp. 201-207 (2010).
Rubboli, F., et al., "Distribution of Neuronal Nicotinic Receptor Subunits in Human Brain," *Neurochemistry International*, vol. 25, No. 1, pp. 69-71 (1994).
Sanberg, Paul R., et al., "Nicotine for the Treatment of Tourette's Syndrome," *Pharmacology & Therapeutics*, vol. 74, No. 1, pp. 21-25 (1997).
Schuller, Hildegard M., et al., "Interaction of tobacco-specific toxicants with the neuronal α$_7$ nicotinic acetylcholine receptor and its associated mitogenic signal transduction pathway: potential role in lung carcinogenesis and pediatric lung disorders," *European Journal of Pharmacology*, vol. 393, pp. 265-277 (2000).
Silva, A.L., et al., "A Simple Preparation of N,N-Dimethyl-N'-Alkyl (Aryl) : Sulfonylformamidines," *Organic Preparations and Procedures International: The New Journal for Organic Synthesis*, vol. 34, No. 5, pp. 545-549 (2002).
Solinas, Marcello, et al., "Nicotinic α$_7$ Receptors as a New Target for Treatment of Cannabis Abuse," *The Journal of Neuroscience*, vol. 27, No. 21, pp. 5615-5620 (May 23, 2007).
Stahl, P. Heinrich, et al., *Handbook of Pharmaceutical Salts: Properties, Selection, and Use*, Wiley-VCH, Weinheim, pp. 1-374 (2002).
Suemaru, K, et al., "Involvement of neuronal nicotinic receptor in psychiatric disorders," *Nihon Yakurigaku Zasshi*, vol. 119, No. 5, pp. 295-300 (May 2002).
Szoka, Jr., Francis, et al., "Comparative Properties and Methods of Preparation of Lipid Vesicles (Liposomes)," *Annual Review of Biophysics & Bioengineering*, vol. 9, pp. 467-508 (1980).
Taguchi. Kazuhiko, et al., "Synthesis of quinolines from amino alcohol and ketones catalyzed by [IrCl(cod)]$_2$ or IrCl$_3$ under solvent-free conditions," *Tetrahedron Letters*, vol. 46, pp. 4539-4542 (2005).
Tatsumi, Ryo, et al., "(+)-3-[2-(Benzo[*b*]thiophen-2-yl)-2-oxoethyl]1-azabicyclo[2.2.2]-octane as potent agonists for the α7 nicotinic acetylcholine receptor," *Bioorganic & Medicinal Chemistry Letters*, vol. 14, pp. 3781-3784 (2004).
Tatsumi, Ryo, et al., "(*R*)-3'-(3-Methylbenzo[*b*]thiophen-5-yl)spiro[1-azabicyclo[2,2,2]octane-3,5'-oxazolidin]-2'-one, a Novel and Potent α7 Nicotinic Acetylcholine Receptor Partial Agonist Displays Cognitive Enhancing Properties," *Journal of Medicinal Chemistry*, vol. 49, pp. 4374-4383 (2006).
Thomsen, Morten S., et al., "Cognitive Improvement by Activation of α$_7$ Nicotinic Acetylcholine Receptors: From Animal Models to Human Pathophysiology," *Current Pharmaceutical Design*, vol. 16, pp. 323-343 (2010).
Timmermann, Daniel B., et al., "An Allosteric Modulator of the α7 Nicotinic Acetylcholine Receptor Possessing Cognition-Enhancing Properties In Vivo," *The Journal of Pharmacology and Experimental Therapeutics*, vol. 323, No. 1 pp. 294-307 (2007).
Tsuang, Debby W., et al., "Examination of Genetic Linkage of Chromosome 15 to Schizophrenia in a Large Veterans Affairs Cooperative Study Sample," *American Journal of Medical Genetics (Neuropsychiatric Genetics)*, vol. 105, pp. 662-668 (2001).
Tusco, Salvatore J., et al. "Intravenous Admixtures," *Remington's Pharmaceutical Sciences*, 17th Edition, Chapter 86, Mack Publishing Company, Easton, PA, pp. 1542-1552 (1985).

(56) References Cited

OTHER PUBLICATIONS

Van Kampen, Marja, et al., "AR-R 17779 improves social recognition in rats by activation of nicotinic $\alpha_7$ receptors," *Psychopharmacology*, vol. 172, pp. 375-383 (2004).

Verbois, S.L., et al. "Chronic nicotine treatment attenuates α7 nicotinic receptor deficits following traumatic brain injury," *Neuropharmacology*, vol. 44, pp. 224-233 (2003).

Wang, Hoau-Yan, et al., "Dissociating β-Amyloid from α7 Nicotinic Acetylcholine Receptor by a Novei Therapeutic Agent, S 24795, Normalizes α7 Nicotinic Acetylcholine and NMDA Receptor Function in Alzheimer's Disease Brain," *The Journal of Neuroscience*, vol. 29, No. 35, pp. 10961-10973 (Sep. 2, 2009).

Wang, Juan, et al., "Huperzine A improves Chronic Inflammation and Cognitive Decline in Rats With Cerebral Hypoperfusion," *Journal of Neuroscience Research*, vol. 88, pp. 807-815 (2010).

Wasserman, Todd H., et al., "Clinical Comparison of the Nitrosoureas," *Cancer*, vol. 36, pp. 1258-1268 (1975).

Weiss, Robert B., et al., "A Candidate Gene Approach Identifies the *CHRNA5-A3-B4* Region as a Risk Factor for Age-Dependent Nicotine Addition," *PLoS Genetics*, vol. 4, No. 7, e1000125, pp. 1-11 (Jul. 2008).

Westman, M., et al., "Cell Specific Synovial Expression of Nicotinic Alpha 7 Acetylcholine Receptor in Rheumatoid Arthritis and Psoriatic Arthritis," *Scandinavian Journal of Immunology*, vol. 70, p. 136-140 (2009).

Wilens, Timothy E., et al., "Neuronal Nicotinic Receptor Agonists for the Treatment of Attention-Deficit/Hyperactivity Disorder: Focus on Cognition," *Biochemical Pharmacology*, vol. 74, No. 8, pp. 1212-1223 (Oct. 15, 2007).

Xu, Liang, et al., "Oxidative cyclization of *N*-alkyl-*o*-methyl-arenesulfonamides to biologically important saccharin derivatives," *Tetrahedron*, vol. 62, pp. 7902-7910 (2006).

Yang, Lei, et al., "Heterpoly acids: a green and efficient heterogeneous Bronsted acidic catalyst for the intermolecular hydroamination of olefins," *Tetrahedron Letters*, vol. 49, pp. 2882-2885 (2008).

Young, Jared W., et al., "Impaired attention is central to the cognitive deficits observed in alpha 7 deficient mice," *European Neuropsychopharmacology*, vol. 17, pp. 145-155 (2007).

Young, Jared W., et al., "Nicotine Improves Sustained Attention in Mice: Evidence for Involvement of the α7 Nicotinic Acetylcholine Receptor," *Neuropsychopharmacology*, vol. 29, pp. 891-900 (2004).

Zhao, Xilong, et al., "Post-Stroke Dementia: Nootropic Drug Modulation of Neuronal Nicotinic Acetylcholine Receptors,"*Annais New York Academy of Sciences*, vol. 939, pp. 179-186 (2001).

International Search Report in corresponding International Application No. PCT/IB2013/051455, mailed Jul. 1, 2013.

Deamici, M., et al., "Analogues of the low-efficacy partial $GABA_A$ agonist 4-PIOL. Synthesis and in vitro pharmalogical studies," *European Journal of Medicinal Chemistry*, vol. 26, pp. 625-631 (1991).

Deluca, Patrick P., et al., "Parenteral Drug-Delivery Systems," *Pharmaceutics and Pharmacy Practice*, Chapter 8, J.B. Lippincott Company, Philadelphia, PA, pp. 238-250 (1982).

Kaur, Kirandeep, et al., "Design, synthesis and activity of novel derivatives of Oxybutynin and Tolterodine," *Bioorganic & Medicinal Chemistry Letters*, vol. 15, pp. 2093-2096 (2005).

Richardson, Christine M., et al., "Discovery of a potent CDK2 inhibitor with a novel binding mode, using virtual screening and initial, structure-guided lead scoping" *Bioorganic & Medicinal Chemistry Letters*, vol. 17, pp. 3880-3885 (2007).

Roger, Julien, et al., "Regioselective C-2 or C-5 Direct Arylation of Pyrroles with Aryl Bromides using a Ligand-Free Palladium Catalyst," *Advanced Synthesis & Cataysis*, vol. 351, pp. 1977-1990 (2009).

Trissel, Lawrence A., "Intravenous Infusion Solutions," *ASHP Handbok on Injectable Drugs*, Fourth Edition, American Society of Hospital Pharmacists, Inc., Bethesda, MD, pp. 622-630 (1986).

\* cited by examiner

HETEROARYL DERIVATIVES AS ALPHA7 NACHR MODULATORS

CROSS-REFERENCE TO RELATED APPLICATIONS

This patent application is a U.S. National Phase Application of copending International Application No. PCT/IB2012/050806, filed Feb. 22, 2012, which claims the benefit of Indian Patent Application Nos. 242/KOL/2011, filed Feb. 23, 2011 and 1184/KOL/2011, filed Sep. 9, 2011, the disclosures of which are hereby incorporated by reference in their entireties.

FIELD OF THE INVENTION

The present invention is related to novel compounds of the general formula I,

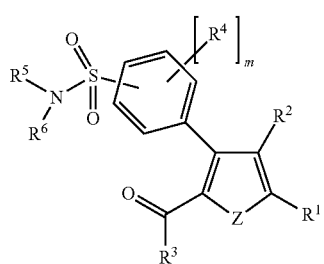

their tautomeric forms, their stereoisomers, their analogues, their prodrugs, their isotopically labeled analogues, their N-oxides, their metabolites, their pharmaceutically acceptable salts, polymorphs, solvates, optical isomers, clathrates, co-crystals, combinations with suitable medicament, pharmaceutical compositions containing them, methods of making of the above compounds, and their use as nicotinic acetylcholine receptor α7 subunit (α7 nAChR) modulator.

BACKGROUND OF THE INVENTION

Cholinergic neurotransmission, mediated primarily through the neurotransmitter acetylcholine (ACh), is a predominant regulator of the physiological functions of the body via the central and autonomic nervous system. ACh acts on the synapses of the neurons present in of all the autonomic ganglia, neuromuscular junctions and the central nervous system. Two distinct classes of ACh target receptors viz. muscarinic (mAChRs) and the nicotinic (nAChRs) have been identified in brain, forming a significant component of receptors carrying its mnemonic and other vital physiological functions.

Neural nicotinic ACh receptors (NNRs) belong to the class of ligand-gated ion channels (LGIC) comprising of five subunits (α2-α10, β2-β4) arranged in heteropentameric (α4β2) or homopertameric (α7) configuration (Paterson D et al., Prog. Neurobiol., 2000, 61, 75-111). α4β2 and α7 nAChR constitute the predominant subtypes expressed in the mammalian brain. α7 nAChR has attained prominence as a therapeutic target due to its abundant expression in the learning and memory centers of brain, hippocampus and the cerebral cortex (Rubboli F et al., Neurochem. Int., 1994, 25, 69-71). Particularly, α7 nAChR is characterized by a high $Ca^{2+}$ ion permeability, which is responsible for neurotransmitter release and consequent modulation of excitatory and inhibitory neurotransmission (Alkondon M et al., Eur. J. Pharmacol., 2000, 393, 59-67; Dajas-Bailador F et al., Trends Pharmacol. Sci., 2004, 25, 317-324). Furthermore, high $Ca^{2+}$ ion influx also has implications on the long-term potentiation of memory via alterations in gene expression (Bitner R S et al., J. Neurosci., 2007, 27, 10578-10587; McKay B E et al., Biochem. Pharmacol., 2007, 74, 1120-1133).

Several recent studies have confirmed the role of α7 nAChR in neural processes like attention, memory and cognition (Mansvelder H D et al., Psychopharmacology (Berl), 2006, 184, 292-305; Chan W K et al., Neuropharmacology, 2007, 52, 1641-1649; Young J W et al., Eur. Neuropsychopharmacol., 2007, 17, 145-155). Gene polymorphisms associated with the α7 nAChR protein CHRNA7 have been implicated in the genetic transmission of schizophrenia, related neurophysiological sensory gating deficits and resultant cognitive impairment (Freedman R et al., Biol. Psychiatry, 1995, 38, 22-33; Tsuang D W et al., Am. J. Med. Genet., 2001, 105, 662-668). Also, preclinical studies in α 7 nAChR knock-out and anti-sense oligonucleotide treated mice have demonstrated impaired attention and defective cognition underscoring the prominent role of α7 nAChR in cognition (Curzon P et al., Neurosci. Lett., 2006, 410, 15-19; Young J W et al., Neuropsychopharmacology., 2004, 29, 891-900). Additionally, pharmacological blockade of α 7 nAChR impairs memory and its activation enhances same in preclinical rodent models implicating α7 nAChR as target for cognitive enhancement (Hashimoto K et al., Biol. Psychiatry, 2008, 63, 92-97).

Pathological brain function in sensory-deficit disorders has been associated with nicotinic cholinergic transmission particularly through α7 receptors (Freedman R et al., Biol. Psychiatry, 1995, 38, 22-33; Tsuang D W et al., Am. J. Med. Genet., 2001, 105, 662-668; Carson R et al., Neuromolecular, 2008, Med. 10, 377-384; Leonard S et al., Pharmacol. Biochem. Behav., 2001, 70, 561-570; Freedman R et al., Curr. Psychiatry Rep., 2003, 5, 155-161; Cannon T D et al., Curr. Opin. Psychiatry, 2005, 18, 135-140). A defective pre-attention processing of sensory information is understood to be the basis of cognitive fragmentation in schizophrenia and related neuropsychiatric disorders (Leiser S C et al., Pharmacol. Ther., 2009, 122, 302-311). Genetic linkage studies have traced sharing of the α7 gene locus for several affective, attention, anxiety and psychotic disorders (Leonard S et al., Pharmacol. Biochem. Behav., 2001, 70, 561-570; Suemaru K et al., Nippon Yakurigaku Zasshi, 2002, 119, 295-300).

Perturbations in the cholinergic and glutamatergic homeostasis, has long been implicated as causative factors for host of neurological disease, including dementia(s) (Nizri E et al., Drug News Perspect., 2007, 20, 421-429). Dementia is a severe, progressive, multi-factorial cognitive disorder affecting memory, attention, language and problem solving. Nicotinic ACh receptor, particularly the interaction of α7 receptor to $\alpha\beta_{1-42}$ is implicated as an up-stream pathogenic event in Alzheimer's disease, a major causative factor for dementia (Wang H Y et al., J. Neurosci., 2009, 29, 10961-10973). Moreover, gene polymorphisms in CHRNA7 have been implicated in dementia with lewy bodies (DLB) and Pick's disease (Feher A et al., Dement. Geriatr. Cogn. Disord., 2009, 28, 56-62).

Disease modification potential of nAChRs particularly the α7 receptor has application for disease-modification of Alzheimer's disease (AD) and Parkinson's disease (PD) by enhancing neuron survival and preventing neurodegeneration (Wang et al. 2009; Nagele R G et al., Neuroscience, 2002, 110, 199-211; Jeyarasasingam G et al., Neuroscience, 2002, 109, 275-285). Additionally, α7 nAChR induced activation of anti-apoptotic (BCL-2) and anti-inflammatory pathways in brain could have neuroprotective effects in neurodegenerative diseases (Marrero M B et al., Brain. Res., 2009, 1256, 1-7). Dopamine containing neurons of ventral tegmental area (VTA) and laterodorsal tegmental nucleus (LDT) are known to express nicotinic ACh receptors, particularly α4, α3, β2, β3, β4 subunits (Kuzmin A et al., Psychopharmacology (Berl), 2009, 203, 99-108). Nicotinic ACh receptors, α4β2 and α3β4 have been identified with candidate-gene approach to have strong mechanistic link for nicotine addiction (Weiss R B et al., PLoS Genet., 2008, 4, e1000125). α7 nAChR has particularly been studied for a putative role in cannabis addiction (Solinas M et al., J. Neurosci., 2007, 27, 5615-5620). Varenicline, a partial agonist at α4β2, has demonstrated better efficacy in reducing the smoking addiction and relapse prevention in comparison to buproprion (Ebbert J O et al., Patient. Prefer. Adherence, 2010, 4, 355-362).

Presence of a high-affinity nicotine binding site at α4β2 nAChR, in the descending inhibitory pathways from brainstem has sparked interest in the antinociceptive properties of nicotinic ACh receptor agonists like epibatidine (Decker M W et al., Expert. Opin. Investig. Drugs, 2001, 10, 1819-1830). Several new developments have opened the area for use of nicotinic modulators for therapy of pain (Rowbotham M C et al., Pain, 2009, 146, 245-252). Appropriate modulation of the nicotinic ACh receptors could provide for remedial approach to pain related states.

Another key role of the α7 nAChR is the ability to modulate the production of pro-inflammatory cytokines, like interleukins (IL), tumor necrosis factor alpha (TNF-α), and high mobility group box (HMGB-1) in the central nervous system. Consequently, an anti-inflammatory and antinociceptive effect in pain disorders have been demonstrated (Damaj M I et al., Neuropharmacology, 2000, 39, 2785-2791). Additionally, 'cholinergic anti-inflammatory pathway' is proposed to be a regulatory of local and systemic inflammation and neuro-immune interactions through neural and humoral pathways (Gallowitsch-Puerta M et al., Life Sci., 2007, 80, 2325-2329; Gallowitsch-Puerta and Pavlov 2007; Rosas-Ballina M et al., Mol. Med., 2009, 15, 195-202; Rosas-Ballina M et al., J. Intern. Med., 2009, 265, 663-679). Selective modulators of nicotinic ACh receptors, particularly α7 type, like GTS-21, attenuate cytokine production and IL-1β after endotoxin exposure. Furthermore, α7 nAChR are understood to have a central role in arthritis pathogenesis and potential therapeutic strategy for treatment of joint inflammation (Westman M et al., Scand. J. Immunol., 2009, 70, 136-140). A putative role for α7 nAChR has also been implicated in severe sepsis, endotoxemic shock and systemic inflammation (Jin Y et al. (2010) Int. J. Immunogenet., Liu C et al., Crit. Care. Med., 2009, 37, 634-641).

Angiogenesis, is a critical physiological process for the cell survival and pathologically important for cancer proliferation; several non-neural nicotinic ACh receptors, particularly α7, α5, α3, β2, β4, are involved (Arias H R et al., Int. J. Biochem. Cell. Biol., 2009, 41, 1441-1451; Heeschen C et al., J. Clin. Invest., 2002, 110, 527-536). A role of nicotinic ACh receptors in the development of cervical cancer, lung carcinogenesis and paediatric lung disorders in smoking-exposed population has also been studied (Calleja-Macias I E et al., Int. J. Cancer., 2009, 124, 1090-1096; Schuller H M et al., Eur. J. Pharmacol., 2000, 393, 265-277). Several α7 nAChR agonists, partial agonists, have been characterized for their efficacy in clinical and preclinical studies. EVP-6124, an agonist at α7 nAChR, has demonstrated significant improvement in sensory processing and cognition biomarkers in Phase Ib study with patients suffering from schizophrenia (EnVivo Pharmaceuticals press release 2009, Jan. 12). GTS-21 (DMXB-Anabaseine), an α7 nAChR agonist, in the P II clinical trials, has shown efficacy in improving cognitive deficits in schizophrenia and inhibition of endotoxin-induced TNF-α release (Olincy A et al., Biol. Psychiatry, 2005, 57(8, Suppl.), Abst 44; Olincy A et al., Arch. Gen. Psychiatry, 2006, 63, 630-638; Goldstein R et al., Acad. Emerg. Med., 2007, 14 (15, Suppl. 1), Abst 474). CP-810123, a α7 nAChR agonist, exhibits protection against the scopolamine-induced dementia and inhibition of amphetamine-induced auditory evoked potentials in preclinical studies (O'Donnell C J et al., J. Med. Chem., 2010, 53, 1222-1237). SSR-180711A, also an α7 nAChR agonist, enhances learning and memory, and protects against MK-801/Scopolamine-induced memory loss and prepulse inhibition in preclinical studies (Redrobe J P et al., Eur. J. Pharmacol., 2009, 602, 58-65; Dunlop J et al., J. Pharmacol. Exp. Ther., 2009, 328, 766-776; Pichat P et al., Neuropsychopharmacology, 2007, 32, 17-34). SEN-12333, protected against scopolamine-induced amnesia in passive avoidance test in preclinical studies (Roncarati R et al., J. Pharmacol. Exp. Ther., 2009, 329, 459-468). AR-R-17779, an agonist at α7 nAChR, exhibits improvement in the social recognition task performed in rats (Van K M et al., Psychopharmacology (Berl), 2004, 172, 375-383). ABBF, an agonist at α7 nAChR, improves social recognition memory and working memory in Morris maze task in rats (Boess F G et al., J. Pharmacol. Exp. Ther., 2007, 321, 716-725). TC-5619, a selective α7 nAChR agonist has demonstrated efficacy in animal models of positive and negative symptoms and cognitive dysfunction in schizophrenia (Hauser T A et al., Biochem. Pharmacol., 2009, 78, 803-812).

An alternative strategy to reinforce or potentiate the endogenous cholinergic neurotransmission of ACh without directly stimulating the target receptor is the positive allosteric modulation (PAM) of α7 nAChR (Albuquerque E X et al., Alzheimer Dis. Assoc. Disord., 2001, 15 Suppl 1, S19-S25). Several PAMs have been characterized, albeit in the preclinical stages of discovery. A-86774, α7 nAChR PAM, improves sensory gating in DBA/2 mice by significantly reducing the T:C ratio in a preclinical model of schizophrenia (Faghih R et al., J. Med. Chem., 2009, 52, 3377-3384). XY-4083, an α7 nAChR PAM, normalizes the sensorimotor gating deficits in the DBA/2 mice and memory acquisition in 8-arm radial maze without altering the receptor desensitization kinetics (Ng H J et al., Proc. Natl. Acad. Sci., U.S. A., 2007, 104, 8059-8064). Yet another PAM, PNU-120596, profoundly alters α7 nAChR desensitization kinetics and simultaneously protecting against the disruption of prepulse inhibition by MK-801. NS-1738, another PAM, has exhibited efficacy in-vivo in the animal models of social recognition and spatial memory acquisition in the Morris maze task (Timmermann D B et al., J. Pharmacol. Exp. Ther., 2007, 323, 294-307). In addition, several patents/applications published are listed below— US20060142349, US20070142450, US20090253691, WO2007031440, WO2009115547, WO2009135944, WO2009127678, WO2009127679, WO2009043780, WO2009043784, U.S. Pat. No. 7,683,084, U.S. Pat. No. 7,741,364, WO2009145996, US20100240707, WO2011064288, US20100222398, US20100227869, EP1866314, WO2010130768, WO2011036167, US20100190819 disclose efficacy of allosteric modulators of nicotinic ACh receptors and underscoring their therapeutic potential.

SUMMARY OF THE INVENTION

According to one aspect of the present invention there is provided compounds represented by the general formula I, its tautomeric forms, its stereoisomers, its analogues, its prodrugs, its isotopically substituted analogues, its metabolites, its pharmaceutically acceptable salts, its polymorphs, its solvates, its clathrates, its optical isomers, its co-crystals, their combinations with suitable medicament and pharmaceutical compositions containing them.

Thus the present invention further provides a pharmaceutical composition, containing the compounds of the general formula (I) as defined herein, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically employed carriers, diluents and the like are useful for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The present invention also provides a pharmaceutical composition, containing the compounds of the general formula (I) as defined herein, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically employed carriers, diluents and the like are useful for the treatment and/or prophylaxis of diseases or disorder or condition classified or diagnosed as major or minor neurocognitive disorders, or disorders arising due to neurodegeneration.

The present invention also provides method of administering a compound of formula I, as defined herein in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provides method of administering a compound of formula I, as defined herein in combination with or as an adjunct to acetylcholinesterase inhibitors, disease modifying drugs or biologics for neurodegenerative disorders, dopaminergic drugs, antidepressants, typical or an atypical antipsychotic.

The present invention also provides use of a compound of formula I as defined herein in the preparation of a medicament for treating a disease or disorder or condition selected from the group classified or diagnosed as major or minor neurocognitive disorders, or disorders arising due to neurodegeneration.

The present invention also provides use of a compound of formula I as defined herein in the preparation of a medicament for treating a disease or disorder or condition selected from the group consisting of attention deficit hyperactivity disorders, schizophrenia, cognitive disorders, Alzheimer's disease, Parkinson's dementia, vascular dementia or dementia associated with Lewy bodies, and traumatic brain injury.

The present invention also provides use of compound of formula I as defined herein in combination with or as an adjunct to acetylcholinesterase inhibitors, disease modifying drugs or biologics for neurodegenerative disorders, dopaminergic drugs, antidepressants, or a typical or atypical antipsychotic.

DETAILED DESCRIPTION OF THE INVENTION

The present invention relates to novel compounds of the general formula I, its tautomeric forms, its stereoisomers, its analogues, its prodrugs, its isotopically substituted analogues, its metabolites, its sulfoxides, its N-oxides, its pharmaceutically acceptable salts, its polymorphs, its solvates, its optical isomers, its clathrates, its co-crystals, their combinations with suitable medicament and pharmaceutical compositions containing them.

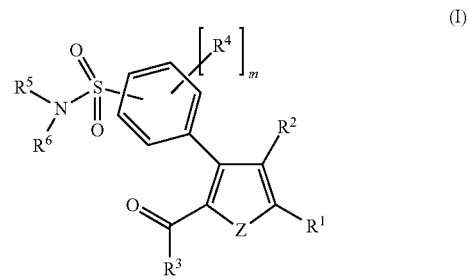

(I)

wherein, in the compound of formula I,

Z is selected from the group consisting of —S—, —O— and —N($R^a$)—;

$R^a$ is selected from the group consisting of hydrogen, optionally substituted alkyl, optionally substituted alkenyl, optionally substituted alkynyl, optionally substituted cycloalkyl, optionally substituted aryl, optionally substituted heteroaryl, optionally substituted heterocyclyl;

$R^1$ is selected from the group consisting of optionally substituted aryl, optionally substituted heteroaryl, optionally substituted cycloalkyl, optionally substituted heterocyclyl;

$R^2$ is selected from the group consisting of hydrogen, optionally substituted alkyl, optionally substituted alkenyl, optionally substituted alkynyl, halogen, perhaloalkyl, optionally substituted cycloalkyl, cyano, nitro, $(R^7)(R^8)N$—, $R^{7a}C(=O)N(R^7)$—, $(R^7)(R^8)NC(=A^1)N(R^9)$—, $R^{7a}OC(=O)NR^9$—, $R^{7a}SO_2N(R^8)$—, $R^7A^1$-, and $R^{7a}C(=O)$—;

$R^3$ is selected from the group consisting of optionally substituted alkyl, optionally substituted alkenyl, optionally substituted alkynyl, optionally substituted cycloalkyl, optionally substituted heterocyclyl, wherein each of the said optionally substituted cycloalkyl and optionally substituted heterocyclyl is optionally annulated or optionally bridged, $(R^7)(R^8)N-$, $(R^7)N(OR^8)-$, and $R^{7a}A^1-$;

$[R^4]_m$ is 'm' times repetition of '$R^4$' groups, each $R^4$ is independently selected from the group consisting of halogen, cyano, optionally substituted alkyl, optionally substituted alkenyl, optionally substituted alkynyl, optionally substituted heteroalkyl, optionally substituted cycloalkyl, optionally substituted heterocyclyl, $R^{7a}C(=O)-$, $R^{7a}SO_2-$, $R^{7}A^1-$, $(R^{7a})C(=O)N(R^9)-$, $(R^7)(R^8)N-$, $(R^7)(R^8)NC(=A^1)N(R^9)-$; wherein m=0 to 3; or two $R^4$ groups and the carbon atoms to which they are attached together form an optionally substituted 5- to 6-membered cyclic system which optionally contains 1 to 4 hetero atoms/groups selected from the group consisting of $-N-$, $-S-$, $-O-$, $-C(=O)-$, and $-C(=S)-$;

$R^5$ and $R^6$ are independently selected from the group consisting of hydrogen, $R^{7a}C(=O)-$, optionally substituted alkyl, optionally substituted alkenyl, optionally substituted alkynyl, optionally substituted cycloalkyl, optionally substituted heterocyclyl, optionally substituted aryl, and optionally substituted heteroaryl; or $R^5$ and $R^6$ together with the nitrogen atom to which they are attached form a 3- to 10-membered optionally substituted saturated/unsaturated heterocyclic ring system containing one to three hetero atoms/groups selected from the group consisting of $-S-$, $-N-$, $-O-$, $-C(=O)-$, and $-C(=S)-$;

wherein $R^7$, $R^8$, and $R^9$ are independently selected from the group consisting of hydrogen, optionally substituted alkyl, optionally substituted alkenyl, optionally substituted alkynyl, optionally substituted heteroalkyl, optionally substituted aryl, optionally substituted heteroaryl, optionally substituted cycloalkyl, and optionally substituted heterocyclyl;

$A^1$ is selected from the group consisting of O and S;

$R^{7a}$ is selected from the group consisting of optionally substituted alkyl, optionally substituted alkenyl, optionally substituted alkynyl, optionally substituted heteroalkyl, optionally substituted aryl, optionally substituted heteroaryl, optionally substituted cycloalkyl, and optionally substituted heterocyclyl;

wherein, the term "optionally substituted alkyl", means a alkyl group unsubstituted or substituted with 1 to 6 substituents selected independently from the group consisting of oxo, halogen, nitro, cyano, aryl, hereroaryl, cycloalkyl, $R^{10a}SO_2-$, $R^{10}A^1-$, $R^{10a}OC(=O)-$, $R^{10a}C(=O)O-$, $(R^{10})(H)NC(=O)-$, $(R^{10})(alkyl)NC(=O)-$, $R^{10a}C(=O)N(H)-$, $(R^{10})(H)N-$, $(R^{10})(alkyl)N-$, $(R^{10})(H)NC(=A^1)N(H)-$, and $(R^{10})(alkyl)NC(=A^1)N(H)-$;

the term "optionally substituted alkenyl", means a alkenyl group unsubstituted or substituted with 1 to 6 substituents selected independently from the group consisting of oxo, halogen, nitro, cyano, aryl, hereroaryl, cycloalkyl, $R^{10a}SO_2-$, $R^{10}A^1-$, $R^{10a}OC(=O)-$, $R^{10a}C(=O)O-$, $(R^{10})(H)NC(=O)-$, $(R^{10})(alkyl)NC(=O)-$, $R^{10a}C(=O)N(H)-$, $(R^{10})(H)N-$, $(R^{10})(alkyl)N-$, $(R^{10})(H)NC(=A^1)N(H)-$, and $(R^{10})(alkyl)NC(=A^1)N(H)-$;

the term "optionally substituted alkynyl", means a alkynyl group unsubstituted or substituted with 1 to 6 substituents selected independently from the group consisting of oxo, halogen, nitro, cyano, aryl, hereroaryl, cycloalkyl, $R^{10a}SO_2-$, $R^{10}A^1-$, $R^{10a}OC(=O)-$, $R^{10a}C(=O)O-$, $(R^{10})(H)NC(=O)-$, $(R^{10})(alkyl)NC(=O)-$, $R^{10a}C(=O)N(H)-$, $(R^{10})(H)N-$, $(R^{10})(alkyl)N-$, $(R^{10})(H)NC(=A^1)N(H)-$, and $(R^{10})(alkyl)NC(=A^1)N(H)-$;

the term "optionally substituted heteroalkyl" means a heteroalkyl group unsubstituted or substituted with 1 to 6 substituents selected independently from the group consisting of oxo, halogen, nitro, cyano, aryl, hereroaryl, and cycloalkyl;

the term "optionally substituted cycloalkyl" means a cycloalkyl group unsubstituted or substituted with 1 to 6 substituents selected independently from the group consisting of oxo, halogen, nitro, cyano, aryl, hereroaryl, alkyl, alkenyl, alkynyl, $R^{10a}C(=O)-$, $R^{10a}SO_2-$, $R^{10}A^1-$, $R^{10a}OC(=O)-$, $R^{10a}C(=O)O-$, $(R^{10})(H)NC(=O)-$, $(R^{10})(alkyl)NC(=O)-$, $R^{10a}C(=O)N(H)-$, $(R^{10})(H)N-$, $(R^{10})(alkyl)N-$, $(R^{10})(H)NC(=A^1)N(H)-$, and $(R^{10})(alkyl)NC(=A^1)N(H)-$;

the term "optionally substituted aryl" means (i) an aryl group unsubstituted or substituted with 1 to 3 substituents selected independently from the group consisting of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N-$, alkyl-$SO_2-$, perhaloalkyl-$SO_2-$, alkyl-C(=O)N(alkyl)-, alkyl-C(=O)N(H)—, alkyl-N(alkyl)C(=O)—, alkyl-N(H)C(=O)—, $H_2NC(=O)-$, alkyl-N(alkyl)$SO_2-$, alkyl-N(H)$SO_2-$, $H_2NSO_2-$, 3- to 6-membered heterocycle containing 1 to 2 heteroatoms selected from the group consisting of N, O and S, wherein the said 3- to 6-membered heterocycle is optionally substituted with alkyl, alkenyl, alkynyl, or alkyl-C(=O)— or (ii) the said substituted or unsubstituted aryl ring optionally fused with cycloalkane ring or heterocycle ring containing 1 to 3 heteroatoms selected from S, O, N, across a bond, wherein the said cycloalkane ring or heterocycle ring is optionally substituted with oxo, alkyl, alkenyl, alkynyl or alkyl-C(=O)—;

the term "optionally substituted heterocyclyl" means a (i) heterocyclyl group unsubstituted or substituted on ring carbons with 1 to 6 substituents selected independently from the group consisting of oxo, halogen, nitro, cyano, aryl, hereroaryl, alkyl, alkenyl, alkynyl, $R^{10}A^1-$, $R^{10a}OC(=O)-$, $R^{10a}C(=O)O-$, $(R^{10})(H)NC(=O)-$, $(R^{10})(alkyl)NC(O)-$, $R^{10a}C(=O)N(H)-$, $(R^{10})(H)N-$, $(R^{10})(alkyl)N-$, $(R^{10})(H)NC(=A^1)N(H)-$, and $(R^{10})(alkyl)NC(=A^1)N(H)-$; (ii) heterocyclyl group optionally substituted on ring nitrogen(s) with one or more substituents selected from the group consisting of hereroaryl, alkyl, alkenyl, alkynyl, $R^{10a}C(=O)-$, $R^{10a}SO_2-$, $R^{10a}OC(=O)-$, $(R^{10})(H)NC(=O)-$, $(R^{10})(alkyl)NC(=O)-$, and aryl unsubstituted or substituted with 1 to 3 substituents selected independently from halogen, alkyl, alkenyl, alkynyl, cyano or nitro;

the term "optionally substituted heteroaryl" means a heteroaryl group unsubstituted or substituted with 1 to 3 substituents selected independently from the group consisting of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N-$, alkyl-$SO_2-$, perhaloalkyl-$SO_2-$, alkyl-C (=O)N(alkyl)-, alkyl-C(=O)N(H)—, alkyl-N(alkyl)C(=O)—, alkyl-N(H)C(=O)—, H$_2$NC(=O)—, alkyl-N(alkyl)SO$_2$—, alkyl-N(H)SO$_2$—, H$_2$NSO$_2$—, and 3- to 6-membered heterocycle containing 1 to 2 heteroatoms selected from the group consisting of N, O and S, wherein the heterocycle is optionally substituted with one to four substituents selected from the group consisting of alkyl alkenyl, alkynyl, or alkyl-C(=O)—;

the term "optionally substituted 5- to 6-membered cyclic system" means the 5- to 6-membered cyclic system unsubstituted or substituted with 1 to 3 substituents selected from the group consisting of oxo, halogen, nitro, cyano, aryl, hereroaryl, alkyl, alkenyl, alkynyl, R$^{10a}$C(=O)—, R$^{10a}$SO$_2$—, R$^{10}$A$^1$-, R$^{10a}$OC(=O)—, R$^{10a}$C(=O)O—, (R$^{10}$)(H)NC(=O)—, (R$^{10}$)(alkyl)NC(=O)—, R$^{10a}$C(=O)N(H)—, (R$^{10}$)(H)N—, (R$^{10}$)(alkyl)N—, (R$^{10}$)(H)NC(=A$^1$)N(H)—, and (R$^{10}$)(alkyl)NC(=A')N(H)—;

the term "3- to 10-membered optionally substituted saturated/unsaturated heterocyclic ring system" the 3- to 10-membered saturated/unsaturated heterocyclic ring system unsubstituted or substituted with 1 to 3 substituents selected from the group consisting of oxo, halogen, nitro, cyano, aryl, hereroaryl, alkyl, alkenyl, alkynyl, R$^{10a}$C(=O)—, R$^{10a}$SO$_2$—, R$^{10}$A$^1$-, R$^{10a}$OC(=O)—, R$^{10a}$C(=O)O—, (R$^{10}$)(H)NC(=O)—, (R$^{10}$)(alkyl)NC(=O)—, R$^{10a}$C(=O)N(H)—, (R$^{10}$)(H)N—, (R$^{10}$)(alkyl)N—, (R$^{10}$)(H)NC(=A$^1$)N(H)—, and (R$^{10}$)(alkyl)NC(=A')N(H)—;

wherein R$^{10}$ is selected from hydrogen, alkyl, alkenyl, alkynyl, aryl, heteroaryl, cycloalkyl or heterocyclyl;

and R$^{10a}$ is selected from the group consisting of alkyl, alkenyl, alkynyl, perhaloalkyl, aryl, heteroaryl, cycloalkyl or heterocyclyl.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

One of the embodiment of the present invention is compound of formula Ia;

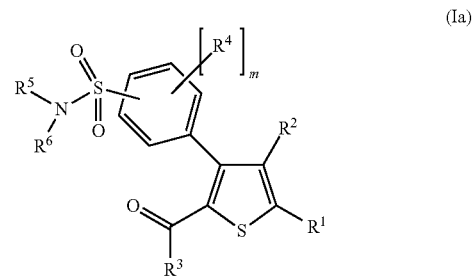

wherein R$^1$, R$^2$, R$^3$, R$^4$, R$^5$, R$^6$ and m are as defined above.

Another embodiment of the present invention is compound of formula Ib;

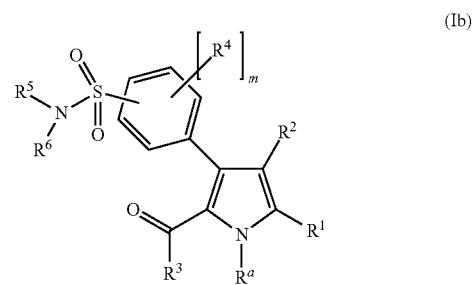

wherein R$^1$, R$^2$, R$^3$, R$^4$, R$^5$, R$^6$, R$^a$ and m are as defined above.

Yet another embodiment of the present invention is compound of formula Ic;

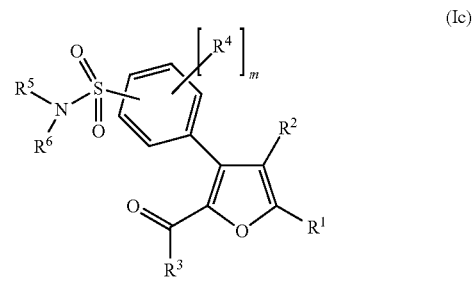

wherein R$^1$, R$^2$, R$^3$, R$^4$, R$^5$, R$^6$ and m are as defined above.

In any of the embodiments of the invention described above, R$^1$ is particularly selected from the group consisting of pyridyl, furanyl, indolyl, N-methylisoindolyl, benzofuranyl, piperazinyl, 4-(4-fluorophenyl)piperazinyl, morpholinyl, indolinyl, 2-oxoindolinyl, 2,3-dihydrobenzo[b][1,4]dioxinyl, benzopyranyl, or phenyl optionally substituted with 1 to 2 substituents selected from group comprising of halo, cyclopropyl, trifluoromethyl, methoxy, ethoxy, trifluoromethoxy, methyl, ethyl, dimethylamino, monomethylamino, tert-butyl and 4-methylpiperazinyl.

In any of the embodiments described above, R$^2$ is particularly selected from the group consisting of hydrogen, methyl, dimethylamino and dimethylaminomethyl.

In any of the embodiments described above, R$^3$ is particularly selected from the group consisting of methyl, ethyl, n-propyl, methoxy, ethoxy, dimethylamino, N-methoxy-N-methyl amino, N-(2-hydroxy ethyl)-N-propyl amino, acetylaminomethyl and piperidinyl.

In any of the embodiments described above, R$^5$ and R$^6$ are particularly selected independently from the group consisting of hydrogen and methyl, or $R^4$ and $R^5$ together with the nitrogen atom to which they are attached form a piperidine ring.

In any of the embodiments described above, m is particularly selected from 0, 1 or 2, and $R^4$ is selected from methyl or two Ws together with the carbon atoms to which they are attached forming a six membered carbocycle.

In any of the embodiments described above, $R^a$ is particularly selected from the group consisting of hydrogen, methyl, ethyl and cyclopropylmethyl.

In any of the embodiments of the present invention of the compound of formula I, $R^1$ is selected from the group consisting of pyridyl, furanyl, indolyl, N-methylisoindolyl, benzofuranyl, piperazinyl, 4-(4-fluorophenyl)piperazinyl, morpholinyl, indolinyl, 2-oxoindolinyl, 2,3-dihydrobenzo[b][1,4]dioxinyl, benzopyranyl, and phenyl optionally substituted with 1 to 2 substituents selected from group consisting of halo, cyclopropyl, trifluoromethyl, methoxy, ethoxy, trifluoromethoxy, methyl, ethyl, dimethylamino, monomethylamino and tert-butyl, 4-methylpiperazinyl; $R^2$ is selected from the group consisting of hydrogen, methyl, dimethylamino and dimethylaminomethyl; $R^3$ is selected from the group consisting of methyl, ethyl, n-propyl, methoxy, ethoxy, dimethylamino, N-methoxy-N-methyl amino, N-(2-hydroxy ethyl)-N-propyl amino, acetylaminomethyl, piperidinyl; $R^5$ and $R^6$ are selected independently from hydrogen and methyl, or $R^5$ and $R^6$ together with the nitrogen atom to which they are attached form a piperidine ring; m is selected from 0, 1 or 2, and $R^4$ is selected from methyl or two $R^4$s together with the carbon atoms to which they are attached form a six membered carbocycle; and $R^a$ is selected from the group consisting of hydrogen, methyl, ethyl and cyclopropylmethyl.

In any of the embodiments described above, $R^1$ is particularly selected from the group consisting of 4-chlorophenyl, 2-chlorophenyl, 3-chlorophenyl, 4-fluorophenyl, 4-cyclopropylphenyl, 4-trifluoromethylphenyl, 4-methoxyphenyl, 4-ethoxyphenyl, 3-ethoxyphenyl, 4-tolyl, 4-tert-butyl phenyl, 4-dimethylaminophenyl, 3-fluorophenyl, phenyl, 4-ethylphenyl, 3,4-dichlorophenyl, 2,4-dichlorophenyl, 2,4-difluorophenyl, 3-chloro-4-fluorophenyl, 3-chloro-4-methoxyphenyl, piperazin-1-yl, 4-(fluorophenyl)piperazinyl, morpholino, yl, furan-3-yl, 1H-indol-5-yl, 1-methyl-1H-indol-5-yl, benzofuran-5-yl, indolin-5-yl, 4-(4-methylpiperaziny-1-yl)phenyl, and 2,3-dihydrobenzo[b][1,4]dioxin-6-yl).

In any of the embodiments described above, Z is particularly selected as S.

General terms used in formula can be defined as follows; however, the meaning stated should not be interpreted as limiting the scope of the term per se.

The term "alkyl", as used herein, means a straight chain or branched hydrocarbon containing from 1 to 20 carbon atoms. Preferably the alkyl chain may contain 1 to 10 carbon atoms. More preferably alkyl chain may contain up to 6 carbon atoms. Representative examples of alkyl include, but are not limited to, methyl, ethyl. n-propyl. iso-propyl. n-butyl, sec-butyl, iso-butyl, tert-butyl, n-pentyl, isopentyl, neopentyl and n-hexyl.

The term "alkenyl" as used herein, means an 'alkyl' group as defined hereinabove containing 2 to 20 carbon atoms and containing at least one double bond.

The term "alkynyl" as used herein, means an 'alkyl' group as defined hereinabove containing 2 to 20 carbon atoms and containing at least one triple bond.

'Alkyl', 'alkenyl' or 'alkynyl' as defined hereinabove may be optionally substituted with one or more substituents selected independently from the group comprising of oxo, halogen, nitro, cyano, aryl, hereroaryl, cycloalkyl, $R^{10a}SO_2$—, $R^{10}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, $(R^{10})(alkyl)NC(=A^1)N(H)$—; wherein $R^{10}$ is selected from hydrogen, alkyl, alkenyl, alkynyl, aryl, heteroaryl, cycloalkyl or heterocyclyl; and $A^1$ is selected from S and O; and $R^{10a}$ is selected from alkyl, alkenyl, alkynyl perhaloalkyl, aryl, heteroaryl, cycloalkyl or heterocyclyl.

The term "perhaloalkyl" used herein means an alkyl group as defined hereinabove wherein all the hydrogen atoms of the said alkyl group are substituted with halogen. The perhaloalkyl group is exemplified by trifluoromethyl, pentafluoroethyl and the like.

The term "heteroalkyl" as used herein means hetero modified 'alkyl' group, where a $CH_2$ group is modified (or replaced) by —O—, —S—, —S(O$_2$)—, —S(O)—, —N(R$^m$)—, Si(R$^m$)R$^n$— wherein, R$^m$ and R$^n$ are independently selected from hydrogen, alkyl, alkenyl, alkynyl, aryl, heteroaryl, cycloalkyl, and heterocyclyl. The group there by includes the linkages like $CH_3$—S—, $CH_3$—$CH_2$—O—, $CH_3$—O—$CH_2$—, $CH_3$—S—$CH_2$—, $CH_3$—N(R$^m$)—$CH_2$—, $CH_3$—Si(R$^m$)R$^n$—$CH_2$— and the like.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems are also exemplified by a bridged monocyclic ring system in which two non-adjacent carbon atoms of the monocyclic ring are linked by an alkylene bridge. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, bicyclo[3.3.2]decane, bicyclo[3.1.0]hexane, bicyclo[410]heptane, bicyclo[3.2.0]heptanes, octahydro-1H-indene. Tricyclic ring systems are also exemplified by a bicyclic ring system in which two non-adjacent carbon atoms of the bicyclic ring are linked by a bond or an alkylene bridge. Representative examples of tricyclic-ring systems include, but are not limited to, tricyclo[3.3.1.0$^{3.7}$]nonane and tricyclo[3.3.1.1$^{3.7}$]decane (adamantane). The term cycloalkyl also include spiro systems wherein one of the ring is annulated on a single carbon atom such ring systems are exemplified by spiro[2.5]octane, spiro[4.5]decane, spiro[bicyclo[4.1.0]heptane-2,1'-cyclopentane], hexahydro-2'H-spiro[cyclopropane-1,1'-pentalene].

cycloalkyl as defined hereinabove may be optionally substituted with one or more substituents selected independently from the group comprising of oxo, halogen, nitro, cyano, aryl, hereroaryl, alkyl, alkenyl, alkynyl, $R^{10a}C(=O)$—, $R^{10a}SO_2$—, $R^{10}A^1$-, $R^{10a}OC(=O)$—, $R^{10a}C(=O)O$—, $(R^{10})(H)NC(=O)$—, $(R^{10})$ (alkyl)NC(=O)—, $R^{10a}C(=O)N(H)$—$(R^{10})(H)N$—, $(R^{10})(alkyl)N$—, $(R^{10})(H)NC(=A^1)N$ (H)—, $(R^{10})$(alkyl)NC(=$A^1$)N(H)—; wherein $R^{10}$ is selected from hydrogen, alkyl, alkenyl, alkynyl, aryl, heteroaryl, cycloalkyl or heterocyclyl; and $A^1$ is selected from S and O; and $R^{10a}$ is selected from alkyl, alkenyl, alkynyl, perhaloalkyl, aryl, heteroaryl, cycloalkyl or heterocyclyl The term "aryl" refers to a monovalent monocyclic, bicyclic or tricyclic aromatic. hydrocarbon ring system. Examples of aryl groups include phenyl, naphthyl, anthracenyl, fluorenyl, indenyl, azulenyl, and the like. Aryl group also include partially saturated bicyclic and tricyclic aromatic hydrocarbons such as tetrahydro-naphthalene. The said aryl group also includes aryl rings fused with heteroaryl or heterocyclic rings such as 2,3-dihydro-benzo[1,4]dioxin-6-yl; 2,3-dihydro-benzo[1,4]dioxin-5-yl; 2,3-dihydro-benzofuran-5-yl; 2,3-dihydro-benzofuran-4-yl; 2,3-dihydro-benzofuran-6-yl; 2,3-dihydro-benzofuran-6-yl; 2,3-dihydro-1H-indol-5-yl; 2,3-dihydro-1H-indol-4-yl; 2,3-dihydro-1H-indol-6-yl; 2,3-dihydro-1H-indol-7-yl; benzo[1,3]dioxol-4-yl; benzo[1,3]dioxol-5-yl; 1,2,3,4-tetrahydroquinolinyl; 1,2,3,4-tetrahydroisoquinolinyl; 2,3-dihydrobenzothien-4-yl, 2-oxoindolin-5-yl.

Aryl as defined hereinabove may be optionally substituted with one or more substituents selected independently from the group comprising of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2$N—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2$NC(=O)—, alkyl-N(alkyl)$SO_2$—, alkyl-N(H)$SO_2$—, $H_2$N$SO_2$—, 3 to 6 membered heterocycle containing 1 to 2 heteroatoms selected from N, O and S optionally substituted with alkyl, alkenyl, alkynyl, or alkyl-C(=O)—.

The term "heteroaryl" refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl. triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo[b]thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl and the like.

heteroaryl as defined hereinabove may be optionally substituted with one or more substituents selected independently from the group comprising of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2$N—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2$NC(=O)—, alkyl-N(alkyl)$SO_2$—, alkyl-N(H)$SO_2$—, $H_2$N$SO_2$—, 3 to 6 membered heterocycle containing 1 to 2 heteroatoms selected from N, O and S optionally substituted with alkyl, alkenyl, alkynyl or alkyl-C(=O)—.

The term "heterocycle" or "heterocyclic" as used herein, means a 'cycloalkyl' group wherein one or more of the carbon atoms replaced by —O—, —S—, —S($O_2$)—, —S(O)—, —N($R'''$)—, —Si($R'''$)$R''$—, wherein, $R'''$ and $R''$ are independently selected from hydrogen, alkyl, alkenyl, alkynyl, aryl, heteroaryl, cycloalkyl, and heterocyclyl. The heterocycle may be connected to the parent molecular moiety through any carbon atom or any nitrogen atom contained within the heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl. oxadiazolidinyl, oxazolinyl, oxazolidinyl, piperazinyl, piperidinyl, pyranyl, pyrazolinyl, pyrazolidinyl. pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone). thiopyranyl, and trithianyl. Representative examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclic systems such as azabicyclo[3.2.1]octane, azabicyclo[3.3.1]nonane and the like.

Heterocyclyl group may optionally be substituted on ring carbons with one or more substituents selected independently from the group comprising of oxo, halogen, nitro, cyano, aryl, hereroaryl, alkyl, alkenyl, alkynyl, $R^{10}A^1$-, $R^{10a}$OC(=O)—, $R^{10a}$C(=O)O—, $(R^{10})$(H)NC(=O)—, $(R^{10})$(alkyl)NC(O)—, $R^{10a}$C(=O)N(H)—, $(R^{10})$(H)N—$(R^{10})$(alkyl)N—, $(R^{10})$(H)NC(=$A^1$)N(H)—, $(R^{10})$(alkyl)NC(=$A^1$)N(H)—; wherein $R^{10}$ is selected from hydrogen, alkyl, alkenyl, alkynyl, aryl, heteroaryl, cycloalkyl or heterocyclyl; and $A^1$ is selected from S and O; and $R^{10a}$ is selected from alkyl, alkenyl, alkynyl, perhaloalkyl, aryl, heteroaryl, cycloalkyl or heterocyclyl.

Heterocyclyl group may further optionally be substituted on ring nitrogen(s) with substituents selected from the group comprising of aryl, hereroaryl, alkyl, alkenyl, alkynyl, $R^{10a}$C(=O)—, $R^{10a}SO_2$—, $R^{10a}$OC(=O)—, $(R^{10})$(H)NC(=O)—, $(R^{10})$(alkyl)NC(=O)—; wherein $R^{10}$ is selected from hydrogen, alkyl, alkenyl, alkynyl, aryl, heteroaryl, cycloalkyl or heterocyclyl; and $R^{10a}$ is selected from alkyl, alkenyl, alkynyl, perhaloalkyl, aryl, heteroaryl, cycloalkyl or heterocyclyl.

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is annulated with another ring either at a carbon atom of the cyclic system or across a bond of the cyclic system as in the case of fused or spiro ring systems.

The term 'bridged' means the ring system under consideration contain an alkylene bridge having 1 to 4 methylene units joining two non adjacent ring atoms.

A compound its stereoisomers, racemates, pharmaceutically acceptable salt thereof as described hereinabove wherein the compound of general formula I is selected from:
1. 4-(5-(4-chlorophenyl)-4-methyl-2-propionylthiophen-3-yl)benzene sulfonamide.

2. 4-(5-(2-chlorophenyl)-4-methyl-2-propionylthiophen-3-yl)benzene sulfonamide.
3. 4-(5-(3-chlorophenyl)-4-methyl-2-propionylthiophen-3-yl)benzene sulfonamide.
4. 4-(5-(4-fluorophenyl)-4-methyl-2-propionylthiophen-3-yl)benzene sulfonamide.
5. 4-(5-(4-cyclopropylphenyl)-4-methyl-2-propionylthiophen-3-yl)benzene sulfonamide.
6. 4-(4-methyl-2-propionyl-5-(4-(trifluoromethyl)phenyl)thiophen-3-yl)benzene sulfonamide.
7. 4-(5-(4-methoxyphenyl)-4-methyl-2-propionylthiophen-3-yl)benzene sulfonamide.
8. 4-(5-(4-ethoxyphenyl)-4-methyl-2-propionylthiophen-3-yl)benzene sulfonamide.
9. 4-(4-methyl-2-propionyl-5-(4-(trifluoromethoxy)phenyl)thiophen-3-yl)benzene sulfonamide.
10. 4-(4-methyl-2-propionyl-5-(4-tolyl)thiophen-3-yl)benzenesulfonamide.
11. 4-(5-(4-(tert-butyl)phenyl)-4-methyl-2-propionylthiophen-3-yl)benzene sulfonamide.
12. 4-((5-(4-dimethylamino)phenyl)-4-methyl-2-propionylthiophen-3-yl)benzene sulfonamide.
13. 4-(5-(3-fluorophenyl)-4-methyl-2-propionylthiophen-3-yl)benzene sulfonamide.
14. 4-(4-methyl-5-phenyl-2-propionylthiophen-3-yl)benzenesulfonamide.
15. 4-(5-(3-ethoxyphenyl)-4-methyl-2-propionylthiophen-3-yl)benzene sulfonamide.
16. 4-(5-(4-ethylphenyl)-4-methyl-2-propionylthiophen-3-yl)benzene sulfonamide.
17. 4-(5-(3,4-dichlorophenyl)-4-methyl-2-propionylthiophen-3-yl)benzene sulfonamide.
18. 4-(5-(2,4-dichlorophenyl)-4-methyl-2-propionylthiophen-3-yl)benzene sulfonamide.
19. 4-(5-(2,4-difluorophenyl)-4-methyl-2-propionylthiophen-3-yl)benzene sulfonamide.
20. 4-(5-(3-chloro-4-fluorophenyl)-4-methyl-2-propionylthiophen-3-yl)benzene sulfonamide.
21. 4-(5-(3-chloro-4-methoxyphenyl)-4-methyl-2-propionylthiophen-3-yl)benzene sulfonamide.
22. 4-(4-methyl-5-(piperazin-1-yl)-2-propionylthiophen-3-yl)benzene sulfonamide.
23. 4-(5-(4-(4-fluorophenyl)piperazin-1-yl)-4-methyl-2-propionylthiophen-3-yl)benzenesulfonamide.
24. 4-(4-methyl-5-morpholino-2-propionylthiophen-3-yl)benzenesulfonamide.
25. 4-(4-methyl-2-propionyl-5-(pyridin-4-yl)thiophen-3-yl)benzenesulfonamide.
26. 4-(4-methyl-2-propionyl-5-(pyridin-3-yl)thiophen-3-yl)benzenesulfonamide.
27. 4-(5-(furan-3-yl)-4-methyl-2-propionylthiophen-3-yl)benzenesulfonamide.
28. 4-(5-(1H-indol-5-yl)-4-methyl-2-propionylthiophen-3-yl)benzene sulfonamide.
29. 4-(4-methyl-5-(1-methyl-1H-indol-5-yl)-2-propionylthiophen-3-yl)benzene sulfonamide.
30. 4-(5-(benzofuran-5-yl)-4-methyl-2-propionylthiophen-3-yl)benzene sulfonamide.
31. 4-(5-(indolin-5-yl)-4-methyl-2-propionylthiophen-3-yl)benzenesulfonamide.
32. 4-(4-methyl-5-(4-(4-methylpiperazin-1-yl)phenyl)-2-propionylthiophen-3-yl)benzenesulfonamide.
33. 4-(5-(4-chlorophenyl)-2-propionylthiophen-3-yl)benzenesulfonamide.
34. 4-(5-(4-chlorophenyl)-4-(dimethylamino)-2-propionylthiophen-3-yl)benzene sulfonamide.
35. 4-(5-(4-chlorophenyl)-4-((dimethylamino)methyl)-2-propionylthiophen-3-yl)benzenesulfonamide.
36. 5-(4-chlorophenyl)-N,N,4-trimethyl-3-(4-sulphamoylphenyl)thiophene-2-carboxamide.
37. 5-(4-chlorophenyl)-N-methoxy-N,4-dimethyl-3-(4-sulphamoylphenyl)thiophene-2-carboxamide.
38. 5-(4-chlorophenyl)-N-(2-hydroxyethyl)-4-methyl-N-propyl-3-(4-sulphamoyl phenyl)thiophene-2-carboxamide.
39. 4-(5-(4-chlorophenyl)-4-methyl-2-(piperidine-1-carbonyl)thiophen-3-yl)benzenesulfonamide.
40. 4-(2-acetyl-5-(4-chlorophenyl)-4-methylthiophen-3-yl)benzenesulfonamide.
41. 4-(5-(4-chlorophenyl)-4-methyl-2-propionylthiophen-3-yl)-2-methylbenzene sulfonamide.
42. methyl 4-methyl-5-(2-oxoindolin-5-yl)-3-(4-sulfamoylphenyl)thiophene-2-carboxylate.
43. ethyl 4-methyl-5-(2-oxoindolin-5-yl)-3-(4-sulfamoylphenyl)thiophene-2-carboxylate.
44. 4-(4-methyl-5-(4-methylaminophenyl)-2-propionylthiophen-3-yl)benzene sulfonamide.
45. 4-(5-(4-chlorophenyl)-4-methyl-2-propionylthiophen-3-yl)-N,N-dimethylbenzenesulfonamide.
46. 4-(5-(4-chlorophenyl)-4-methyl-2-propionylthiophen-3-yl)-N-methylbenzene sulfonamide.
47. 4-(5-(3,4-difluorophenyl)-4-methyl-2-propionylthiophen-3-yl)benzene sulfonamide.
48. 1-(5-(4-chlorophenyl)-4-methyl-3-(4-(piperidin-1-ylsulfonyl)phenyl)thiophen-2-yl)propan-1-one
49. 4-(5-(4-chlorophenyl)-1,4-dimethyl-2-propionyl-1H-pyrrol-3-yl)benzene sulfonamide.
50. 5-(4-chlorophenyl)-N,N,1,4-tetramethyl-3-(4-sulfamoylphenyl)-1H-pyrrol-2-carboxamide.
51. 4-(5-(4-chlorophenyl)-1-ethyl-4-methyl-2-propionyl-1H-pyrrol-3-yl)benzene sulfonamide.
52. 4-(5-(4-chlorophenyl)-1-(cyclopropylmethyl)-4-methyl-2-propionyl-1H-pyrrol-3-yl)benzene sulfonamide.
53. 4-(5-(4-chlorophenyl)-4-methyl-2-propionyl-1H-pyrrol-3-yl)benzene sulfonamide.
54. 4-(5-(4-fluorophenyl)-1,4-dimethyl-2-propionyl-1H-pyrrol-3-yl)benzene sulfonamide.
55. 4-(5-(4-methoxyphenyl)-1,4-dimethyl-2-propionyl-1H-pyrrol-3-yl)benzene sulfonamide.
56. 4-(2-butyryl-5-(4-chlorophenyl)-1,4-dimethyl-1H-pyrrol-3-yl)benzene sulfonamide.
57. 4-(5-(2,4-dichlorophenyl)-1,4-dimethyl-2-propionyl-1H-pyrrol-3-yl)benzene sulfonamide.
58. 4-(5-(2,3-dihydrobenzo[b][1,4]dioxin-6-yl)-1,4-dimethyl-2-propionyl-1H-pyrrol-3-yl)benzene sulfonamide.
59. ethyl 5-(4-chlorophenyl)-4-methyl-3-(4-sulfamoyl-5,6,7,8-tetrahydro naphthalen-1-yl)thiophene-2-carboxylate.
60. ethyl 5-(4-chlorophenyl)-3-(4-sulfamoylphenyl)furan-2-carboxylate According to another aspect of the present invention, the compounds of general formula I where all the symbols are as defined earlier were prepared by methods described below. However, the invention is not limited to these methods; the compounds may also be prepared by using procedures described for structurally related compounds in the literature.

Scheme 1 shows a method of preparation of a compound in accordance with an embodiment of the formula Ia. Compound of formula Ia can be prepared from compound of formula VI, where $R^1$, $R^2$, $R^4$, $R^5$, $R^6$ and m are same as described under generic formula Ia.

SCHEME 1

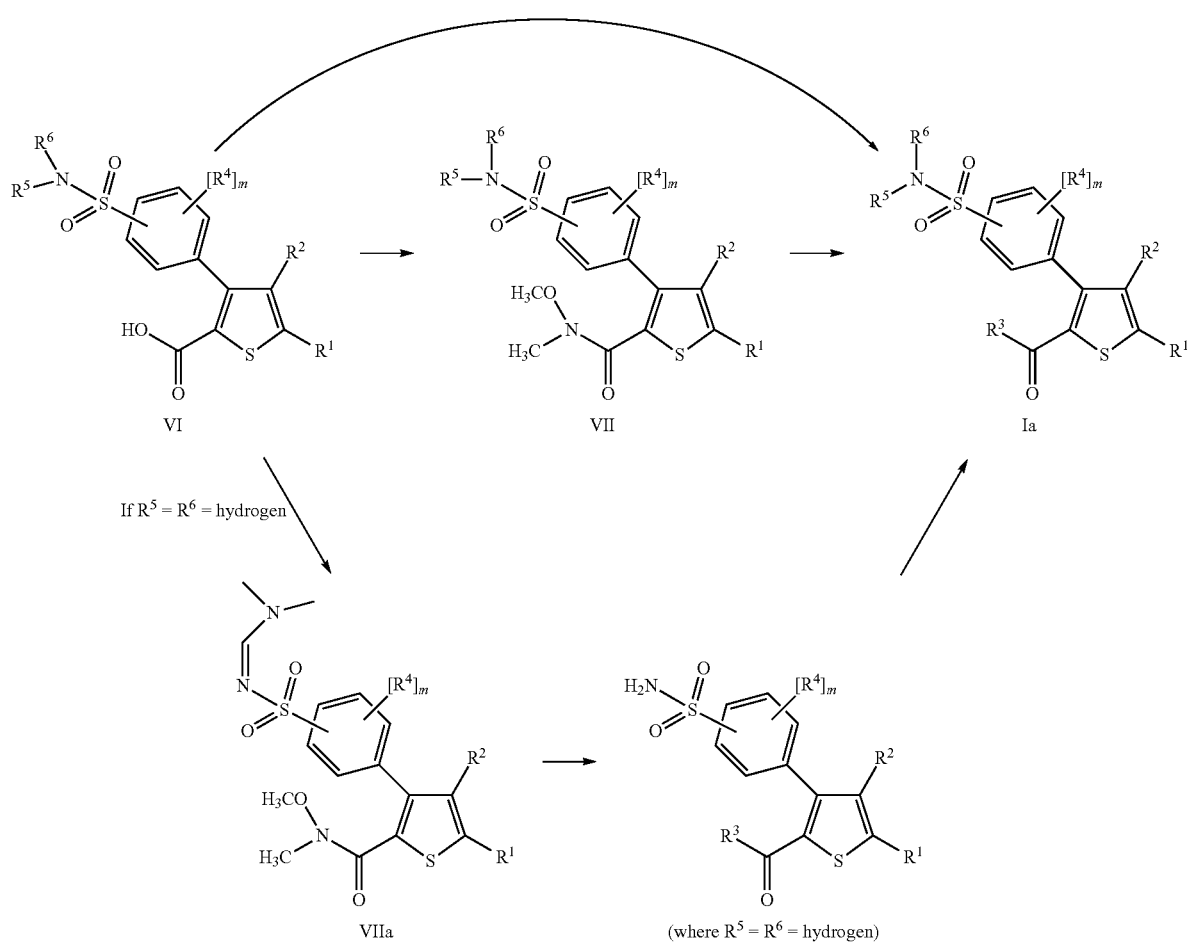

Compound of formula VI can be converted to its corresponding acid chloride using standard procedures known in synthetic organic chemistry or preferably by reaction with oxalyl chloride in dichloromethane along with DMF followed by reaction with N,O-dimethylhydroxylamine hydrochloride in presence of triethylamine in dichloromethane to provide compound of formula VII.

Compound of the formula VII is reacted with a Grignard reagent $R^3MgX^1$ wherein $R^3$ is selected from optionally substituted alkyl, optionally substituted alkenyl, optionally substituted alkynyl, optionally substituted cycloalkyl, optionally substituted hererocyclyl which may be optionally annulated or optionally bridged, and $X^1$ is a halogen, to obtain compound of formula Ia, where $R^3$ is selected from optionally substituted alkyl, optionally substituted alkenyl, optionally substituted alkynyl, optionally substituted cycloalkyl, optionally substituted hererocyclyl which may be optionally annulated or optionally bridged, and $R^5$ and $R^6$ are same as described under general formula I or Ia. The reaction of compound of formula VII with $R^3MgX^1$ may be carried out according to the procedure given in literature such as J. Med. Chem., 2009, 52, 3377.

Compound of formula VI, where $R^5=R^6$=hydrogen, can be converted to acid chloride using oxalyl chloride in dichloromethane along with DMF followed by reaction with N,O-dimethylhydroxylamine hydrochloride in presence of triethylamine in dichloromethane to provide compound of formula VIIa, which can then be further converted to compound of formula Ia by reacting with $R^3MgX^1$ as described herein above.

Compound of formula VI is alternatively reacted with ($R^7$)($R^8$)NH, ($R^7$)($OR^8$)NH, or $R^7OH$, where $R^7$ and $R^8$ are as defined under definition of $R^3$ in general formula Ia or I, to obtain compound of formula Ia, where $R^5$ and $R^6$ are same as described under compound of formula I or Ia and $R^3$ is selected from the group consisting of ($R^7$)($R^8$)N—, ($R^7$)($OR^8$)N—, and $R^7O$—, wherein $R^7$ and $R^8$ are as defined under definition of $R^3$ in general formula Ia or I. The reaction was carried out according to the conditions known in converting carboxylic acids to amides and esters as known to one skilled in the art. The reaction may be carried out in the presence of solvents, for example, DMF, THF, a halogenated hydrocarbon such as chloroform and dichloromethane, an aromatic hydrocarbon such as xylene, benzene, toluene, or mixtures thereof or the like, in the presence of suitable base such as triethylamine, diisopropylethylamine, pyridine or the like at a temperature between 0-50° C. using reagents such as 1-(3-dimethylaminopropyl)-3-ethylcarbodiimide hydrochloride (EDCI), 1,3-dicyclohexylcarbodiimide (DCC), and auxiliary reagents such as 1-hydroxy-7-azabenzotriazole (HOAT), hydroxybenzotriazole hydrate (HOBT) or the like.

Compound of formula Ia where $R^1$, $R^2$, and $R^3$ are the same as described under compound of formula I or Ia, and $R^5$ and $R^6$ are as described under formula I or Ia excluding hydrogen were prepared by further reaction of compounds of formula Ia where $R^5$ and $R^6$ are hydrogen, with the reagents selected from $R^5L^1$ and $R^6L^1$, where $L^1$ is halogen or $-B(OH)_2$ in presence of a base or using appropriate conditions given in literature such as Tetrahedron letters 2005, 46(43), 7295-7298, Tetrahedron letters 2003, 44(16), 3385-3386, US2003236413, Synthetic Communications 2009, 39(12), 2082-2092, Tetrahedron letters 2010, 51(15), 2048-2051, Tetrahedron letters 2008, 49(18), 2882-2885, and J. Amer. Chem. Soc. 2005, 127(36), 12640-12646.

Scheme 2 shows a method of preparation of compound of formula VI from compound of formula II and an alternative method for compound VI from compound of formula VIII.

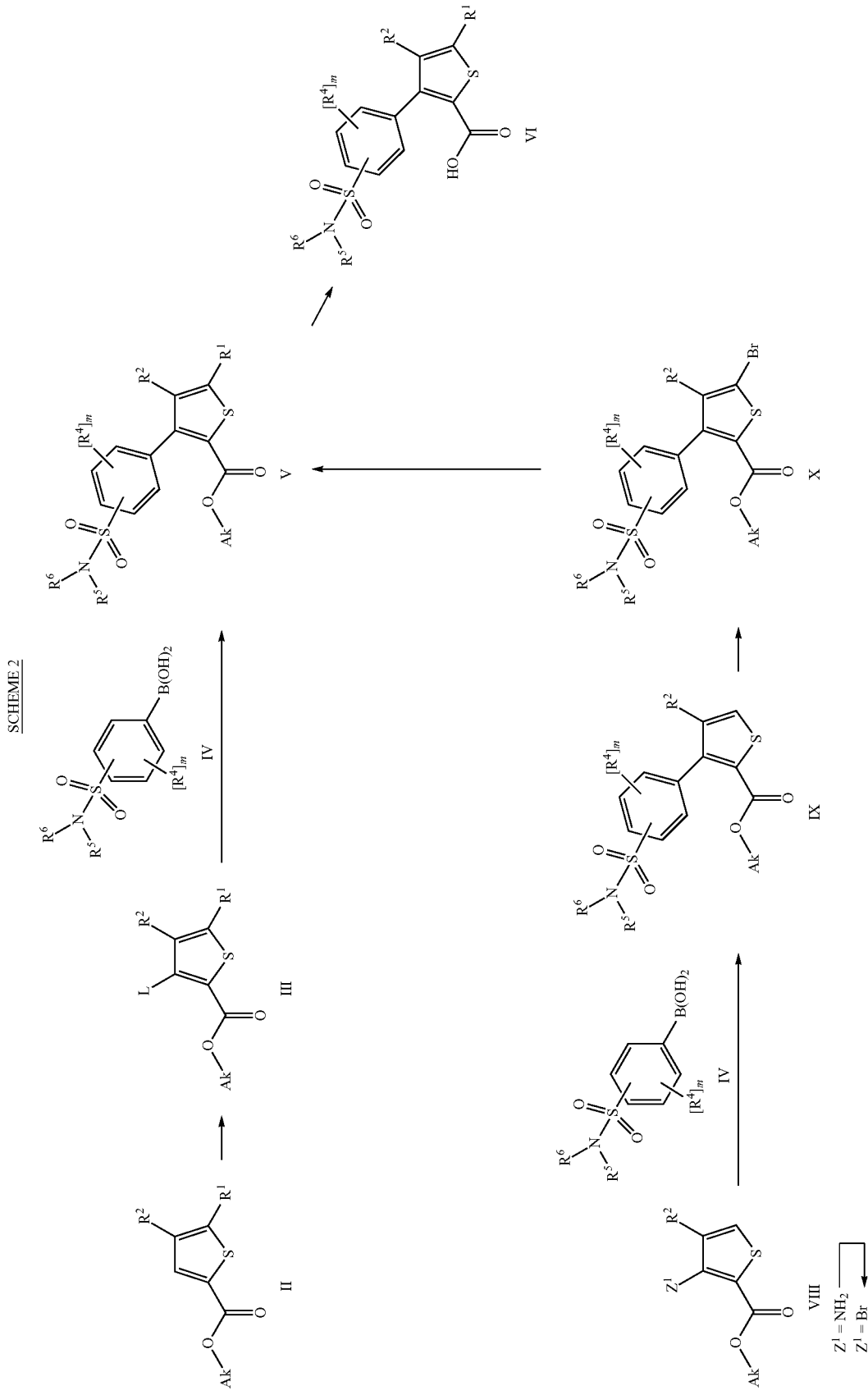

Compound of formula VI, where $R^1$ is as described under compound of generic formula Ia and $R^2$ is selected from optionally substituted alkyl, optionally substituted alkenyl, optionally substituted alkynyl, perhaloalkyl, optionally substituted cycloalkyl, $R^7A^1$- and $R^{7a}C(=O)$—, can be prepared from compound represented by general formula II, where Ak is alkyl group, $R^1$ is optionally substituted, optionally fused aryl; optionally substituted, optionally fused heteroaryl; wherein, aryl and hereroaryl include the fused ring systems wherein the aryl or heteroaryl ring is fused with saturated cyclic system; and $R^2$ is selected from optionally substituted alkyl, optionally substituted alkenyl, optionally substituted alkynyl, perhaloalkyl, optionally substituted cycloalkyl, $R^7A^1$- and $R^{7a}C(=O)$—. Compound of formula II was in turn prepared by the procedures described in the literature such as U.S. Pat. No. 5,608,082 and WO2007092751. Groups covered under $R^2$ can be transformed from one to other in any of the succeeding steps of Scheme 1 or 2 by general group transformation method.

Compound of formula II on halogenation gave compound of formula III, where L is a halogen and other symbols are the same as defined earlier for compound of formula II. Halogenation can be carried out under a condition generally used in the synthetic organic chemistry using halogenating agents such as bromine, phosphorous tribromide, bromine chloride, aluminium tribromide, hydrogen iodide/iodine, iodine chloride, N-iodosuccinimide, iodine/sulfuric acid and N-chlorosuccinimide. The inventors have carried out bromination using bromine in the presence of zinc chloride.

Compound of formula III as obtained in the previous step was subjected to Suzuki coupling with compound of formula IV, where $R^4$, $R^5$, $R^6$ and m are same as defined earlier in compound of formula Ia or I, to obtain compound of formula V where the symbols $R^1$ and $R^2$ are same as defined for compound of formula II and $R^4$, $R^5$, $R^6$ and m are same as defined in general formula Ia or I. Suzuki coupling can be carried out under different coupling conditions with boronic acids and boronic esters well known in the art. Preferably, the Suzuki coupling is carried out in a mixture of water, ethanol, methanol and toluene, in presence of base such as potassium phosphate or potassium carbonate or the like, palladium catalyst such as tetrakis(triphenylphosphine)palladium(0) at 50° C. or higher temperature. Boronic acid used in this reaction can be prepared by the methods well known in the art by hydrolysing the corresponding boronate. Boronates are generally commercially available. Besides, such boronates can also be prepared by reacting an appropriate iodo- or bromo compound with an alkyl lithium such as butyl lithium and then reacting with a borate ester or by methods well known in the art (EP 1012142; Review article by N. Miyaura and A. Suzuki, Chem. Rev., 1995, 95, 2547).

Ester hydrolysis of compound of formula V gave compound of formula VI, where $R^1$, $R^2$, $R^4$ $R^5$, $R^6$ and m are the same as defined hereinabove for compound of formula V. Ester hydrolysis may be carried out using standard procedure generally used in synthetic organic chemistry or well known in the art with reagents such as sodium hydroxide, potassium hydroxide, lithium hydroxide or the like in solvents such as water, alcohol, THF or the like or mixtures thereof. Preferably aqueous solution of sodium hydroxide and ethanol were used for the reaction.

Alternatively, compound of formula VI can be prepared starting from compound of formula VIII, where $R^2$ is selected from the group consisting of optionally substituted alkyl, optionally substituted alkenyl, optionally substituted alkynyl, perhaloalkyl, optionally substituted cycloalkyl, $R^7A^1$- and $R^{7a}C(=O)$—; Ak is alkyl group; and $Z^1$ is bromo or amino, as follows.

Compound of formula VIII with $Z^1$ as bromo, was obtained by converting the amino group (the said amino compound is commercially available) to the corresponding bromo group under a condition usually applied in Sandmayer's reaction. This involves diazotization by reacting the corresponding amino compound with a nitrite eg. tert-butyl nitrite or the like, followed by halogen exchange, which may be conveniently accomplished by reaction with a copper halide, preferably copper(II)bromide.

Compound of the formula VIII with $Z^1$ as bromo was subjected to Suzuki coupling with the compound of formula IV, to obtain compound IX where the symbol $R^2$ is the same as defined for compound of formula VIII above, and $R^4$, $R^5$, $R^6$ and m are same as defined in general formula Ia.

Compound of the formula IX on bromination gave compound of formula X. Bromination can be carried out under a condition generally used in the synthetic organic chemistry using brominating agents. The inverters have carried out bromination using bromine.

Compound of the formula X was subjected to Suzuki Coupling with $R^1B(OH)_2$, wherein $R^1$ is as defined in the generic formula Ia having point of attachment on carbon atom, to give compound of formula V where all the symbols $R^2$, $R^4$, $R^5$, $R^6$ and m are the same as defined in compound of formula IX and $R^1$ is as defined in the generic formula Ia having point of attachment on carbon atom. Ester hydrolysis of compound of formula V to compound of formula VI is carried out by following the same procedure and reaction conditions as described earlier. Compound of formula VI so obtained was then converted to compound of formula Ia using the process described hereinabove in Scheme 1. The groups covered under $R^2$ can be introduced or transformed from one to another to arrive at the required groups as covered in compound of formula Ia at the stage of compound of formula V or in the succeeding steps also.

Scheme 3 shows a method of preparation of a compound of formula VI, where, $R^2$ is selected from the group consisting of $(R^7)(R^8)N$—, $R^{7a}C(=O)N(R^7)$—, $(R^7)(R^8)NC(=A^1)N(R^9)$—, $R^{7a}OC(=O)N(R^9)$—, $R^{7a}SO_2N(R^7)$—, cyano, nitro and halogen from dibromo compound of formula XI, where Ak is alkyl group.

SCHEME 3

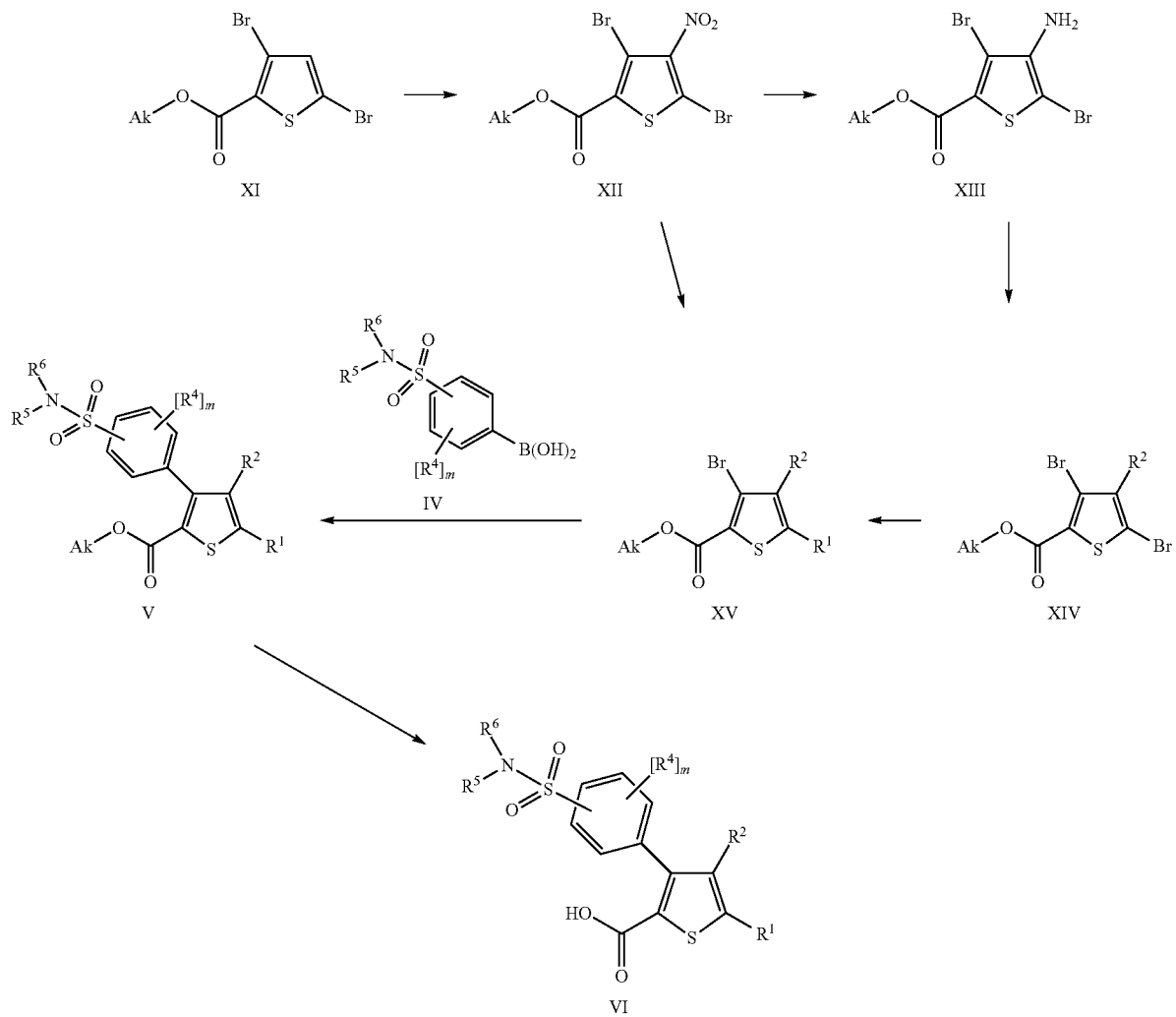

Compound VI, where $R^2$ is selected from $(R^7)(R^8)N-$, $R^8C(=O)N(R^7)-$, $(R^7)(R^8)NC(=O)N(R^9)-$, $(R^7)OC(=O)N(R^8)-$, $-R^7SO_2N(R^8)-$, cyano, halogen or Nitro Compound of the formula VI, where, $R^2$ is selected from $(R^7)(R^8)N-$, $R^{7a}C(=O)N(R^7)-$, $(R^7)(R^8)NC(=O)N(R^9)-$, $R^{7a}OC(=O)N(R^9)-$, $R^{7a}SO_2N(R^7)-$, cyano, nitro and halogen can be prepared starting from the dibromo compound of formula XI as follows. Compound XI can be prepared by following the process provided in J. Chem. Soc. Perkin Trans.: Organic and Bioorganic chemistry (1972-1999), 1973, pages 1766-1770.

Compound of the formula XI on nitration gave compound XII, which upon reduction of the nitro group to an amino group gave compound of formula XIII. Nitration and its further reduction can be carried out under the conditions according to procedures generally known or used in synthetic organic chemistry. The inventers have carried out nitration using nitric acid, and reduction by the use of iron powder and acetic acid.

Compound of the formula XIII was further reacted with the reagents selected from $R^7L$, $R^8L$, $R^9L$, where $R^7$, $R^{7a}$, $R^8$ and $R^9$ are as defined earlier except being hydrogen, and L is halogen, and/or reacted with the reagents selected from the group consisting of $R^{7a}C(=O)L$, $R^{7a}N=C=O$, $R^{7a}N=C=S$ and $(R^7)(R^8)NC(=O)L$, $R^{7a}A^1C(=O)L$, and $R^{7a}SO_2L$, wherein $R^7$, $R^{7a}$ and $R^8$ are as defined earlier under general formula I or Ia, and L is halogen, to obtain compound of formula XIV with $R^2$ as $(R^7)(R^8)N-$, $R^{7a}C(=O)N(R^7)-$, $(R^7)(R^8)NC(=A^1)N(R^9)-$, $R^{7a}OC(=O)NR^9-$, $R^{7a}SO_2N(R^7)-$, $R^{7a}A^1-$, or $R^{7a}C(=O)-$. $R^2$ in compound of formula XIV where $R^2$ is $R^{7a}OC(=O)NR^9-$ was conveniently converted to $(R^7)(R^8)NC(=O)N(R^9)-$ by reaction with the amine of formula $(R^7)(R^8)NH$ in the presence of a suitable base such as alkalimetal alkoxides or triethylamine or by using an aluminum amide [Tetrahedron 60 (2004) 3439-43] in non-polar organic solvent such as toluene or a polar solvent such as tetrahydrofuran.

Compound of formula XIV or compound of formula XII were subjected to Suzuki coupling with boronic acid of the formula '$R^1B(OH)_2$', where $R^1$ is the same as defined in general formula Ia, under standard Suzuki coupling conditions in presence of a base selected from potassium phosphate, potassium carbonate and the like, and a palladium catalyst tetrakis(triphenylphosphine)palladium(0) in a solvent selected from water, ethanol, methanol, toluene and mixtures thereof in any suitable proportion, to obtain compound of formula XV, where the definition of $R^1$ is the same as defined in general formula Ia and $R^2$ is $(R^7)(R^8)N-$, $R^{7a}C(=O)N(R^7)-$, $(R^7)(R^8)NC(=A^1)N(R^9)-$, $R^{7a}OC(=O)NR^9-$, $R^{7a}SO_2N(R^7)-$, $R^{7a}A^1-$, $R^{7a}C(=O)-$ or nitro.

Compound of the formula XV was then subjected to Suzuki coupling with compound of formula IV to obtain compound of formula V where $R^1$, $R^4$, $R^5$, $R^6$ and m are the same as defined in general formula Ia, and $R^2$ is $(R^7)(R^8)N-$, $R^{7a}C(=O)N(R^7)-$, $(R^7)(R^8)NC(=A^1)N(R^9)-$, $R^{7a}OC(=O)NR^9-$, $R^{7a}SO_2N(R^7)-$, $R^7A^1-$, $R^{7a}C(=O)-$ or nitro. Suzuki coupling has been carried out by following the same procedure as described earlier. The compound of formula V was further converted to the compound of formula VI by the application of procedures described hereinabove. Compound of formula V, where $R^2$ is nitro, the nitro group of the said compound can be further converted to cyano or halogen by known functional group conversion methods.

Scheme 4 shows method of preparation of a compound of formula VI, where, $R^2$ is hydrogen, from dibromo compound of formula XI, where Ak is alkyl group.

SCHEME 4

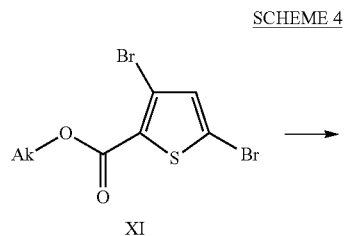

XI

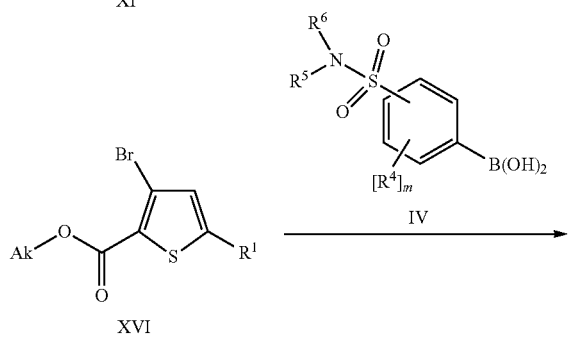

XVI

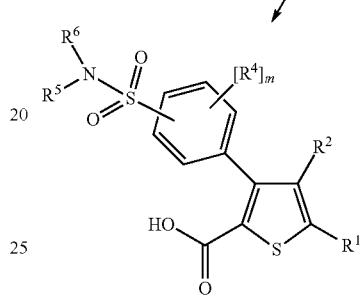

V

Compound V, where $R^2$ is Hydrogen

VI

Compound VI, where $R^2$ is Hydrogen

Compound of formula XI was first coupled with boronic acid of formula '$R^1B(OH)_2$', where $R^1$ is the same as defined in general formula Ia having point of attachment as carbon atom by Suzuki coupling to obtain compound of formula XVI, which was then subjected to Suzuki coupling with compound of formula IV to give the compound of formula V, where $R^2$ is hydrogen. Compound of formula V was converted to compound of formula VI, where $R^1$, $R^4$, $R^5$, $R^6$ and m are same as defined in general formula Ia and $R^2$ is hydrogen using the procedure described earlier.

SCHEME 5

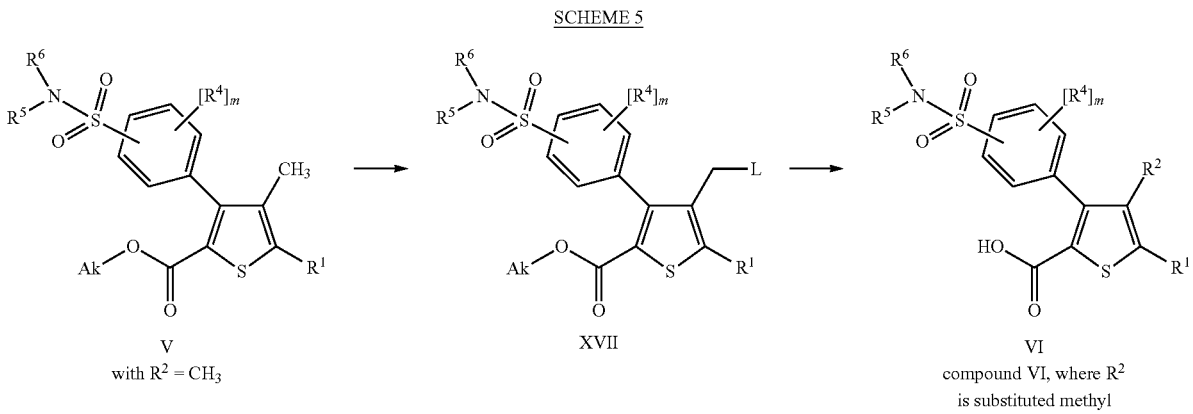

V
with $R^2$ = CH$_3$

XVII

VI
compound VI, where $R^2$
is substituted methyl if $R^5$ = $R^6$ = hydrogren
in compound XI

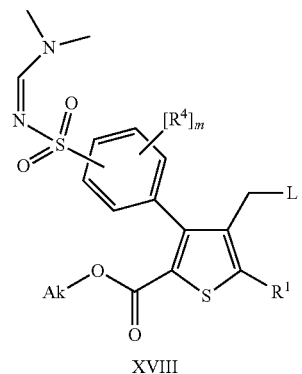

XVIII

In another embodiment of compound of formula V, where the symbols W, $R^5$, $R^6$ and m are the same as defined in general formula Ia; $R^4$ is selected from the group consisting of halogen, cyano, $R^{7a}SO_2$—, $R^7A^1$-, $(R^{7a})C(=O)N(R^9)$—, $(R^7)(R^8)N$— and $(R^7)(R^8)NC(=A^1)N(R^9)$—; Ak is the same as defined for compound of formula II; and $R^2$ is methyl, on bromination gave compound of formula XVII (Scheme 5). The compound of formula XVII, where the symbols W, $R^5$, $R^6$ and m are the same as defined in general formula Ia; and $R^4$ is selected from the group consisting of halogen, cyano, $R^{7a}SO_2$—, $R^7A^1$-, $(R^{7a})C(=O)N(R^9)$—, $(R^7)(R^8)N$— and $(R^7)(R^8)NC(=A^1)N(R^9)$—; Ak is as defined for compound of formula II and L is bromo on reaction with $(R^{10})NH_2$, $(R^{10})$(alkyl)NH or $R^{10}A^1H$, where $R^{10}$ is the same as defined under compound of formula I and/or Ia, and further ester hydrolysis provide a compound of formula VI, where $R^2$ is alkyl (e.g., methyl) substituted with $(R^{10})(H)N$—, $(R^{10})$(alkyl)N— or $R^{10}A^1$-. Synthesis of compound of formula Ia from compound of formula VI was carried out by following the same procedure and reaction conditions as described earlier. If the compound of formula V has $R^5=R^6$=hydrogen, then the sulfonamide group needs to be protected using an appropriate protecting group such as N,N-dimethylformamide dimethyl acetal to obtain compound of formula XVIII, which can then be reacted with $(R^{10})(H)N$—, $(R^{10})$(alkyl)N— or $R^{10}A^1H$, where $R^{10}$ is the same as defined under compound of formula I and/or Ia.

Alternatively, the compounds of the formula Ia where all the substituents are the same as described under generic formula except $R^2$ being selected from hydrogen or optionally substituted alkyl, optionally substituted alkenyl, optionally substituted alkynyl, perhaloalkyl, optionally substituted cycloalkyl, cyano, nitro, $(R^7)(R^8)N$—, $R^{7a}C(=O)N(R^7)$—, $(R^7)(R^8)NC(=A^1)N(R^9)$—, $R^{7a}OC(=O)NR^9$—, $R^{7a}SO_2N(R^8)$—, $R^7A^1$- or $R^{7a}C(=O)$— can be prepared starting from compounds represented by general formula (a) as per the route provided in Scheme 6 as follows—

SCHEME 6

(a)    (f)

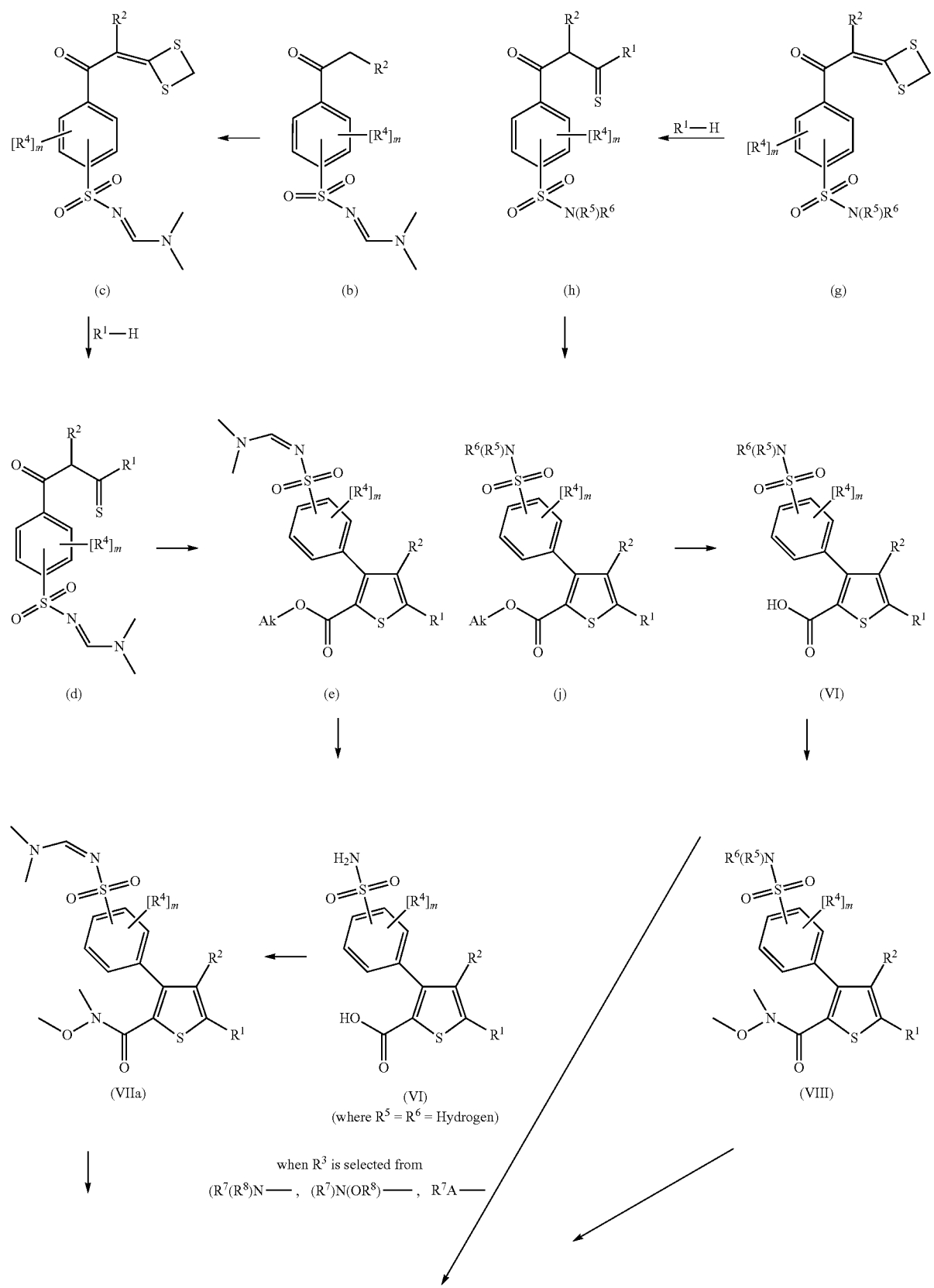

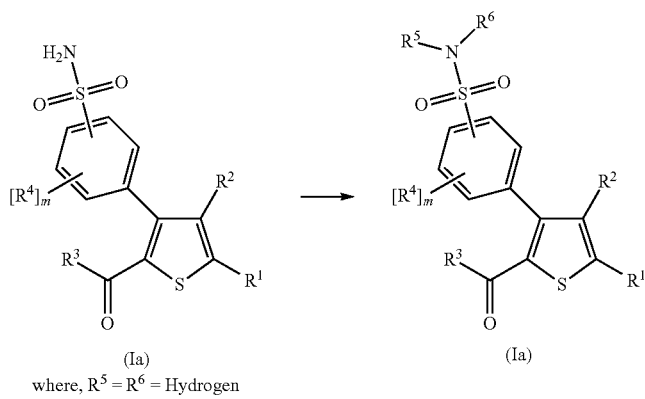

(Ia)

(Ia)

where, R⁵ = R⁶ = Hydrogen

Wherein,

R¹—H is 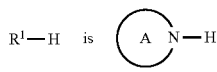

wherein, 'A' is a 3 to 10 membered optionally substituted saturated/unsaturated monocyclic/bicyclic or optionally bridged heterocyclic ring system containing one to three hetero atoms/groups such as S, N, O, C(═O), C(═S); wherein, the heterocyclic ring may optionally be further annulated with cycloalkyl, heterocyclyl, aryl or heteroaryl ring systems.

Compounds of formula (a) and (f) were prepared by adopting the procedure described in the literature such as Bioorganic chemistry, 22, 387-394 (1994). Compound of the formula (a) where the symbol $R^2$ is selected from hydrogen or optionally substituted alkyl, optionally substituted alkenyl, optionally substituted alkynyl, perhaloalkyl, optionally substituted cycloalkyl, cyano or nitro was protected using N,N-dimethylformamide acetal to give compound of formula (b). Protection may be carried out using a procedure given in literature such as EP 1790640. The inventers have done protection using N,N-dimethylformamide dimethyl acetal in the presence of DMF.

Compound of the formula (b) was reacted with carbondisulfide and dibromoethane in the presence of a base such as potassium carbonate, potassium tert. butoxide or the like in a solvent such as acetone or the like, to form dithietane ring as represented by formula (c).

Compound of the formula (c) was further reacted with $R^1$—H, where $R^1$ is a heterocycle 'A' with a point of attachment on nitrogen atom; viz.

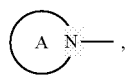

wherein A is a 3 to 10 membered optionally substituted heterocyclic ring system containing one to three hetero atoms/groups such as S, N, O, C(═O) or C(═S); wherein, the heterocyclic ring may optionally be further annulated with cycloalkyl, heterocyclyl, aryl or heteroaryl ring systems; to give compound of formula (d).

Compound of formula (d) was further cyclized to obtain compound of formula (e). The inventers have carried out cyclization by reacting compound (d) with ethyl iodoacetate in the presence of a base such as potassium carbonate or the like.

Hydrolysis of compounds of the formula (e) gave compound of formula VI with W selected as heterocycle attached through nitrogen atom, $R^2$, $R^4$ and m are as defined earlier under generic formula Ia or I, and Ak is alkyl group. The hydrolysis may be carried out by standard procedure generally used in synthetic organic chemistry or well known in the art with reagents such as sodium hydroxide, potassium hydroxide and lithium hydroxide in solvents such as alcohol or THF or the like. Preferably, the hydrolysis is carried out using aqueous solution of sodium hydroxide and ethanol. Compounds of formula VI, so obtained, was further converted to compound of formula Ia, where $R^1$ is a heterocycle connected through nitrogen atom, using the process described hereinbefore.

Compound of formula Ia, where $R^2$ is nitro, the nitro group of the said compound can be further converted to $(R^7)(R^8)N—$, $R^{7a}C(═O)N(R^7)—$, $(R^7)(R^8)NC(═A^1)N(R^9)—$, $R^{7a}OC(═O)NR^9—$, $R^{7a}SO_2N(R^8)—$ using the known functional group transformation methods.

Compound of formula (f), where the nitrogen of the sulfonamido function has nonhydrogen substituents thereon, can be analogously converted to compound of formula VI following the chemistry described for conversion of compound of formula (a) to compound of formula VI, however such conversion does not require protection of the sulfonamido function as shown in Scheme 6.

According to another feature of the present invention, the compounds of general formula Ib where all the symbols are as defined earlier, were prepared by method described below in Scheme 7.

SCHEME 7

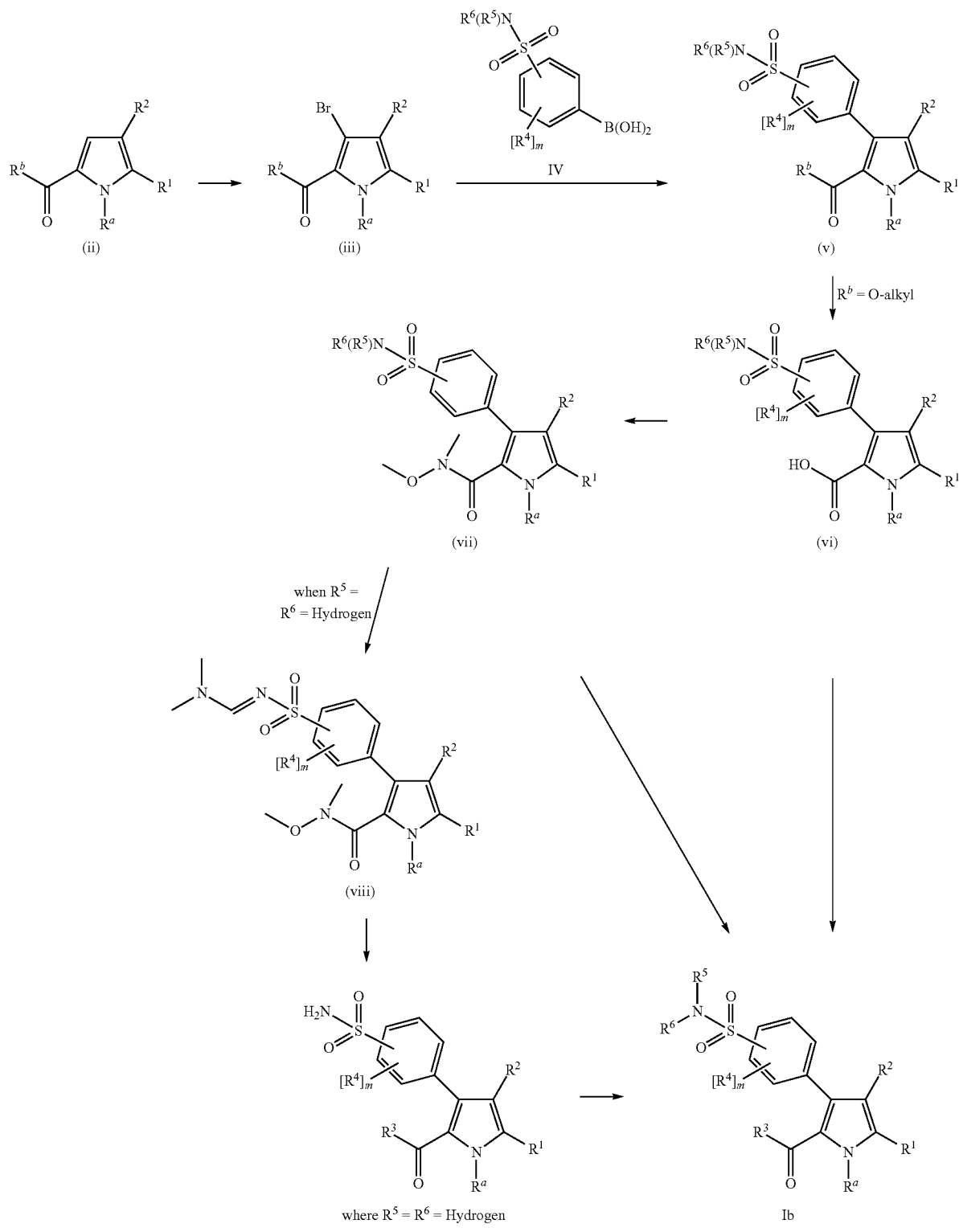

when $R^b$ is alkyl, compound (v) = compound Ib
$R^b$ = O-alkyl or alkyl

Compound of the formula Ib can be prepared starting from compound represented by general formula (II) wherein $R^1$, $R^2$, and $R^a$ are the same as defined under general formula I or Ib and $R^b$ is alkyl or —O-alkyl; which in turn can be prepared by adopting the procedures described in literature such as Tetrahedron Letters 2005, 46, 4539-4542, WO2005105789, Tetrahedron Letters 2010, 51, 1693-1695; J. Org. Chem. 2009, 74(2), 903-905; Organic Letters 2007, 9(25), 5191-5194; Tetrahedron 2006, 62, 8243-8255 or methods well known in the art. Groups covered under $R^2$ can be introduced or transformed into a suitable group of choice in any of the succeeding steps of Scheme 7 by general functional group transformation methods known to a person skilled in the relevant art.

Compound of the formula (II) when $R^b$=O-alkyl or alkyl and other symbols are same as defined in general formula Ib or I, on bromination can provide compound of formula (iii). Bromination can be carried out under a condition according to a procedure generally known in the literature using brominating agents such as bromine, N-bromo succinimide, phosphorous tribromide or the like (Synlett 2002, 7, 1152-1154).

Compound of the formula (iii) where all the symbols are the same as defined earlier in general formula Ib or I is subjected to Suzuki coupling with compound of formula IV, where $R^4$, $R^5$, $R^6$ and m are the same as defined under general formula Ib or I, to obtain compound of formula (v). Compound of formula (v), wherein $R^b$ is alkyl, is nothing but a compound of formula Ib where $R^3$ is selected as alkyl group. Suzuki coupling can be carried out under suitable coupling conditions with boronic acids and boronic esters as well known in the art. Preferably, the coupling reaction is carried out in a mixture of water, ethanol, methanol and toluene, the in presence of a base such as potassium phosphate, potassium carbonate, or the like, and a palladium catalyst such as tetrakis (triphenylphosphine) palladium(0) at a temperature of about 50° C. or higher. Boronic acid used in this reaction can be prepared by methods well known in the art, for example, by hydrolyzing the corresponding boronate. Boronates are generally commercially available. Besides, such boronates can also be prepared by reacting an appropriate iodo- or bromo compound with an alkyl lithium compound such as butyl lithium and then by reacting with a borate ester or by methods well known in the art (WO200530715; EP 1012142; Review article by N. Miyaura and A. Suzuki, Chem. Rev. 1995, 95, 2547).

Ester hydrolysis of compound of formula (v), when $R^b$=O-alkyl, gave compound of formula (vi) where $R^1$, $R^2$, $R^4$, $R^5$, $R^6$ and m are the same as defined hereinbefore for compounds of formula (iii) and (iv). Ester hydrolysis may be carried out using standard procedures generally used in synthetic organic chemistry or well known in the art with reagents such as sodium hydroxide, potassium hydroxide, lithium hydroxide or the like in solvents such as alcohol, THF, or the like. Preferably, aqueous solution of sodium hydroxide and ethanol are used for this reaction.

Compound of formula (vi) where all the symbols are the same as defined earlier is converted to its corresponding amide of formula (vii) according to the conditions known to convert carboxylic acids to amides. The reaction can be carried out preferably with N,O-dimethylhydroxylamine hydrochloride and triethylamine in DMF using reagents such as 1-(3-dimethylaminopropyl)-3-ethylcarbodimide hydrochloride (EDCI), benzotriazole hydrate (HOBT) or the like.

In the case of compound of formula (vii) where $R^4$=$R^5$=hydrogen, the sulfonamido group should be protected before proceeding ahead with other subsequent reaction steps to prepare the compound of formula Ib. The protection of the sulfonamido group can be carried out under a condition known to a person skilled in the art or by utilizing the teaching provided in Organic Preparations and Procedures International 2002, 37(5), 545-549. The inventors have done protection using N,N-dimethylformamide dimethyl acetal in the presence of DMF to obtain compound of formula (viii).

Compound of the formula (viii) or a compound of formula (vii), which did not need protection of the sulfonamide group is reacted with a Grignard reagent $R^3MgX^1$ where $R^3$ is selected from the group consisting of optionally substituted alkyl, optionally substituted alkenyl, optionally substituted alkynyl, optionally substituted cycloalkyl, and optionally substituted hererocyclyl, wherein each of the said optionally substituted cycloalkyl and optionally substituted heterocyclyl is optionally annulated or optionally bridged, and $X^1$ is a halogen, to obtain a compound of formula Ib. The reaction may be carried out under a suitable condition known to a person skilled in the art or by utilizing the teaching provided in J. Med. Chem., 2009, 52, 3377.

Compound of formula (vi) is alternatively reacted with $(R^7)(R^8)NH$, $(R^7)N(OR^8)H$, or $R^7A^1H$, where $R^7$ and $R^8$ are as defined under definition of $R^3$ in general formula Ib or I, to obtain the compound of formula Ib, where $R^5$ and $R^6$ are same as defined earlier in general formula I or Ib and $R^3$ is selected from the group consisting of $(R^7)(R^8)N$—, $(R^7)N(OR^8)$—, and $R^7A^1$-, where $R^7$ and $R^8$ are as defined under definition of $R^3$ in general formula Ib or I. The reaction can be carried out according to the conditions known in converting carboxylic acids to amides and esters as known to one skilled in the art. The reaction may be carried out in the presence of suitable solvents, for example, DMF, THF, a halogenated hydrocarbon such as chloroform and dichloromethane, an aromatic hydrocarbon such as xylene, benzene, toluene, or mixtures thereof, or the like, in the presence of suitable base such as triethylamine, diisopropylethylamine, pyridine, or the like at a temperature between 0-50° C. using reagents such as 1-(3-dimethylaminopropyl)-3-ethylcarbodiimide hydrochloride (EDCI), 1,3-dicyclohexylcarbodiimide (DCC), and auxiliary reagents such as 1-hydroxy-7-azabenzotriazole (HOAT), hydroxybenzotriazole hydrate (HOBT), or the like.

Compound of the formula Ib where $R^5$ and/or $R^6$ are hydrogen, can be converted to compound of formula Ib where $R^5$ and/or $R^6$ are same as defined in general formula Ib excluding hydrogen by reaction with corresponding alkyl halides, alkenyl halides, alkynyl halides, alkanoyl halides or anhydride, aryl halides or boronic acids in presence of a base or by using appropriate conditions given in technical literature.

Compound of formula Ic may also be prepared by using a suitable starting material by adopting the chemistry provided for compounds of formula Ia and Ib hereinabove.

The term 'room temperature' denotes any temperature ranging between about 20° C. to about 40° C., except and otherwise it is specifically mentioned in the specification.

The intermediates and the compounds of the present invention may obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g., flash chromatography) on a suitable support material such as alumina or silica gel using eluent such as dichloromethane, ethyl acetate, hexane, methanol, acetone and their combinations. Preparative LC-MS method is also used for the purification of molecules described herein.

Salts of compound of formula I can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G. wermuth, Wiley-VCH (2002). Lists of suitable salts can also be found in *Remington's Pharmaceutical Sciences*, 18th ed., Mack Publishing Company, Easton, Pa., 1990, p. 1445, and *Journal of Pharmaceutical Science*, 66, 2-19 (1977). For example, they can be a salt of an alkali metal (e.g., sodium or potassium), alkaline earth metal (e.g., calcium), or ammonium of salt.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula I of the present invention may be prepared by stereospecific syntheses or resolution of the achiral compound using an optically active amine, acid or complex forming agent, and separating the diastereomeric salt/complex by fractional crystallization or by column chromatography.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched lower alkyl ester moieties, e.g., ethyl esters, lower alkenyl esters, di-lower alkylamino lower-alkyl esters, e.g., dimethylaminoethyl ester, acylamino lower alkyl esters, acyloxy lower alkyl esters (e.g., pivaloyloxymethyl ester), aryl esters, e.g., phenyl ester, aryl-lower alkyl esters, e.g., benzyl ester, optionally substituted, e.g., with methyl, halo, or methoxy substituents aryl and aryl-lower alkyl esters, amides, lower-alkyl amides, di-lower alkyl amides, and hydroxy amides.

Modulation of the nicotinic cholinergic receptors, particularly $\alpha 7$ may provide for efficacy in a range of cognitive states, right from pre-attention to attention and subsequently working, reference and recognition memory. Accordingly, this invention may find application in the treatment and prophylaxis of multitude of disease conditions including, either one or combinations of, schizophrenia, schizophreniform disorder, cognitive deficits in schizophrenia, brief psychotic disorder, delusional disorder, schizoaffective disorder, shared psychotic disorder, paranoid personality disorder, schizoid personality disorder, schizotypal personality disorder, attention deficit disorder, attention deficit hyperactivity disorder, depression, maniac depression, major depressive disorder, posttraumatic stress disorder, generalized anxiety disorder, tourette's syndrome, cyclothymic disorder, dysthymic disorder, agoraphobia, panic disorder (with or without agoraphobia), phobias (including social phobia) and bipolar disorders (Thomsen M S et al., Curr. Pharm. Des., 2010, 16, 323-343; Peng Z Z et al., Zhonghua Yi Xue Yi Chuan Xue Za Zhi, 2008, 25, 154-158; Young J W et al., Eur. Neuropsychopharmacol., 2007, 17, 145-155; Martin L F et al., Am. J. Med. Genet., B Neuropsychiatr. Genet., 2007, 144B, 611-614; Martin L F et al., Psychopharmacology (Berl), 2004, 174, 54-64; Feher A et al., Dement. Geriatr. Cogn. Disord., 2009, 28, 56-62; Wilens T E et al., Biochem. Pharmacol., 2007, 74, 1212-1223; Verbois S L et al., Neuropharmacology, 2003, 44, 224-233; Sanberg P R et al., Pharmacol. Ther., 1997, 74, 21-25). Cholinergic system, particularly through $\alpha 7$ nAChR seems to have implications in traumatic brain injury-induced psychosis. Chronic nicotine treatment has shown to attenuate same. Thus, this invention may also find application in the treatment of deficits in cholinergic $\alpha 7$ nAChR following traumatic brain injury (Bennouna M et al., Encephale, 2007, 33, 616-620; Verbois S L et al., Neuropharmacology, 2003, 44, 224-233).

Modulation of nicotinic ACh receptors, particularly the $\alpha 7$ subtype could also help supplement the down-regulated cholinergic receptor expression and transmission as in dementia(s), and also slowing disease progression by reduction of $\alpha 7$-$\alpha\beta_{1-42}$ complexation and internalization in AD and Down's syndrome (Nordberg A et al., Neurotox. Res., 2000, 2, 157-165; Haydar S N et al., Bioorg. Med. Chem., 2009, 17, 5247-5258; Deutsch S I et al., Clin. Neuropharmacol., 2003, 26, 277-283). Appropriately, this invention may find application in the treatment and prophylaxis of multitude of disease conditions including, either one or combinations of, dementia(s) due to Alzheimer's disease, dementia with Lewy bodies, Down's syndrome, head trauma, Stroke, hypoperfusion, Parkinson's disease, Huntington's disease, Prion diseases, progressive supranuclear palsy, radiation therapy, brain tumors, normal-pressure hydrocephalus, subdural hematoma, human immunodeficiency virus (HIV) infection, vitamin deficiency, hypothyroidism, drugs, alcohol, lead, mercury, aluminium, heavy metals, syphilis, Lyme disease, viral encephalitis, fungal infection and cryptococcosis (Zhao X et al., Ann. N.Y. Acad. Sci., 2001, 939, 179-186; Perry E et al., Eur. J. Pharmacol., 2000, 393, 215-222; Harrington C R et al., Dementia, 1994, 5, 215-228; Wang J et al., J. Neurosci. Res., 2010, 88, 807-815; Duris K et al., Stroke 2011, 42(12), 3530-6). Thus, this invention may also find application in the prophylaxis and preventive measures immediately after early-stage identification of neurodegenerative disease like Alzheimer's disease and Parkinson's disease.

Modulation of nicotinic ACh receptors particularly $\alpha 4\beta 2$, $\alpha 3\beta 4$ and $\alpha 7$ may have implications in the development of therapies for nicotine, cannabis addiction and relapse prevention. Accordingly, this invention may find application in the prophylaxis or therapy of nicotine addiction, cannabis addiction, and relapse prevention of nicotine or cannabis addiction. Additionally, this invention may also provide for an alternative therapy for non-responding addiction patients, patients having intolerable side-effects with de-addiction therapies or those requiring long-term maintenance therapies. (Kuzmin A et al., Psychopharmacology (Berl), 2009, 203, 99-108; Weiss R B et al., PLoS Genet., 2008, 4, e1000125; Solinas M et al., J. Neurosci., 2007, 27, 5615-5620; Ebbert J O et al., Patient. Prefer. Adherence, 2010, 4, 355-362)

This invention may also find application in the treatment and prophylaxis of multitude of pain conditions including, either one or combinations of, pain arising from, peripheral nervous system (PNS), post-diabetic neuralgia (PDN), post-herpetic neuralgia (PHN), multiple sclerosis, Parkinson's disease, low-back pain, fibromyalgia, post-operative pain, acute pain, chronic pain, mononeuropathy, primary lateral sclerosis, pseudobulbar palsy, progressive muscular palsy, progressive bulbar palsy, postpolio syndrome, diabetes induced polyneuropathy, acute demyelinating polyneuropathy (Guillain-Barre syndrome), acute spinal muscular atrophy (Werdnig-Hoffman disease) and secondary neurodegeneration (Donnelly-Roberts D L et al., J. Pharmacol. Exp. Ther., 1998, 285, 777-786; Rowley T J et al., Br. J. Anaesth., 2010, 105, 201-207; Bruchfeld A et al., J. Intern. Med., 2010, 268, 94-101).

This invention may find application in the treatment and prophylaxis of plethora of inflammation and pain related states involving TNF-α and thus providing symptomatic relief in either any one or combination of, rheumatoid arthritis, bone resorption diseases, atherosclerosis, inflammatory bowel disease, Crohn's disease, inflammation, cancer pain, muscle degeneration, osteoarthritis, osteoporosis, ulcerative colitis, rhinitis, pancreatitis, spondylitis, acute respiratory distress syndrome (ARDS), joint inflammation, anaphylaxis, ischemia reperfusion injury, multiple sclerosis, cerebral malaria, septic shock, tissue rejection of graft, brain trauma, toxic shock syndrome, herpes virus infection (HSV-1 & HSV-2), herpes zoster infection, sepsis, fever, myalgias, asthma, uveititis, contact dermatitis, obesity-related disease and endotoxemia (Giebelen I A T et al., Shock, 2007, 27, 443-447; Pena G et al., Eur. J. Immunol., 2010, 40, 2580-2589).

Thus the present invention further provides a pharmaceutical composition, containing the compounds of the general formula (I) as defined above, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically acceptable carriers, diluents and the like.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

An compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as 20% to 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837, 028, and 5,019,369.

The compounds or pharmaceutical compositions are useful, in an embodiment, for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

In another embodiment, the pharmaceutical compositions are useful for the treatment and/or prophylaxis of diseases or disorder or condition classified or diagnosed as major or minor neurocognitive disorders, or disorders arising due to neurodegeneration.

The present invention also provide method of administering a compound of formula I, as defined hereinabove in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provide method of administering a compound of formula I, as defined hereinabove in combination with or as an adjunct to acetylcholinesterase inhibitors, disease modifying drugs or biologics for neurodegenerative disorders, dopaminergic drugs, antidepressants, typical or an atypical antipsychotic.

Accordingly, compound of formula I is useful for preventing or treating a disorder mediated by nicotinic acetylcholine receptors. Such compounds can be administered to a subject having such a disorder or susceptible to such disorders in a therapeutically effective amount. The compounds are particularly useful for a method of treating a mammal having a condition where modulation of nicotinic acetylcholine receptor activity is of therapeutic benefit, wherein the method is accomplished by administering a therapeutically effective amount of a compound of formula I to a subject having, or susceptible to, such a disorder.

The present invention also provides a pharmaceutical composition, containing the compounds of the general formula (I) as defined above, its tautomeric forms, its stereoisomers, its analogs, its prodrugs, its isotopes, its metabolites, its pharmaceutically acceptable salts, its polymorphs, its solvates, its optical isomers, its clathrates and its co-crystals in combination with the usual pharmaceutically employed carriers, diluents and the like, and for use in any of the methods described herein.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson P D R (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

In accordance with embodiments, the present invention provides methods of treating, preventing, ameliorating, and/or inhibiting a condition modulated by the nicotinic acetylcholine receptor comprising administering a compound of formula (I) or a salt thereof.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Following are the abbreviations used and meaning thereof in the specification:
ACh: Acetylcholine.
AD: Alzheimer's disease.
ADC: AIDS dementia complex.
ADHD: attention deficit hyperactivity disorder.
AIDS: Acquired immunodeficiency syndrome.
ARDS: acute respiratory distress syndrome.
DCC: 1,3-dicyclohexylcarbodiimide.
DCE: dichloroethane.
DCM: dichloromethane.
DIPEA: diisopropyl ethyl amine
DLB: dementia with Lewy bodies.
DMF: N,N-dimethylformamide.
EDCI: 1-(3-dimethylaminopropyl)-3-ethylcarbodiimide hydrochloride.
FLIPR: Fluorometric Imaging Plate Reader.
HATU: 2-(1H-7-Azabenzotriazol-1-yl)-1,1,3,3-tetramethyl uronium hexafluorophosphate.
HBSS: Hank's balanced salt solution.

HEPES: 4-(2-hydroxyethyl)piperazine-1-ethanesulfonic acid.
HMGB: high mobility group box.
HOAT: 1-hydroxy-7-azabenzotriazole.
HOBT: hydroxybenzotriazole hydrate.
HPLC: High Performance liquid chromatography.
IL: interleukins.
LDT: laterodorsal tegmental nucleus.
LGIC: ligand-gated ion channels.
MCI: mild cognitive impairment.
NBS: N-bromosuccinimide.
NCS: N-chlorosuccinimide.
NIS: N-iodosuccinamide
NNRs: Neural nicotinic ACh receptors.
PAM: positive allosteric modulation.
PD: Parkinson's disease.
PDN: post-diabetic neuralgia.
PHN: post-herpetic neuralgia.
PMBO: p-methoxy benzyloxy.
PNS: peripheral nervous system.
TBI: traumatic brain injury.
THF: Tetrahydrofuran.
TLC: Thin layer chromatography.
TMS: tetramethylsilane.
TNF-α: tumor necrosis factor alpha.
VTA: ventral tegmental area.
α7 nAChR: nicotinic acetylcholine receptor α7 subunit.

The following examples are provided to further illustrate the present invention and therefore should not be construed in any way to limit the scope of the present invention. All $^1$HNMR spectra were determined in the solvents indicated and chemical shifts are reported in δ units downfield from the internal standard tetramethylsilane (TMS) and interproton coupling constants are reported in Hertz (Hz).

Example 1

Preparation of 4-(5-(4-chlorophenyl)-4-methyl-2-propionylthiophen-3-yl)benzenesulfonamide (Compound 1)

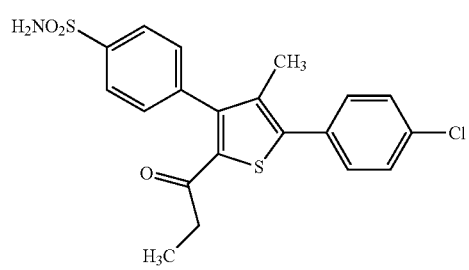

Step 1: Methyl-3-bromo-5-(4-chlorophenyl)-4-methylthiophene-2-carboxylate (1a)

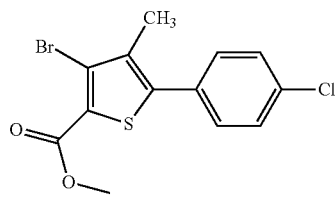 [SMILES: COC(=O)c1sc(-c2ccc(Cl)cc2)c(C)c1Br]

To a stirred solution of methyl-5-(4-chlorophenyl)-4-methylthiophene-2-carboxylate (prepared according to the procedure reported in WO 2007092751, 4.0 g, 15.0 mmol) in chloroform (50 ml) at 25° C. was added zinc chloride (2.06 g, 15.0 mmol) followed by the addition of bromine (2.64 g, 0.85 ml, 16.5 mmol) in a dropwise manner under a nitrogen atmosphere. The resulting mixture was stirred at 60-65° C. for 1.5 hr. The progress of the reaction was monitored by TLC. The reaction mixture was cooled to 0° C. and quenched with water (30 ml). The resulting organic layer was washed with 10% aqueous sodium bicarbonate solution (2×50 ml) and dried over anhydrous $Na_2SO_4$. The solvent in the organic layer was evaporated under reduced pressure to obtain a crude product, which was then purified by column chromatography over silica gel (100-200 mesh) using 3% ethyl acetate in hexanes as an eluent to obtain the title compound (2.2 g, 42.53%);

MS: m/z 345 (M+1),
$^1$HNMR ($CDCl_3$, 400 MHz): δ 7.43 (d, J=8.4 Hz, 2H), 7.36 (d, J=8.4 Hz, 2H), 3.9 (s, 3H), 2.28 (s, 3H).

The compounds given below were prepared by procedure similar to those described above for compound '1a' with appropriate variations of reactants, reaction conditions and quantities of reagents 2a. Methyl-3-bromo-5-(2-chlorophenyl)-4-methylthiophene-2-carboxylate MS: m/z 345 (M+1)

4a. Methyl-3-bromo-5-(4-fluorophenyl)-4-methylthiophene-2-carboxylate

MS: m/z 330 (M+1)

11a. Methyl-3-bromo-5-(4-(tert-butyl)phenyl)-4-methylthiophene-2-carboxylate

MS: m/z 368 (M+1)

17a. Methyl-3-bromo-5-(3,4-dichlorophenyl)-4-methylthiophene-2-carboxylate

MS: m/z 381 (M+1)

18a. Methyl-3-bromo-5-(2,4-dichlorophenyl)-4-methylthiophene-2-carboxylate

MS: m/z 381 (M+1)

19a. Methyl-3-bromo-5-(2,4-difluorophenyl)-4-methylthiophene-2-carboxylate

MS: m/z 370 (M+23)

20a. Methyl-3 bromo-5-(3-chloro-4-fluorophenyl)-4-methylthiophene-2-carboxylate

MS: m/z 365 (M+1)

21a. Methyl-3-bromo-5-(3-chloro-4-methoxyphenyl)-4-methylthiophene-2-carboxyate

MS: m/z 377 (M+1)

47a. Ethyl-3-bromo-5-(3,4-difluorophenyl)-4-methylthiophene-2-carboxylate

MS: m/z 384 (M+23)

Step 2: Ethyl-5-(4-chlorophenyl)-4-methyl-3-(4-sulfamoylphenyl)thiophene-2-carboxylate (1b)

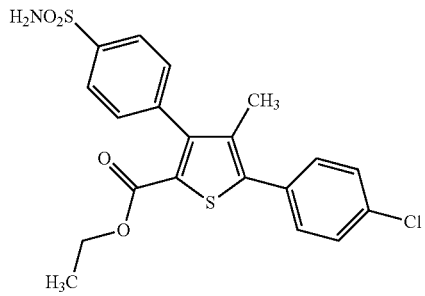 [SMILES: CCOC(=O)c1sc(-c2ccc(Cl)cc2)c(C)c1-c1ccc(S(N)(=O)=O)cc1]

To a solution of methyl-3-bromo-5-(4-chlorophenyl)-4-methylthiophene-2-carboxylate (compound 1a, 2.2 g, 6.3 mmol) in a mixture of toluene:ethanol (10:30 ml) were added 4-aminosulfonylbenzene boronic acid (prepared according to the procedure given in EP 1012142, 1.28 g, 6.3 mmol) and potassium carbonate (1.76 g, 12.7 mmol) at 25° C. in a sealed tube and nitrogen gas was bubbled through the reaction mixture for 15 minutes. To this was added tetrakis(triphenylphosphine)palladium(0) (0.370 g, 0.318 mmol) under nitrogen and the reaction mixture was heated at about 95-about 100° C. for 18 hr under stirring. The progress of the reaction was monitored by TLC. The reaction mixture was cooled to 25° C. and filtered through celite. The filtrate was concentrated under reduced pressure to obtain a crude product, which was purified by column chromatography over silica gel (100-200 mesh) using 40% ethyl acetate in hexanes as an eluent to obtain the title compound (1.3 g, 48%).

MS: m/z 436 (M+1),
$^1$HNMR (CDCl$_3$, 400 MHz): δ 8.01 (d, J=8.4 Hz, 2H), 7.46-7.41 (m, 6H). 4.89 (bs, 2H), 4.17 (q, J=7.2 Hz, 2H), 1.99 (s, 3H), 1.9 (t, J=7.2 Hz, 3H).

The compounds given below were prepared by procedure similar to the one described above for compound '1b' with appropriate variations of reactants, reaction conditions and quantities of reagents.

2b. Ethyl-5-(2-chlorophenyl)-4-methyl-3-(4-sulfamoylphenyl)thiophene-2-carboxylate MS: m/z 436 (M+1), 4b. Ethyl 5-(4-fluorophenyl)-4-methyl-3-(4-sulfamoylphenyl)thiophene-2-carboxylate MS: m/z 420 (M+1)

11b. Ethyl 5-(4-(tert-butyl)phenyl)-4-methyl-3-(4-sulfamoylphenyl)thiophene-2-carboxylate MS: m/z 458 (M+1)

17b. Ethyl 5-(3,4-dichlorophenyl)-4-methyl-3-(4-sulfamoylphenyl)thiophene-2-carboxylate MS: m/z 470 (M+1)

18b. Ethyl 5-(2,4-dichlorophenyl)-4-methyl-3-(4-sulfamoylphenyl)thiophene-2-carboxylate MS: m/z 470 (M+1)

19b. Ethyl 5-(2,4-difluorophenyl)-4-methyl-3-(4-sulfamoylphenyl)thiophene-2-carboxylate MS: m/z 438 (M+1)

20b. Ethyl 5-(3-chloro-4-fluorophenyl)-4-methyl-3-(4-sulfamoylphenyl)thiophene-2-carboxylate MS: m/z 454 (M+1)

21b. Ethyl 5-(3-chloro-4-methoxyphenyl)-4-methyl-3-(4-sulfamoylphenyl)thiophene-2-carboxyate MS: m/z 466 (M+1)

47b. Ethyl 5-(3,4-difluorophenyl)-4-methyl-3-(4-sulfamoylphenyl)thiophene-2-carboxylate MS: m/z 438 (M+1)

Step 3: 5-(4-chlorophenyl)-4-methyl-3-(4-sulfamoylphenyl)thiophene-2-carboxylic acid (1c)

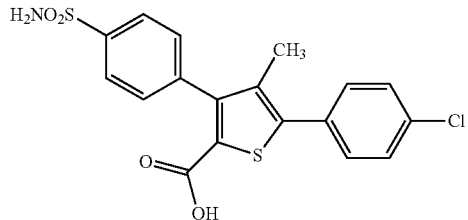 [SMILES: Cc1c(-c2ccc(Cl)cc2)sc(C(=O)O)c1-c1ccc(S(N)(=O)=O)cc1]

Ethyl-5-(4-chlorophenyl)-4-methyl-3-(4-sulfamoylphenyl)thiophene-2-carboxylate (compound 1b, 1.9 g, 4.36 mmol) was suspended in ethanol (40 ml) and treated with 1N solution of NaOH (0.9 ml) at 25° C. The reaction mixture was heated at 50-55° C. under stirring for 30-40 minutes. The progress of reaction was monitored by TLC. The reaction mixture was then concentrated under reduced pressure. The residue obtained was diluted with a mixture of ethylacetate:water (100:50 ml) To the resulting diluted mixture was added aqueous 10% HCl to bring the pH of the mixture to between 5 and 6. The aqueous layer was extracted with ethyl acetate (2×50 ml). The combined organic layer was dried over anhydrous Na₂SO₄. The solvent in the organic layer was evaporated under reduced pressure to obtain the title compound. (1.72 g, 97%).

MS: m/z 408 (M+1),

¹HNMR (DMSO, 400 MHz): δ 12.87 (bs, 1H), 7.88 (d, J=8.4 Hz, 2H), 7.56 (bs, 4H). 7.5 (d, J=8.4 Hz, 2H), 7.45 (s, 2H), 1.95 (s, 3H).

The compounds given below were prepared by procedure similar to the one described above for compound '1c' with appropriate variations of reactants, reaction conditions and quantities of reagents.

2c. 5-(2-chlorophenyl)-4-methyl-3-(4-sulfamoylphenyl)thiophene-2-carboxylic acid MS: m/z 408 (M+1).

4c. 5-(4-fluorophenyl)-4-methyl-3-(4-sulfamoylphenyl)thiophene-2-carboxylic acid MS: m/z 392 (M+1).

11c. 5-(4-(tert-butyl)phenyl)-4-methyl-3-(4-sulfamoylphenyl)thiophene-2-carboxylic acid MS: m/z 430 (M+1).

17c. 5-(3,4-dichlorophenyl)-4-methyl-3-(4-sulfamoylphenyl)thiophene-2-carboxylic acid MS: m/z 442 (M+1).

18c. 5-(2,4-dichlorophenyl)-4-methyl-3-(4-sulfamoylphenyl)thiophene-2-carboxylic acid MS: m/z 442 (M+1).

19c. 5-(2,4-difluorophenyl)-4-methyl-3-(4-sulfamoylphenyl)thiophene-2-carboxylic acid MS: m/z 410 (M+1).

20c. 5-(3-chloro-4-fluorophenyl)-4-methyl-3-(4-sulfamoylphenyl)thiophene-2-carboxylic acid MS: m/z 426 (M+1).

21c. 5-(3-chloro-4-methoxyphenyl)-4-methyl-3-(4-sulfamoylphenyl)thiophene-2-carboxylic acid MS: m/z 438 (M+1).

47c. 5-(3,4-difluorophenyl)-4-methyl-3-(4-sulfamoylphenyl)thiophene-2-carboxylic acid MS: m/z 410 (M+1).

Step 4: 5-(4-chlorophenyl)-3-(4-(N-((dimethylamino)methylene)sulfamoyl)phenyl)-N-methoxy-N, 4-dimethylthiophene-2-carboxamide (1d)

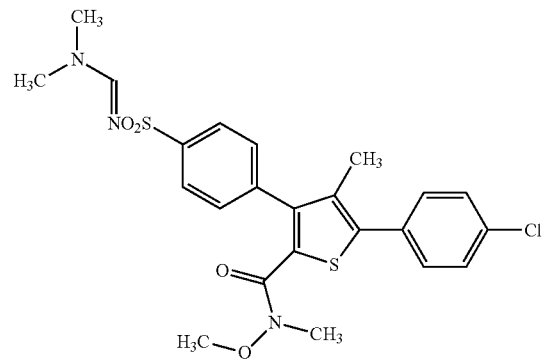

Oxalyl chloride (2.1 g, 1.4 ml, 16.2 mmol) was added dropwise at 0° C. to a solution of 5-(4-chlorophenyl)-4-methyl-3-(4-sulfamoylphenyl)thiophene-2-carboxylic acid (compound 1c, 2.2 g, 5.4 mmol) in a mixture of dichloromethane (40 ml) and DMF (0.8 g, 0.8 ml, 10.8 m mol). The resulting mixture was allowed to warm to room temperature and stirred for 1.5 hr, under a nitrogen atmosphere. The progress of reaction was monitored by TLC. The reaction mixture was concentrated under reduced pressure and used directly for further reaction. The residue so obtained was dissolved in dry dichloromethane (40 ml) and to this was added triethylamine (2.8 g, 3.9 ml, 27.0 mmol) followed by the addition of N,O-dimethylhydroxylamine hydrochloride (1.06 g, 10.8 mmol) under stirring. The reaction mixture was stirred at room temperature for 2 hr. The progress of reaction was monitored by TLC. The reaction mixture was washed with water (2×20 ml) and the organic layer obtained was dried over anhydrous sodium sulphate, and concentrated under reduced pressure to obtain a crude product. The crude product was further purified by column chromatography over silica gel (100-200 mesh) using 80% ethylacetate in hexane as an eluent to obtain the title compound (2.36 g, 86%).

MS: m/z 506 (M+1),

¹HNMR (CDCl₃, 400 MHz): δ 8.14 (s, 1H), 7.95 (d, J=8.4 Hz, 2H), 7.42 (bs, 4H). 7.37 (d, J=8.4 Hz, 2H), 3.68 (s, 3H), 3.17 (s, 3H), 3.13 (s, 3H), 3.05 (s, 3H), 1.98 (s, 3H).

The compounds given below were prepared by procedure similar to the one described above for compound '1d' with appropriate variations of reactants, reaction conditions and quantities of reagents 2d. 5-(2-chlorophenyl)-3-(4-(N-((dimethylamino)methylene)sulfamoyl)phenyl)-N-methoxy-N,4-dimethylthiophene-2-carboxamide MS: m/z 506 (M+1)

4d. 3-(4-(N-((dimethylamino)methylene)sulfamoyl)phenyl)-5-(4-Fluoro phenyl)-N-methoxy-N,4-dimethylthiophene-2-carboxamide MS: m/z 490 (M+1).

11d. 5-(4-(tert-butyl)phenyl)-3-(4-(N-((dimethylamino)methylene)sulfamoyl)phenyl)-N-methoxy-N, 4-dimethylthiophene-2-carboxamide MS: m/z 528 (M+1).

17d. 5-(3,4-dichlorophenyl)-3-(4-(N-((dimethylamino)methylene)sulfamoyl)phenyl)-N-methoxy-N,4-dimethylthiophene-2-carboxamide MS: m/z 540 (M+1).

18d. 5-(2,4-dichlorophenyl)-3-(4-(N-((dimethylamino)methylene)sulfamoyl)phenyl)-N-methoxy-N,4-dimethylthiophene-2-carboxamide MS: m/z 540 (M+1).

19d. 5-(2,4-Difluoro phenyl)-3-(4-(N-((dimethylamino)methylene)sulfamoyl)phenyl)-N-methoxy-N,4-dimethylthiophene-2-carboxamide MS: m/z 508 (M+1).

20d. 5-(3-Chloro-4-fluoro phenyl)-3-(4-(N-((dimethylamino)methylene)sulfamoyl)phenyl)-N-methoxy-N,4-dimethylthiophene-2-carboxamide MS: m/z 524 (M+1).

21d. 5-(3-Chloro-4-methoxyphenyl)-3-(4-(N-((dimethylamino)methylene)sulfamoyl)phenyl)-N-methoxy-N,4-dimethylthiophene-2-carboxamide MS: m/z 536 (M+1).

47d. 5-(3,4-Difluoro phenyl)-3-(4-(N-((dimethylamino)methylene)sulfamoyl)phenyl)-N-methoxy-N,4-dimethylthiophene-2-carboxamide MS: m/z 508 (M+1).

Step 5: Preparation of 4-(5-(4-chlorophenyl)-4-methyl-2-propionylthiophen-3-yl)benzenesulfonamide (Compound 1)

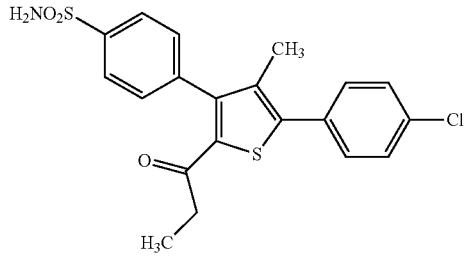 [SMILES: CCC(=O)c1sc(-c2ccc(Cl)cc2)c(C)c1-c1ccc(S(N)(=O)=O)cc1]

To a stirred solution of 5-(4-chlorophenyl)-3-(4-(N-((dimethylamino)methylene) sulfamoyl)phenyl)-N-methoxy-N,4-dimethylthiophene-2-carboxamide (compound 1d, 2.3 g, 4.55 mmol) in anhydrous THF (40 ml) at 25° C., Grignard reagent (ethyl magnesium bromide, 3.04 g, 22.8 ml, 22.77 mmol) was added dropwise and the reaction mixture was heated at 70-75° C. for 1 hr. The progress of the reaction was monitored by TLC. After cooling the reaction mixture to 0° C., the reaction mixture was quenched by adding a solution of saturated ammonium chloride (40 ml) and the resulting mixture was extracted with ethyl acetate (3×50 ml). The combined organic layer was dried over anhydrous $Na_2SO_4$. The solvent was evaporated from the dried organic layer under reduced pressure to obtain a crude product; which was purified by column chromatography over silica gel (100-200 mesh) using 30-35% ethyl acetate in hexane as an eluent to obtain the title compound which was further purified by precipitation by dissolving 1.1 g of the compound in dichloromethane (10 ml) and precipitating it by slow addition of diisopropyl ether. (0.89 g, 47%)

MS: m/z 420 (M+1),
$^1$HNMR (DMSO, 400 MHz): δ 7.95 (d, J=8.4 Hz, 2H), 7.59 (bs, 4H). 7.56 (d, J=8.4 Hz, 2H), 7.45 (s, 2H), 2.37 (q, J=6.8 Hz, 2H), 1.92 (s, 3H), 0.88 (t, J=6.8 Hz, 3H),

The following compounds were prepared according to the procedure described above but with appropriate changes to the reactants.

4-(5-(2-Chlorophenyl)-4-methyl-2-propionylthiophen-3-yl)benzenesulfonamide (Compound 2)

MS: m/z 420 (M+1),
$^1$HNMR (DMSO, 400 MHz): δ 7.88 (d, J=8.4 Hz, 2H), 7.56-7.58 (m, 1H), 7.43-7.47 (m, 7H), 2.34 (q, J=7.2 Hz, 2H), 1.70 (s, 3H), 0.89 (t, J=7.2 Hz, 3H).

4-(5-(4-Fluorophenyl)-4-methyl-2-propionylthiophen-3-yl)benzenesulfonamide. (Compound 4)

MS: m/z 404 (M+1),
$^1$HNMR (DMSO, 400 MHz): δ 7.94 (d, J=8.4 Hz, 2H), 7.56-7.64 (m, 4H), 7.49 (bs-exchanges with $D_2O$, 2H), 7.36-7.40 (m, 2H), 2.38 (q, J=7.2 Hz, 2H), 1.92 (s, 3H), 0.89 (t, J=7.2 Hz, 3H).

4-(5-((4-tert butyl)phenyl)-4-methyl-2-propionylthiophen-3-yl)benzene sulfonamide (Compound 11)

MS: m/z 442 (M+1),
$^1$HNMR ($CDCl_3$, 400 MHz): δ 8.02 (d, J=8.4 Hz, 2H), 7.42-7.49 (m, 6H), 4.92 (bs-exchanges with $D_2O$, 2H), 2.56 (q, J=7.2 Hz, 2H), 1.97 (s, 3H), 1.36 (s, 9H), 1.06 (t, J=7.2 Hz, 3H).

4-(5-(3,4-Dichlorophenyl)-4-methyl-2-propionylthiophen-3-yl)benzenesulfonamide (Compound 17)

MS: MS: m/z 454 (M+1),
$^1$HNMR ($CDCl_3$, 400 MHz): δ 8.03 (d, J=8.4 Hz, 2H), 7.59 (d, J=2.0 Hz, 1H), 7.54 (d, J=8.4 Hz, 1H), 7.42 (d, J=8.4 Hz, 2H), 7.32 (dd, J=8.4, 2.0 Hz, 1H), 4.91 (bs-exchanges with $D_2O$, 2H), 2.52 (q, J=7.2 Hz, 2H), 1.95 (s, 3H), 1.04 (t, J=7.2 Hz, 3H).

4-(5-(2,4-Dichlorophenyl)-4-methyl-2-propionylthiophen-3-yl)benzenesulfonamide (Compound 18)

MS: MS: m/z 454 (M+1),
$^1$HNMR ($CDCl_3$, 400 MHz): δ 8.04 (d, J=8.4 Hz, 2H), 7.53-7.54 (m, 1H), 7.44 (d, J=8.4 Hz, 2H), 7.32-7.42 (m, 2H), 4.89 (bs-exchanges with $D_2O$, 2H), 2.55 (q, J=7.2 Hz, 2H), 1.76 (s, 3H), 1.04 (t, J=7.2 Hz, 3H).

4-(5-(2,4-Difluorophenyl)-4-methyl-2-propionylthiophen-3-yl)benzenesulfonamide (Compound 19)

MS: m/z 422 (M+1),
$^1$HNMR ($CDCl_3$, 400 MHz): δ 8.04 (d, J=8.4 Hz, 2H), 7.47 (d, J=8.4 Hz, 2H), 7.38-7.44 (m, 1H) 6.98-7.04 (m, 2H), 5.01 (bs-exchanges with $D_2O$, 2H), 2.54 (q, J=7.2 Hz, 2H), 1.83 (s, 3H), 1.05 (t, J=7.2 Hz, 3H).

4-(5-(3-Chloro-4-fluorophenyl)-4-methyl-2-propionylthiophen-3-yl)benzenesulfonamide (Compound 20)

MS: m/z 438 (M+1), $^1$HNMR (CDCl$_3$, 400 MHz): δ 8.04 (d, J=8.4 Hz, 2H), 7.54 (dd, J=6.8, 2.4 Hz, 1H), 7.42 (d, J=8.4 Hz, 2H), 7.35-7.38 (m, 1H), 7.25 (t, J=8.4 Hz, 1H), 4.92 (bs-exchanges with D$_2$O, 2H), 2.54 (q, J=7.2 Hz, 2H), 1.94 (s, 3H), 1.04 (t, J=7.2 Hz, 3H).

4-(5-(3-Chloro-4-methoxyphenyl)-4-methyl-2-propionylthiophen-3-yl)benzene sulfonamide (Compound 21)

MS: m/z 450 (M+1), $^1$HNMR (DMSO, 400 MHz): δ 7.93 (d, J=8.4 Hz, 2H), 7.61 (d, J=2.4 Hz, 1H), 7.54 (d, J=8.4 Hz, 2H), 7.50 (d, J=2.4 Hz, 1H), 7.49 (bs-exchanges with D$_2$O, 2H), 7.29 (d, J=8.8 Hz, 1H), 3.92 (s, 3H), 2.35 (q, J=7.2 Hz, 2H), 1.91 (s, 3H), 0.87 (t, J=7.2 Hz, 3H).

4-(2-Acetyl-5-(4-chlorophenyl)-4-methylthiophen-3-yl)benzenesulfonamide (Compound 40)

MS: m/z 406 (M+1), $^1$HNMR (DMSO, 400 MHz): δ 7.95 (d, J=8.4 Hz, 2H), 7.57-7.59 (m, 6H), 7.50 (bs-exchanges with D$_2$O, 2H), 1.99 (s, 3H), 1.93 (s, 3H).

4-(5-(3,4-Difluorophenyl)-4-methyl-2-propionylthiophen-3-yl)benzenesulfonamide (Compound 47)

MS: m/z 422 (M+1), $^1$HNMR (CDCl$_3$, 400 MHz): δ 8.03 (d, J=8.4 Hz, 2H), 7.42 (d, J=8.4 Hz, 2H), 7.25-7.33 (m, 3H), 4.98 (bs-exchanges with D$_2$O, 2H), 2.52 (q, J=7.2 Hz, 2H), 1.94 (s, 3H), 1.04 (t, J=7.2 Hz, 3H).

Example 2

Preparation of 4-(4-methyl-5-morpholino-2-propionylthiophen-3-yl)benzenesulfonamide (Compound 24)

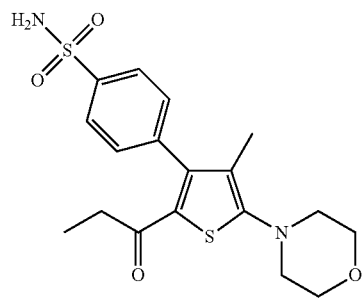 [SMILES: CCC(=O)c1sc(N2CCOCC2)c(C)c1-c1ccc(S(N)(=O)=O)cc1]

Step 1: Preparation of N,N-dimethyl-N'-((4-propionylphenyl)sulfonyl) formimidamide (24a)

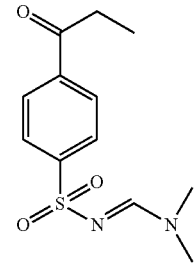 [SMILES: CCC(=O)c1ccc(S(=O)(=O)/N=C/N(C)C)cc1]

To a stirred solution of 4-propionylbenzenesulfonamide (prepared according to the procedure reported in Bioorganic Chemistry 1994, 22, 387-394), 2.2 g (10.3 mmol) in ethylacetate (20 ml) was added DMF (2.0 ml) followed by the addition of N,N-dimethylformamidedimethyl acetal (1.36 g, 1.51 ml, 11.36 mmol) in a dropwise manner at room temperature. The resulting mixture was stirred at room temperature for 4 hr. The progress of the reaction was monitored by TLC. The reaction mixture was concentrated under reduced pressure to obtain a solid product, which was washed with diisopropylether to obtain the title compound (2.6 g, 94%).

MS: m/z 269 (M+1), $^1$HNMR (DMSO, 400 MHz): δ 8.25 (s, 1H), 8.08 (d, J=8.8 Hz, 2H), 7.90 (d, J=8.4 Hz, 2H), 3.15 (s, 3H), 3.09 (q, J=7.2 Hz, 2H), 2.91 (s, 3H), 1.08 (t, J=7.2 Hz, 3H).

Step 2: Preparation of N'-((4-(2-(1,3-dithiatan-2-ylidene)propanoyl)phenyl)sulfonyl)-N,N-dimethylformimidamide (24b)

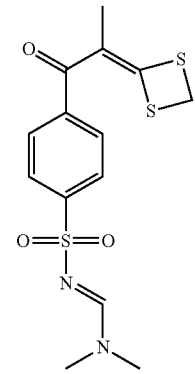 [SMILES: CC(C(=O)c1ccc(S(=O)(=O)/N=C/N(C)C)cc1)=C1SCS1]

To a stirred solution of N,N-dimethyl-N'-((4-propionylphenyl)sulfonyl) formimidamide (compound 24a, 1.0 g, 3.73 mmol) in dry THF (30 ml) was added potassium tert.butoxide (0.837 g, 7.46 mmol) at 0° C. under a nitrogen atmosphere. The resulting mixture was stirred at room temperature for 1 hr. The reaction mixture was cooled to 0° C. and to the cooled reaction mixture was added carbon disulfide (0.425 g, 0.34 ml, 5.59 mmol) in a dropwise manner at 0° C. The resulting reaction mixture was stirred at room temperature for 30 minutes. The reaction mixture was cooled to 0° C. and to the cooled reaction mixture was added dibromomethane (1.3 g, 0.85 ml, 7.46 mmol) in a dropwise manner at 0° C. The resulting reaction mixture was stirred at room temperature for 20 hr. The progress of the reaction was monitored by TLC. The reaction mixture was poured into cold water (50 ml) and extracted with ethyl acetate (3×50 ml). The combined organic layer was dried over anhydrous Na$_2$SO$_4$. The solvent was evaporated under reduced pressure from the dried organic layer to obtain a crude product, which was further purified by column chromatography over silica gel (100-200 mesh) using 2% methanol in dichloromethane as an eluent to obtain the title compound (0.65 g, 49%).

MS: m/z 357 (M+1), $^1$HNMR (CDCl$_3$, 400 MHz): δ 8.13 (s, 1H), 7.93 (d, J=8.8 Hz, 2H), 7.59 (d, J=8.4 Hz, 2H), 4.16 (s, 2H), 3.15 (s, 3H), 3.04 (s, 3H), 1.83 (s, 3H).

Step 3: Preparation of N,N-dimethyl-N'-((4-(2-methyl-3-morpholino-3-thioxopropanoyl)phenyl)sulfonyl)formimidamide (24c)

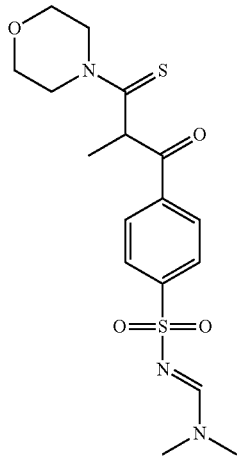 [SMILES: CC(C(=O)c1ccc(S(=O)(=O)/N=C/N(C)C)cc1)C(=S)N1CCOCC1]

To a stirred solution of N'-((4-(2-(1,3-dithiatan-2-ylidene)propanoyl)phenyl)sulfonyl)-N,N-dimethylformimidamide (compound 24b, 0.53 g, 1.48 mmol) in toluene (20 ml) was added morpholine (0.39 g, 4.4 mmol) at room temperature. The reaction mixture was stirred at 115-120° C. for 3 hr. The progress of the reaction was monitored by TLC. The reaction mixture was concentrated under reduced pressure to obtain a crude product, which was purified by column chromatography over silica gel (100-200 mesh) using 2% methanol in dichloromethane as an eluent to obtain the title compound (0.191 g, 32.3%)

MS: m/z 398 (M+1), $^1$HNMR (DMSO, 400 MHz): δ 8.23 (s, 1H), 7.85 (brs, 4H), 5.19 (q, J=6.4 Hz, 1H), 3.5-4.0 (m, 8H), 3.14 (s, 3H), 2.91 (s, 3H), 1.33 (d, J=6.4 Hz, 3H).

The compounds given below were prepared by procedure similar to the one described above for compound '24c' with appropriate variations of reactants, reaction conditions and quantities of reagents.

22c. tert-butyl 4-(3-(4-(N-((dimethylamino)methylene)sulfamoyl)phenyl)-2-methyl-3-oxopropanethioyl)piperazine-1-carboxylate MS: m/z 519 (M+23)

23c. N'-((4-(3-(4-(4-fluorophenyl)piperazin-1-yl)-2-methyl-3-thioxopropanoyl)phenyl)sulfonyl)-N,N-dimethylformimidamide MS: m/z 491 (M+1), Step 4: Preparation of ethyl-3-(4-(N-((dimethylamino)methylene) sulfamoyl)phenyl)-4-methyl-5-morpholinothiophene-2-carboxylate (24d)

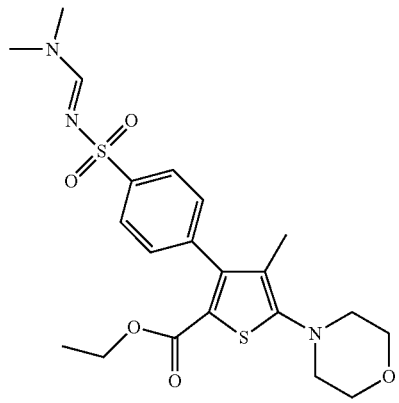 [SMILES: CCOC(=O)c1sc(N2CCOCC2)c(C)c1-c1ccc(S(=O)(=O)/N=C/N(C)C)cc1]

To a stirred solution of N,N-dimethyl-N'-((4-(2-methyl-3-morpholino-3-thioxopropanoyl)phenyl)sulfonyl)formimidamide (compound 24c, 0.180 g, 0.45 mmol) in dry acetone (15 ml) was added potassium carbonate (0.45 g, 3.17 mmol) at room temperature. The resulting mixture was stirred at 55-60° C. for 2 hr. The reaction mixture was cooled to 0° C. and to this was added ethyl iodoacetate (0.097 g, 0.053 ml, 0.45 mmol) in a dropwise manner. The reaction mixture was stirred at reflux temperature for 4 hr. The progress of the reaction was monitored by TLC. The reaction mixture was allowed to warm to room temperature and filtered through a celite pad. The celite pad was washed with acetone (2×10 ml). The filtrate was concentrated under reduced pressure to obtain a crude product, which was purified by column chromatography over silica gel (100-200 mesh) using 50-55% ethyl acetate in hexanes as an eluent to obtain the title compound (0.091 g, 43%)

MS: m/z 466 (M+1), $^1$HNMR (CDCl$_3$, 400 MHz): δ 8.19 (s, 1H), 7.90 (d, J=8.4 Hz, 2H), 7.31 (d, J=8.4 Hz, 2H), 4.10 (q, J=7.2 Hz, 2H), 3.87-3.84 (m, 4H), 3.16 (s, 3H), 3.07 (s, 3H), 3.07-3.04 (m, 4H), 1.88 (s, 3H), 1.15 (t, J=7.2 Hz, 3H).

The compounds given below were prepared by procedure similar to the one described above for compound '24d' with appropriate variations of reactants, reaction conditions and quantities of reagents 22d. tert-butyl 4-(4-(4-(N-((dimethylamino)methylene)sulfamoyl)phenyl)-5-(ethoxycarbonyl)-3-methylthiophen-2-yl)piperazine-1-carboxylate MS: m/z 565 (M+1)

23d. Ethyl-3-(4-(N-((dimethylamino)methylene) sulfamoyl)phenyl)-5-(4-(4-fluorophenyl)piperazin-1-yl)-4-methyl-thiophene-2-carboxylate MS: m/z 559 (M+1)

Step 5: Preparation of 4-methyl-5-morpholino-3-(4-sulfamoylphenyl)thiophene-2-carboxylic acid (24e)

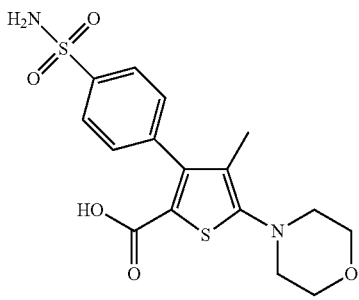 [SMILES: Cc1c(N2CCOCC2)sc(C(=O)O)c1-c1ccc(S(N)(=O)=O)cc1]

Ethyl-3-(4-(N-((dimethylamino)methylene) sulfamoyl)phenyl)-4-methyl-5-morpholinothiophene-2-carboxylate (compound 24d, 0.36 g, 0.77 mmol) was suspended in ethanol (20 ml) and combined with 2N solution of NaOH (1.55 ml) at 25° C. The reaction mixture was heated at 95-100° C. under stirring for 1 hr. The progress of the reaction was monitored by TLC. The resulting reaction mixture was concentrated at a reduced pressure. The residue obtained was diluted with mixture of ethylacetate:water (30:15 ml). To this was added aqueous 10% HCl to bring the pH to between 5 and 6. The aqueous layer was extracted with ethyl acetate (2×20 ml). The combined organic layer was dried over anhydrous $Na_2SO_4$. The solvent was evaporated under reduced pressure from the dried organic layer to obtain the title compound (0.196 g, 66%).

MS: m/z 383 (M+1), $^1$HNMR (DMSO, 400 MHz): δ 12.44 (bs, 1H), 7.83 (d, J=8.4 Hz, 2H), 7.42 (s, 2H), 7.41 (d, J=8.4 Hz, 2H), 3.75 (t, J=4.8 Hz, 4H), 2.98 (t, J=4.4 Hz, 4H), 1.79 (s, 3H).

The compounds given below were prepared by procedure similar to the one described above for compound '24e' with appropriate variations of reactants, reaction conditions and quantities of reagents 22e. 5-(4-(tert-butoxycarbonyl)piperazin-1-yl)-4-methyl-3-(4-sulfamoylphenyl)thiophene-2-carboxylic acid MS: m/z 482 (M+1)

23e. 5-(4-(4-fluorophenyl)piperazin-1-yl)-4-methyl-3-(4-sulfamoylphenyl)thiophene-2-carboxylic acid MS: m/z 476 (M+1)

Step 6: Preparation of 3-(4-(N-((dimethylamino)methylene)sulfamoyl)phenyl)-N-methoxy-N,4-dimethyl-5-morpholinothiophene-2-carboxamide (24f)

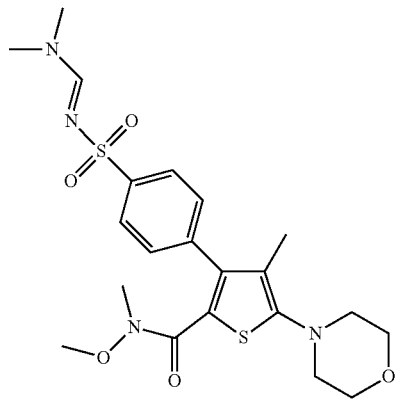 [SMILES: CON(C)C(=O)c1sc(N2CCOCC2)c(C)c1-c1ccc(S(=O)(=O)/N=C/N(C)C)cc1]

Oxalyl chloride (0.19 g, 0.13 ml, 1.49 mmol) was added dropwise at 0° C. to a solution of 4-methyl-5-morpholino-3-(4-sulfamoylphenyl)thiophene-2-carboxylic acid (compound 24e, 0.19 g, 0.497 mmol) in a mixture of dichloromethane (15 ml) and DMF (0.073 g, 0.08 ml, 0.99 m mol). The resulting mixture was allowed to warm to room temperature and stirred for 1.5 hr, under a nitrogen atmosphere. The progress of the reaction was monitored by TLC. The reaction mixture was concentrated under reduced pressure and used directly for further reaction. The residue so obtained was dissolved in dry dichloromethane (15 ml) and to this was added triethylamine (0.251 g, 0.35 ml, 2.48 mmol) followed by the addition of N,O-dimethylhydroxylamine hydrochloride (0.098 g, 0.99 mmol) under stirring at 0° C. The reaction mixture was stirred at room temperature for 2 hr. The progress of reaction was monitored by TLC. The reaction mixture was washed with water (2×10 ml) and the resulting organic layer was dried over anhydrous sodium sulphate and concentrated under reduced pressure to obtain a crude product. The crude product was further purified by column chromatography over silica gel (100-200 mesh) using 1% methanol in dichloromethane as an eluent to obtain the title compound (0.127 g, 53%).

MS: m/z 481 (M+1), $^1$HNMR (CDCl$_3$, 400 MHz): δ 8.13 (s, 1H), 7.89 (d, J=8.4 Hz, 2H), 7.29 (d, J=8.4 Hz, 2H), 3.86 (brs, 4H), 3.65 (s, 3H), 3.14 (s, 3H), 3.13 (s, 3H), 3.03-3.05 (m, 7H), 1.85 (s, 3H).

The compounds given below were prepared by procedure similar to the one described above for compound '24f' with appropriate variations of reactants, reaction conditions and quantities of reagents.

22f. tert-butyl 4-(4-(4-(N-((dimethylamino)methylene)sulfamoyl)phenyl)-5-(methoxy(methyl)carbamoyl)-3-methylthiophen-2-yl)piperazine-1-carboxylate MS: m/z 580 (M+1).

23f. 3-(4-(N-((dimethylamino)methylene)sulfamoyl)phenyl)-5-(4-(4-fluorophenyl)piperazin-1-yl)-N-methoxy-N,4-dimethylthiophene-2-carboxamide MS: m/z 574 (M+1).

Step 7: Preparation of 4-(4-methyl-5-morpholino-2-propionylthiophene-3-yl)benzenesulfonamide (compound 24)

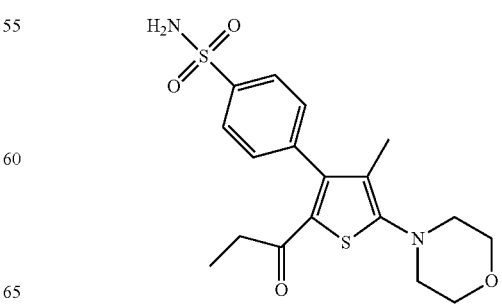

To a stirred solution of 3-(4-(N-((dimethylamino)methylene) sulfamoyl)phenyl)-N-methoxy-N,4-dimethyl-5-morpholinothiophene-2-carboxamide (compound 24f, 0.120 g, 0.25 mmol) in anhydrous THF (10 ml) at 25° C., Grignard reagent (ethyl magnesium bromide, 0.17 g, 1.25 ml, 1.25 mmol) was added dropwise and the reaction mixture was heated to 70-75° C. for 1 hr. The progress of the reaction was monitored by TLC. After cooling the reaction mixture to 0° C., reaction mixture was quenched by adding a saturated ammonium chloride solution (10 ml) and the resulting mixture was extracted with ethyl acetate (2×20 ml). The combined organic layer was dried over anhydrous $Na_2SO_4$. The solvent in the dried organic layer was evaporated under a reduced pressure to obtain a crude product, which was purified by column chromatography over silica gel (100-200 mesh) using 40-45% ethyl acetate in hexane as an eluent to obtain the title compound which was further purified by precipitation by dissolving 0.056 g of this compound in ethyl acetate (1.0 ml) and precipitating it by the slow addition of diisopropyl ether. The precipitate was filtered to obtain the title compound. (0.047 g, 48%).

MS: m/z 395 (M+1),
$^1$HNMR (DMSO, 400 MHz): δ 7.88 (d, J=8.4 Hz, 2H), 7.46-7.48 (m, 4H), 3.74-3.76 (m, 4H), 3.00-3.03 (m, 4H), 2.24 (q, J=7.2 Hz, 2H), 1.75 (s, 3H), 0.83 (t, J=7.2 Hz, 3H).

The following compounds were prepared according to the procedure described above but with appropriate changes to the reactants.

4-(4-methyl-5-(piperazin-1-yl)-2-propionylthiophen-3-yl)benzenesulfonamide (Compound 22)

MS: MS: m/z 394 (M+1),
$^1$HNMR (CDCl$_3$, 400 MHz): δ 7.84 (d, J=8.4 Hz, 2H), 7.18 (d, J=8.4 Hz, 2H), 6.31 (bs-exchanges with D$_2$O, 2H), 2.84-2.89 (m, 8H), 2.36 (bs-exchanges with D$_2$O, 1H), 2.16 (q, J=7.2 Hz, 2H), 1.63 (s, 3H), 0.80 (t, J=7.2 Hz, 3H).

4-(5-(4-(4-Fluorophenyl)piperazin-1-yl)-4-methyl-2-propionylthiophen-3-yl)benzene sulfonamide (Compound 23)

MS: m/z 488 (M+1),
$^1$HNMR (DMSO, 400 MHz): δ 7.88 (d, J=8.4 Hz, 2H), 7.47-7.49 (m, 4H), 7.00-7.10 (m, 4H), 3.34-3.36 (m, 4H), 3.24-3.26 (m, 2H), 3.16-3.19 (m, 2H), 2.24 (q, J=7.2 Hz, 2H), 1.78 (s, 3H), 0.83 (t, J=7.2 Hz, 3H).

Example 3

Preparation of 4-(5-(4-methoxyphenyl)-4-methyl-2-propionylthiophen-3-yl)benzenesulfonamide (Compound 7)

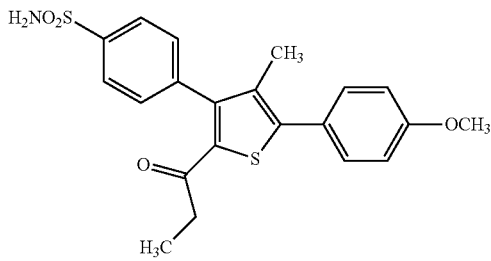 [SMILES: CCC(=O)c1sc(-c2ccc(OC)cc2)c(C)c1-c1ccc(S(N)(=O)=O)cc1]

Step 1: Methyl 3-bromo-4-methylthiophene-2-carboxylate (7a)

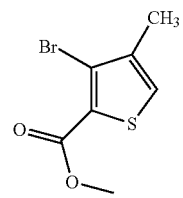

To a stirred suspension of copper (II) bromide (14.3 g, 64.0 mmol) in acetonitrile (70 ml), t-butyl nitrite (7.83 g, 9.21 ml, 76.0 mmol) was added under a nitrogen atmosphere at room temperature (25° C.). To this suspension solution of methyl 3-amino-4-methylthiophene-2-carboxylate (10.0 g, 58.0 mmol) in acetonitrile (30 ml) was added at 20° C. in drop wise manner over a period of 2 hr. The reaction mixture was stirred at 25° C. for 2 hr. The progress of the reaction was monitored by TLC. The reaction mixture was then slowly added to 150 ml 2N HCl and extracted with ethyl acetate (2×150 ml). The resulting organic layer was washed with water (1×50 ml), brine (1×50 ml) and dried over sodium sulfate and concentrated under reduced pressure to obtain crude product as semi-solid (10.5 g), which was then purified by column chromatography over silica gel (100-200 mesh) using 7% ethyl acetate in hexanes as an eluent to obtain the title compound (9.0 g, 65.55%).

MS: m/z 236 (M+1),
$^1$HNMR (CDCl$_3$, 400 MHz): δ 7.19 (s, 1H), 3.87 (s, 3H), 2.24 (s, 3H).

Step 2: Methyl 4-methyl-3-(4-sulfamoylphenyl)thiophene-2-carboxylate. (7b)

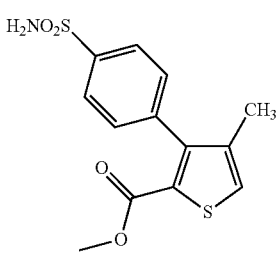 [SMILES: COC(=O)c1scc(C)c1-c1ccc(S(N)(=O)=O)cc1]

To a stirred suspension of methyl 3-bromo-4-methylthiophene-2-carboxylate (compound 7a, 9.0 g, 38.0 mmol) in ethanol:toluene (100:30 ml) in sealed tube, (4-sulfamoylphenyl) boronic acid (8.46 g, 42.0 mmol) and potassium carbonate (10.57 g, 76.0 mmol) were added under a nitrogen atmosphere at room temperature (about 25° C.). Nitrogen gas was purged to this suspension for further minute at room temperature (about 25° C.) and tetrakis(triphenyl phosphine)palladium(0) (2.21 g, 1.9 mmol) was added at 25° C. and sealed tube was closed. The reaction mixture was stirred at 105° C. for 15 hr and the progress of the reaction was monitored by TLC. Reaction mixture was filtered and washed with ethyl acetate (2×100 ml). Organic layer was concentrated under reduced pressure to obtain crude product as semi-solid (11.2 g); which was purified by column chromatography over silica gel (100-200 mesh) using 50% ethyl acetate in hexanes as an eluent to obtain the title compound (20% ethyl ester as trans esterified product was observed) (8.8 g, 70.70%).

MS: m/z 312 (M+1), $^1$HNMR (CDCl$_3$, 400 MHz): δ 7.97 (d, J=8.4 Hz, 2H), 7.38 (d, J=8.4 Hz, 2H), 7.23 (s, 1H), 4.91 (bs-exchanges with D$_2$O, 2H) 3.71 (s, 3H), 2.20 (s, 3H).

Step 3: Methyl 5-bromo-4-methyl-3-(4-sulfamoylphenyl)thiophene-2-carboxylate. (7c)

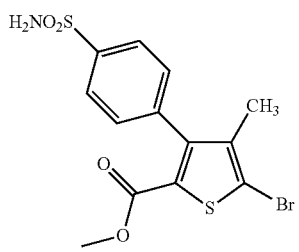 [SMILES: COC(=O)c1sc(Br)c(C)c1-c1ccc(S(N)(=O)=O)cc1]

To a stirred suspension of methyl 4-methyl-3-(4-sulfamoylphenyl)thiophene-2-carboxylate (compound 7b, 8.80 g, 27.0 mmol) in DCM (150 ml), bromine (5.19 g, 1.67 ml, 32.0 mmol) was added at 0° C. in a drop wise manner. The reaction mixture was stirred at 25° C. for 2 hr and the progress of the reaction was monitored by TLC. The reaction mixture was then concentrated completely and again dissolved in DCM (250 ml). The organic layer so obtained was washed with water (2×50 ml), brine (1×50 ml) and dried over sodium sulfate and concentrated under reduced pressure to obtain crude product as semi-solid (10.2 g), which was then purified by column chromatography over silica gel (100-200 mesh) using 50% ethyl acetate in hexanes as an eluent to obtain the title compound (20% ethyl ester as trans esterified product was observed) (9.0 g, 82.34%).

MS: m/z 391 (M+1), $^1$HNMR (CDCl$_3$, 400 MHz): δ 8.01 (d, J=8.4 Hz, 2H), 7.39 (d, J=8.4 Hz, 2H), 4.93 (bs-exchanges with D$_2$O, 2H), 3.72 (s, 3H), 1.95 (s, 3H).

Step 4: Methyl 5-(4-methoxyphenyl)-4-methyl-3-(4-sulfamoylphenyl)thiophene-2-carboxylate. (7d)

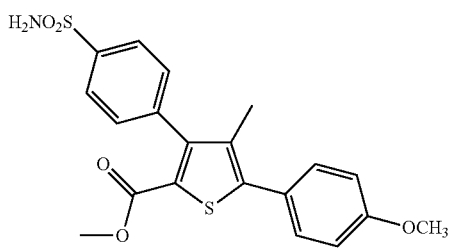 [SMILES: COC(=O)c1sc(-c2ccc(OC)cc2)c(C)c1-c1ccc(S(N)(=O)=O)cc1]

To the solution of methyl 5-bromo-4-methyl-3-(4-sulfamoylphenyl)thiophene-2-carboxylate (compound 7c, 3.0 g, 7.69 mmol) in a mixture of toluene:ethanol (25:75 ml) was added (4-methoxyphenyl)boronic acid (1.28 g, 8.46 mmol) and potassium carbonate (3.18 g, 23.07 mmol) at 25° C. Nitrogen gas was bubbled through reaction mixture for 15 minutes. To this was added tetrakis(triphenylphosphine)palladium(0) (0.487 g, 0.422 mmol) under nitrogen and reaction mixture was heated at 95-100° C. for 1 hr under stirring. The progress of reaction was monitored by TLC. The reaction mixture was cooled to 25° C. and filtered through celite, and then washed with ethyl acetate (50 ml). The filtrate was concentrated under reduced pressure to obtain a crude product, that was then purified by column chromatography over silica gel (100-200 mesh) using 50% ethyl acetate in hexanes as an eluent to obtain the title compound (20% ethyl ester as trans esterified product was observed) (2.69 g, 84%).

MS: m/z 418 (M+1), $^1$HNMR (CDCl$_3$, 400 MHz): δ 8.01 (d, J=8.4 Hz, 2H), 7.41-7.46 (m, 4H), 7.00 (d, J=8.4 Hz, 2H). 4.96 (bs-exchanges with D$_2$O, 2H), 3.87 (s, 3H), 3.73 (s, 3H), 1.99 (s, 3H).

The compounds given below were prepared by procedure similar to the one described above for compound '7d' with appropriate variations of reactants, reaction conditions and quantities of reagents.

3d. Ethyl 5-(3-chlorophenyl)-4-methyl-3-(4-sulfamoylphenyl)thiophene-2-carboxylate MS: m/z 436 (M+1).

5d. Ethyl 5-(4-Cyclopropylphenyl)-4-methyl-3-(4-sulfamoylphenyl)thiophene-2-carboxylate MS: m/z 442 (M+1).

6d. Ethyl 4-Methyl-3-(4-sulfamoylphenyl)-5-(4-trifluoromethyl)phenyl)thiophene-2-carboxylate MS: m/z 468 (M−1).

8d. Ethyl 5-(4-ethoxyphenyl)-4-methyl-3-(4-sulfamoylphenyl)thiophene-2-carboxylate MS: m/z 446 (M+1).

9d. Ethyl 4-Methyl-3-(4-sulfamoylphenyl)-5-(4-trifluoromethoxy)phenyl)thiophene-2-carboxylate MS: m/z 486 (M+1).

10d. Ethyl 4-Methyl-3-(4-sulfamoylphenyl)-5-(p-tolyl)thiophene-2-carboxylate

MS: m/z 416 (M+1).

12d. Ethyl 5-(4-(dimethylamino)phenyl)-4-methyl-3-(4-sulfamoylphenyl)thiophene-2-carboxylate MS: m/z 445 (M+1).

13d. Ethyl 5-(3-Fluorophenyl)-4-methyl-3-(4-sulfamoylphenyl)thiophene-2-carboxylate MS: m/z 420 (M+1).

14d. Ethyl 4-methyl-5-phenyl-3-(4-sulfamoylphenyl) thiophene-2-carboxylate

MS: m/z 402 (M+1).

15d. Ethyl 5-(3-Ethoxyphenyl)-4-methyl-3-(4-sulfamoylphenyl)thiophene-2-carboxylate MS: m/z 446 (M+1).

16d. Ethyl 5-(4-Ethylphenyl)-4-methyl-3-(4-sulfamoylphenyl)thiophene-2-carboxylate MS: m/z 430 (M+1).

25d. Ethyl 4-methyl-5-(pyridin-4-yl)-3-(4-sulfamoylphenyl)thiophene-2-carboxylate MS: m/z 403 (M+1).

26d. Ethyl 4-methyl-5-(pyridin-3-yl)-3-(4-sulfamoylphenyl)thiophene-2-carboxylate MS: m/z 403 (M+1).

27d. Ethyl 5-(Furan-3-yl)-4-methyl-3-(4-sulfamoylphenyl)thiophene-2-carboxylate

MS: m/z 392 (M+1).

28d. Ethyl 5-(1H-indol-5-yl)-4-methyl-3-(4-sulfamoylphenyl)thiophene-2-carboxylate MS: m/z 441 (M+1).

29d. Ethyl 4-methyl-5-(1-methyl-1H-indol-5-yl)-3-(4-sulfamoylphenyl)thiophene-2-carboxylate MS: m/z 455 (M+1).

30d. Ethyl 5-(benzofuran-5-yl)-4-methyl-3-(4-sulfamoylphenyl)thiophene-2-carboxylate MS: m/z 442 (M+1).

31d. Ethyl 5-(1-acetylindolin-5-yl)-4-methyl-3-(4-sulfamoylphenyl)thiophene-2-carboxylate MS: m/z 485 (M+1).

44d. Ethyl-5-(4-((tert-butoxycarbonyl)methyl)amino)phenyl)-4-methyl-3-(4-sulfamoylphenyl)thiophene-2-carboxylate MS: m/z 531 (M+1).

Step 5: 5-(4-Methoxyphenyl)-4-methyl-3-(4-sulfamoylphenyl)thiophene-2-carboxylic acid. (7e)

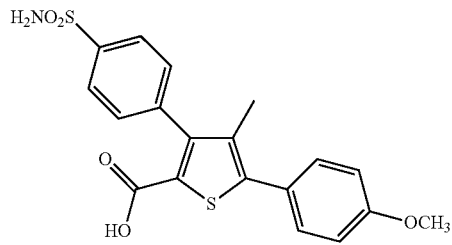 [SMILES: COc1ccc(-c2sc(C(=O)O)c(-c3ccc(S(N)(=O)=O)cc3)c2C)cc1]

Methyl 5-(4-methoxyphenyl)-4-methyl-3-(4-sulfamoylphenyl)thiophene-2-carboxylate (compound 7d, 3.02 g, 7.24 mmol) was suspended in ethanol (50 ml) and NaOH (1.44 g, 36.2 mmol) in water 10 ml was added at 25° C. The reaction mixture was heated at 50-55° C. under stirring for 2 hr. The progress of reaction was monitored by TLC. The reaction mixture was then concentrated under reduced pressure. Water, 50 ml was added to the residue so obtained and the mixture was cooled using icebath. Aqueous hydrochloric acid (10%) was then added to the mixture to bring the pH to between 5 and 6. The mixture was then extracted with ethyl acetate (2×75 ml). The combined organic layer was dried over anhydrous $Na_2SO_4$. The solvent was evaporated under reduced pressure to obtain a product (2.83 g, 97%).

MS: m/z 404 (M+1), $^1$HNMR (DMSO, 400 MHz): δ 12.85 (bs-exchanges with $D_2O$, 1H), 7.86 (d, J=8.4 Hz, 2H), 7.45-7.50 (m, 4H). 7.45 (bs-exchanges with $D_2O$, 2H), 7.07 (d, J=8.4 Hz, 2H), 3.81 (s, 3H), 1.90 (s, 3H).

The compounds given below were prepared by procedure similar to the one described above for compound '7e' with appropriate variations of reactants, reaction conditions and quantities of reagents.

3e. 5-(3-chlorophenyl)-4-methyl-3-(4-sulfamoylphenyl)thiophene-2-carboxylic acid MS: m/z 408 (M+1).

5e. 5-(4-Cyclopropylphenyl)-4-methyl-3-(4-sulfamoylphenyl)thiophene-2-carboxylic acid MS: m/z 414 (M+1).

6e. 4-Methyl-3-(4-sulfamoylphenyl)-5-(4-trifluoromethyl)phenyl)thiophene-2-carboxylic acid MS: m/z 442 (M+1).

8e. 5-(4-Ethoxyphenyl)-4-methyl-3-(4-sulfamoylphenyl)thiophene-2-carboxylic acid MS: m/z 418 (M+1).

9e. 4-Methyl-3-(4-sulfamoylphenyl)-5-(4-trifluoromethoxy)phenyl)thiophene-2-carboxylic acid MS: m/z 458 (M+1).

10e. 4-Methyl-3-(4-sulfamoylphenyl)-5-(p-tolyl)thiophene-2-carboxylic acid

MS: m/z 388 (M+1).

12e. 5-(4-(dimethylamino)phenyl)-4-methyl-3-(4-sulfamoylphenyl)thiophene-2-carboxylic acid MS: m/z 417 (M+1).

13e. 5-(3-Fluorophenyl)-4-methyl-3-(4-sulfamoylphenyl)thiophene-2-carboxylic acid MS: m/z 392 (M+1).

14e. 4-methyl-5-phenyl-3-(4-sulfamoylphenyl)thiophene-2-carboxylic acid

MS: m/z 374 (M+1).

15e. 5-(3-Ethoxyphenyl)-4-methyl-3-(4-sulfamoylphenyl)thiophene-2-carboxylic acid MS: m/z 418 (M+1).

16e. 5-(4-Ethylphenyl)-4-methyl-3-(4-sulfamoylphenyl)thiophene-2-carboxylic acid MS: m/z 402 (M+1).

25e. 4-methyl-5-(pyridin-4-yl)-3-(4-sulfamoylphenyl)thiophene-2-carboxylic acid

MS: m/z 375 (M+1).

26e. 4-methyl-5-(pyridin-3-yl)-3-(4-sulfamoylphenyl)thiophene-2-carboxylic acid

MS: m/z 375 (M+1).

27e. 5-(Furan-3-yl)-4-methyl-3-(4-sulfamoylphenyl)thiophene-2-carboxylic acid

MS: m/z 364 (M+1).

28e. 5-(1H-indol-5-yl)-4-methyl-3-(4-sulfamoylphenyl)thiophene-2-carboxylic acid MS: m/z 413 (M+1).

29e. 4-methyl-5-(1-methyl-1H-indol-5-yl)-3-(4-sulfamoylphenyl)thiophene-2-carboxylic acid MS: m/z 427 (M+1).

30e. 5-(benzofuran-5-yl)-4-methyl-3-(4-sulfamoylphenyl)thiophene-2-carboxylic acid MS: m/z 414 (M+1).

31e. 5-(1-acetylindolin-5-yl)-4-methyl-3-(4-sulfamoylphenyl)thiophene-2-carboxylic acid MS: m/z 457 (M+1).

44e. 5-(4-((tert-butoxycarbonyl)methyl)amino)phenyl)-4-methyl-3-(4-sulfamoylphenyl)thiophene-2-carboxylic acid MS: m/z 503 (M+1).

Step 6: 3-(4-(N-((dimethylamino)methylene)sulfamoyl)phenyl)-N-methoxy-5-(4-methoxyphenyl)-N,4-dimethylthiophene-2-carboxamide. (7f)

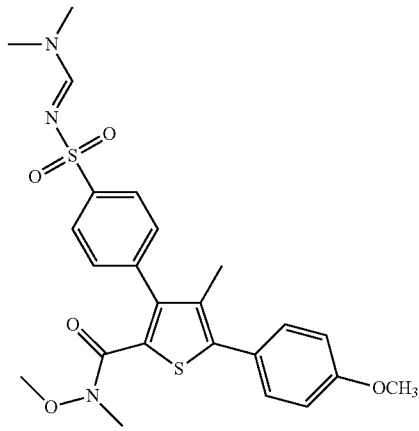 [SMILES: COc1ccc(-c2sc(C(=O)N(C)OC)c(-c3ccc(S(=O)(=O)/N=C/N(C)C)cc3)c2C)cc1]

Oxalyl chloride (1.77 g, 1.2 ml, 13.9 mmol) was added drop wise at 0° C. to a solution of 5-(4-methoxyphenyl)-4-methyl-3-(4-sulfamoylphenyl)thiophene-2-carboxylic acid (compound 7e, 2.8 g, 6.94 mmol) in a mixture of dichloromethane (75 ml) and DMF (1.01 g, 1.1 ml, 13.89 mmol). The so obtained mixture was allowed to come at room temperature and stirred for 1.5 hr under a nitrogen atmosphere. The progress of the reaction was monitored by TLC. The reaction mixture was then concentrated under reduced pressure. The residue so obtained was dissolved in dry dichloromethane (75 ml) and to this was added triethylamine (2.8 g, 3.9 ml, 27.76 mmol) followed by the addition of N,O-dimethylhydroxylamine hydrochloride (1.35 g, 13.89 mmol) under stirring. The reaction mixture was then stirred at room temperature for 2 hr. The progress of the reaction was monitored by TLC. The reaction mixture was then washed with water (2×25 ml) and the organic layer so obtained was dried over anhydrous sodium sulphate and concentrated under reduced pressure to obtain crude product. The crude product was further purified by column chromatography over silica gel (100-200 mesh) using 80% ethyl acetate in hexane as an eluent to obtain the title compound (2.73 g, 78%).

MS: m/z 502 (M+1),
$^1$HNMR (CDCl$_3$, 400 MHz): δ 8.16 (s, 1H), 7.95 (d, J=8.4 Hz, 2H), 7.45 (d, J=8.4 Hz, 2H), 7.39 (d, J=8.4 Hz, 2H), 7.00 (d, J=8.4 Hz, 2H), 3.88 (s, 3H), 3.70 (s, 3H), 3.19 (s, 3H), 3.17 (s, 3H), 3.07 (s, 3H), 2.00 (s, 3H).

The compounds given below were prepared by procedure similar to the one described above for compound '7f' with appropriate variations of reactants, reaction conditions and quantities of reagents 3f. 5-(3-chlorophenyl)-3-(4-(N-((dimethylamino)methylene)sulfamoyl)phenyl)-N-methoxy-N,4-dimethylthiophene-2-carboxamide MS: m/z 506 (M+1).

5f. 5-(4-(Cyclopropylphenyl)-3-(4-(N-((dimethylamino)methylene)sulfamoyl)phenyl)-N-methoxy-N,4-dimethylthiophene-2-carboxamide MS: m/z 512 (M+1).

6f. 3-(4-(N-((dimethylamino)methylene)sulfamoyl)phenyl)-N-methoxy-N,4-dimethyl-5-(4-(trifluoromethyl)phenyl)thiophene-2-carboxamide MS: m/z 540 (M+1).

8f. 3-(4-(N-((dimethylamino)methylene)sulfamoyl)phenyl)-5-(4-ethoxyphenyl)-N-methoxy-N,4-dimethyl thiophene-2-carboxamide MS: m/z 516 (M+1).

9f. 3-(4-(N-((dimethylamino)methylene)sulfamoyl)phenyl)-N-methoxy-N,4-dimethyl-phenyl)-5-(4-(trifluoromethoxy)phenyl)thiophene-2-carboxamide MS: m/z 556 (M+1).

10f. 3-(4-(N-((dimethylamino)methylene)sulfamoyl)phenyl)-N-methoxy-N,4-dimethyl-phenyl)-5-(4-(p-tolyl)thiophene-2-carboxamide MS: m/z 486 (M+1).

12f. 3-(4-(N-((dimethylamino)methylene)sulfamoyl)phenyl)-5-(4-(dimethylamino)phenyl)-N-methoxy-N,4-dimethylthiophene-2-carboxamide MS: m/z 515 (M+1).

13f. 3-(4-(N-((dimethylamino)methylene)sulfamoyl)phenyl)-5-(3-Fluoro phenyl)-N-methoxy-N,4-dimethylthiophene-2-carboxamide MS: m/z 490 (M+1).

14f. 3-(4-(N-((dimethylamino)methylene)sulfamoyl)phenyl)-N-methoxy-N,4-dimethyl-5-phenylthiophene-2-carboxamide MS: m/z 472 (M+1).

15f. 3-(4-(N-((dimethylamino)methylene)sulfamoyl)phenyl)-5-(3-ethoxyphenyl)-N-methoxy-N,4-dimethylthiophene-2-carboxamide MS: m/z 516 (M+1).

16f. 3-(4-(N-((dimethylamino)methylene)sulfamoyl)phenyl)-5-(4-ethylphenyl)-N-methoxy-N,4-dimethylthiophene-2-carboxamide MS: m/z 500 (M+1).

25f. 3-(4-(N-((dimethylamino)methylene)sulfamoyl)phenyl)-N-methoxy-N,4-dimethyl-5-(pyridin-4-yl)thiophene-2-carboxamide MS: m/z 473 (M+1).

26f. 3-(4-(N-((dimethylamino)methylene)sulfamoyl)phenyl)-N-methoxy-N,4-dimethyl-5-(pyridin-3-yl)thiophene-2-carboxamide MS: m/z 473 (M+1).

27f. 3-(4-(N-((dimethylamino)methylene)sulfamoyl)phenyl)-5-(furan-3-yl)-N-methoxy-N,4-dimethyl thiophene-2-carboxamide MS: m/z 462 (M+1).

28f. 3-(4-(N-((dimethylamino)methylene)sulfamoyl)phenyl)-5-(1H-indol-5-yl)-N-methoxy-N,4-dimethyl thiophene-2-carboxamide MS: m/z 511 (M+1).

29f. 3-(4-(N-((dimethylamino)methylene)sulfamoyl)phenyl)-N-methoxy-N,4-dimethyl-5-(1-methyl-1H-indol-5-yl)thiophene-2-carboxamide MS: m/z 525 (M+1).

30f. 5-(Benzofuran-5-yl)-3-(4-(N-((dimethylamino)methylene)sulfamoyl)phenyl)-N-methoxy-N,4-dimethylthiophene-2-carboxamide MS: m/z 512 (M+1).

31f. 5-(1-acetylindolin-5-yl)-3-(4-(N-((dimethylamino)methylene)sulfamoyl)phenyl)-N-methoxy-N,4-dimethylthiophene-2-carboxamide MS: m/z 555 (M+1).

44f. tert-butyl (4-(4-(4-(N-((dimethylamino)methylene)sulfamoyl)phenyl)-5-(methoxy(methyl)carbamoyl)-3-methylthiophen-2-yl)phenyl)(methyl)carbamate MS: m/z 601 (M+1).

Step 7: 4-(5-(4-methoxyphenyl)-4-methyl-2-propionylthiophen-3-yl)benzene sulfonamide (compound 7)

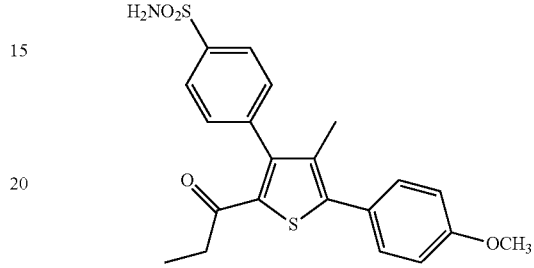

Grignard reagent (ethyl magnesium bromide, 3.59 g, 26.8 ml, 26.94 mmol) was added drop wise to a stirred solution of 3-(4-(N-((dimethylamino)methylene)sulfamoyl)phenyl)-N-methoxy-5-(4-methoxyphenyl)-N,4-dimethylthiophene-2-carboxamide (compound 7f, 2.7 g, 5.8 mmol) in anhydrous THF (100 ml) at 25° C., and the reaction mixture was heated at about 70 to about 75° C. for 1 hr. The progress of the reaction was monitored by TLC. After cooling the reaction mixture to 0° C., the reaction mixture was quenched by adding a solution of saturated ammonium chloride (50 ml) and the resulting mixture was extracted with ethyl acetate (2×100 ml). The combined organic layer was dried over anhydrous Na$_2$SO$_4$. The solvent was evaporated from the dried organic layer under reduced pressure to obtain a crude product; which was purified by Preparative HPLC to obtain the title compound (0.84 g, 37%).

MS: m/z 416 (M+1),
$^1$HNMR (CDCl$_3$, 400 MHz): δ 8.00 (d, J=8.4 Hz, 2H), 7.40-7.43 (m, 4H). 6.97 (d, J=8.4 Hz, 2H), 4.87 (bs-exchanges with D$_2$O, 2H), 3.85 (s, 3H), 2.53 (q, J=7.2 Hz, 2H), 1.93 (s, 3H), 1.03 (t, J=7.2 Hz, 3H).

The following compounds were prepared according to the procedure described above but with appropriate changes to the reactants.

4-(5-(3-Chlorophenyl)-4-methyl-2-propionylthiophen-3-yl)benzenesulfonamide (Compound 3)

MS: m/z 420 (M+1),
$^1$HNMR (DMSO, 400 MHz): δ 7.93 (d, J=8.4 Hz, 2H), 7.62 (t, J=2.4 Hz, 1H), 7.53-7.56 (m, 5H), 7.49 (bs-exchanges with D$_2$O, 2H), 2.38 (q, J=7.2 Hz, 2H), 1.93 (s, 3H), 0.88 (t, J=7.2 Hz, 3H).

4-(5-(4-cyclopropylphenyl)-4-methyl-2-propionylthiophen-3-yl)benzenesulfonamide (Compound 5)

MS: m/z 426 (M+1),
$^1$HNMR (CDCl$_3$, 400 MHz): δ 8.01 (d, J=8.4 Hz, 2H), 7.43 (d, J=8.4 Hz, 2H), 7.38 (d, J=8.0 Hz, 2H). 7.15 (d, J=8.0 Hz, 2H), 4.87 (bs-exchanges with D$_2$O, 2H), 2.55 (q, J=7.2 Hz, 2H), 1.91-1.97 (m, 4H), 1.01-1.06 (m, 5H), 0.75-0.78 (m, 2H).

4-(4-methyl-2-propionyl-5-(4-(trifluoromethyl)phenyl)thiophen-3-yl)benzenesulfonamide (Compound 6)

MS: m/z 454 (M+1),
$^1$HNMR (CDCl$_3$, 400 MHz): δ 8.03 (d, J=8.4 Hz, 2H), 7.72 (d, J=8.0 Hz, 2H), 7.61 (d, J=8.4 Hz, 2H). 7.43 (d, J=8.0 Hz, 2H), 5.02 (bs-exchanges with D$_2$O, 2H), 2.54 (q, J=7.2 Hz, 2H), 1.97 (s, 3H), 1.04 (t, J=7.2 Hz, 3H).

4-(5-(4-Ethoxyphenyl)-4-methyl-2-propionylthiophen-3-yl)benzenesulfonamide (Compound 8)

MS: m/z 430 (M+1),
$^1$HNMR (CDCl$_3$, 400 MHz): δ 8.01 (d, J=8.8 Hz, 2H), 7.42 (d, J=8.4 Hz, 2H), 7.40 (d, J=8.4 Hz, 2H), 6.95 (d, J=8.8 Hz, 2H), 4.88 (bs-exchanges with D$_2$O, 2H), 4.08 (q, J=6.8 Hz, 2H), 2.54 (q, J=7.2 Hz, 2H), 1.93 (s, 3H), 1.44 (t, J=6.8 Hz, 3H), 1.03 (t, J=7.2 Hz, 3H).

4-(4-methyl-2-propionyl-5-(4-(trifluoromethoxy)phenyl)thiophen-3-yl)benzenesulfonamide (Compound 9)

MS: m/z 470 (M+1),
$^1$HNMR (CDCl$_3$, 400 MHz): δ 8.04 (d, J=8.4 Hz, 2H), 7.52 (d, J=8.0 Hz, 2H), 7.44 (d, J=8.4 Hz, 2H). 7.31 (d, J=8.0 Hz, 2H), 4.98 (bs-exchanges with D$_2$O, 2H), 2.55 (q, J=7.2 Hz, 2H), 1.95 (s, 3H), 1.05 (t, J=7.2 Hz, 3H).

4-(4-methyl-2-propionyl-5-(4-tolyl)thiophen-3-yl)benzenesulfonamide (Compound 10)

MS: m/z 400 (M+1),
$^1$HNMR (DMSO, 400 MHz): δ 7.92 (d, J=8.4 Hz, 2H), 7.55 (d, J=8.4 Hz, 2H), 7.49 (bs-exchanges with D$_2$O, 2H), 7.45 (d, J=8.4 Hz, 2H), 7.33 (d, J=8.4 Hz, 2H), 2.33-2.36 (m, 5H), 1.92 (s, 3H), 0.87 (t, J=7.2 Hz, 3H).

4-(5-((4-tert butyl)phenyl)-4-methyl-2-propionylthiophen-3-yl)benzenesulfonamide (Compound 11)

MS: m/z 442 (M+1),
$^1$HNMR (CDCl$_3$, 400 MHz): δ 8.02 (d, J=8.4 Hz, 2H), 7.42-7.49 (m, 6H), 4.92 (bs-exchanges with D$_2$O, 2H), 2.56 (q, J=7.2 Hz, 2H), 1.97 (s, 3H), 1.36 (s, 9H), 1.06 (t, J=7.2 Hz, 3H).

4-((5-(4-Dimethylamino)phenyl)-4-methyl-2-propionylthiophen-3-yl)benzenesulfonamide (Compound 12)

MS: m/z 429 (M+1), $^1$HNMR (CDCl$_3$, 400 MHz): δ 8.01 (d, J=8.4 Hz, 2H), 7.44 (d, J=8.4 Hz, 2H), 7.40 (d, J=8.8 Hz, 2H). 6.77 (d, J=8.8 Hz, 2H), 4.83 (bs-exchanges with D$_2$O, 2H), 3.03 (s, 6H), 2.55 (q, J=7.2 Hz, 2H), 1.97 (s, 3H), 1.05 (t, J=7.2 Hz, 3H).

4-(5-(3-Fluorophenyl)-4-methyl-2-propionylthiophen-3-yl)benzenesulfonamide (Compound 13)

MS: m/z 404 (M+1),
$^1$HNMR (CDCl$_3$, 400 MHz): δ 8.02 (d, J=8.4 Hz, 2H), 7.40-7.46 (m, 3H), 7.26-7.29 (m, 1H), 7.18-7.21 (m, 1H), 7.09-7.14 (m, 1H), 5.09 (bs-exchanges with D$_2$O, 2H), 2.55 (q, J=7.2 Hz, 2H), 1.96 (s, 3H), 1.03 (t, J=7.2 Hz, 3H).

4-(4-methyl-5-phenyl-2-propionylthiophen-3-yl)benzenesulfonamide (Compound 14)

MS: m/z 386 (M+1),
$^1$HNMR (DMSO, 400 MHz): δ 7.93 (d, J=8.4 Hz, 2H), 7.45-7.57 (m, 9H), 2.36 (q, J=7.2 Hz, 2H), 1.93 (s, 3H), 0.88 (t, J=7.2 Hz, 3H).

4-(5-(3-Ethoxyphenyl)-4-methyl-2-propionylthiophen-3-yl)benzenesulfonamide (Compound 15)

MS: m/z 430 (M+1),
$^1$HNMR (CDCl$_3$, 400 MHz): δ 8.01 (d, J=8.4 Hz, 2H), 7.42 (d, J=8.4 Hz, 2H), 7.34 (t, J=8.0 Hz, 1H), 7.05 (dd, J=8.0, 2.0 Hz, 1H), 6.99 (t, J=2.0 Hz, 1H), 6.92 (dd, J=8.0, 2.0 Hz, 1H), 5.07 (bs-exchanges with D$_2$O, 2H), 4.06 (q, J=7.2 Hz, 2H), 2.53 (q, J=7.2 Hz, 2H), 1.95 (s, 3H), 1.42 (t, J=7.2 Hz, 3H), 1.02 (t, J=7.2 Hz, 3H).

4-(5-(4-Ethylphenyl)-4-methyl-2-propionylthiophen-3-yl)benzenesulfonamide (Compound 16)

MS: m/z 414 (M+1),
$^1$HNMR (CDCl$_3$, 400 MHz): δ 8.02 (d, J=8.4 Hz, 2H), 7.45 (d, J=8.0 Hz, 2H), 7.42 (t, J=8.0 Hz, 2H), 7.29 (d, J=8.4 Hz, 2H), 5.00 (bs-exchanges with D$_2$O, 2H), 2.72 (q, J=7.6 Hz, 2H), 2.54 (q, J=7.2 Hz, 2H), 1.96 (s, 3H), 1.28 (t, J=7.6 Hz, 3H), 1.04 (t, J=7.2 Hz, 3H).

4-(4-methyl-2-propionyl-5-(pyridin-4-yl)thiophen-3-yl)benzenesulfonamide (Compound 25)

MS: m/z 387 (M+1),
$^1$HNMR (DMSO, 400 MHz): δ 8.71 (d, J=8.4 Hz, 2H), 7.93 (d, J=8.4 Hz, 2H), 7.57-7.59 (m, 4H), 7.50 (bs-exchanges with D$_2$O, 2H), 2.39 (q, J=7.2 Hz, 2H), 1.98 (s, 3H), 0.88 (t, J=7.2 Hz, 3H).

4-(4-methyl-2-propionyl-5-(pyridin-3-yl)thiophen-3-yl)benzenesulfonamide (Compound 26)

MS: m/z 387 (M+1),
$^1$HNMR (DMSO, 400 MHz): δ 8.77-8.78 (m, 1H), 8.66 (dd, J=8.8, 1.6 Hz, 1H), 7.99-8.02 (m, 1H), 7.94 (d, J=8.8 Hz, 2H), 7.54-7.58 (m, 3H),), 7.50 (bs-exchanges with D$_2$O, 2H), 2.38 (q, J=7.2 Hz, 2H), 1.94 (s, 3H), 0.88 (t, J=7.2 Hz, 3H).

4-(5-(Furan-3-yl)-4-methyl-2-propionylthiophen-3-yl)benzenesulfonamide (Compound 27)

MS: m/z 376 (M+1),
$^1$HNMR (CDCl$_3$, 400 MHz): δ 8.01 (d, J=8.8 Hz, 2H), 7.68-7.69 (m, 1H), 7.51 (t, J=1.6 Hz, 1H), 7.38 (d, J=8.4 Hz, 2H), 6.64-6.65 (m, 1H), 4.88 (bs-exchanges with D$_2$O, 2H), 2.49 (q, J=7.2 Hz, 2H), 1.96 (s, 3H), 1.02 (t, J=7.2 Hz, 3H).

4-(5-(1H-indol-5-yl)-4-methyl-2-propionylthiophen-3-yl)benzenesulfonamide (Compound 28)

MS: m/z 425 (M+1), $^1$HNMR (DMSO, 400 MHz): δ 11.3 (bs-exchanges with D$_2$O, 1H), 7.92 (d, J=8.4 Hz, 2H), 7.74-7.75 (m, 1H), 7.58 (d, J=8.4 Hz, 2H), 7.52 (d, J=8.4 Hz, 1H), 7.49 (bs-exchanges with D$_2$O, 2H), 7.45 (t, J=2.8 Hz, 1H), 7.27 (dd, J=8.4, 1.6 Hz, 1H), 6.52-6.53 (m, 1H), 2.36 (q, J=7.2 Hz, 2H), 1.96 (s, 3H), 0.85 (t, J=7.2 Hz, 3H).

4-(4-methyl-5-(1-methyl-1H-indol-5-yl)-2-propionylthiophen-3-yl)benzenesulfonamide (Compound 29)

MS: m/z 439 (M+1), $^1$HNMR (DMSO, 400 MHz): δ 7.92 (d, J=8.4 Hz, 2H), 7.75 (s, 1H), 7.56-7.58 (m, 3H), 7.49 (bs-exchanges with D$_2$O, 2H), 7.43 (d, J=2.8 Hz, 1H), 7.34 (d, J=8.4 Hz, 1H), 6.52 (d, J=2.8 Hz, 1H), 3.83 (s, 3H), 2.37 (q, J=7.2 Hz, 2H), 1.96 (s, 3H), 0.88 (t, J=7.2 Hz, 3H).

4-(5-(Benzofuran-5-yl)-4-methyl-2-propionylthiophen-3-yl)benzenesulfonamide (Compound 30)

MS: m/z 426 (M+1),
$^1$HNMR (DMSO, 400 MHz): δ 8.10 (s, 1H), 7.93 (d, J=8.0 Hz, 2H), 7.86 (s, 1H), 7.75 (d, J=8.4 Hz, 1H), 7.58 (d, J=8.0 Hz, 2H), 7.48 (m, 3H), 7.05 (s, 1H), 2.37 (q, J=7.2 Hz, 2H), 1.95 (s, 3H), 0.89 (t, J=7.2 Hz, 3H).

4-(5-(Indolin-5-yl)-4-methyl-2-propionylthiophen-3-yl)benzenesulfonamide (Compound 31)

MS: m/z 427 (M+1),
$^1$HNMR (CDCl$_3$, 400 MHz): δ 7.99 (d, J=8.4 Hz, 2H), 7.40 (d, J=8.4 Hz, 2H), 7.23 (s, 1H), 7.14-7.16 (m, 1H), 6.66 (d, J=8.0 Hz, 1H), 5.72 (bs-exchanges with D$_2$O, 2H), 3.63 (t, J=8.4 Hz, 2H), 3.08 (t, J=8.4 Hz, 2H), 2.46 (q, J=7.2 Hz, 2H), 2.01 (bs-exchanges with D$_2$O, 1H), 1.93 (s, 3H), 1.01 (t, J=7.2 Hz, 3H).

4-(4-methyl-5-(4-(4-methylpiperazin-1-yl)phenyl)-2-propionylthiophen-3-yl)benzenesulfonamide (Compound 32)

MS: m/z 484 (M+1),
$^1$HNMR (DMSO, 400 MHz): δ 7.90 (d, J=8.4 Hz, 2H), 7.49 (d, J=8.4 Hz, 2H), 7.41 (d, J=8.4 Hz, 2H), 7.04 (d, J=8.4 Hz, 2H), 5.04 (bs-exchanges with D$_2$O, 2H), 3.28-3.29 (m, 4H), 2.74-2.75 (m, 4H), 2.41 (s, 3H), 2.33 (q, J=7.2 Hz, 2H), 1.88 (s, 3H), 0.85 (t, J=7.2 Hz, 3H).

4-(4-Methyl-5-(4-methylaminophenyl)-2-propionylthiophen-3-yl)benzenesulfonamide (Compound 44)

MS: m/z 415 (M+1)
$^1$HNMR (DMSO, 400 MHz): δ 7.90 (d, J=8.4 Hz, 2H), 7.52 (d, J=8.4 Hz, 2H), 7.47 (bs-exchanges with D$_2$O, 2H) 7.31 (d, J=8.4 Hz, 2H). 6.63 (d, J=8.4 Hz, 2H), 6.11 (q, J=4.8 Hz-exchanges with D$_2$O, 1H), 2.72 (d, J=4.8 Hz, 3H), 2.34 (q, J=7.2 Hz, 2H), 1.90 (s, 3H), 0.87 (t, J=7.2 Hz, 3H).

Example 4

Preparation of Methyl 4-methyl-5-(2-oxoindolin-5-yl)-3-(4-sulfamoyl phenyl)thiophen-2-carboxylate (Compound 42) and Ethyl 4-methyl-5-(2-oxoindolin-5-yl)-3-(4-sulfamoylphenyl)thiophen-2-carboxylate (Compound 43)

Following a procedure analogous to the one provided for compound of formula 7d (Step 4 of example 3) and replacing 4-methoxyphenyl boronic acid with an appropriate boronic acid or a similar reagent compounds of formula 42 and 43 were prepared.

Methyl 4-methyl-5-(2-oxoindolin-5-yl)-3-(4-sulfamoylphenyl)thiophen-2-carboxylate (Compound 42)

MS: m/z 443 (M+1),
$^1$HNMR (DMSO, 400 MHz): δ 10.60 (bs-exchanges with D$_2$O, 1H), 7.88 (d, J=8.4 Hz, 2H), 7.49 (d, J=8.4 Hz, 2H), 7.40 (bs-exchanges with D$_2$O, 2H), 7.37-7.39 (m, 2H), 6.94 (d, J=8.0 Hz, 1H), 3.64 (s, 3H), 3.56 (s, 2H), 1.96 (s, 3H).

Ethyl 4-methyl-5-(2-oxoindolin-5-yl)-3-(4-sulfamoylphenyl)thiophen-2-carboxylate (Compound 43)

MS: m/z 457 (M+1),
$^1$HNMR (DMSO, 400 MHz): δ 10.59 (bs-exchanges with D$_2$O, 1H), 7.86 (d, J=8.4 Hz, 2H), 7.49 (d, J=8.4 Hz, 2H), 7.41 (bs-exchanges with D$_2$O, 2H), 7.37-7.39 (m, 2H), 6.94 (d, J=8.0 Hz, 1H), 4.08 (q, J=7.2 Hz, 2H), 3.56 (s, 2H), 1.96 (s, 3H), 1.07 (t, J=7.2 Hz, 3H).

Example 5

Preparation of 4-(5-(4-chlorophenyl)-4-methyl-2-propionylthiophen-3-yl)-N,N-dimethylbenzenesulfonamide (Compound 45)

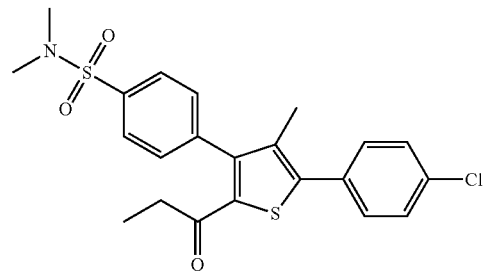 [SMILES: CCC(=O)c1sc(-c2ccc(Cl)cc2)c(C)c1-c1ccc(S(=O)(=O)N(C)C)cc1]

And 4-(5-(4-chlorophenyl)-4-methyl-2-propionylthiophen-3-yl)-N-methylbenzenesulfonamide (Compound 46)

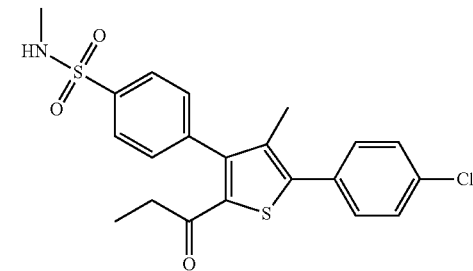 [SMILES: CCC(=O)c1sc(-c2ccc(Cl)cc2)c(C)c1-c1ccc(S(=O)(=O)NC)cc1]

To a solution of 4-(5-(4-chlorophenyl)-4-methyl-2-propionylthiophen-3-yl)benzenesulfonamide (Compound 1, 0.50 g, 1.19 mmol) in acetonitrile (15 ml) was added K$_2$CO$_3$ (0.25 g, 1.84 mmol) at room temperature and stirred for 15 minutes. To this was added methyl iodide (0.20 g, 0.08 ml, 1.42 mmol). The so obtained mixture was stirred at room temperature for 15 hr. The progress of the reaction was monitored by TLC. The reaction mixture was then concentrated under reduced pressure. The concentrated mass was diluted with water (20 ml). The mixture so obtained was extracted with ethyl acetate (3×30 ml). The combined organic layer was dried over anhydrous sodium sulphate and concentrated under reduced pressure to obtain a crude product. The crude product so obtained was purified by column chromatography over silica gel (100-200 mesh) using 40% ethyl acetate in hexanes as an eluent to obtain first title compound (0.05 g, 9.38%) and second title compound (0.045 g, 8.7%).

First Title Compound 4-(5-(4-chlorophenyl)-4-methyl-2-propionylthiophen-3-yl)-N,N-dimethylbenzenesulfonamide (Compound 45)

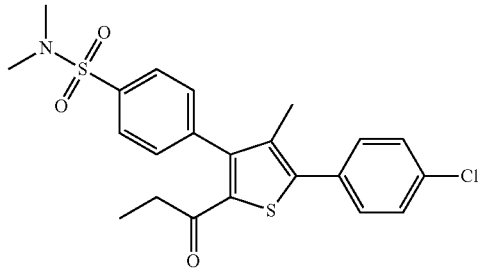 [SMILES: CCC(=O)c1sc(-c2ccc(Cl)cc2)c(C)c1-c1ccc(S(=O)(=O)N(C)C)cc1]

MS: m/z 448 (M+1)

$^1$HNMR (DMSO, 400 MHz): δ 7.86 (d, J=8.4 Hz, 2H), 7.60-7.65 (m, 6H), 2.65 (s, 6H), 2.32 (q, J=7.2 Hz, 2H), 1.94 (s, 3H), 0.86 (t, J=7.2 Hz, 3H).

Second Title Compound 4-(5-(4-chlorophenyl)-4-methyl-2-propionylthiophen-3-yl)-N-methylbenzenesulfonamide (Compound 46)

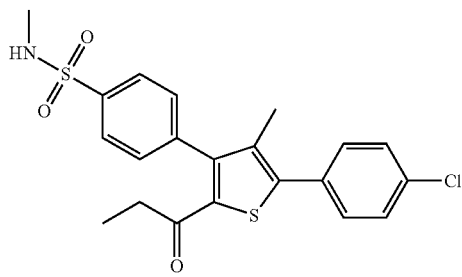 [SMILES: CCC(=O)c1sc(-c2ccc(Cl)cc2)c(C)c1-c1ccc(S(=O)(=O)NC)cc1]

MS: m/z 434 (M+1)

$^1$HNMR (DMSO, 400 MHz): δ 7.87 (d, J=8.4 Hz, 2H), 7.55-7.65 (m, 7H), 2.46 (d, J=4.8 Hz, 3H), 2.34 (q, J=7.2 Hz, 2H), 1.93 (s, 3H), 0.86 (t, J=7.2 Hz, 3H).

Example 6

Preparation of 4-(5-(4-chlorophenyl)-4-((dimethylamino)methyl)-2-propionylthiophen-3-yl)benzenesulfonamide (Compound 35)

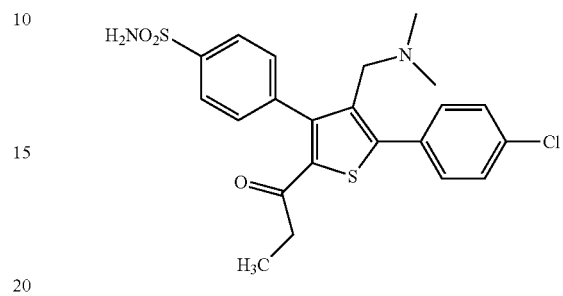

Step 1: Ethyl 4-(bromomethyl)-5-(4-chlorophenyl)-3-(4-sulfamoylphenyl)thiophene-2-carboxylate. (35a)

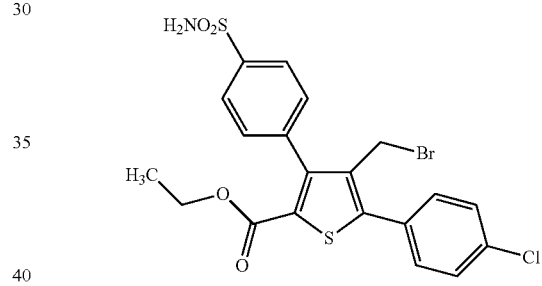

To a stirred solution of Ethyl 5-(4-chlorophenyl)-4-methyl-3-(4-sulfamoylphenyl)thiophene-2-carboxylate (Compound 1b, 4.0 g, 9.17 mmol) in chlorobenzene (50 ml) were added NBS (1.77 g, 10.09 mmol) and AIBN (1.65 g, 10.09 mmol) at 25° C. The reaction mixture was then stirred at 85° C. for 4 hr. The progress of the reaction was monitored by TLC. The reaction mixture was then cooled to room temperature and was quenched in aqueous sodium chloride solution (50 ml). The mixture so obtained was then extracted with Ethyl acetate (2×50 ml). The organic layer was washed with brine (1×50 ml) and dried over sodium sulfate and concentrated under reduced pressure to obtain crude product (4.0 g). The crude product was then purified by column chromatography over silica gel (100-200 mesh) using 40% ethyl acetate in hexanes as an eluent to obtain the title compound (2.8 g, 59.32%).

MS: m/z 516 (M+1), $^1$HNMR (DMSO, 400 MHz): δ 7.90 (d, J=8.4 Hz, 2H), 7.59-7.71 (m, 4H), 7.58 (d, J=8.4 Hz, 2H), 7.51 (bs-exchanges with D$_2$O, 2H) 4.29 (s, 2H), 4.10 (q, J=6.8 Hz, 2H), 1.06 (t, J=6.8 Hz, 3H).

Step 2: Ethyl 4-(bromomethyl)-5-(4-chlorophenyl)-3-(4-(N-((dimethylamino)methylene)sulfamoyl)phenyl)thiophene-2-carboxylate. (35b)

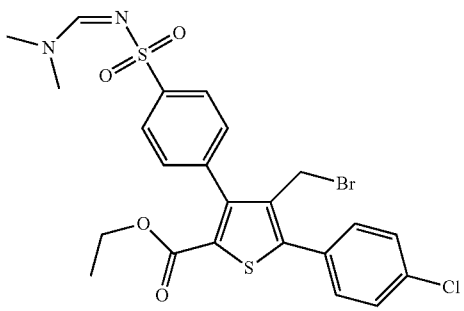 [SMILES: CCOC(=O)c1sc(-c2ccc(Cl)cc2)c(CBr)c1-c1ccc(S(=O)(=O)/N=C\N(C)C)cc1]

To a stirred suspension of Ethyl 4-(bromomethyl)-5-(4-chlorophenyl)-3-(4-sulfamoylphenyl)thiophene-2-carboxylate (compound 35a, 2.7 g, 5.24 mmol) in ethyl acetate (30 ml) were added DMF (1.91 g, 2.01 ml, 26.2 mmol) and N,N-Dimethylformamide dimethyl acetal (DMF-acetal) (0.69 g, 0.76 ml, 5.76 mmol) under a nitrogen atmosphere at room temperature (about 25° C.). The reaction mixture was then stirred at room temperature (about 25° C.) for 4 hr. The progress of the reaction was monitored by TLC. The reaction mixture was concentrated under reduced pressure to obtain 2.9 g of crude product. The crude product so obtained was then purified by column chromatography over silica gel (100-200 mesh) using 1.5% methanol in DCM as an eluent to obtain the title compound (2.2 g, 73.82%).

MS: m/z 571 (M+1),
$^1$HNMR (DMSO, 400 MHz): δ 8.23 (s, 1H) 7.85 (d, J=8.4 Hz, 2H), 7.62-7.75 (m, 4H), 7.52 (d, J=8.4 Hz, 2H), 4.29 (s, 2H), 4.07 (q, J=7.2 Hz, 2H), 3.15 (s, 3H) 2.94 (s, 3H), 1.01 (t, J=7.2 Hz, 3H).

Step 3: Ethyl 5-(4-chlorophenyl)-4-((dimethylamino)methyl)-3-(4-(N-((dimethylamino)methylene)sulfamoyl)phenyl)thiophene-2-carboxylate. (35c)

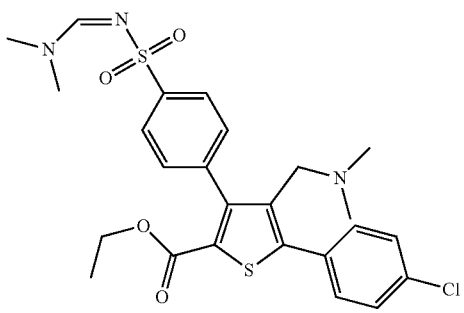 [SMILES: CCOC(=O)c1sc(-c2ccc(Cl)cc2)c(CN(C)C)c1-c1ccc(S(=O)(=O)/N=C\N(C)C)cc1]

To a stirred suspension of Ethyl 4-(bromomethyl)-5-(4-chlorophenyl)-3-(4-(N-((dimethylamino)methylene)sulfamoyl)phenyl)thiophene-2-carboxylate (compound 35b, 2.20 g, 3.86 mmol) in benzene (30 ml), dimethyl amine (0.69 g, 7.6 ml 2M solution in THF, 15.4 mmol) was added at 0° C. in a drop wise manner. The reaction mixture was then stirred at room temperature (about 25° C.) for 16 hr. The progress of the reaction was monitored by TLC. The reaction mixture was then concentrated to obtain the crude product as semi-solid (2.38 g). The crude product so obtained was purified by column chromatography over silica gel (100-200 mesh) using 1.2 methanol in DCM as an eluent to obtain the title compound (1.1 g, 53.39%).

MS: m/z 534 (M+1),
$^1$HNMR (CDCl$_3$, 400 MHz): δ 8.16 (s, 1H), 7.93 (d, J=8.4 Hz, 2H), 7.66 (d, J=8.4 Hz, 2H), 7.39-7.42 (m, 4H), 4.14 (q, J=7.2 Hz, 2H), 3.15 (s, 3H), 3.07 (s, 2H), 3.04 (s, 3H), 1.85 (s, 6H), 1.13 (t, J=7.2 Hz, 3H).

Step 4: 5-(4-chlorophenyl)-4-((dimethylamino)methyl)-3-(4sulfamoylphenyl)thiophene-2-carboxylic acid (35d)

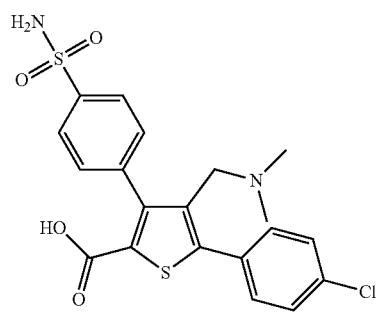 [SMILES: CN(C)Cc1c(-c2ccc(Cl)cc2)sc(C(=O)O)c1-c1ccc(S(N)(=O)=O)cc1]

Ethyl 5-(4-chlorophenyl)-4-((dimethylamino)methyl)-3-(4-(N-((dimethylamino)methylene)sulfamoyl)phenyl)thiophene-2-carboxylate (compound 35c, 1.0 g, 1.87 mmol) was suspended in ethanol (20 ml) and a solution of NaOH (0.37 g, 9.36 mmol) in water (2 ml) was added to it at 25° C. The reaction mixture was heated at 75° C. under stirring for 2 hr. The progress of the reaction was monitored by TLC. The reaction mixture was concentrated under reduced pressure. The residue so obtained was then diluted with water (5 ml) and cooled using ice bath. To the cooled mixture was then added aqueous 10% HCl to bring pH of the mixture to between 5 and 6. The resulting solid was filtered and dried under reduced pressure to obtain the title compound (0.8 g, 94.78%).

MS: m/z 451 (M+1),
$^1$HNMR (DMSO, 400 MHz): δ 12.85 (bs-exchanges with D$_2$O, 1H), 7.86 (d, J=8.0 Hz, 2H), 7.70 (d, J=8.0 Hz, 2H) 7.52-7.60 (m, 4H), 7.49 (bs-exchanges with D$_2$O, 2H), 3.61 (s, 2H), 1.97 (s, 6H).

Step 5: 5-(4-chlorophenyl)-4-((dimethylamino)methyl)-3-(4-(N-((dimethylamino)methylene)sulfamoyl)phenyl)-N-methoxy-N-methylthiophene-2-carboxamide. (35e)

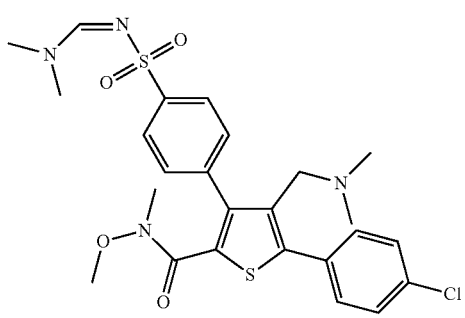 [SMILES: CON(C)C(=O)c1sc(-c2ccc(Cl)cc2)c(CN(C)C)c1-c1ccc(S(=O)(=O)/N=C\N(C)C)cc1]

Oxalyl chloride (0.39 g, 0.26 ml, 3.1 mmol) was added drop wise at 0° C. to a solution of 5-(4-chlorophenyl)-4-((dimethylamino)methyl)-3-(4sulfamoylphenyl)thiophene-2-carboxylic acid (compound 35d, 0.7 g, 1.55 mmol) in a mixture of dichloromethane (25 ml) and DMF (0.27 g, 0.24 ml, 3.10 mmol). The mixture so obtained was allowed to come at room temperature and stirred for 1.5 hr under a nitrogen atmosphere. The progress of the reaction was monitored by TLC. The reaction mixture was then concentrated under reduced pressure. The residue so obtained was dissolved in dry dichloromethane (25 ml), cooled to 0° C. and to this was added triethylamine (0.94 g, 1.3 ml, 9.31 mmol) followed by the addition of N,O-dimethylhydroxylamine hydrochloride (0.3 g, 3.1 mmol) under stirring. The reaction mixture was then stirred at room temperature for 2 hr. The progress of the reaction was monitored by TLC. The reaction mixture was then diluted with DCM (25 ml) and washed with water (2×25 ml), the organic layer so obtained was dried over anhydrous sodium sulphate, and concentrated under reduced pressure to obtain a crude product. The crude product so obtained was purified by column chromatography over silica gel (100-200 mesh) using 6% methanol in DCM as an eluent to obtain the title compound (0.45 g, 52.81%).

MS: m/z 549 (M+1), $^1$HNMR (DMSO, 400 MHz): δ 8.28 (s, 1H), 7.78 (d, J=8.0 Hz, 2H), 7.72 (d, J=8.4 Hz, 2H), 7.58 (d, J=8.0 Hz, 2H), 7.46 (d, J=8.4 Hz, 2H), 3.63 (s, 3H), 3.47 (s, 3H), 3.38 (s, 2H), 3.17 (s, 3H), 3.09 (s, 3H), 2.94 (s, 6H).

Step 6: 4-(5-(4-chlorophenyl)-4-((dimethylamino) methyl)-2-propionylthiophen-3-yl)benzenesulfonamide (Compound 35)

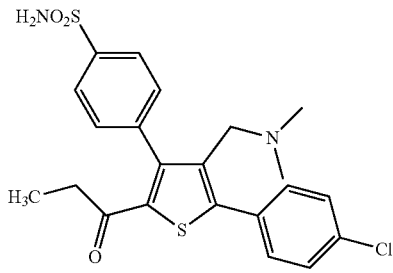 [SMILES: CCC(=O)c1sc(-c2ccc(Cl)cc2)c(CN(C)C)c1-c1ccc(S(N)(=O)=O)cc1]

Grignard reagent (ethyl magnesium bromide, 0.48 g, 3.6 ml 1M solution in THF, 3.64 mmol) was added drop wise to a stirred solution of 5-(4-chlorophenyl)-4-((dimethylamino) methyl)-3-(4-(N-((dimethylamino)methylene)sulfamoyl) phenyl)-N-methoxy-N-methylthiophene-2-carboxamide (compound 35e, 0.4 g, 0.72 mmol) in anhydrous THF (20 ml) at 25° C. The reaction mixture was then heated at about 70 to about 75° C. for 2 hr. The progress of the reaction was monitored by TLC. After cooling the reaction mixture to 0° C., the reaction mixture was quenched by addition of a saturated solution of ammonium chloride (15 ml). The mixture so formed was then extracted with ethyl acetate (2×30 ml). The combined organic layer was dried over anhydrous Na$_2$SO$_4$. The solvent from the dried organic layer was evaporated under reduced pressure to obtain a crude product, which was then purified by column chromatography over silica gel (100-200 mesh) using 60% ethyl acetate in hexanes as an eluent to obtain the title compound (0.065 g, 19.28%)

MS: m/z 463 (M+1), $^1$HNMR (CDCl$_3$, 400 MHz): δ 7.99 (d, J=8.4 Hz, 2H), 7.63 (d, J=8.4 Hz, 2H), 7.48 (d, J=8.4 Hz, 2H), 7.42 (d, J=8.4 Hz, 2H), 4.95 (bs-exchanges with D$_2$O, 2H), 3.05 (s, 2H), 2.51 (q, J=7.2 Hz, 2H) 1.85 (s, 6H), 1.05 (t, J=7.2 Hz, 3H)

Example 7

Preparation of 4-(5-(4-chlorophenyl)-2-propionylthiophen-3-yl)benzenesulfonamide (Compound 33)

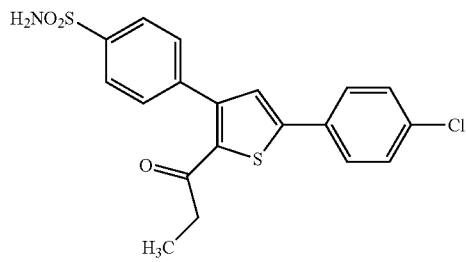 [SMILES: CCC(=O)c1sc(-c2ccc(Cl)cc2)cc1-c1ccc(S(N)(=O)=O)cc1]

Step 1: Ethyl 3-bromo-5-(4-chlorophenyl)thiophene-2-carboxylate. (33a)

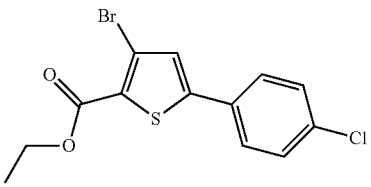 [SMILES: CCOC(=O)c1sc(-c2ccc(Cl)cc2)cc1Br]

To a solution of ethyl 3,5-dibromothiophene-2-carboxylate (Prepared according to procedure reported in J. Chem. Soc. Perkin Trans-1: Organic and Bioorganic Chemistry (1972-1999), 1973, p 1766-1770), 2.0 g (6.36 mmol) in a mixture of toluene:water (35:2 ml) was added (4-chlorophenyl)boronic acid [0.99 g, 6.36 mmol] and potassium carbonate (1.76 g, 12.73 mmol) at 25° C. Nitrogen gas was bubbled through reaction mixture for 15 minutes. To the reaction mixture was then added tetrakis(triphenylphosphine)palladium(0) (0.37 g, 0.31 mmol) under nitrogen atmosphere and the reaction mixture was heated at about 95 to about 100° C. for 3 hr under stirring. The progress of the reaction was monitored by TLC. The reaction mixture was then cooled to 25° C. and filtered through celite and the celite cake was washed with ethyl acetate (50 ml). The filtrate so obtained was concentrated under reduced pressure to obtain a crude product, which was then purified by flash column chromatography using and 6% ethyl acetate in hexanes as an eluent to obtain the title compound (1.5 g, 68.18%).

MS: m/z 347 (M+1), $^1$HNMR (CDCl$_3$, 400 MHz): δ 7.52 (d, J=8.4 Hz, 2H), 7.39 (d, J=8.4 Hz, 2H), 7.26 (s, 1H), 4.38 (q, J=7.2 Hz, 2H), 1.40 (t, J=7.2 Hz, 3H).

Step 2: Ethyl 5-(4-chlorophenyl)-3-(4-sulfamoylphenyl)thiophene-2-carboxylate. (33b)

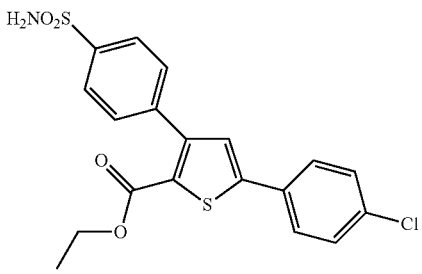 [SMILES: CCOC(=O)c1sc(-c2ccc(Cl)cc2)cc1-c1ccc(S(N)(=O)=O)cc1]

To the solution of Ethyl 3-bromo-5-(4-chlorophenyl) thiophene-2-carboxylate (compound 33a, 1.45 g, 4.19 mmol) in a mixture of toluene:ethanol (10:40 ml) was added (4-sulfamoylphenyl)boronic acid (0.84 g, 4.19 mmol) and potassium carbonate (1.16 g, 8.39 mmol) at 25° C. Nitrogen gas was bubbled through the reaction mixture for 15 minutes. To the reaction mixture was then added tetrakis(triphenylphosphine)palladium(0) (0.24 g, 0.20 mmol) under nitrogen atmosphere and the reaction mixture was heated at about 95 to about 100° C. for 16 hr under stirring. The progress of the reaction was monitored by TLC. The reaction mixture was then cooled to 25° C. and filtered through celite, the celite cake was washed with Ethanol (2×25 ml). The filtrate so obtained was concentrated under reduced pressure to obtain a crude product, which was then purified by column chromatography over silica gel (100-200 mesh) using 50% ethyl acetate in hexanes as an eluent to obtain the title compound (1.35 g, 76.27%).

MS: m/z 422 (M+1), $^1$HNMR (DMSO, 400 MHz): δ 7.83-7.87 (m, 4H), 7.68-7.70 (m, 3H), 7.54 (d, J=8.4 Hz, 2H). 7.54 (bs-exchanges with D$_2$O, 2H), 4.19 (q, J=7.2 Hz, 2H), 1.17 (t, J=7.2 Hz, 3H).

Step 3: 5-(4-chlorophenyl)-3-(4-sulfamoylphenyl) thiophene-2-carboxylic acid. (33c)

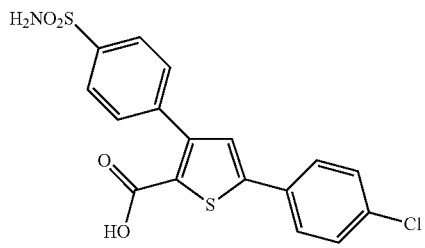 [SMILES: NS(=O)(=O)c1ccc(-c2cc(-c3ccc(Cl)cc3)sc2C(=O)O)cc1]

Ethyl 5-(4-chlorophenyl)-3-(4-sulfamoylphenyl) thiophene-2-carboxylate (compound 33b, 1.3 g, 3.08 mmol) was suspended in ethanol (30 ml) and solution of NaOH (0.61 g, 15.4 mmol) in water (3 ml) was added to it at 25° C. The reaction mixture was then heated at about 75° C. under stirring for 3 hr. The progress of the reaction was monitored by TLC. The reaction mixture was then concentrated under reduced pressure. The residue so obtained was diluted with water (5 ml) and cooled using ice bath. To the cooled mixture was then added aqueous 10% HCl to bring pH to between 5 and 6. The mixture so obtained was extracted with ethyl acetate (3×25 ml). The combined organic layer was dried over anhydrous Na$_2$SO$_4$. The solvent was evaporated from the dried organic layer under reduced pressure to obtain the title compound (1.10 g, 90.9%).

MS: m/z 394M+1), $^1$HNMR (DMSO, 400 MHz): δ 12.85 (bs-exchanges with D$_2$O, 1H), 7.81-7.86 (m, 4H), 7.70-7.72 (m, 3H), 7.53 (d, J=8.4 Hz, 2H), 7.44 (bs-exchanges with D$_2$O, 2H).

Step 4: 5-(4-chlorophenyl)-3-(4-(N-((dimethylamino)methylene)sulfamoyl)phenyl)-N-methoxy-N-methylthiophene-2-carboxamide. (33d)

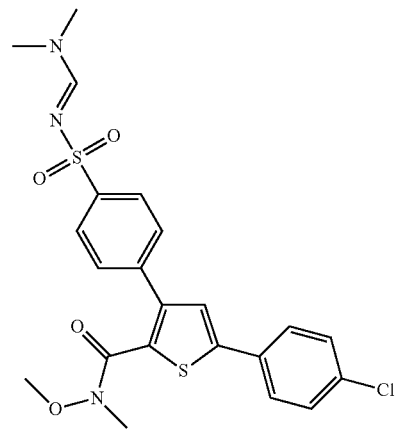 [SMILES: CON(C)C(=O)c1sc(-c2ccc(Cl)cc2)cc1-c1ccc(S(=O)(=O)/N=C/N(C)C)cc1]

Oxalyl chloride (0.70 g, 0.48 ml, 5.58 mmol) was added drop wise at 0° C. to a solution of 5-(4-chlorophenyl)-3-(4-sulfamoylphenyl)thiophene-2-carboxylic acid (compound 33c, 1.10 g, 2.79 mmol) in a mixture of dichloromethane (30 ml) and DMF (0.40 g, 0.43 ml, 5.58 mmol). The mixture was then allowed to warm to room temperature and stirred for 1.5 hr under a nitrogen atmosphere. The progress of the reaction was monitored by TLC. The reaction mixture was then concentrated under reduced pressure. The residue so obtained was dissolved in dry dichloromethane (30 ml) and the mixture was then cooled to 0° C. To the cooled mixture was added triethylamine (1.69 g, 2.32 ml, 16.75 mmol) followed by the addition of N,O-dimethylhydroxylamine hydrochloride (0.54 g, 5.58 mmol) under stirring. The reaction mixture was then stirred at room temperature for 2 hr. The progress of the reaction was monitored by TLC. The reaction mixture was then diluted with DCM (25 ml) and washed with water (2×25 ml) and organic layer so obtained was dried over anhydrous sodium sulphate, and concentrated under reduced pressure to obtain a crude product. The crude product was then purified by flash column chromatography using 0.8% methanol in DCM as an eluent to obtain the title compound (0.9 g, 65.69%).

MS: m/z 492 (M+1), $^1$HNMR (CDCl$_3$, 400 MHz): δ 8.14 (s, 1H), 7.91 (d, J=8.4 Hz, 2H), 7.51-7.58 (m, 4H), 7.38 (d, J=8.4 Hz, 2H), 7.26 (s, 1H), 3.65 (s, 3H), 3.22 (s, 3H), 3.13 (s, 3H), 3.02 (s, 3H).

Step 5: 4-(5-(4-chlorophenyl)-2-propionylthiophen-3-yl)benzenesulfonamide. (Compound 33)

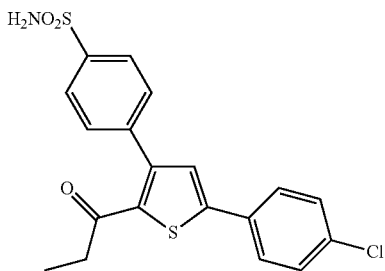 [SMILES: CCC(=O)c1sc(-c2ccc(Cl)cc2)cc1-c1ccc(S(N)(=O)=O)cc1]

Grignard reagent (ethyl magnesium bromide, 0.67 g, 5.0 ml 1M solution in THF, 5.08 mmol) was added drop wise to a stirred solution of 5-(4-chlorophenyl)-3-(4-(N-((dimethylamino)methylene)sulfamoyl)phenyl)-N-methoxy-N-methylthiophene-2-carboxamide (compound 33d, 0.5 g, 1.01 mmol) in anhydrous THF (15 ml) at 25° C. The reaction mixture was then heated to about 70 to about 75° C. for 2 hr. The progress of the reaction was monitored by TLC. After cooling the reaction mixture to 0° C., the reaction mixture was quenched by addition of a saturated solution of ammonium chloride (10 ml). The mixture so obtained was extracted with ethyl acetate (2×30 ml). the combined organic layer was dried over anhydrous $Na_2SO_4$. The solvent was evaporated from the dried organic layer under reduced pressure to obtain a crude product, which was then purified by column chromatography over silica gel (100-200 mesh) using 40% ethyl acetate in hexanes as an eluent to obtain the title compound (0.06 g, 14.6%).

MS: m/z 406 (M+1), $^1$HNMR (DMSO, 400 MHz): δ 7.88 (d, J=8.4 Hz, 2H), 7.85 (d, J=8.8 Hz, 2H). 7.69-7.71 (m, 3H) 7.55 (d, J=8.4 Hz, 2H), 7.48 (bs-exchanges with $D_2O$, 2H), 2.58 (q, J=7.2 Hz, 2H), 0.95 (t, J=7.2 Hz, 3H).

Example 8

Preparation of 4-(5-(4-chlorophenyl)-4-(dimethylamino)-2-propionyl thiophen-3-yl)benzenesulfonamide (Compound 34)

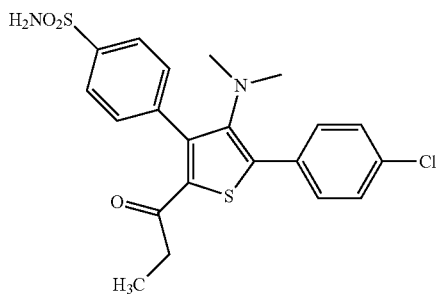 [SMILES: CCC(=O)c1sc(-c2ccc(Cl)cc2)c(N(C)C)c1-c1ccc(S(N)(=O)=O)cc1]

Step 1: Ethyl 3,5-dibromo-4-nitrothiophene-2-carboxylate. (34a)

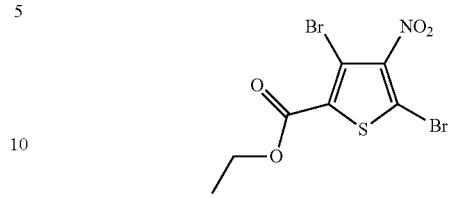

Sulfuric acid (27.6 g, 15.0 ml, 281.0 mmol) was added in a dropwise manner to ethyl 3,5-dibromothiophene-2-carboxylate (Prepared according to procedure reported in *JCS Perkin Trans*-1: Organic and Bioorganic Chemistry (1972-1999), 1973, p 1766-1770), 5.0 g (15.92 mmol), at room temperature (about 25° C.). The reaction mixture was then cooled to −5° C. and to the cooled mixture was added nitric acid (2.0 g, 2.04 ml, 31.84 mmol) slowly. The reaction mixture was then stirred at 0° C. for 1 hr. The progress of the reaction was monitored by TLC. The reaction mixture was then poured onto ice-water (150 ml). The mixture so obtained was extracted with ethyl acetate (2×100 ml). The combined organic layer was dried over sodium sulphate and was concentrated under reduced pressure to obtain a crude product, which was then purified by column chromatography over silica gel (100-200 mesh) using 2% ethyl acetate in hexanes as an eluent to obtain the title compound (3.40 g, 59.54%).

MS: m/z 359 (M+1), $^1$HNMR (CDCl$_3$, 400 MHz): δ 4.40 (q, J=7.2 Hz, 2H), 1.40 (t, J=7.2 Hz, 3H).

Step 2: Ethyl 4-amino-3,5-dibromothiophene-2-carboxylate. (34b)

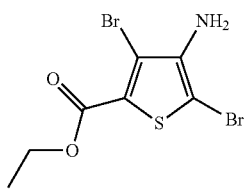

To the solution of Ethyl 3,5-dibromo-4-nitrothiophene-2-carboxylate (compound 34a, 10.0 g, 27.85 mmol) in acetic acid (100 ml) was added iron powder (7.77 g, 139.27 mmol). The reaction mixture was then heated at 60° C. for 35 min under stirring. The progress of the reaction was monitored by TLC. The reaction mixture was then cooled to 25° C. Acetic acid from the reaction mixture was then evaporated under reduced pressure. The pH of the resulting reaction mass was brought to between 8 and 9 by adding to it saturated sodium bicarbonate solution. To the mixture so obtained was added ethyl acetate (150 ml), the resulting emulsion was filtered and then the organic layer was separated. The aqueous layer remaining behind was re-extracted with ethyl acetate (2×100 ml). The combined organic layers were dried over sodium sulphate and the dried organic layer was concentrated under reduced pressure to obtain a crude product, which was then purified by column chromatography over silica gel (100-200 mesh) using 2% ethyl acetate in hexanes as an eluent to obtain the title compound (6.00 g, 65.50%).

MS: m/z 330 (M+1),

¹HNMR (CDCl₃, 400 MHz): δ 4.34 (q, J=7.2 Hz, 2H), 4.03 (bs-exchanges with D₂O, 2H), 1.36 (t, J=7.2 Hz, 3H).

Step 3: Ethyl 3,5-dibromo-4-(dimethylamino) thiophene-2-carboxylate (34c)

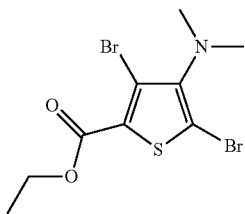

To a solution of Ethyl 4-amino-3,5-dibromothiophene-2-carboxylate (compound 34b, 5.0 g, 15.19 mmol) in DMF (25 ml) was added NaH (60% suspension in mineral oil) (1.82 g, 45.49 mmol) in portion wise manner at a temperature of about −5° C. The reaction mixture was then stirred at −5° C. for 20 min. To the reaction mixture was then added iodomethane (6.47 g, 2.83 ml, 45.59 mmol) and stirring was continued for 40 min at −5° C. The progress of the reaction was monitored by TLC. The reaction mixture was then quenched by addition of cold water (50 ml). the mixture so obtained was then extracted with ethyl acetate (3×100 ml). The combined organic layer was then dried over sodium sulphate and concentrated under reduced pressure to obtain a crude product, which was then purified by flash column chromatography using 2.5% ethyl acetate in hexanes as an eluent to obtain the title compound (3.2 g, 58.97%).

MS: m/z 358 (M+1),
¹HNMR (CDCl₃, 400 MHz): δ 4.33 (q, J=7.2 Hz, 2H), 2.89 (s, 6H), 1.35 (t, J=7.2 Hz, 3H).

Step 4: Ethyl 3-bromo-5-(4-chlorophenyl)-4-(dimethylamino)thiophene-2-carboxylate. (34d)

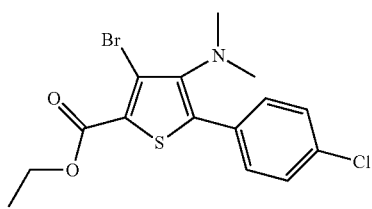 [SMILES: CCOC(=O)c1sc(-c2ccc(Cl)cc2)c(N(C)C)c1Br]

To a solution of Ethyl 3,5-dibromo-4-(dimethylamino) thiophene-2-carboxylate (compound 34c, 3.0 g, 8.40 mmol) in a mixture of toluene:ethanol (5 ml:30 ml) was added (4-chlorophenyl)boronic acid [1.44 g, 9.24 mmol] and potassium carbonate (2.32 g, 16.80 mmol) at 25° C. Nitrogen gas was bubbled through the reaction mixture for 15 minutes. To the reaction mixture was then added tetrakis(triphenylphosphine)palladium(0) (0.48 g, 0.42 mmol) under nitrogen atmosphere and the reaction mixture was heated at about 95 to 100° C. for 3 hr under stirring. The progress of the reaction was monitored by TLC. The reaction mixture was then cooled to 25° C. and filtered through celite, the celite cake was then washed with ethyl acetate (50 ml). The filtrate so obtained was then concentrated under reduced pressure to obtain a crude product, which was then purified by flash column chromatography using 12% ethyl acetate in hexanes as an eluent to obtain the title compound (2.5 g, 76.56%).

MS: m/z 389 (M+1),
¹HNMR (CDCl₃, 400 MHz): δ 7.47 (d, J=8.8 Hz, 2H), 7.40 (d, J=8.8 Hz, 2H) 4.38 (q, J=7.2 Hz, 2H), 2.78 (s, 6H), 1.40 (t, J=7.2 Hz, 3H).

Step 5: Ethyl 5-(4-chlorophenyl)-4-(dimethylamino)-3-(4-sulfamoylphenyl)thiophene-2-carboxylate. (34e)

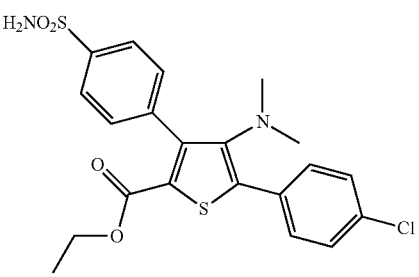 [SMILES: CCOC(=O)c1sc(-c2ccc(Cl)cc2)c(N(C)C)c1-c1ccc(S(N)(=O)=O)cc1]

To a solution of Ethyl 3-bromo-5-(4-chlorophenyl)-4-(dimethylamino)thiophene-2-carboxylate (compound 34d, 2.20 g, 5.65 mmol) in a mixture of toluene:ethanol (10 ml:30 ml) was added (4-sulfamoylphenyl)boronic acid (1.25 g, 6.22 mmol) and potassium carbonate (1.56 g, 11.30 mmol) at 25° C. Nitrogen gas was bubbled through the reaction mixture for 15 minutes. To the reaction mixture was then added tetrakis(triphenylphosphine)palladium(0) (0.32 g, 0.28 mmol) under nitrogen and the reaction mixture was heated at about 95 to about 100° C. for 16 hr under stirring. The progress of the reaction was monitored by TLC. The reaction mixture was then cooled to 25° C. and filtered through celite. The celite cake was then washed with ethanol (2×25 ml). The combined filtrate was concentrated under reduced pressure to obtain a crude product, which was then purified by flash column chromatography using 55% ethyl acetate in hexanes as an eluent to obtain the title compound (2.0 g, 76.05%).

MS: m/z 465 (M+1),
¹HNMR (DMSO, 400 MHz): δ 7.85 (d, J=8.4 Hz, 2H), 7.60 (d, J=8.8 Hz, 2H), 7.52-7.55 (m, 4H). 7.44 (bs-exchanges with D₂O, 2H), 4.07 (q, J=7.2 Hz, 2H) 2.33 (s, 6H), 1.07 (t, J=7.24 Hz, 3H)

Step 6: 5-(4-chlorophenyl)-4-(dimethylamino)-3-(4-sulfamoylphenyl)thiophene-2-carboxylic acid. (34 f)

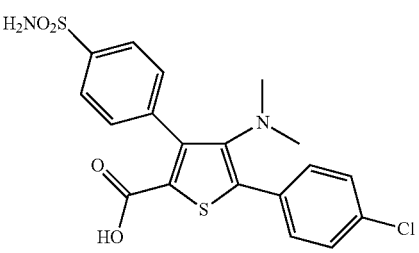 [SMILES: CN(C)c1c(-c2ccc(Cl)cc2)sc(C(=O)O)c1-c1ccc(S(N)(=O)=O)cc1]

Ethyl 5-(4-chlorophenyl)-4-(dimethylamino)-3-(4-sulfamoylphenyl)thiophene-2-carboxylate (compound 34e, 2.00 g, 4.30 mmol) was suspended in ethanol (30 ml) and solution of NaOH (0.86 g, 21.5 mmol) in water (4 ml) was added to it at 25° C. The reaction mixture was then heated at 75° C. under stirring for 2 hr. The progress of the reaction was monitored by TLC. The reaction mixture was then concentrated under reduced pressure. The residue so obtained was diluted with water (10 ml) and cooled using ice bath. To the cooled mixture was added aqueous 10% HCl to bring the pH of the solution to about 6. The mixture so obtained was extracted with ethyl acetate (3×30 ml). The combined organic layer was then dried over anhydrous $Na_2SO_4$. The solvent was evaporated from the dried organic layer under reduced pressure to obtain the title compound (1.60 g, 85.1%)

MS: m/z 437 (M+1), $^1$HNMR (DMSO, 400 MHz): δ 12.97 (bs-exchanges with $D_2O$, 1H), 7.84 (d, J=8.4 Hz, 2H), 7.58 (d, J=8.4 Hz, 2H), 7.52-7.54 (m, 4H), 7.44 (bs-exchanges with $D_2O$, 2H), 2.32 (s, 6H)

Step 7: 5-(4-chlorophenyl)-4-(dimethylamino)-3-(4-(N-((dimethylamino)methylene) sulfamoyl)phenyl)-N-methoxy-N-methylthiophene-2-carboxamide. (34g)

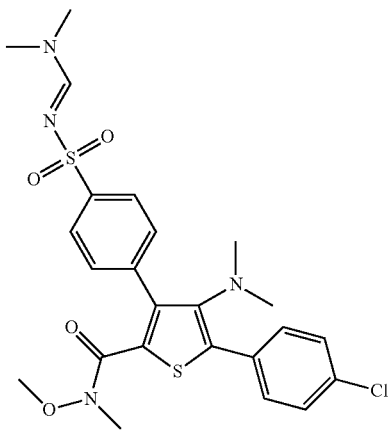 [SMILES: CON(C)C(=O)c1sc(-c2ccc(Cl)cc2)c(N(C)C)c1-c1ccc(S(=O)(=O)/N=C/N(C)C)cc1]

Oxalyl chloride (0.58 g, 0.39 ml, 4.57 mmol) was added drop wise to a solution of 5-(4-chlorophenyl)-4-(dimethylamino)-3-(4-sulfamoylphenyl)thiophene-2-carboxylic acid (compound 34f, 1.00 g, 2.28 mmol) in a mixture of dichloromethane (30 ml) and DMF (0.33 g, 0.35 ml, 4.57 mmol) at 0° C. The reaction mixture was then allowed to warm to room temperature and stirred for 1.5 hr under a nitrogen atmosphere. The progress of the reaction was monitored by TLC. The mixture was then concentrated under reduced pressure. The residue so obtained was dissolved in dry dichloromethane (30 ml) and cooled to 0° C. To the cooled reaction mixture was then added triethylamine (1.38 g, 1.90 ml, 13.68 mmol) followed by the addition of N,O-dimethylhydroxylamine hydrochloride (0.40 g, 4.57 mmol) under stirring. The reaction mixture was then stirred at room temperature for 2 hr. The progress of the reaction was monitored by TLC. The reaction mixture was then diluted with DCM (25 ml) and washed with water (2×25 ml). The combined organic layer was then dried over anhydrous sodium sulphate, and concentrated under reduced pressure to obtain a crude product, which was then purified by column chromatography over silica gel (100-200 mesh) using 1.6% methanol in DCM as an eluent to obtain the title compound (0.8 g, 65.35%).

MS: m/z 535 (M+1), $^1$HNMR (DMSO 400 MHz): δ 8.27 (s, 1H), 7.77 (d, J=8.4 Hz, 2H), 7.54 (m, 4H) 7.44 (d, J=8.4 Hz, 2H), 3.62 (s, 3H), 3.17 (s, 3H), 3.08 (s, 3H), 2.94 (s, 3H), 2.34 (s, 6H).

Step 8: 4-(5-(4-chlorophenyl)-4-(dimethylamino)-2-propionylthiophen-3-yl)benzene sulfonamide. (Compound 34)

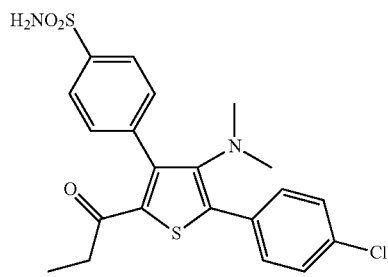 [SMILES: CCC(=O)c1sc(-c2ccc(Cl)cc2)c(N(C)C)c1-c1ccc(S(N)(=O)=O)cc1]

Grignard reagent (ethyl magnesium bromide, 0.62 g, 4.66 ml 1M solution in THF, 4.67 mmol) was added drop wise to a stirred solution of 5-(4-chlorophenyl)-4-(dimethylamino)-3-(4-(N-((dimethylamino)methylene)sulfamoyl)phenyl)-N-methoxy-N-methylthiophene-2-carboxamide (compound 34g, 0.5 g, 0.93 mmol) in anhydrous THF (30 ml) at 25° C. The reaction mixture was then heated at about 70 to 75° C. for 2 hr. The progress of the reaction was monitored by TLC. After cooling the reaction mixture to 0° C., the reaction mixture was quenched by addition of saturated solution of ammonium chloride (10 ml). The mixture so obtained was then extracted with ethyl acetate (2×30 ml). The combined organic layer was dried over anhydrous $Na_2SO_4$. The solvent was evaporated from the dried organic layer under reduced pressure to obtain a crude product, which was then purified by column chromatography over silica gel (100-200 mesh) using 40% ethyl acetate in hexanes as an eluent to obtain the title compound (0.27 g, 64.43%). The title compound was then purified by preparative HPLC (0.135 g, 32.2%).

MS: m/z 449 (M+1), $^1$HNMR (DMSO, 400 MHz): δ 7.90 (d, J=8.4 Hz, 2H), 7.60-7.62 (m, 4H). 7.54 (d, J=8.4 Hz, 2H), 7.48 (bs-exchanges with $D_2O$, 2H), 2.32-2.36 (s, 8H), 0.86 (t, J=7.2 Hz, 3H).

Example 9

5-(4-Chlorophenyl)-N,N,4-trimethyl-3-(4-sulphamoylphenyl)thiophene-2-carboxamide. (Compound 36)

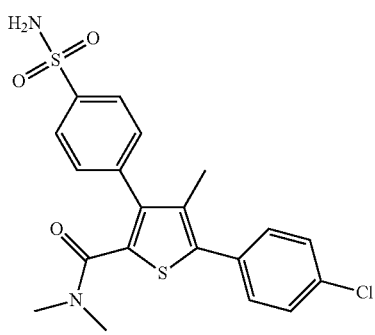 [SMILES: Cc1c(-c2ccc(Cl)cc2)sc(C(=O)N(C)C)c1-c1ccc(S(N)(=O)=O)cc1]

Dimethyl amine (0.055 g, 0.61 ml 2M solution in THF, 1.22 mmol) was added drop wise to a solution of 5-(4-chlorophenyl)-4-methyl-3-(4-sulfamoylphenyl)thiophene-2-carboxylic acid (compound 1c, 0.25 g, 0.61 mmol) in dry THF (15 ml) under a nitrogen atmosphere at 0° C. To the reaction mixture HATU (0.26 g, 0.67 mmol) and DIPEA (0.16 g, 0.21 ml, 1.24 mmol) were added at 0° C. with stirring. The mixture was then allowed to warm to 10° C. and stirred for 2 hr. The progress of the reaction was monitored by TLC. The reaction mixture was then concentrated under reduced pressure. The concentrated mass so obtained was diluted with ethyl acetate (30 ml) and washed with saturated sodium bicarbonate solution (2×15 ml) and brine (1×15 ml). The organic layer obtained was then dried over anhydrous sodium sulphate, and concentrated under reduced pressure to obtain a crude product, which was then purified by flash column chromatography using 25% ethyl acetate in hexanes as an eluent to obtain the title compound (0.06 g, 22.50%).

MS: m/z 435 (M+1), $^1$HNMR (DMSO, 400 MHz): δ 7.89 (d, J=8.4 Hz, 2H), 7.57 (s, 4H), 7.49 (d, J=8.4 Hz, 2H), 7.46 (bs-exchanges with D$_2$O, 2H), 3.61 (m, 3H), 3.13 (m, 3H), 2.11 (s, 3H).

The following compounds were prepared according to the procedure described above but with appropriate changes to the reactants.

5-(4-Chlorophenyl)-N-methoxy-N,4-dimethyl-3-(4-sulphamoylphenyl)thiophene-2-carboxamide (Compound 37)

MS: m/z 451 (M+1), $^1$HNMR (DMSO, 400 MHz): δ 7.85 (d, J=8.4 Hz, 2H), 7.58 (s, 4H), 7.44 (d, J=8.4 Hz, 2H), 7.43 (bs-exchanges with D$_2$O, 2H), 3.64 (s, 3H), 3.09 (s, 3H), 2.01 (s, 3H).

5-(4-Chlorophenyl)-N-(2-hydroxyethyl)-4-methyl-N-propyl-3-(4-sulphamoylphenyl)thiophene-2-carboxamide (Compound 38)

MS: m/z 493 (M+1), $^1$HNMR (DMSO, 400 MHz): δ 7.87 (d, J=8.4 Hz, 2H), 7.55-7.57 (m, 4H), 7.52 (d, J=8.4 Hz, 2H), 7.45 (bs-exchanges with D$_2$O, 2H), 4.71 (bs-exchanges with D$_2$O, 1H), 3.25-3.30 (m, 4H), 3.16-3.21 (m, 2H), 2.11 (s, 3H), 1.27-1.29 (m, 2H), 1.02 (d, J=6.0 Hz, 3H).

4-(5-(4-Chlorophenyl)-4-methyl-2-(piperidine-1-carbonyl)thiophen-3-yl)benzene sulfonamide (Compound 39)

MS: m/z 475 (M+1), $^1$HNMR (DMSO, 400 MHz): δ 7.89 (d, J=8.4 Hz, 2H), 7.56-7.60 (m, 4H), 7.54 (d, J=8.4 Hz, 2H), 7.46 (bs-exchanges with D$_2$O, 2H), 3.59-3.64 (m, 2H), 3.12-3.16 (m, 2H), 2.12 (s, 3H), 1.22-1.27 (m, 6H).

Example 10

Preparation of 4-(5-(4-chlorophenyl)-1,4-dimethyl-2-propionyl-1H-pyrrol-3-yl)benzenesulfonamide (Compound 49)

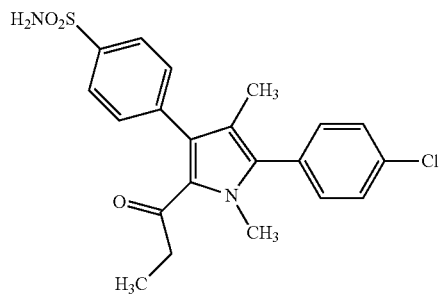 [SMILES: CCC(=O)c1c(-c2ccc(S(N)(=O)=O)cc2)c(C)c(-c2ccc(Cl)cc2)n1C]

Step 1: Methyl-5-(4-chlorophenyl)-1,4-dimethyl-1H-pyrrole-2-carboxylate. (49α)

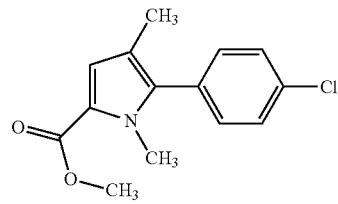 [SMILES: COC(=O)c1cc(C)c(-c2ccc(Cl)cc2)n1C]

To a stirred solution of sodium hydride (60% suspension in mineral oil) (0.529 g, 13.22 mmol) in DMF (5 ml) at 0° C. was added a solution of methyl-5-(4-chlorophenyl)-4-methyl-1H-pyrrole-2-carboxylate (prepared according to the procedure reported in J. org. Chem., 2009, 74(2), 903-905, Org. Lett. 2007, 9(25), 5191-5194, 2.20 g, 8.81 mmol) in DMF (10 ml), which was then followed by the addition of methyl iodide (1.88 g, 0.83 ml, 13.22 mmol). The resulting reaction mixture was stirred at room temperature for 45 minutes. The progress of the reaction was monitored by TLC. The reaction mixture was then quenched with water (10 ml). The mixture so obtained was then extracted with ethyl acetate (2×50 ml). The combined organic layer was dried over anhydrous Na$_2$SO$_4$. The solvent was evaporated from the dried organic layer under reduced pressure to obtain a crude product, which was then purified by column chromatography over silica gel (100-200 mesh) using 15-20% ethyl acetate in hexanes as an eluent to obtain the title compound (1.9 g, 81.9%)

MS: m/z 264 (M+1)

$^1$HNMR (DMSO, 400 MHz): δ 7.55 (d, J=8.4 Hz, 2H), 7.39 (d, J=8.4 Hz, 2H), 6.48 (s, 1H), 3.74 (s, 3H), 3.67 (s, 3H), 1.94 (s, 3H).

Step 2: Methyl-3-bromo-5-(4-chlorophenyl)-1,4-dimethyl-1H-pyrrole-2-carboxylate. (49β)

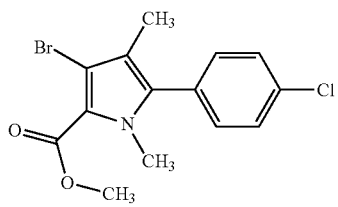 [SMILES: COC(=O)c1c(Br)c(C)c(-c2ccc(Cl)cc2)n1C]

Bromine (1.69 g, 0.54 ml, 10.54 mmol) was added dropwise to a stirred solution of methyl-5-(4-chlorophenyl)-1,4-dimethyl-1H-pyrrole-2-carboxylate (compound 49α, 1.85 g, 7.03 mmol) in acetic acid (20 ml) at 10° C. The resulting reaction mixture was stirred at room temperature for 15 hr. The progress of the reaction was monitored by TLC. Acetic acid was removed from the reaction mixture under reduced pressure and residue obtained was dissolved in ethyl acetate (150 ml). The mixture so obtained was washed with saturated sodium bicarbonate solution (50 ml) followed by washing with brine (50 ml). The combined organic layer was dried over anhydrous $Na_2SO_4$. The solvent was evaporated from the dried organic layer under reduced pressure to obtain a crude product, which was washed with a mixture of ethyl acetate in hexanes (10:90) to obtain the title compound (2.1 g, 87.5%)

$^1$HNMR ($CDCl_3$, 400 MHz): δ 7.43 (d, J=8.4 Hz, 2H), 7.20 (d, J=8.4 Hz, 2H), 3.88 (s, 3H), 3.67 (s, 3H), 1.94 (s, 3H).

Step 3: Methyl-5-(4-chlorophenyl)-1,4-dimethyl-3-(4-sulfamoylphenyl)-1H-pyrrole-2-carboxylate. (49γ)

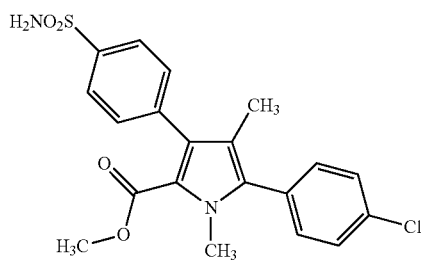 [SMILES: COC(=O)c1c(-c2ccc(S(N)(=O)=O)cc2)c(C)c(-c2ccc(Cl)cc2)n1C]

To the solution of methyl-3-bromo-5-(4-chlorophenyl)-1,4-dimethyl-1H-pyrrole-2-carboxylate (compound 49β, 2.0 g, 5.84 mmol) in a mixture of toluene:ethanol (15:40 ml) was added 4-aminosulfonylbenzene boronic acid (1.41 g, 7.01 mmol) and potassium carbonate (2.42 g, 17.52 mmol) at 25° C. in a sealed tube and a nitrogen gas was bubbled through the resulting mixture for 15 minutes. To the reaction mixture was then added tetrakis(triphenylphosphine)palladium(0) (0.349 g, 0.29 mmol) under nitrogen and reaction mixture was heated at about 95 to about 100° C. for 15 hr under stirring. The progress of the reaction was monitored by TLC. The reaction mixture was then cooled to 25° C. and filtered through celite. The celite cake was washed with ethanol (100 ml) and ethyl acetate (50 ml). The combined filtrate was concentrated under reduced pressure to obtain a crude product, which was then purified by column chromatography over silica gel (100-200 mesh) using 40% ethyl acetate in hexanes as an eluent to obtain the title compound (1.7 g, 69.6%).

MS: m/z 419 (M+1),

HNMR ($CDCl_3$, 400 MHz): δ 7.92 (d, J=8.4 Hz, 2H), 7.46 (d, J=8.8 Hz, 2H), 7.42 (d, J=8.4 Hz, 2H), 7.29 (d, J=8.8 Hz, 2H), 4.86 (bs, exchange with $D_2O$, 2H), 3.74 (s, 3H), 3.58 (s, 3H), 1.79 (s, 3H).

Step 4: 5-(4-chlorophenyl)-1,4-dimethyl-3-(4-sulfamoylphenyl)-1H-pyrrole-2-carboxylic acid. (49ε)

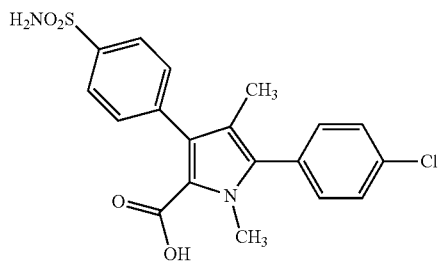 [SMILES: Cc1c(-c2ccc(S(N)(=O)=O)cc2)c(C(=O)O)n(C)c1-c1ccc(Cl)cc1]

Methyl 5-(4-chlorophenyl)-1,4-dimethyl-3-(4-sulfamoylphenyl)-1H-pyrrole-2-carboxylate (compound 49γ, 1.6 g, 3.82 mmol) was suspended in ethanol (100 ml) and treated with solution of NaOH (0.76 g 19.13 mmol) in water (20 ml) at 0° C. The reaction mixture was then heated at 80° C. under stirring for 15 h. The progress of the reaction was monitored by TLC. The reaction mixture was then concentrated under reduced pressure. The reaction mixture was then treated with dilute HCl to bring pH of the mixture to between 6 and 7. The obtained mixture was then extracted with ethyl acetate (2×100 ml). The combined organic layer was then dried over anhydrous $Na_2SO_4$. The solvent was evaporated from the dried organic layer under reduced pressure to obtain the title compound (1.3 g, 84.4%).

MS: m/z 405 (M+1), $^1$HNMR (DMSO, 400 MHz): δ 11.89 (bs, exchanges with $D_2O$, 1H), 7.79 (d, J=8.4 Hz, 2H), 7.59 (d, J=8.4 Hz, 2H), 7.47 (d, J=8.4 Hz, 2H), 7.42 (d, J=8.4 Hz, 2H), 7.31 (bs, exchanges with $D_2O$, 2H), 3.67 (s, 3H), 1.77 (s, 3H).

Step 5: 5-(4-chlorophenyl)-N-methoxy-N,1,4-trimethyl-3-(4-sulfamoylphenyl)-1H-pyrrole-2-carboxamide. (49φ)

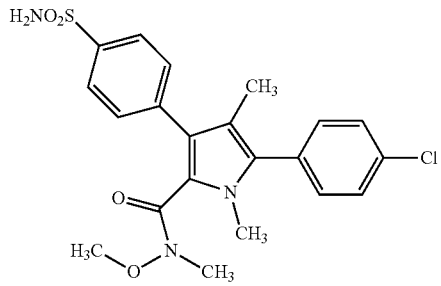 [SMILES: CON(C)C(=O)c1c(-c2ccc(S(N)(=O)=O)cc2)c(C)c(-c2ccc(Cl)cc2)n1C]

To a stirred solution of 5-(4-chlorophenyl)-1,4-dimethyl-3-(4-sulfamoylphenyl)-1H-pyrrole-2-carboxylic acid (compound 49ε, 0.800 g, 1.98 mmol) in DMF (15 ml) was added HOBT (0.333 g, 2.17 mmol) at room temperature followed by the addition of N,O-dimethylhydroxylamine hydrochloride (0.386 g, 3.96 mmol). The reaction mixture was then cooled to 0° C., and to the cooled reaction mixture was added EDC (0.570 g, 2.97 mmol) and triethylamine (0.80 g, 1.10 ml, 7.92 mmol). The reaction mixture was then stirred at room temperature for 15 hr. The progress of the reaction was monitored by TLC. The reaction mixture was then concentrated under reduced pressure. The residue so obtained was taken in ethyl acetate (100 ml) and washed with saturated sodium bicarbonate solution (20 ml) followed by washing with brine (20 ml). The organic layer obtained was dried over anhydrous sodium sulphate, and concentrated under reduced pressure to obtain a crude product. The crude product was then purified by column chromatography over silica gel (100-200 mesh) using 50% ethyl acetate in hexanes as an eluent to obtain the title compound (0.680 g, 76.8%).

MS: m/z 448 (M+1), $^1$HNMR (DMSO, 400 MHz): δ 7.83 (d, J=8.4 Hz, 2H), 7.59 (d, J=8.8 Hz, 2H), 7.46 (d, J=8.4 Hz, 2H), 7.42 (d, J=8.8 Hz, 2H), 7.35 (bs, exchanges with $D_2O$, 2H), 3.43 (s, 6H), 2.99 (s, 3H), 1.96 (s, 3H).

Step 6: 5-(4-chlorophenyl)-3-(4-(N-((dimethylamino)methylene)sulfamoyl)phenyl)-N-methoxy-N,1,4-trimethyl-1H-pyrrole-2-carboxamide. (49ω)

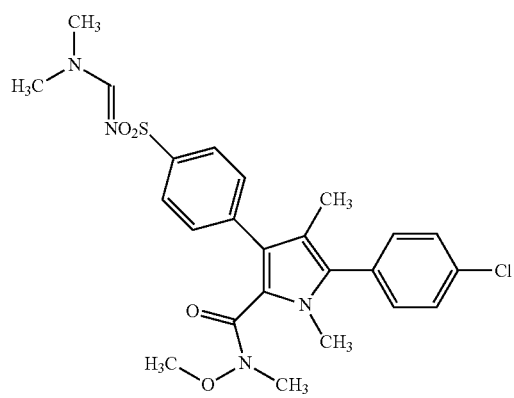

To a stirred solution of 5-(4-chlorophenyl)-N-methoxy-N,1,4-trimethyl-3-(4-sulfamoylphenyl)-1H-pyrrole-2-carboxamide (compound 49φ, 0.650 g, 1.45 mmol) in ethyl acetate (12 ml) was added DMF (0.65 ml) and DMF acetal (0.207 g, 0.233 ml, 1.74 mmol) sequentially at room temperature. The reaction mixture was then stirred at room temperature for 15 hr under a nitrogen atmosphere. The progress of the reaction was monitored by TLC. The precipitated out product was filtered and washed with ether (10 ml) to obtain the title compound (0.600 g, 82.19%).

MS: m/z 503 (M+1), $^1$HNMR (DMSO, 400 MHz): δ 8.24 (s, 1H), 7.77 (d, J=8.4 Hz, 2H), 7.57 (d, J=8.4 Hz, 2H), 7.47 (d, J=8.4 Hz, 2H), 7.41 (d, J=8.4 Hz, 2H), 3.43 (s, 6H), 3.15 (s, 3H), 3.00 (s, 3H), 2.92 (s, 3H), 1.95 (s, 3H).

Step 7: 4-(5-(4-chlorophenyl)-1,4-dimethyl-2-propionyl-1H-pyrrol-3-yl)benzene sulfonamide (Compound 49)

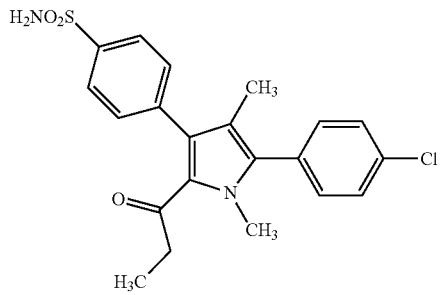 [SMILES: CCC(=O)c1c(-c2ccc(S(N)(=O)=O)cc2)c(C)c(-c2ccc(Cl)cc2)n1C]

Grignard reagent (ethyl magnesium bromide, 0.531 g, 3.98 ml, 1M soln. In THF, 3.98 mmol) was added dropwise under a nitrogen atmosphere to a stirred solution of 5-(4-chlorophenyl)-3-(4-(N-((dimethylamino)methylene)sulfamoyl)phenyl)-N-methoxy-N,1,4-trimethyl-1H-pyrrole-2-carboxamide (compound 49ω, 0.400 g, 0.79 mmol) in anhydrous THF (15 ml) at 25° C., and the reaction mixture was then heated to about 70 to about 75° C. for 1 hr. The progress of the reaction was monitored by TLC. After cooling the reaction mixture to 0° C., the cooled reaction mixture was quenched by addition of saturated solution of ammonium chloride (10 ml). The mixture so formed was extracted with ethyl acetate (2×50 ml). The combined organic layer was dried over anhydrous $Na_2SO_4$. The solvent from the dried organic solution was evaporated under reduced pressure to obtain a crude product, which was then purified by preparative HPLC to obtain the title compound (0.070 g, 21.08%)

MS: m/z 417 (M+1), $^1$HNMR ($CDCl_3$, 400 MHz): δ 8.01 (d, J=8.4 Hz, 2H), 7.47 (d, J=8.4 Hz, 2H), 7.45 (d, J=8.4 Hz, 2H), 7.28 (d, J=8.4 Hz, 2H), 4.93 (bs, exchanges with $D_2O$, 2H), 3.69 (s, 3H), 2.16 (q, J=7.2 Hz, 2H), 1.76 (s, 3H), 0.93 (t, J=7.2 Hz, 3H).

Example 11

Preparation of 4-(5-(4-chlorophenyl)-1,4-dimethyl-2-propionyl-1H-pyrrol-3-yl)benzenesulfonamide (Compound 49) (Alternative method)

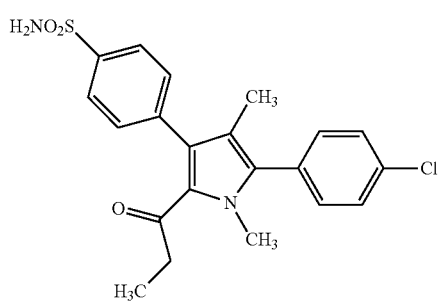 [SMILES: CCC(=O)c1c(-c2ccc(S(N)(=O)=O)cc2)c(C)c(-c2ccc(Cl)cc2)n1C]

Step 1: 1-(5-(4-chlorophenyl)-1,4-dimethyl-1H-pyrrol-2-yl)propan-1-one (49a)

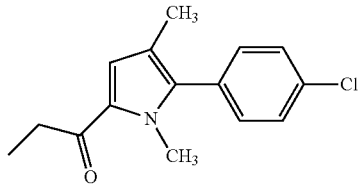

N,N-dimethyl propionamide (3.24 g, 3.52 ml, 32.08 mmol) was cooled at 0-5° C. and and to this was added POCl$_3$ (4.9 g, 2.9 ml, 32.08 mmol) slowly in a dropwise manner. The resulting mixture was then stirred at room temperature (about 25° C.) for 20 minutes. The reaction mixture was then diluted with 1,2-dichloroethane (60 ml) and cooled to 0° C. To the cooled reaction mixture was then added a solution of 2-(4-chlorophenyl)-1,3-dimethyl-1H-pyrrole (prepared according to the procedure given in Tetrahedron Letters 46 (2005) 4539-4542, 6.0 g, 29.17 mmol) in 1,2-dichloroethane (60 ml) dropwise. The reaction mixture was then heated to reflux for 30 minutes. The progress of the reaction was monitored by TLC. The mixture so obtained was allowed to cool to room temperature and was diluted with aqueous solution of sodium acetate trihydrate (21.8 g, 160.4 mmol in 45 ml water). The mixture so obtained was further heated to reflux for 30 minutes, two layers were separated. The aqueous layer was extracted with dichloromethane (3×100 ml). The combined organic layer was washed with water (1×100 ml) and dried over anhydrous Na$_2$SO$_4$. The solvent from the reaction mixture was evaporated under reduced pressure to obtain a crude product. This crude product was purified by column chromatography over silica gel (100-200 mesh) using 4-6% ethyl acetate in hexanes as an eluent to obtain the title compound (6.55 g, 85.8%)

MS: m/z 262 (M+1),
$^1$HNMR (CDCl$_3$, 400 MHz): δ 7.45 (d, J=8.8 Hz, 2H), 7.24 (d, J=8.8 Hz, 2H), 6.89 (s, 1H), 3.76 (s, 3H), 2.83 (q, J=7.6 Hz, 2H), 2.02 (s, 3H), 1.21 (t, J=7.6 Hz, 3H).

The compounds given below were prepared by procedure similar to the one described above for compound '49a' with appropriate variations of reactants, reaction conditions and quantities of reagents.

54a. 1-(5-(4-Fluorophenyl)-1,4-dimethyl-1H-pyrrol-2-yl)propan-1-one

MS: m/z 246 (M+1),

55a. 1-(5-(4-Methoxyphenyl)-1,4-dimethyl-1H-pyrrol-2-yl)propan-1-one

MS: m/z 258 (M+1),

56a. 1-(5-(4-chlorophenyl)-1,4-dimethyl-1H-pyrrol-2-yl)butan-1-one

MS: m/z 276 (M+1),

57a. 1-(5-(2,4-dichlorophenyl)-1,4-dimethyl-1H-pyrrol-2-yl)propan-1-one

MS: m/z 297 (M+1),

58a. 1-(5-(2,3-dihydrobenzo[b][1,4]dioxin-6-yl)-1,4-dimethyl-1H-pyrrol-2-yl)propan-1-one MS: m/z 286 (M+1),

Step 2: 1-(3-Bromo-5-(4-chlorophenyl)-1,4-dimethyl-1H-pyrrol-2-yl)propan-1-one. (49b)

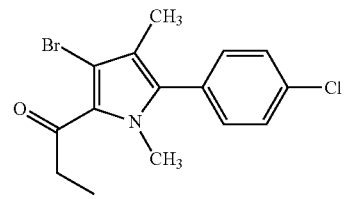 [SMILES: CCC(=O)c1c(Br)c(C)c(-c2ccc(Cl)cc2)n1C]

A solution of N-bromosuccinimide (4.42 g, 24.83 mmol) in THF (62.5 ml) was added dropwise to a stirred solution of 1-(5-(4-chlorophenyl)-1,4-dimethyl-1H-pyrrol-2-yl)propan-1-one (compound 49a, 6.5 g, 24.83 mmol) in THF (100 ml) at −78° C. The resulting reaction mixture was then stirred at a temperature of −78° C. for 5 hr. The reaction mixture was allowed to warm to 25° C. slowly during further 3 to 4 hr. The progress of the reaction was monitored by TLC. The solvent from the reaction mixture was evaporated under reduced pressure and residue so obtained was mixed in ethyl acetate (200 ml). The resulting mixture was washed with saturated sodium bicarbonate solution (1×100 ml) which was followed by washing with water (1×100 ml). The combined organic layer was dried over anhydrous Na$_2$SO$_4$. The solvent was evaporated from the dried organic layer under reduced pressure to obtain a crude product, which was then purified by flash column chromatography using 10% ethyl acetate in hexanes to obtain the title compound (7.58 g, 90%).

MS: m/z 342 (M+1),
$^1$HNMR (CDCl$_3$, 400 MHz): δ 7.45 (d, J=8.4 Hz, 2H), 7.22 (d, J=8.4 Hz, 2H), 3.67 (s, 3H), 3.12 (q, J=7.2 Hz, 2H), 1.96 (s, 3H), 1.21 (t, J=7.2 Hz, 3H).

The compounds given below were prepared by procedure similar to the one described above for compound '49b' with appropriate variations of reactants, reaction conditions and quantities of reagents.

54b. 1-(3-Bromo-5-(4-Fluorophenyl)-1,4-dimethyl-1H-pyrrol-2-yl)propan-1-one

MS: m/z 325 (M+1).

55b. 1-(3-Bromo-5-(4-Methoxyphenyl)-1,4-dimethyl-1H-pyrrol-2-yl)propan-1-one MS: m/z 336 (M+1),

56b. 1-(3-Bromo-5-(4-chlorophenyl)-1,4-dimethyl-1H-pyrrol-2-yl)butan-1-one

MS: m/z 356 (M+1),

57b. 1-(3-Bromo-5-(2,4-dichlorophenyl)-1,4-dimethyl-1H-pyrrol-2-yl)propan-1-one MS: m/z 376 (M+1),

58b. 1-(3-Bromo-5-(2,3-dihydrobenzo[b][1,4]dioxin-6-yl)-1,4-dimethyl-1H-pyrrol-2-yl)propan-1-one MS: m/z 365 (M+1),

Step 3: 4-(5-(4-chlorophenyl)-1,4-dimethyl-2-propionyl-1H-pyrrol-3-yl)benzene sulfonamide. (Compound 49)

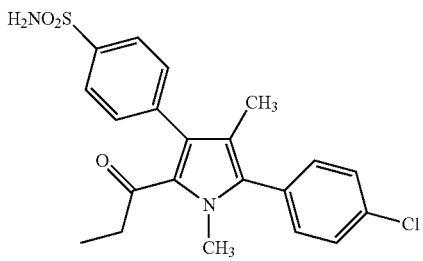 [SMILES: CCC(=O)c1c(-c2ccc(S(N)(=O)=O)cc2)c(C)c(-c2ccc(Cl)cc2)n1C]

To a solution of 1-(3-bromo-5-(4-chlorophenyl)-1,4-dimethyl-1H-pyrrol-2-yl)propan-1-one (compound 49b, 3.0 g, 8.81 mmol) in a mixture of toluene:ethanol (15 ml:45 ml) were added 4-aminosulfonylbenzene boronic acid (1.947 g, 9.69 mmol) and potassium carbonate (2.43 g, 17.61 mmol) at 25° C. in a sealed tube and a nitrogen gas was bubbled through it for 15 minutes. To the reaction mixture was the added tetrakis(triphenylphosphine)palladium(0) (0.51 g, 0.44 mmol) under nitrogen atmosphere and reaction mixture was heated at about 90 to about 95° C. for 18 hr under stirring. The progress of the reaction was monitored by TLC. The reaction mixture was then cooled to 25° C. and filtered through celite. The celite cake was washed with 10% methanol in dichloromethane. The combined filtrate so obtained was concentrated under reduced pressure to obtain a crude product, which was then purified by flash column chromatography using 40% ethyl acetate in hexanes as an eluent to obtain the title compound (1.22 g, 33.2%).

MS: m/z 417 (M+1),
$^1$HNMR (CDCl$_3$, 400 MHz): δ 8.02 (d, J=8.4 Hz, 2H), 7.48 (d, J=8.4 Hz, 2H), 7.47 (d, J=8.4 Hz, 2H), 7.30 (d, J=8.4 Hz, 2H), 5.11 (bs, exchanges with D$_2$O, 2H), 3.71 (s, 3H), 2.17 (q, J=7.2 Hz, 2H), 1.75 (s, 3H), 0.94 (t, J=7.2 Hz, 3H).

The following compounds were prepared according to the procedure described above but with appropriate changes to the reactants.

4-(5-(4-Fluorophenyl)-1,4-dimethyl-2-propionyl-1H-pyrrol-3-yl)benzene sulfonamide (Compound 54)

MS: m/z 401 (M+1),
$^1$HNMR (CDCl$_3$, 400 MHz): δ 8.01 (d, J=8.4 Hz, 2H), 7.48 (d, J=8.4 Hz, 2H), 7.31-7.35 (m, 2H), 7.21 (t, J=8.4 Hz, 2H), 4.98 (bs-exchanges with D$_2$O, 2H), 3.70 (s, 3H), 2.18 (q, J=7.2 Hz, 2H), 1.74 (s, 3H), 0.94 (t, J=7.2 Hz, 3H).

4-(5-(4-Methoxyphenyl)-1,4-dimethyl-2-propionyl-1H-pyrrol-3-yl)benzene sulfonamide (Compound 55)

MS: m/z 413 (M+1),
$^1$HNMR (CDCl$_3$, 400 MHz): δ 8.01 (d, J=8.4 Hz, 2H), 7.40 (d, J=8.4 Hz, 2H), 7.29 (d, J=8.4 Hz, 2H), 7.03 (d, J=8.4 Hz, 2H), 4.89 (bs-exchanges with D$_2$O, 2H), 3.88 (s, 3H), 3.71 (s, 3H), 2.18 (q, J=7.2 Hz, 2H), 1.76 (s, 3H), 0.92 (t, J=7.2 Hz, 3H).

4-(2-butyryl-5-(4-chlorophenyl)-1,4-dimethyl-1H-pyrrol-3-yl)benzene sulfonamide (Compound 56)

MS: m/z 431 (M+1),
$^1$HNMR (CDCl$_3$, 400 MHz): δ 8.01 (d, J=8.4 Hz, 2H), 7.46-7.49 (m, 4H), 7.31 (d, J=8.4 Hz, 2H), 4.96 (bs-exchanges with D$_2$O, 2H), 3.71 (s, 3H), 2.13 (t, J=7.2 Hz, 2H), 1.76 (s, 3H), 1.45-1.52 (m, 2H), 0.71 (t, J=7.2 Hz, 3H).

4-(5-(2,4-Dichlorophenyl)-1,4-dimethyl-2-propionyl-1H-pyrrol-3-yl)benzene sulfonamide (Compound 57)

MS: m/z 452 (M+1),
$^1$HNMR (CDCl$_3$, 400 MHz): δ 8.01 (d, J=8.4 Hz, 2H), 7.58 (d, J=2.0 Hz, 1H), 7.49 (d, J=8.4 Hz, 2H), 7.39 (dd, J=8.4, 2.0 Hz, 1H), 7.26-7.28 (m, 1H), 4.93 (bs-exchanges with D$_2$O, 2H), 3.64 (s, 3H), 2.19 (q, J=7.2 Hz, 2H), 1.66 (s, 3H), 0.95 (t, J=7.2 Hz, 3H).

4-(5-(2,3-Dihydrobenzo[b][1,4]dioxin-6-yl)-1,4-dimethyl-2-propionyl-1H-pyrrol-3-yl)benzene sulfonamide (Compound 58)

MS: m/z 441 (M+1),
$^1$HNMR (DMSO, 400 MHz): δ 7.89 (d, J=8.0 Hz, 2H), 7.49 (d, J=8.0 Hz, 2H), 7.44 (bs-exchanges with D$_2$O, 2H), 6.99 (d, J=8.4 Hz, 1H), 6.86-6.91 (m, 2H), 4.30 (s, 4H), 3.61 (s, 3H), 2.12 (q, J=7.2 Hz, 2H), 1.71 (s, 3H), 0.83 (t, J=7.2 Hz, 3H).

Example 12

Preparation of 4-(5-(4-chlorophenyl)-4-methyl-2-propionyl-1H-pyrrol-3-yl)benzenesulfonamide (Compound 53)

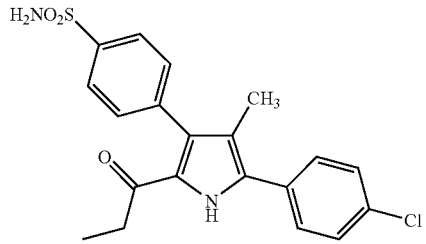 [SMILES: CCC(=O)c1[nH]c(-c2ccc(Cl)cc2)c(C)c1-c1ccc(S(N)(=O)=O)cc1]

Step 1: 1-(5-(4-chlorophenyl)-4-methyl-1H-pyrrol-2-yl)propan-1-one. (53a)

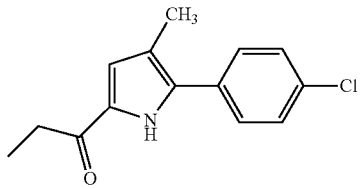 [SMILES: CCC(=O)c1cc(C)c(-c2ccc(Cl)cc2)[nH]1]

phosphorus oxychloride (1.496 g, 0.896 ml, 9.76 mmol) was added dropwise to previously cooled (0 to 5° C.) N,N-dimethyl propionamide (0.987 g, 1.073 ml, 9.76 mmol) maintaining the temperature between about 0° C. to about 5° C. The resulting reaction mixture was then allowed to warm to room temperature (about 25° C.), which was then stirred at room temperature (about 25° C.) for 15 minutes. The reaction mixture was then diluted with 1,2-dichloroethane (17 ml), the resulting mixture was cooled to 0° C., to it was then added 2-(4-chlorophenyl)-3-methyl-1H-pyrrole (prepared according to the procedure given in Tetrahedron Letters 46 (2005) 4539-4542, 1.7 g, 8.87 mmol) in 1,2-dichloroethane (17 ml) dropwise. The reaction mixture so formed was heated to reflux for 30 minutes. The progress of the reaction was monitored by TLC. The reaction mixture was then allowed to cool to room temperature, and to it was then added a solution of sodium acetate trihydrate (6.64 g, 48.8 mmol) in 14 ml water. The reaction mixture so obtained was heated to reflux for 30 minutes. Two phases formed in the reaction mixture were then separated. The aqueous layer was extracted with dichloromethane (3×50 ml). The combined organic layer was washed with saturated sodium bicarbonate solution (1×50 ml) followed by washing with water (1×50 ml), and then the organic layer was dried over anhydrous $Na_2SO_4$. The solvent was evaporated from the dried organic layer under reduced pressure to obtain a crude product. The crude product was then purified by flash column chromatography using 10% ethyl acetate in hexanes as an eluent to obtain the title compound (1.82 g, 83%)

MS: m/z 247 (M+1), $^1$HNMR (CDCl$_3$, 400 MHz): δ 9.75 (bs, exchanges with D$_2$O, 1H), 7.47 (d, J=8.8 Hz, 2H), 7.41 (d, J=8.8 Hz, 2H), 6.81 (d, J=2.4 Hz, 1H), 2.79 (q, J=7.2 Hz, 2H), 2.26 (s, 3H), 1.21 (t, J=7.2 Hz, 3H).

Step 2: 1-(3-Bromo-5-(4-chlorophenyl)-4-methyl-1H-pyrrol-2-yl)propan-1-one. (53b)

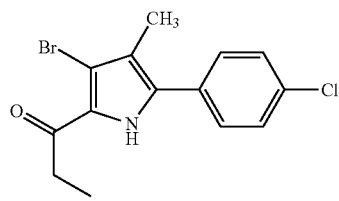 [SMILES: CCC(=O)c1[nH]c(-c2ccc(Cl)cc2)c(C)c1Br]

A solution of N-bromosuccinimide (1.25 g, 7.06 mmol) in THF (20 ml) was added dropwise to a stirred solution of 1-(5-(4-chlorophenyl)-4-methyl-1H-pyrrol-2-yl)propan-1-one (compound 53a, 1.75 g, 7.06 mmol) in THF (40 ml) at about −78° C. The resulting reaction mixture was stirred at about −78° C. for 5 hr. The reaction mixture was then allowed to warm to 25° C. slowly during further 3 to 4 hr. The progress of the reaction was monitored by TLC. The solvent was evaporated from the reaction mixture under reduced pressure and to the residue so obtained was added ethyl acetate (200 ml). The mixture so obtained was washed with saturated sodium bicarbonate solution (1×50 ml) followed by washing with water (1×50 ml). The combined organic layer was then dried over anhydrous Na$_2$SO$_4$. The solvent was evaporated from the dried organic layer under reduced pressure to obtain a crude product, which was then purified by flash column chromatography using 10 ethyl acetate in hexanes to obtain the title compound (1.77 g, 77%)

MS: m/z 327 (M+1), $^1$HNMR (CDCl$_3$, 400 MHz): δ 9.67 (bs, exchangeable with D$_2$O, 1H) 7.43 (m, 4H), 3.05 (q, J=7.2 Hz, 2H), 2.21 (s, 3H), 1.20 (t, J=7.2 Hz, 3H).

Step 3: 4-(5-(4-chlorophenyl)-4-methyl-2-propionyl-1H-pyrrol-3-yl)benzene sulfonamide. (Compound 53)

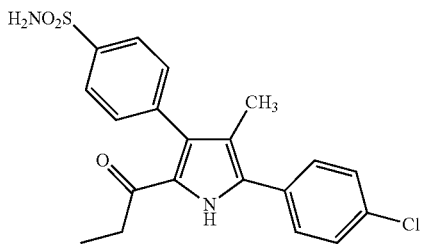 [SMILES: CCC(=O)c1[nH]c(-c2ccc(Cl)cc2)c(C)c1-c1ccc(S(N)(=O)=O)cc1]

To the solution of 1-(3-bromo-5-(4-chlorophenyl)-4-methyl-1H-pyrrol-2-yl)propan-1-one (compound 53b, 1.0 g, 3.06 mmol) in a mixture of toluene:ethanol (5:15 ml) was added 4-aminosulfonylbenzene boronic acid (0.67 g, 3.37 mmol) and potassium carbonate (1.26 g, 9.19 mmol) at a temperature of about 25° C. in a sealed tube and a nitrogen gas was bubbled through the resulting reaction mixture for 15 minutes. To the reaction mixture was then added tetrakis(triphenylphosphine)palladium(0) (0.17 g, 0.153 mmol) under nitrogen atmosphere and the reaction mixture was heated at about 90° C. to 95° C. for 18 hr under stirring. The progress of the reaction was monitored by TLC. The reaction mixture was then cooled to 25° C. and filtered through celite. The celite cake was washed with 10% methanol in dichloromethane (3×25 ml). The combined filtrate was concentrated under reduced pressure to obtain a crude product, which was then purified by flash column chromatography using 40% ethyl acetate in hexanes as an eluent to obtain the title compound (0.082 g, 6.65%).

MS: m/z 403 (M+1), $^1$HNMR (DMSO, 400 MHz): δ 11.83 (bs, exchanges with D$_2$O, 1H) 7.87 (d, J=8.4 Hz, 2H), 7.61 (d, J=8.4 Hz, 2H), 7.53 (d, J=8.4 Hz, 2H), 7.51 (d, J=8.4 Hz, 2H), 7.42 (bs, exchanges with D$_2$O, 2H), 2.40 (q, J=7.2 Hz, 2H), 1.91 (s, 3H), 0.91 (t, J=7.2 Hz, 3H).

Example 13

4-(5-(4-chlorophenyl)-1-ethyl-4-methyl-2-propionyl-1H-pyrrol-3-yl)benzenesulfonamide (Compound 51)

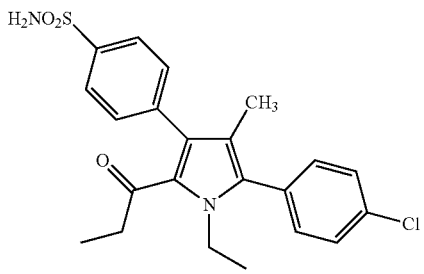 [SMILES: CCC(=O)c1c(-c2ccc(S(N)(=O)=O)cc2)c(C)c(-c2ccc(Cl)cc2)n1CC]

Step 1: 2-(4-chlorophenyl)-1-ethyl-3-methyl-1H-pyrrole. (51a)

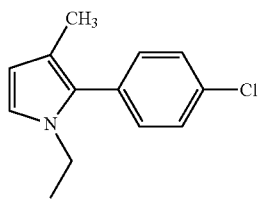

A solution of 2-(4-chlorophenyl)-3-methyl-1H-pyrrole (prepared according to the procedure given in Tetrahedron Letters 46 (2005) 4539-4542, 1.0 g, 5.22 mmol) in DMF (10 ml) was added dropwise to a stirred suspension of Sodium hydride (0.23 g, 5.74 mmol, 60% dispersion in mineral oil) in 20 ml DMF at 0° C. under a nitrogen atmosphere. The reaction mixture was then stirred at about 0° C. for 30 min. Ethyl iodide (0.89 g, 0.47 ml, 5.74 mmol) was then added to the reaction mixture maintaining the temperature at 0° C. The reaction mixture was then stirred at 25° C. for 3 hrs. The progress of the reaction was monitored by TLC. The reaction mixture was slowly quenched with cold water (30 ml) and the resulting mixture was then extracted with ethyl acetate (2×30 ml). The combined organic layer was then washed with brine (1× 30 ml) and dried over sodium sulfate. The dried organic layer was then concentrated under reduced pressure to obtain crude product as semi-solid mass (0.8 g), which was then purified by flash column chromatography using 5% ethyl acetate in hexanes as an eluent to obtain the title compound (0.6 g, 52.3%).

MS: m/z 220 (M+1), $^1$HNMR (CDCl$_3$, 400 MHz): δ 7.42 (d, J=8.4 Hz, 2H), 7.24 (d, J=8.4 Hz, 2H), 6.71 (d, J=2.8 Hz, 1H), 6.10 (d, J=2.8 Hz, 1H), 3.83 (q, J=7.2 Hz, 2H), 2.05 (s, 3H), 1.24 (t, J=7.2 Hz, 3H).

Step 2: 1-(5-(4-chlorophenyl)-1-ethyl-4-methyl-1H-pyrrol-2-yl)propan-1-one. (51b)

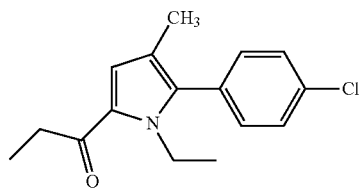 [SMILES: CCC(=O)c1cc(C)c(-c2ccc(Cl)cc2)n1CC]

Phosphorus oxychloride (0.47 g, 0.28 ml, 3.00 mmol) was added dropwise to previously cooled (0 to 5° C.) N,N-dimethyl propionamide (0.30 g, 0.27 ml, 3.00 mmol) maintaining the temperature between about 0° C. to about 5° C. The resulting reaction mixture was then allowed to warm to room temperature (about 25° C.), which was then stirred at room temperature (about 25° C.) for 20 minutes. The reaction mixture was then diluted with 1,2-dichloroethane (15 ml), the resulting mixture was cooled to 0° C., to it was then added 2-(4-chlorophenyl)-1-ethyl-3-methyl-1H-pyrrole (compound 51a, 0.6 g, 2.73 mmol) in 1,2-dichloroethane (15 ml) dropwise. The reaction mixture so formed was heated to reflux for 30 minutes. The progress of the reaction was monitored by TLC. The reaction mixture was then allowed to cool to room temperature, and to it was then added a solution of sodium acetate trihydrate (1.23 g, 15.0 mmol) in 14 ml water. The reaction mixture so obtained was heated to reflux for 30 minutes. Two phases formed in the reaction mixture were then separated. The aqueous layer was extracted with dichloromethane (3×30 ml). The combined organic layer was washed with water (1×30 ml) and dried over anhydrous Na$_2$SO$_4$. The solvent was evaporated from the dried organic layer under reduced pressure to obtain a crude product, which was then purified by flash column chromatography using 10% ethyl acetate in hexanes as an eluent to obtain the title compound (0.5 g, 66.4%).

MS: m/z 276 (M+1), $^1$HNMR (CDCl$_3$, 400 MHz): δ 7.46 (d, J=8.4 Hz, 2H), 7.23 (d, J=8.4 Hz, 2H), 6.90 (s, 1H), 4.23 (q, J=7.2 Hz, 2H), 2.85 (q, J=7.2 Hz, 2H), 1.95 (s, 3H), 1.22 (t, J=7.2 Hz, 3H), 1.16 (t, J=7.2 Hz, 3H).

Step 3: 1-(3-bromo-5-(4-chlorophenyl)-1-ethyl-4-methyl-1H-pyrrol-2-yl)propan-1-one. (51c)

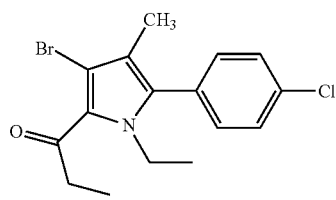 [SMILES: CCC(=O)c1c(Br)c(C)c(-c2ccc(Cl)cc2)n1CC]

A solution of N-bromosuccinimide (0.35 g, 1.99 mmol) in THF (10 ml) was added dropwise to a stirred solution of 1-(5-(4-chlorophenyl)-1-ethyl-4-methyl-1H-pyrrol-2-yl) propan-1-one (compound 51b, 0.5 g, 1.81 mmol) in THF (25 ml) at about −78° C. The resulting reaction mixture was stirred at about −78° C. for 5 hr. The reaction mixture was then allowed to warm to 25° C. slowly during further 3 to 4 hr. The progress of the reaction was monitored by TLC. The solvent was evaporated from the reaction mixture under reduced pressure and to the residue so obtained was added ethyl acetate (50 ml). The mixture so obtained was washed with saturated sodium bicarbonate solution (1×30 ml) followed by washing with water (1×30 ml). The combined organic layer was then dried over anhydrous Na$_2$SO$_4$. The solvent was evaporated from the dried organic layer under reduced pressure to obtain a crude product, which was then purified by flash column chromatography 10% ethyl acetate in hexanes as an eluent to obtain the title compound (0.5 g, 78.0%).

$^1$HNMR (CDCl$_3$, 400 MHz): δ 7.45 (d, J=8.4 Hz, 2H), 7.22 (d, J=8.4 Hz, 2H), 4.20 (q, J=6.8 Hz, 2H), 3.14 (q, J=7.2 Hz, 2H), 1.91 (s, 3H), 1.22 (t, J=7.2 Hz, 3H), 1.12 (t, J=6.8 Hz, 3H).

Step 4: 4-(5-(4-chlorophenyl)-1-ethyl-4-methyl-2-propionyl-1H-pyrrol-3-yl)benzene sulfonamide. (Compound 51)

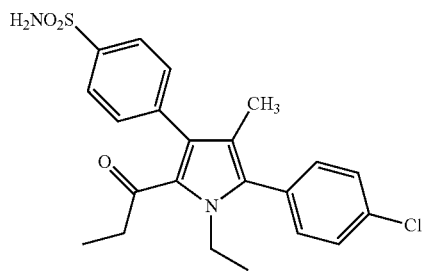 [SMILES: CCC(=O)c1c(-c2ccc(S(N)(=O)=O)cc2)c(C)c(-c2ccc(Cl)cc2)n1CC]

To the solution of 1-(3-bromo-5-(4-chlorophenyl)-1-ethyl-4-methyl-1H-pyrrol-2-yl)propan-1-one (compound 51c, 0.5 g, 1.41 mmol) in a mixture of toluene:ethanol (3:12 ml) was added 4-aminosulfonylbenzene boronic acid (0.34 g, 1.69 mmol) and potassium carbonate (0.48 g, 3.52 mmol) at a temperature of about 25° C. in a sealed tube and a nitrogen gas was bubbled through the reaction mixture for 15 minutes. To the reaction mixture was then added tetrakis(triphenylphosphine)palladium(0) (0.16 g, 0.14 mmol) under nitrogen atmosphere and the reaction mixture was heated at about 90° C. to 95° C. for 18 hr under stirring. The progress of the reaction was monitored by TLC. The reaction mixture was then cooled to 25° C. and filtered through celite. The celite cake was washed with 10% methanol in dichloromethane (2×20 ml). The combined filtrate was concentrated under reduced pressure to obtain a crude product, which was then purified by column chromatography over silicagel (100-200 mesh) using 30-35% ethyl acetate in hexanes as an eluent to obtain the title compound (0.2 g, 32.9%).

MS: m/z 431 (M+1), $^1$HNMR (CDCl$_3$, 400 MHz): δ 8.02 (d, J=8.4 Hz, 2H), 7.47-7.49 (m, 4H), 7.29 (d, J=8.4 Hz, 2H), 4.94 (bs-exchanges with D$_2$O, 2H), 4.21 (q, J=6.8 Hz, 2H), 2.18 (q, J=7.2 Hz, 2H), 1.69 (s, 3H), 1.16 (t, J=6.8 Hz, 3H), 0.95 (t, J=7.2 Hz, 3H).

Analogously, by practicing the above procedure with appropriate change in the reactants, following compound was prepared

4-(5-(4-Chlorophenyl)-1-(cyclopropylmethyl)-4-methyl-2-propionyl-1H-pyrrol-3-yl)benzene sulfonamide (Compound 52)

MS: m/z 457 (M+1), $^1$HNMR (CDCl$_3$, 400 MHz): δ 8.01 (d, J=8.4 Hz, 2H), 7.46-7.50 (m, 4H), 7.30 (d, J=8.4 Hz, 2H), 4.97 (bs-exchanges with D$_2$O, 2H), 4.14 (q, J=6.8 Hz, 2H), 2.20 (q, J=7.2 Hz, 2H), 1.72 (s, 3H), 0.96 (t, J=7.2 Hz, 3H), 0.86-0.87 (m, 1H), 0.31-0.34 (m, 2H), −0.08-0.04 (m, 2H).

Example 14

Preparation of 4-(5-(4-chlorophenyl)-4-methyl-2-propionylthiophen-3-yl)-2-methylbenzenesulfonamide. (compound 41)

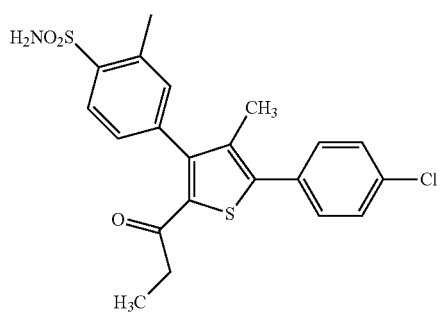 [SMILES: CCC(=O)c1sc(-c2ccc(Cl)cc2)c(C)c1-c1ccc(S(N)(=O)=O)c(C)c1]

Step 1: Methyl 3-(4-(N-(tert-butyl)sulfamoyl)-3-methylphenyl)-4-methylthiophene-2-carboxylate (41a)

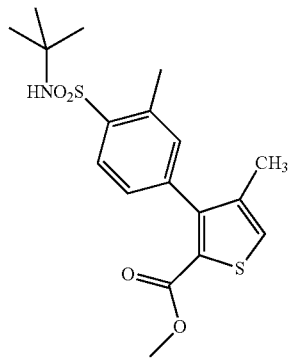

4-bromo-N-(tert-butyl)-2-methylbenzenesulfonamide (Prepared according to the procedure reported in the literature, Tetrahedron, 2006, 62, 7902-7910, 1.43 g, 4.68 mmol) and Potassium phosphate (2.25 g, 10.63 mmol) were added to a stirred suspension of methyl 4-methyl-3-(4,4,5,5-tetramethyl-1,3,2-dioxaborolan-2-yl)thiophene-2-carboxylate (Prepared according to the procedure reported in the literature, J. Org. Chem., 2010, 75, 3855-3858, 1.2 g, 4.25 mmol) in a mixture of 20 ml of THF and 4 ml of water in a tube under a nitrogen atmosphere at room temperature (25° C.). Nitrogen was purging was continued to this suspension for 15 minute at room temperature (25° C.). Triphenyl phospine (0.056 g, 0.21 mmol) and palladium (II) acetate (0.02 g, 0.08 mmol) were then added to it at 25° C. and the tube was sealed. Reaction mixture was stirred at 70° C. for 20 hours. The progress of the reaction was monitored by TLC. The reaction mixture was then filtered and washed with ethyl acetate (2×30 ml). The organic layer was concentrated under reduced pressure to obtain a crude product, which was then purified by flash column chromatography using 40% ethyl acetate in hexanes as an eluent to obtain the title compound (0.7 g, 43.10%).

MS: m/z 382 (M+1)

$^1$HNMR (CDCl$_3$, 400 MHz): δ 8.09 (d, J=8.0 Hz, 1H), 7.16-7.23 (m, 3H), 4.52 (bs-exchanges with D$_2$O, 1H), 3.69 (s, 3H), 2.70 (s, 3H), 2.00 (s, 3H), 1.27 (s, 9H).

Step 2: Methyl 5-bromo-4-methyl-3-(3-methyl-4-sulfamoylphenyl)thiophene-2-carboxylate (41b)

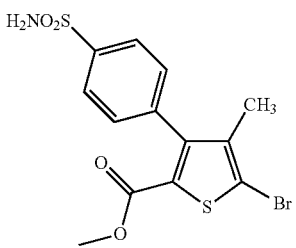

Bromine (0.35 g, 0.11 ml, 2.2 mmol) was added drop wise to a stirred suspension of methyl 3-(4-(N-(tert-butyl)sulfamoyl)-3-methylphenyl)-4-methylthiophene-2-carboxylate (41a, 0.70 g, 1.83 mmol) in DCM (15 ml) at 0° C. The reaction mixture was then stirred at 25° C. for 3 hours. The progress of the reaction was monitored by TLC. The reaction mixture was then concentrated. DCM (50 ml) was added to the residue. The mixture so obtained was washed with water (2×20 ml), brine (lx 20 ml) and dried over sodium sulfate. The dried organic layer was then concentrated under reduced pressure to obtain a crude product as semi-solid (0.7 g), which was then purified by flash column chromatography using 40% ethyl acetate in hexanes as an eluent to obtain the title compound (0.63 g, 85.13%).

MS: m/z 405 (M+1)

$^1$HNMR (CDCl$_3$, 400 MHz): δ 8.09 (d, J=8.0 Hz, 1H), 7.17-7.23 (m, 2H), 4.91 (bs-exchanges with D$_2$O, 2H), 3.73 (s, 3H), 2.72 (s, 3H), 1.95 (s, 3H).

Step 3: Ethyl 5-(4-chlorophenyl)-4-methyl-3-(3-methyl-4-sulfamoylphenyl)thiophene-2-carboxylate. (41c)

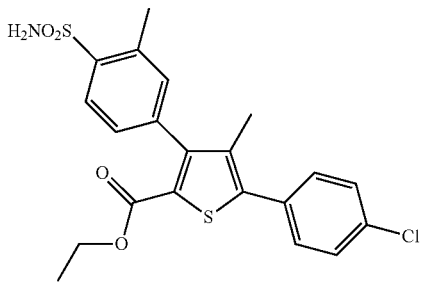 [SMILES: CCOC(=O)c1sc(-c2ccc(Cl)cc2)c(C)c1-c1ccc(S(N)(=O)=O)c(C)c1]

(4-chlorophenyl)boronic acid [0.29 g, 1.85 mmol] and potassium carbonate (0.43 g, 3.09 mmol) were added to a solution of methyl 5-bromo-4-methyl-3-(3-methyl-4-sulfamoylphenyl)thiophene-2-carboxylate (41b, 0.62 g, 1.54 mmol) in a mixture of 5 ml of toluene and 20 ml ethanol at 25° C. A nitrogen gas was bubbled through reaction mixture for 15 minutes. To the reaction mixture was then added tetrakis (triphenylphosphine)palladium(0) (0.09 g, 0.08 mmol) under nitrogen atmosphere and the reaction mixture was heated at a temperature between about 95° C. to 100° C. for 3 hr under stirring. The progress of the reaction was monitored by TLC. The reaction mixture was then cooled to 25° C. and filtered through celite. The celite cake was washed with ethyl acetate (20 ml). The combined filtrate was then concentrated under reduced pressure to obtain a crude product, which was then purified by flash column chromatography using 30% ethyl acetate in hexanes as an eluent to obtain the title compound (0.53 g, 76.8%).

MS: m/z 450 (M+1)

$^1$HNMR (CDCl$_3$, 400 MHz): δ 8.09 (d, J=8.4 Hz, 1H), 7.41-7.46 (m, 4H), 7.21-7.24 (m, 2H), 4.88 (bs-exchanges with D$_2$O, 2H), 4.17 (q, J=6.8 Hz, 2H), 2.73 (s, 3H), 1.99 (s, 3H), 1.19 (t, J=6.8 Hz, 3H).

Step-4: 5-(4-chlorophenyl)-4-methyl-3-(3-methyl-4-sulfamoylphenyl)thiophene-2-carboxylic acid. (41d)

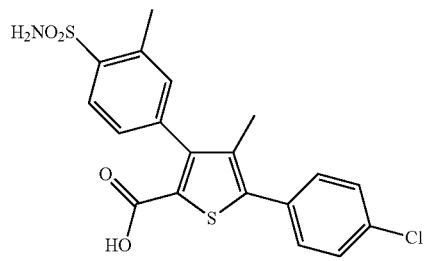 [SMILES: Cc1cc(-c2c(C(=O)O)sc(-c3ccc(Cl)cc3)c2C)ccc1S(N)(=O)=O]

Ethyl 5-(4-chlorophenyl)-4-methyl-3-(3-methyl-4-sulfamoylphenyl)thiophene-2-carboxylate (41c, 0.6 g, 1.33 mmol) was suspended in ethanol (20 ml) and a solution of sodiumhydroxide (0.1 g, 2.66 mmol) in water [2 ml] was added to it at 25° C. The reaction mixture was then heated at 75° C. under stirring for 2 hours. The progress of the reaction was monitored by TLC. The reaction mixture was concentrated under reduced pressure. The residue so obtained was then diluted with water (5 ml) and the mixture was cooled using ice bath. To the cooled mixture was added 10% aqueous HCl to bring the pH of the mixture between about 5 and 6. The mixture was then extracted with ethyl acetate (2×35 ml). The combined organic layer was then dried over anhydrous Na$_2$SO$_4$. The solvent was evaporated from the dried organic layer under reduced pressure to obtain the title compound (0.53 g, 94%).

MS: m/z 422 (M+1)

$^1$HNMR (DMSO, 400 MHz): δ 12.52 (bs-exchanges with D$_2$O, 1H), 7.89 (d, J=8.4 Hz, 1H), 7.54-7.58 (m, 4H), 7.46 (bs-exchanges with D$_2$O, 2H), 7.27-7.32 (m, 2H), 2.62 (s, 3H), 1.98 (s, 3H).

Step 5: 5-(4-chlorophenyl)-3-(4-(N-((dimethylamino)methylene)sulfamoyl)-3-methylphenyl)-N-methoxy-N,4-dimethylthiophene-2-carboxamide (41e)

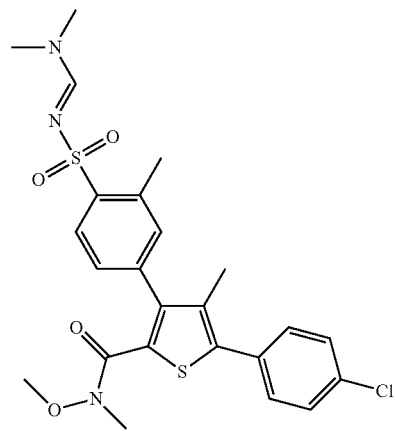 [SMILES: CON(C)C(=O)c1sc(-c2ccc(Cl)cc2)c(C)c1-c1ccc(S(=O)(=O)/N=C/N(C)C)c(C)c1]

Oxalyl chloride (0.47 g, 0.32 ml, 3.7 mmol) was added drop wise to a solution of 5-(4-chlorophenyl)-4-methyl-3-(3-methyl-4-sulfamoylphenyl)thiophene-2-carboxylic acid (41d, 0.52 g, 1.23 mmol) in a mixture of dichloromethane (20 ml) and DMF (0.18 g, 0.19 ml, 2.46 mmol) at 0° C. The mixture was then allowed to warm to room temperature and stirred for 1.5 hr under a nitrogen atmosphere. The progress of the reaction was monitored by TLC. The reaction mixture was then concentrated under reduced pressure. The residue so obtained was then dissolved in dry dichloromethane (20 ml) and cooled to 0° C. To the cooled solution so obtained was then added triethylamine (0.74 g, 1.03 ml, 7.39 mmol), which was then followed by addition of N,O-dimethylhydroxylamine hydrochloride (0.24 g, 2.46 mmol) under stirring. The reaction mixture was then stirred at room temperature for 2 hours. The progress of the reaction was monitored by TLC. The reaction mixture was then diluted with DCM (20 ml) and the mixture so obtained was washed with water (2×10 ml). The organic layer obtained was then dried over anhydrous sodium sulphate, and concentrated under reduced pressure to obtain a crude product. The crude product was then purified by column chromatography over silica gel (100-200 mesh) using 0.8% methanol in DCM as an eluent to obtain the title compound (0.34 g, 53%).

MS: m/z 520 (M+1)

$^1$HNMR (CDCl$_3$, 400 MHz): δ 8.15 (s, 1H), 8.01 (d, J=8.4 Hz, 1H), 7.43-7.44 (m, 4H), 7.15-7.19 (m, 2H), 3.70 (s, 3H), 3.20 (s, 3H), 3.16 (s, 3H), 3.06 (s, 3H), 2.70 (s, 3H), 1.98 (s, 3H).

Step 6: 4-(5-(4-chlorophenyl)-4-methyl-2-propionylthiophen-3-yl)-2-methylbenzene sulfonamide. (Compound 41)

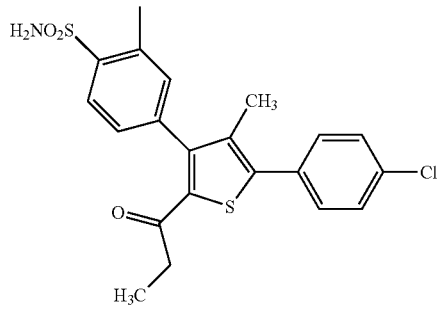 [SMILES: CCC(=O)c1sc(-c2ccc(Cl)cc2)c(C)c1-c1ccc(S(N)(=O)=O)c(C)c1]

Grignard reagent (Ethyl magnesium bromide, 0.42 g, 3.17 ml 1M solution in THF, 3.17 mmol) was added drop wise to a stirred solution of (5-(4-chlorophenyl)-3-(4-(N-((dimethylamino)methylene)sulfamoyl)-3-methylphenyl)-N-methoxy-N,4-dimethylthiophene-2-carboxamide (41e, 0.33 g, 0.63 mmol) in anhydrous THF (20 ml) at 25° C. The reaction mixture was then heated to about 70° C. to 75° C. for 1 hr. The progress of the reaction was monitored by TLC. The reaction mixture was then cooled to 0° C. The cooled reaction mixture was quenched by adding saturated solution of ammonium chloride (10 ml) and the mixture was then extracted with ethyl acetate (2×30 ml). The combined organic layer was dried over anhydrous Na$_2$SO$_4$. The solvent was evaporated from the dried organic layer under reduced pressure to obtain a crude product, which was then purified by preparative HPLC to obtain the title compound (0.05 g, 18.1%)

MS: m/z 434 (M+1)

$^1$HNMR (DMSO, 400 MHz): δ 7.93 (d, J=8.0 Hz, 1H), 7.56-7.59 (m, 4H), 7.51 (bs-exchanges with D$_2$O, 2H), 7.35-7.38 (m, 2H), 2.64 (s, 3H), 2.32 (q, J=7.2 Hz, 2H), 1.92 (s, 3H), 0.87 (t, J=7.2 Hz, 3H).

Example 15

Preparation of 1-(5-(4-chlorophenyl)-4-methyl-3-(4-(piperidin-1-ylsulfonyl)phenyl)thiophen-2-yl)propan-1-one (Compound 48)

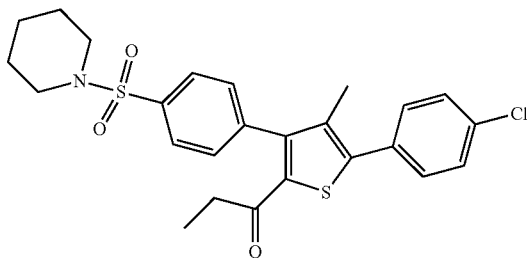 [SMILES: CCC(=O)c1sc(-c2ccc(Cl)cc2)c(C)c1-c1ccc(S(=O)(=O)N2CCCCC2)cc1]

Step 1: Ethyl 4-methyl-3-(4-(piperidin-1-ylsulfonyl)phenyl)thiophene-2-carboxylate (48a)

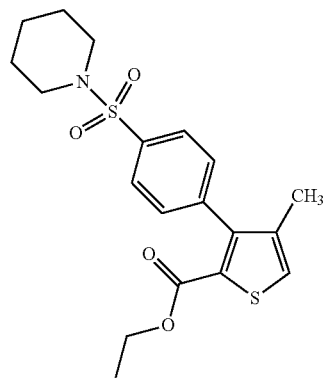 [SMILES: CCOC(=O)c1scc(C)c1-c1ccc(S(=O)(=O)N2CCCCC2)cc1]

(4-(piperidin-1-ylsulfonyl)phenyl) boronic acid (Prepared according to the procedure reported in US20060258670, 4.41 g, 16.38 mmol) and Potassium carbonate (5.15 g, 37.2 mmol) were added to a stirred suspension of methyl 3-bromo-4-methylthiophene-2-carboxylate (7a, 3.5 g, 14.89 mmol) in a mixture of 100 ml of ethanol and 30 ml toluene in a tube under a nitrogen atmosphere at room temperature (25° C.). Nitrogen was purged to this suspension for 15 minute at room temperature (25° C.). The reaction mixture was then added tetrakis(triphenylphosphine)palladium(0) (0.86 g, 0.74 mmol) at a temperature of about 25° C. and the tube was sealed. The reaction mixture was then stirred at 105° C. for 15 hours. The progress of the reaction was monitored by TLC. The reaction mixture was then filtered and washed with ethyl acetate (2×50 ml). The combined organic layer was then concentrated under reduced pressure to obtain crude product, which was then purified by column chromatography over silica gel (100-200 mesh) using 45% ethyl acetate in hexanes as an eluent to obtain the title compound (3.5 g, 62.0%).

MS: m/z 394 (M+1)

$^1$HNMR (DMSO, 400 MHz): δ 7.76 (d, J=8.4 Hz, 2H), 7.68 (s, 1H), 7.50 (d, J=8.4 Hz, 2H), 4.06 (q, J=6.8 Hz, 2H), 2.93 (t, J=4.2 Hz, 4H), 1.98 (s, 3H), 1.54-1.59 (m, 4H), 1.36-1.39 (m, 2H), 1.01 (t, J=6.8 Hz, 3H).

Step 2: ethyl 5-bromo-4-methyl-3-(4-(piperidin-1-ylsulfonyl)phenyl)thiophene-2-carboxylate (48b)

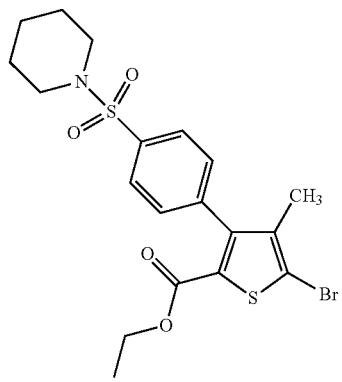 [SMILES: CCOC(=O)c1sc(Br)c(C)c1-c1ccc(S(=O)(=O)N2CCCCC2)cc1]

Prepared by following process provided in example 3 step 3 using 48a as a starting material.
MS: m/z 473 (M+1)

Step 3: Ethyl 5-(4-chlorophenyl)-4-methyl-3-(4-(piperidin-1-ylsulfonyl)phenyl)thiophene-2-carboxylate. (48c)

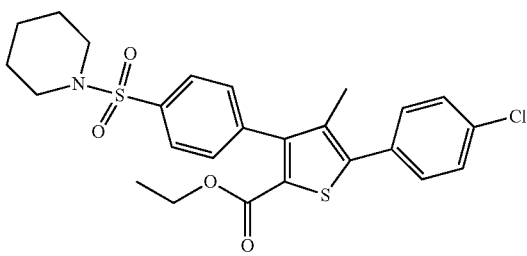 [SMILES: CCOC(=O)c1sc(-c2ccc(Cl)cc2)c(C)c1-c1ccc(S(=O)(=O)N2CCCCC2)cc1]

Prepared by following process provided in example 3 step 4, using 48b and (4-chlorophenyl)boronic acid as reactants.
MS: m/z 504 (M+1).

Step 4: 5-(4-chlorophenyl)-4-methyl-3-(4-(piperidin-1-ylsulfonyl)phenyl)thiophene-2-carboxylic acid (48d)

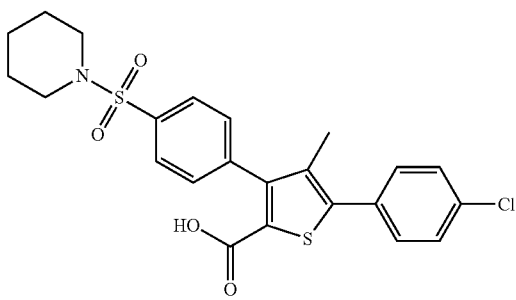 [SMILES: Cc1c(-c2ccc(Cl)cc2)sc(C(=O)O)c1-c1ccc(S(=O)(=O)N2CCCCC2)cc1]

Prepared by following process provided in example 3 step 5 using 48c as a starting material.
MS: m/z 476 (M+1).

Step-3: 5-(4-chlorophenyl)-N-methoxy-N,4-dimethyl-3-(4-(piperidin-1-ylsulfonyl)phenyl)thiophene-2-carboxamide (48e)

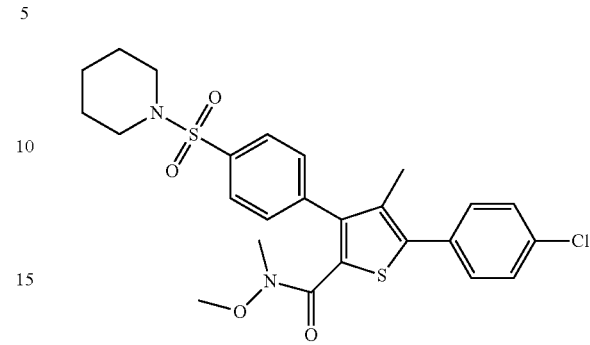

Prepared by following the process provided in example 3 step 6 using 48d as a starting material.
MS: m/z 519 (M+1)

Step-4: 1-(5-(4-chlorophenyl)-4-methyl-3-(4-(piperidin-1-ylsulfonyl)phenyl)thiophen-2-yl)propan-1-one (compound 48)

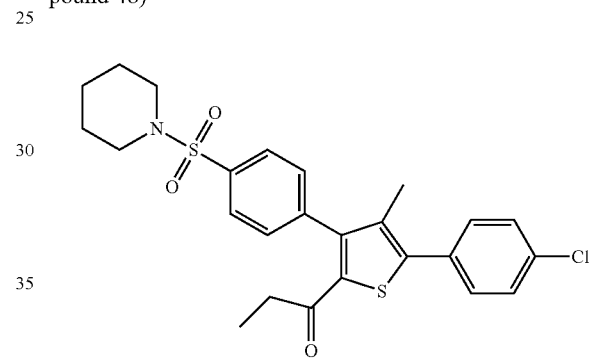

Prepared by following process provided in example 3 step 7 using 48e as a starting material.
MS: m/z 488 (M+1)
$^1$HNMR (DMSO, 400 MHz): δ 7.84 (d, J=8.0 Hz, 2H), 7.63 (d, J=8.0 Hz, 2H), 7.46 (m, 4H), 2.94 (t, J=5.2 Hz, 4H), 2.30 (q, J=7.2 Hz, 2H), 1.94 (s, 3H), 1.52-1.55 (m, 4H), 1.36-1.38 (m, 2H), 0.86 (t, J=7.2 Hz, 3H).

Example 16

Preparation of 5-(4-chlorophenyl)-N,N,1,4-tetramethyl-3-(4-sulfamoylphenyl)-1H-pyrrole-2-carboxamide. (Compound 50)

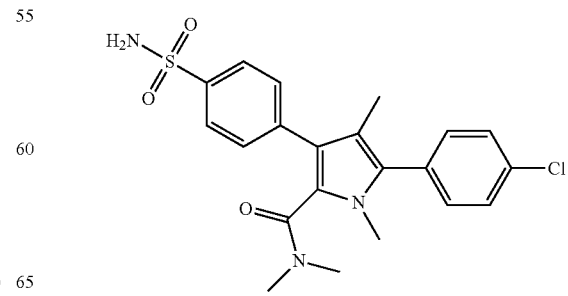

To a stirred solution of 5-(4-chlorophenyl)-1,4-dimethyl-3-(4-sulfamoylphenyl)-1H-pyrrole-2-carboxylic acid (49ε, 1.00 g, 2.47 mmol) in DMF (15 ml) was added θHOBT (0.41 g, 2.72 mmol) at room temperature, which was then followed by the addition of dimethylamine hydrochloride (0.40 g, 4.94 mmol). the reaction mixture was cooled to 0° C. and to the cooled reaction mixture was then added EDC (0.71 g, 3.70 mmol) and triethylamine (1.00 g, 1.37 ml, 9.88 mmol). The reaction mixture was then stirred at room temperature for 16 hours. The progress of the reaction was monitored by TLC. The reaction mixture was then concentrated under reduced pressure. Ethyl acetate (100 ml) was added to the residue so obtained. The mixture so obtained was then washed with saturated sodium bicarbonate solution (20 ml) followed by washing with brine (20 ml). The organic layer obtained was dried over anhydrous sodium sulphate. The dried organic layer was then concentrated under reduced pressure to obtain a crude product. The crude product was purified by column chromatography over silica gel (100-200 mesh) using 90% ethyl acetate in hexanes as an eluent to obtain the title compound (0.94 g, 88.1%).

MS: m/z 432 (M+1)
$^1$HNMR (DMSO, 400 MHz): δ 7.82 (d, J=8.4 Hz, 2H), 7.57 (d, J=8.4 Hz, 2H), 7.46 (d, J=8.4 Hz, 2H), 7.41 (d, J=8.4 Hz, 2H), 7.36 (bs-exchanges with D$_2$O, 2H), 3.40 (s, 3H), 2.87 (s, 3H), 2.56 (s, 3H), 1.98 (s, 3H).

Example 17

Preparation of ethyl 5-(4-chlorophenyl)-4-methyl-3-(4-sulfamoyl-5,6,7,8-tetrahydronaphthalen-1-yl)thiophene-2-carboxylate (Compound 59)

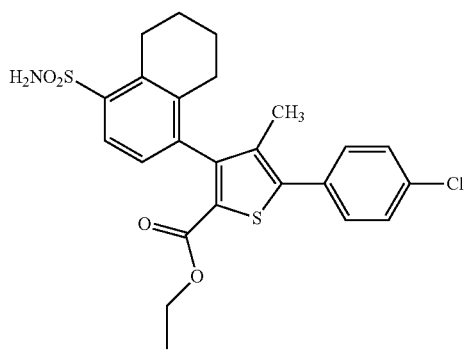 [SMILES: CCOC(=O)c1sc(-c2ccc(Cl)cc2)c(C)c1-c1ccc(S(N)(=O)=O)c2c1CCCC2]

Step 1:
4-bromo-5,6,7,8-tetrahydronaphthalene-1-sulfonyl chloride (59a)

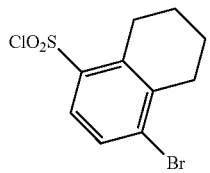 [SMILES: O=S(=O)(Cl)c1ccc(Br)c2c1CCCC2]

Chlorosulfonic acid (13.80 g, 7.93 ml, 118.00 mmol was added dropwise to a stirred solution of 5-bromo-1,2,3,4-tetrahydronaphthalene (Prepared according to the procedure reported in the literature, WO2004/792, 10.0 g, 47.4 mmol) in 50 ml chloroform at 0° C. The reaction mixture was then allowed to warm to about 25° C. and was stirred at the same temperature for 45 min. The progress of the reaction was monitored by TLC. The reaction mixture was then poured in ice-water (50 ml) and the mixture so obtained was extracted with chloroform (2×150 ml). The combined organic layer was dried over sodium sulphate and concentrated under reduced pressure to obtain the title compound (12.0 g, 81.6%), which was taken ahead as such without further purification for the next step.

MS: m/z 310 (M+1)
$^1$HNMR (CDCl$_3$, 400 MHz): δ 7.81 (d, J=8.8 Hz, 1H), 7.64 (d, J=8.8 Hz, 1H), 2.72-7.81 (m, 4H), 1.83-1.89 (m, 4H).

Step 2: 4-bromo-N-(tert-butyl)-5,6,7,8-tetrahydronaphthalene-1-sulfonamide (59b)

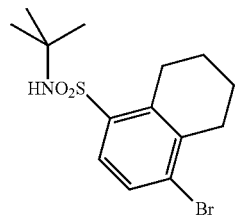

tert-butyl amine [8.5 g, 12.32 ml, 116.0 mmol) was added dropwise to a stirred suspension of 4-bromo-5,6,7,8-tetrahydronaphthalene-1-sulfonyl chloride (59a, 12.0 g, 38.8 mmol) in 150 ml tetrahydrofuran at 0° C. The reaction mixture was then stirred at a temperature of about 25° C. for 2 hours. The progress of the reaction was monitored by TLC. Water (100 ml) was added to the reaction mixture, and the mixture so obtained was extracted with ethyl acetate (2×150 ml). The combined organic layer was then dried over sodium sulphate, and the dried organic layer was concentrated under reduced pressure to obtain a crude product, which was then purified by column chromatography over silica gel (100-200 mesh) using 15% ethyl acetate in hexanes as an eluent to obtain the title compound (2.34 g, 17.4%).

MS: m/z 347 (M+1)
$^1$HNMR (CDCl$_3$, 400 MHz): δ 7.79 (d, J=8.8 Hz, 1H), 7.52 (d, J=8.8 Hz, 1H), 4.53 (bs-exchanges with D$_2$O, 1H), 2.76-7.83 (m, 4H), 1.80-1.85 (m, 4H), 1.22 (s, 9H).

Step 3: Methyl 3-(4-(N-(tert-butyl)sulfamoyl)-5,6,7,8-tetrahydronaphthalen-1-yl)-4-methylthiophene-2-carboxylate (59c)

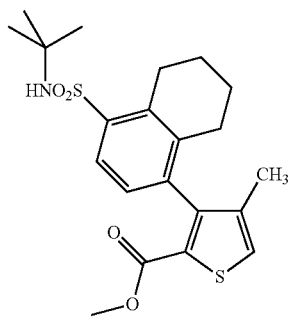

4-bromo-N-(tert-butyl)-5,6,7,8-tetrahydronaphthalene-1-sulfonamide (59b, 1.35 g, 3.90 mmol) and Potassium phosphate (0.75 g, 3.54 mmol) were added to a stirred suspension of methyl 4-methyl-3-(4,4,5,5-tetramethyl-1,3,2-dioxaborolan-2-yl)thiophene-2-carboxylate (Prepared according to the procedure reported in the literature, J. Org. Chem., 2010, 75, 3855-3858, 1.0 g, 3.54 mmol) in a mixture of 20 ml THF and 4 ml water in a tube under a nitrogen atmosphere at room temperature (about 25° C.). A nitrogen gas was purged to this suspension for 15 minute at room temperature (about 25° C.). To the reaction mixture was then added triphenyl phospine (0.028 g, 0.10 mmol) and) Palladium (II) acetate (0.016 g, 0.07 mmol) at 25° C. and the tube was sealed. The reaction mixture was then stirred at about 75° C. for 20 hours. The progress of the reaction was monitored by TLC. The reaction mixture was then filtered and the cake obtained was washed with ethyl acetate (2×30 ml). The combined filtrate was then concentrated under reduced pressure to obtain crude product, which was then purified by flash column chromatography using 30% ethyl acetate in hexanes as an eluent to obtain the title compound (0.11 g, 7.7%)

MS: m/z 422 [M+1]

$^1$HNMR (CDCl$_3$, 400 MHz): δ 7.99 (d, J=8.0 Hz, 1H), 7.26 (s, 1H), 6.98 (d, J=8.0 Hz, 1H), 4.43 (bs-exchanges with D$_2$O, 1H), 3.66 (s, 3H), 3.23 (t, J=6.4 Hz, 2H), 2.21-2.43 (m, 2H), 1.87 (s, 3H), 1.69-1.81 (m, 4H), 1.27 (s, 9H).

Step 4: Methyl 5-bromo-4-methyl-3-(4-sulfamoyl-5,6,7,8-tetrahydronaphthalen-1-yl)thiophene-2-carboxylate (59d)

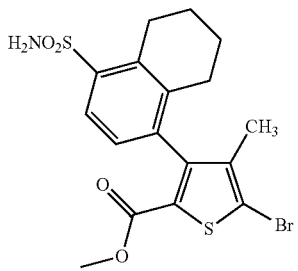 [SMILES: COC(=O)c1sc(Br)c(C)c1-c1ccc(S(N)(=O)=O)c2c1CCCC2]

Bromine (0.045 g, 0.015 ml, 0.28 mmol) was added dropwise to a stirred suspension of methyl 3-(4-(N-(tert-butyl)sulfamoyl)-5,6,7,8-tetrahydronaphthalen-1-yl)-4-methylthiophene-2-carboxylate (59c, 0.10 g, 0.24 mmol) in 15 ml dichloromethane at a temperature of about 0° C. The reaction mixture was then stirred at about 25° C. for 2 hours. the progress of the reaction was monitored by TLC. The reaction mixture was then concentrated. 20 ml of dichloromethane was added to the residue so obtained. The mixture so formed was washed with water (2×10 ml), brine (1×10 ml) and the organic layer so obtained was dried over sodium sulfate. The dried organic layer was then concentrated under reduced pressure to obtain a crude product, which was then purified by flash column chromatography using 20% ethyl acetate in hexanes as an eluent to obtain the title compound (0.08 g, 67.4%).

MS: m/z 445 [M+1]

$^1$HNMR (CDCl$_3$, 400 MHz): δ 7.97 (d, J=8.4 Hz, 1H), 6.97 (d, J=8.4 Hz, 1H), 4.43 (bs-exchanges with D$_2$O, 2H), 3.73 (s, 3H), 3.22-3.28 (m, 2H), 2.24-2.46 (m, 2H), 1.69-1.82 (m, 7H).

Step 5: Ethyl 5-(4-chlorophenyl)-4-methyl-3-(4-sulfamoyl-5,6,7,8-tetrahydronaphthalen-1-yl)thiophene-2-carboxylate (Compound 59)

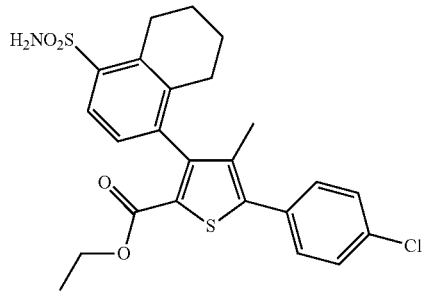 [SMILES: CCOC(=O)c1sc(-c2ccc(Cl)cc2)c(C)c1-c1ccc(S(N)(=O)=O)c2c1CCCC2]

(4-chlorophenyl)boronic acid [0.027 g, 0.17 mmol] and potassium carbonate (0.043 g, 0.31 mmol) were added to a solution of methyl 5-bromo-4-methyl-3-(4-sulfamoyl-5,6,7,8-tetrahydronaphthalen-1-yl)thiophene-2-carboxylate (59d, 0.07 g, 0.16 mmol) in a mixture of 1 ml toluene and 4 ml ethanol at 25° C. A nitrogen gas was bubbled through reaction mixture for 15 minutes. To the reaction mixture was then added tetrakis (triphenylphosphine)palladium(0) (0.009 g, 0.008 mmol) under nitrogen atmosphere and the reaction mixture was heated at a temperature of about 95° C. to about 100° C. for 3 hr under stirring. The progress of the reaction was monitored by TLC. The reaction mixture was then cooled to 25° C. and filtered through celite, the celite cake washed with 10 ml ethyl acetate. The combined filtrate so obtained was then concentrated under reduced pressure to obtain a crude product, which was then purified by flash column chromatography using 30% ethyl acetate in hexanes as an eluent to obtain the title compound (0.027 g, 35.0%).

MS: m/z 490 (M+1)

$^1$HNMR (CDCl$_3$, 400 MHz): δ 7.97 (d, J=8.0 Hz, 1H), 7.45 (s, 4H), 7.05 (d, J=8.0 Hz, 1H), 5.31 (bs-exchanges with D$_2$O, 2H), 4.10-4.20 (m, 2H), 3.25-3.28 (m, 2H), 2.51-2.57 (m, 1H), 2.31-2.37 (m, 1H), 1.78-1.90 (m, 7H), 1.13 (t, J=7.2 Hz, 3H).

Example 18

Preparation of ethyl 5-(4-chlorophenyl)-3-(4-sulfamoylphenyl)furan-2-carboxylate (Compound 60)

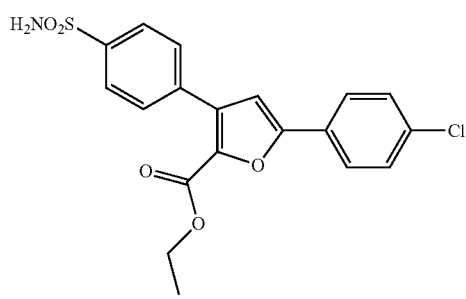 [SMILES: CCOC(=O)c1oc(-c2ccc(Cl)cc2)cc1-c1ccc(S(N)(=O)=O)cc1]

Step 1: ethyl 3-(4-sulfamoylphenyl)furan-2-carboxylate (60a)

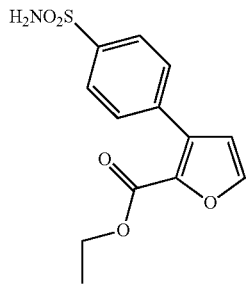 [SMILES: CCOC(=O)c1occc1-c1ccc(S(N)(=O)=O)cc1]

(4-sulfamoylphenyl) boronic acid (1.76. gm, 8.77 mmol) and Potassium carbonate (2.52 gm, 18.26 mmol) were added to a stirred suspension of ethyl 3-bromofuran-2-carboxylate (Prepared according to the procedure reported in the literature EP1489077A1, 2004, 1.6 gm, 7.30 mmol) in a mixture of 80 ml of ethanol and 20 ml of toluene (80 ml:20 ml) under nitrogen atmosphere at room temperature (25° C.) in a tube. A nitrogen gas was purged to the suspension for 15 minute at room temperature (about 25° C.). To the reaction mixture was then added Tetrakis(triphenyl phosphine) Palladium(0) (0.422 gm, 0.365 mmol) at 25° C. and tube was sealed. The reaction mixture was then stirred at 100° C. for 18 hours. The progress of the reaction was monitored by TLC. The reaction mixture was then filtered and washed with ethyl acetate (2×100 ml). The combined organic layer was then concentrated under reduced pressure to obtain a crude product as semi-solid (11.2 gm), which was then purified by column chromatography over silica gel (100-200 mesh) using 50% ethyl acetate in hexanes as an eluent to obtain the title compound (1.2 g, 55.60%)

MS: m/z 296 (M+1)

$^1$HNMR (CDCl$_3$, 400 MHz): δ 7.99 (d, J=8.8 Hz, 2H), 7.76 (d, J=8.8 Hz, 2H), 7.23 (d, J=2.0 Hz 1H), 6.65 (d, J=2.0 Hz, 1H), 4.85 (bs-exchanges with D$_2$O, 2H), 4.35 (q, J=7.2 Hz 2H), 1.33 (t, J=7.2 Hz, 3H).

Step 2: ethyl 5-(4-chlorophenyl)-3-(4-sulfamoylphenyl)furan-2-carboxylate (compound 60)

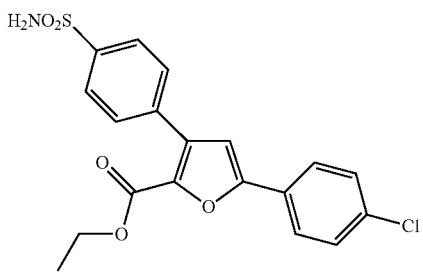 [SMILES: CCOC(=O)c1oc(-c2ccc(Cl)cc2)cc1-c1ccc(S(N)(=O)=O)cc1]

1-bromo-4-chlorobenzene (0.214 g, 1.11 mmol) and potassium acetate (0.199 g, 2.03 mmol) were added to a solution of ethyl 3-(4-sulfamoylphenyl)furan-2-carboxylate (60a, 0.3 g, 1.01 mmol) in dimethyl acetamide (5 ml) at 25° C. in a tube. A nitrogen gas was bubbled through the reaction mixture for 15 minutes. To the reaction mixture was then added palladium (II) acetate (0.023 gm, 0.102 mmol) under nitrogen atmosphere and the tube was sealed. The reaction mixture was then heated at 150° C. for 20 hr with stirring. The progress of the reaction was monitored by TLC. The reaction mixture was then cooled to 25° C. and concentrated under reduced pressure. The residue so obtained was dissolved in ethyl acetate (30 ml). The solution so obtained was then washed with water (2×10 ml), dried over sodium sulphate and concentrated under reduced pressure to obtain a crude product, which was then purified by flash column chromatography using 50% ethyl acetate in hexanes as an eluent to obtain the title compound (0.040 gm, 9.70%).

MS: m/z 406 (M+1)

$^1$HNMR (CDCl$_3$, 400 MHz): δ 8.00 (d, J=8.8 Hz, 2H), 7.75-7.77 (m, 4H), 7.43 (d, J=8.8 Hz, 2H), 6.85 (s, 1H), 5.2 (bs-exchanges with D$_2$O, 2H), 4.35 (q, J=7.2 Hz 2H), 1.34 (t, J=7.2 Hz, 3H).

Example 19

Pharmacological Screening

Compounds were tested in a cell-based real-time kinetic assay in human IMR-32 cells with native expression of α7nAChR. The increase in intracellular Ca$^{2+}$ levels was measured in a Fluorometric Imaging Plate Reader (FLIPR). Test compound and agonist solutions were made in assay buffer (HBSS, pH 7.4, 20 mM HEPES, and 10 mM CaCl$_2$). Briefly, cells were plated into Poly-D-Lysine coated back-walled clear-bottom 96-well microplates at a density of 80,000 to 100,000 cells/well and incubated at 37° C./5% CO$_2$ for 40-48 h prior to the experiment. For evaluation of compound mediated potentiation of agonist response, growth media was removed from the wells and 200 µl of FLIPR calcium 4 dye (Molecular Devices), reconstituted in assay buffer, and was added to the wells. After dye loading, microplates were incubated for 30 min at 37° C. and 30 min at room temperature and then directly transferred to the FLIPR. Baseline fluorescence was monitored for the first 10 to 30 followed by the addition of 25 µl of test compound solution and subsequent monitoring of fluorescence changes for up to 10 min. This was followed by addition of 25 µl of agonist solution (PNU-282987, 10 µM) and measurement of fluorescence for 4 mM. (Faghih R. et al. 2009, J. Med. Chem., 52, 3377-84.)

The compound induced fold increase in agonist response (fold PAM activity) was computed by dividing the maximum effect (Max-Min fluorescence) obtained with test compound in presence of agonist with the agonist-alone effect. EC$_{50}$ of the compound was calculated using GraphPad Prism software version 5.0, by plotting compound concentrations against fold PAM activity.

Fold activity at 1 µM concentration: compounds with activity below 5 folds are grouped as A, the compounds with activity between 5.1 folds and 15 folds are grouped as B and the compounds with activity above 15 folds are grouped as C.

Following table 1 provides fold activity of the compounds of the present invention

TABLE 1

| Sr. No. | Fold activation at 1 µM conc. (Group) | Compound No. |
|---|---|---|
| 1 | A | 2, 3, 11, 13, 14, 15, 17, 20, 21, 22, 23, 24, 25, 26, 27, 28, 29, 31, 32, 33, 34, 35, 36, 37, 38, 39, 42, 43, 48, 50, 52, 53, 54, 57, 58 |
| 2 | B | 4, 5, 8, 9, 18, 19, 30, 40, 51, 55, 56, |
| 3 | C | 1, 6, 7, 10, 12, 16, 44, 49, |

The invention claimed is:
1. A compound of formula I, a tautomer, a stereoisomer, or a pharmaceutically acceptable salt thereof,

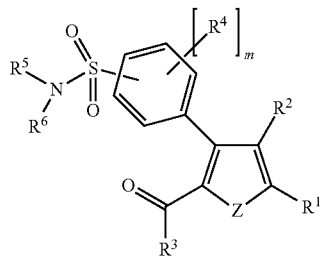
(I)

wherein:
Z is S, O, or $NR^a$, wherein $R^a$ is hydrogen, optionally substituted alkyl, or cycloalkyl;
$R^1$ is selected from the group consisting of optionally substituted aryl, cycloalkyl, optionally substituted heteroaryl, and optionally substituted heterocyclyl;
$R^2$ is selected from the group consisting of hydrogen, halogen, optionally substituted alkyl, perhaloalkyl, cycloalkyl, and $(R^7)(R^8)N—$;
$R^3$ is selected from the group consisting of optionally substituted alkyl, cycloalkyl, heterocyclyl, $(R^7)(R^8)N—$, $(R^7)N(OR^8)—$, and $R^7A^1-$;
$[R^4]_m$ is 'm' times repetition of '$R^4$' groups, each $R^4$ is independently selected from the group consisting of halogen, $R^7A^1-$, and alkyl, wherein m=0, 1 or 2; or two $R^4$ groups and the carbon atoms to which they are attached together form an optionally substituted 5- to 6-membered cyclic system;
$R^5$ and $R^6$ are independently hydrogen or alkyl; or $R^5$ and $R^6$ together with the nitrogen atom to which they are attached form a 3- to 10-membered heterocyclic ring system containing a nitrogen atom;
wherein $R^7$ and $R^8$ are independently selected from the group consisting of hydrogen and optionally substituted alkyl; and
$A^1$ is selected from the group consisting of O and S;
wherein,
the term "optionally substituted alkyl" means an alkyl group unsubstituted or substituted with 1 to 6 substituents selected independently from the group consisting of oxo, halogen, nitro, cyano, aryl, heteroaryl, cycloalkyl, $R^{10a}SO_2—$, $R^{10}A^1-$, $R^{10a}OC(=O)—$, $R^{10a}C(=O)O—$, $(R^{10})(H)NC(=O)—$, $(R^{10})(alkyl)NC(=O)—$, $R^{10a}C(=O)N(H)—$, $(R^{10})(H)N—$, $(R^{10})(alkyl)N—$, $(R^{10})(H)NC(=A^1)N(H)—$, and $(R^{10})(alkyl)NC(=A^1)N(H)—$;
the term "optionally substituted aryl" means (i) an aryl group unsubstituted or substituted with 1 to 3 substituents selected independently from the group consisting of halogen, nitro, cyano, hydroxy, $C_1$ to $C_6$ alkyl, $C_3$ to $C_6$ cycloalkyl, $C_1$ to $C_6$ perhaloalkyl, alkyl-O—, perhaloalkyl-O—, alkyl-N(alkyl)-, alkyl-N(H)—, $H_2N—$, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC(=O)$—, alkyl-N(alkyl)$SO_2$—, alkyl-N(H)$SO_2$—, $H_2NSO_2$—, 3- to 6-membered heterocycle containing 1 to 2 heteroatoms selected from the group consisting of N, O and S, wherein said 3- to 6-membered heterocycle is optionally substituted with alkyl, or alkyl-C(=O)— or (ii) said substituted or unsubstituted aryl ring optionally fused with cycloalkane ring or heterocycle ring containing 1 to 3 heteroatoms selected from S, O, and N across a bond, wherein the said cycloalkane ring or heterocycle ring is optionally substituted with oxo, alkyl, or alkyl-C(=O)—;
the term "optionally substituted heterocyclyl" means a (i) heterocyclyl group unsubstituted or substituted on ring carbons with 1 to 6 substituents selected independently from the group consisting of oxo, halogen, nitro, cyano, aryl, heteroaryl, alkyl, $R^{10}A^1-$, $R^{10a}OC(=O)—$, $R^{10a}C(=O)O—$, $(R^{10})(H)NC(=O)—$, $(R^{10})(alkyl)NC(O)—$, $R^{10a}C(=O)N(H)—$, $(R^{10})(H)N—$, $(R^{10})(alkyl)N—$, $(R^{10})(H)NC(=A^1)N(H)—$, and $(R^{10})(alkyl)NC(=A^1)N(H)—$; (ii) heterocyclyl group optionally substituted on ring nitrogen(s) with one or more substituents selected from the group consisting of heteroaryl, alkyl, $R^{10a}C(=O)—$, $R^{10a}SO_2—$, $R^{10a}OC(=O)—$, $(R^{10})(H)NC(=O)—$, $(R^{10})(alkyl)NC(=O)—$, and aryl unsubstituted or substituted with 1 to 3 substituents selected independently from halogen, alkyl, cyano, and nitro;
the term "optionally substituted heteroaryl" means a heteroaryl group unsubstituted or substituted with 1 to 3 substituents selected independently from the group consisting of halogen, nitro, cyano, hydroxy, $C_1$ to $C_6$ alkyl, $C_3$ to $C_6$ cycloalkyl, $C_1$ to $C_6$ perhaloalkyl, alkyl-O—, perhaloalkyl-O—, alkyl-N(alkyl)-, alkyl-N(H)—, $H_2N—$, alkyl-$SO_2$, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC(=O)$, alkyl-N(alkyl)$SO_2$—, alkyl-N(H)$SO_2$—, $H_2NSO_2$—, and 3- to 6-membered heterocycle containing 1 to 2 heteroatoms selected from the group consisting of N, O, and S, wherein the heterocycle is optionally substituted with one to four substituents selected from the group consisting of alkyl and alkyl-C(=O)—;
the term "optionally substituted 5- to 6-membered cyclic system" means the 5- to 6-membered cyclic system unsubstituted or substituted with 1 to 3 substituents selected from the group consisting of oxo, halogen, nitro, cyano, aryl, heteroaryl, alkyl, $R^{10a}C(=O)—$, $R^{10a}SO_2—$, $R^{10}A^1-$, $R^{10a}OC(=O)—$, $R^{10a}C(=O)O—$, $(R^{10})(H)NC(=O)—$, $(R^{10})(alkyl)NC(=O)—$, $R^{10a}C(=O)N(H)—$, $(R^{10})(H)N—$, $(R^{10})(alkyl)N—$, $(R^{10})(H)NC(=A^1)N(H)—$, and $(R^{10})(alkyl)NC(=A^1)N(H)—$;
the term "3- to 10-membered optionally substituted heterocyclic ring system" means a 3- to 10-membered heterocyclic ring system unsubstituted or substituted with 1 to 3 substituents selected from the group consisting of oxo, halogen, nitro, cyano, aryl, heteroaryl, alkyl, alkenyl, alkynyl, $R^{10a}C(=O)—$, $R^{10a}SO_2—$, $R^{10}A^1-$, $R^{10a}OC(=O)—$, $R^{10a}C(=O)O—$, $(R^{10})(H)NC(=O)—$, $(R^{10})(alkyl)NC(=O)—$, $R^{10a}C(=O)N(H)—$, $(R^{10})(H)N—$, $(R^{10})(alkyl)N—$, $(R^{10})(H)NC(=A^1)N(H)—$, and $(R^{10})(alkyl)NC(=A^1)N(H)—$; wherein $R^{10}$ is selected from hydrogen, alkyl, aryl, heteroaryl, cycloalkyl, and heterocyclyl;
and $R^{10a}$ is selected from the group consisting of alkyl, perhaloalkyl, aryl, heteroaryl, cycloalkyl, and heterocyclyl.

2. The compound of formula I, tautomer, stereoisomer, or pharmaceutically acceptable salt thereof, as claimed in claim 1, wherein Z is S.

3. The compound of formula I, tautomer, stereoisomer, or pharmaceutically acceptable salt thereof, as claimed in claim 2, wherein R² is selected from the group consisting of hydrogen, optionally substituted alkyl, and (R⁷)(R⁸)N—.

4. The compound of formula I, tautomer, stereoisomer, or pharmaceutically acceptable salt thereof, as claimed in claim 3, wherein R² is selected from the group consisting of hydrogen, methyl, dimethylamino, and dimethylaminomethyl.

5. The compound of formula I, tautomer, stereoisomer, or pharmaceutically acceptable salt thereof, as claimed in claim 2, wherein R³ is selected from the group consisting of alkyl, heterocyclyl, R⁷A¹-, (R⁷)(R⁸)N—, and (R⁷)N(OR⁸)—.

6. The compound of formula I, tautomer, stereoisomer, or pharmaceutically acceptable salt thereof, as claimed in claim 5, wherein R³ is selected from the group consisting of methyl, ethyl, n-propyl, methoxy, ethoxy, dimethylamino, N-methoxy-N-methyl amino, N-(2-hydroxyethyl)-N-propyl amino, and piperidinyl.

7. The compound of formula I, tautomer, stereoisomer, or pharmaceutically acceptable salt thereof, as claimed in claim 2, wherein R⁵ and R⁶ are selected independently from the group consisting of hydrogen and alkyl; or R⁵ and R⁶ together with the nitrogen atom to which they are attached form a 6-membered heterocyclic ring system containing a nitrogen atom.

8. The compound of formula I, tautomer, stereoisomer, or pharmaceutically acceptable salt thereof, as claimed in claim 7, wherein R⁵ and R⁶ are independently selected from hydrogen and methyl, or both R⁵ and R⁶ together with the nitrogen atom to which they are attached form a piperidine ring.

9. The compound of formula I, tautomer, stereoisomer, or pharmaceutically acceptable salt thereof, as claimed in claim 2, wherein m is 0, 1, or 2, and R⁴ is or are selected from alkyl group or groups, or two R⁴s together with the carbon atoms to which they are attached form a 6-membered cyclic system.

10. The compound of formula (I), tautomer, stereoisomer, or pharmaceutically acceptable salt thereof, as claimed in claim 9, wherein m is 0, 1, or 2, and R⁴ is or are selected from methyl group or groups, or two R⁴s together with the carbon atom to which they are attached form a 6-membered carbocycle.

11. The compound of formula I, tautomer, stereoisomer, or pharmaceutically acceptable salt thereof, as claimed in claim 2, wherein:
R¹ is selected from the group consisting of optionally substituted phenyl, optionally substituted heteroaryl, and optionally substituted heterocyclyl;
R² is selected from the group consisting of hydrogen, optionally substituted alkyl, and (R⁷)(R⁸)N—;
R³ is selected from the group consisting of alkyl, heterocyclyl, R⁷A¹-, (R⁷)(R⁸)N—, and (R⁷)N(OR⁸)—;
R⁵ and R⁶ are selected independently from the group consisting of hydrogen, alkyl, or R⁵ and R⁶ together with the nitrogen atom to which they are attached form a 6-membered heterocyclic ring system containing a nitrogen atom;
m is 0, 1 or 2; and
R⁴ is or are selected from alkyl group or groups, or two R⁴s together with the carbon atoms to which they are attached form a 6-membered cyclic system.

12. The compound of formula I, tautomer, stereoisomer, or pharmaceutically acceptable salt thereof, as claimed in claim 11, wherein:
R¹ is selected from the group consisting of pyridyl, furanyl, indolyl, N-methylisoindolyl, benzofuranyl, piperazinyl, 4-(4-fluorophenyl)piperazinyl, morpholinyl, indolinyl, 2-oxoindolinyl, 2,3-dihydrobenzo[b][1,4]dioxin-6-yl, benzopyranyl, and phenyl optionally substituted with 1 to 2 substituents selected from group consisting of halo, cyclopropyl, trifluoromethyl, methoxy, ethoxy, trifluoromethoxy, methyl, ethyl, dimethylamino, monomethylamino, tert-butyl and 4-methylpiperazinyl;
R² is selected from the group consisting of hydrogen, methyl; dimethylamino, and dimethylaminomethyl;
R³ is selected from the group consisting of methyl, ethyl, n-propyl, methoxy, ethoxy, dimethylamino, N-methoxy-N-methyl amino, N-(2-hydroxy ethyl)-N-propyl amino, and piperidinyl;
R⁵ and R⁶ are selected independently from the group consisting of hydrogen, methyl, or R⁵ and R⁶ together with nitrogen atom to which they are attached form a piperidine ring;
m is 0, 1 or 2; and
R⁴ is selected from methyl groups or two R⁴s together with the carbon atoms to which they are attached forming a six membered carbocycle.

13. The compound of formula I tautomer, stereoisomer, or pharmaceutically acceptable salt thereof, as claimed in claim 12, wherein R¹ is selected from the group consisting of 4-chlorophenyl, 2-chlorophenyl, 3-chlorophenyl, 4-fluorophenyl, 4-cyclopropylphenyl, 4-trifluoromethylphenyl, 4-methoxyphenyl, 4-ethoxyphenyl, 3-ethoxyphenyl, 4-tolyl, 4-tert-butyl phenyl, 4-dimethylaminophenyl, 3-fluorophenyl, phenyl, 4-ethylphenyl, 3,4-dichlorophenyl, 2,4-dichlorophenyl, 2,4-difluorophenyl, 3-chloro-4-fluorophenyl, 3-chloro-4-methoxyphenyl, piperazin-1-yl, 4-(fluorophenyl)piperazinyl, morpholino, pyridin-4-yl, pyridin-3-yl, furan-3-yl, 1H-indol-5-yl, 1-methyl-1H-indol-5-yl, benzofuran-5-yl, indolin-5-yl, 4-(4-methylpiperaziny-1-yl)phenyl, and 2,3-dihydrobenzo[b][1,4]dioxin-6-yl).

14. The compound of formula I, tautomer, stereoisomer, or pharmaceutically acceptable salt thereof, as claimed in claim 11, wherein the compound is selected from the group consisting of:
4-(5-(4-chlorophenyl)-4-methyl-2-propionylthiophen-3-yl)benzene sulfonamide;
4-(5-(2-chlorophenyl)-4-methyl-2-propionylthiophen-3-yl)benzene sulfonamide;
4-(5-(3-chlorophenyl)-4-methyl-2-propionylthiophen-3-yl)benzene sulfonamide;
4-(5-(4-fluorophenyl)-4-methyl-2-propionylthiophen-3-yl)benzene sulfonamide;
4-(5-(4-cyclopropylphenyl)-4-methyl-2-propionylthiophen-3-yl)benzene sulfonamide;
4-(4-methyl-2-propionyl-5-(4-(trifluoromethyl)phenyl)thiophen-3-yl)benzene sulfonamide;
4-(5-(4-methoxyphenyl)-4-methyl-2-propionylthiophen-3-yl)benzene sulfonamide;
4-(5-(4-ethoxyphenyl)-4-methyl-2-propionylthiophen-3-yl)benzene sulfonamide;
4-(4-methyl-2-propionyl-5-(4-(trifluoromethoxy)phenyl)thiophen-3-yl)benzenesulfonamide;
4-(4-methyl-2-propionyl-5-(4-tolyl)thiophen-3-yl)benzenesulfonamide;
4-(5-(4-(tert-butyl)phenyl)-4-methyl-2-propionylthiophen-3-yl)benzene sulfonamide;
4-((5-(4-dimethylamino)phenyl)-4-methyl-2-propionylthiophen-3-yl)benzene sulfonamide;
4-(5-(3-fluorophenyl)-4-methyl-2-propionylthiophen-3-yl)benzene sulfonamide;
4-(4-methyl-5-phenyl-2-propionylthiophen-3-yl)benzenesulfonamide;
4-(5-(3-ethoxyphenyl)-4-methyl-2-propionylthiophen-3-yl)benzene sulfonamide;
4-(5-(4-ethylphenyl)-4-methyl-2-propionylthiophen-3-yl)benzene sulfonamide;

4-(5-(3,4-dichlorophenyl)-4-methyl-2-propionylthiophen-3-yl)benzene sulfonamide;
4-(5-(2,4-dichlorophenyl)-4-methyl-2-propionylthiophen-3-yl)benzene sulfonamide;
4-(5-(2,4-difluorophenyl)-4-methyl-2-propionylthiophen-3-yl)benzene sulfonamide;
4-(5-(3-chloro-4-fluorophenyl)-4-methyl-2-propionylthiophen-3-yl)benzene sulfonamide;
4-(5-(3-chloro-4-methoxyphenyl)-4-methyl-2-propionylthiophen-3-yl)benzenesulfonamide;
4-(4-methyl-5-(piperazin-1-yl)-2-propionylthiophen-3-yl)benzene sulfonamide;
4-(5-(4-(4-fluorophenyl)piperazin-1-yl)-4-methyl-2-propionylthiophen-3-yl)benzenesulfonamide;
4-(4-methyl-5-morpholino-2-propionylthiophen-3-yl)benzenesulfonamide;
4-(4-methyl-2-propionyl-5-(pyridin-4-yl)thiophen-3-yl)benzenesulfonamide;
4-(4-methyl-2-propionyl-5-(pyridin-3-yl)thiophen-3-yl)benzenesulfonamide;
4-(5-(furan-3-yl)-4-methyl-2-propionylthiophen-3-yl)benzenesulfonamide;
4-(5-(1H-indol-5-yl)-4-methyl-2-propionylthiophen-3-yl)benzene sulfonamide;
4-(4-methyl-5-(1-methyl-1H-indol-5-yl)-2-propionylthiophen-3-yl)benzene sulfonamide;
4-(5-(benzofuran-5-yl)-4-methyl-2-propionylthiophen-3-yl)benzene sulfonamide;
4-(5-(indolin-5-yl)-4-methyl-2-propionylthiophen-3-yl)benzenesulfonamide;
4-(4-methyl-5-(4-(4-methylpiperazin-1-yl)phenyl)-2-propionylthiophen-3-yl)benzenesulfonamide;
4-(5-(4-chlorophenyl)-2-propionylthiophen-3-yl)benzenesulfonamide;
4-(5-(4-chlorophenyl)-4-(dimethylamino)-2-propionylthiophen-3-yl)benzene sulfonamide;
4-(5-(4-chlorophenyl)-4-((dimethylamino)methyl)-2-propionylthiophen-3-yl)benzenesulfonamide;
5-(4-chlorophenyl)-N,N,4-trimethyl-3-(4-sulphamoylphenyl)thiophene-2-carboxamide;
5-(4-chlorophenyl)-N-methoxy-N,4-dimethyl-3-(4-sulphamoylphenyl)thiophene-2-carboxamide;
5-(4-chlorophenyl)-N-(2-hydroxyethyl)-4-methyl-N-propyl-3-(4-sulphamoyl phenyl)thiophene-2-carboxamide;
4-(5-(4-chlorophenyl)-4-methyl-2-(piperidine-1-carbonyl)thiophen-3-yl)benzenesulfonamide;
4-(2-acetyl-5-(4-chlorophenyl)-4-methylthiophen-3-yl)benzenesulfonamide;
4-(5-(4-chlorophenyl)-4-methyl-2-propionylthiophen-3-yl)-2-methylbenzene sulfonamide;
Methyl 4-methyl-5-(2-oxoindolin-5-yl)-3-(4-sulfamoylphenyl)thiophen-2-carboxylate;
Ethyl 4-methyl-5-(2-oxoindolin-5-yl)-3-(4-sulfamoylphenyl)thiophen-2-carboxylate;
4-(4-methyl-5-(4-mehylaminophenyl)-2-propionylthiophen-3-yl)benzene sulfonamide;
4-(5-(4-chlorophenyl)-4-methyl-2-propionylthiophen-3-yl)-N,N-dimethylbenzenesulfonamide;
4-(5-(4-chlorophenyl)-4-methyl-2-propionylthiophen-3-yl)-N-methylbenzenesulfonamide;
4-(5-(3,4-difluorophenyl)-4-methyl-2-propionylthiophen-3-yl)benzene sulfonamide;
1-(5-(4-chlorophenyl)-4-methyl-3-(4-(piperidin-1-ylsulfonyl)phenyl)thiophen-2-yl)propan-1-one; and
Ethyl 5-(4-chlorophenyl)-4-methyl-3-(4-sulfamoyl-5,6,7,8-tetrahydro naphthalen-1-yl)thiophene-2-carboxylate.

15. A pharmaceutical composition comprising a compound of claim 2, tautomer, stereoisomer, or pharmaceutically acceptable salt thereof, and a pharmaceutically acceptable carrier.

16. The compound of formula I, tautomer, stereoisomer, or pharmaceutically acceptable salt thereof, as claimed in claim 1, wherein Z is $NR^a$, wherein $R^a$ is hydrogen or optionally substituted alkyl.

17. The compound of formula I, tautomer, stereoisomer, or pharmaceutically acceptable salt thereof, as claimed in claim 16, wherein Z is $NR^a$ wherein $R^a$ is selected from hydrogen, methyl, ethyl, and cyclopropylmethyl.

18. The compound of formula I, tautomer, stereoisomer, or pharmaceutically acceptable salt thereof, as claimed in claim 16, wherein $R^2$ is hydrogen or alkyl.

19. The compound of formula I, tautomer, stereoisomer, or pharmaceutically acceptable salt thereof, as claimed in claim 18, wherein $R^2$ is hydrogen or methyl.

20. The compound of formula I, tautomer, stereoisomer, or pharmaceutically acceptable salt thereof, as claimed in claim 16, wherein $R^3$ is selected from the group consisting of alkyl, $R^7A^1$-, and $(R^7)(R^8)N$—.

21. The compound of formula I, tautomer, stereoisomer, or pharmaceutically acceptable salt thereof, as claimed in claim 20, wherein $R^3$ is selected from the group consisting of methyl, ethyl, n-propyl, methoxy, ethoxy, and dimethylamino.

22. The compound of formula I, tautomer, stereoisomer, or pharmaceutically acceptable salt thereof, as claimed in claim 16, wherein $R^5$ and $R^6$ are selected from the group consisting of hydrogen and alkyl.

23. The compound of formula I, tautomer, stereoisomer, or pharmaceutically acceptable salt thereof, as claimed in claim 22, wherein $R^5$ and $R^6$ are hydrogen.

24. The compound of formula I, tautomer, stereoisomer, or pharmaceutically acceptable salt thereof, as claimed in claim 16, wherein m is 0, 1, or 2, and $R^4$ is or are selected from alkyl group or groups.

25. The compound of formula I, tautomer, stereoisomer, or pharmaceutically acceptable salt thereof, as claimed in claim 16, wherein:
$R^a$ is selected from the group consisting of hydrogen and optionally substituted alkyl;
$R^1$ is selected from the group consisting of optionally substituted phenyl and optionally substituted heterocyclyl;
$R^2$ is selected from the group consisting of hydrogen and alkyl;
$R^3$ is selected from the group consisting of alkyl, $R^7A^1$, and $(R^7)(R^8)N$—; and
$R^5$ and $R^6$ are selected independently from the group consisting of hydrogen and alkyl;
m is 0, 1 or 2; and
$R^4$ is or are selected from alkyl group or groups.

26. The compound of formula I, tautomer, stereoisomer, or pharmaceutically acceptable salt thereof, as claimed in claim 25, wherein:
$R^a$ is selected from the group consisting of hydrogen, methyl, ethyl, and cyclopropylmethyl;
$R^1$ is selected from the group consisting of 2,3-dihydrobenzo[b][1,4]dioxin-6-yl and phenyl optionally substituted with 1 to 2 substituents selected from group consisting of halo, methoxy, and ethoxy;
$R^2$ is selected from the group consisting of hydrogen and methyl;
$R^3$ is selected from the group consisting of methyl, ethyl, n-propyl, methoxy, ethoxy, and dimethylamino;

$R^5$ and $R^6$ are selected independently from the group consisting of hydrogen and methyl;

m is 0, 1 or 2; and $R^4$ is methyl.

27. The compound of formula I tautomer, stereoisomer, or pharmaceutically acceptable salt thereof, as claimed in claim 26, wherein $R^1$ is selected from the group consisting of 4-chlorophenyl, 4-fluorophenyl, 4-methoxyphenyl, 2,4-dichlorophenyl, and 2,3-dihydrobenzo[b][1,4]dioxin-6-yl.

28. The compound of formula I, tautomer, stereoisomer, or pharmaceutically acceptable salt thereof, as claimed in claim 16, wherein the compound is selected from the group consisting of:

- 4-(5-(4-chlorophenyl)-1,4-dimethyl-2-propionyl-1H-pyrrol-3-yl)benzene sulfonamide;
- 5-(4-chlorophenyl)-N,N,1,4-tetramethyl-3-(4-sulfamoylphenyl)-1H-pyrrol-2-carboxamide;
- 4-(5-(4-chlorophenyl)-1-ethyl-4-methyl-2-propionyl-1H-pyrrol-3-yl)benzene sulfonamide;
- 4-(5-(4-chlorophenyl)-1-(cyclopropylmethyl)-4-methyl-2-propionyl-1H-pyrrol-3-yl)benzene sulfonamide;
- 4-(5-(4-chlorophenyl)-4-methyl-2-propionyl-1H-pyrrol-3-yl)benzene sulfonamide;
- 4-(5-(4-fluorophenyl)-1,4-dimethyl-2-propionyl-1H-pyrrol-3-yl)benzene sulfonamide;
- 4-(5-(4-methoxyphenyl)-1,4-dimethyl-2-propionyl-1H-pyrrol-3-yl)benzene sulfonamide;
- 4-(2-butyryl-5-(4-chlorophenyl)-1,4-dimethyl-1H-pyrrol-3-yl)benzene sulfonamide;
- 4-(5-(2,4-dichlorophenyl)-1,4-dimethyl-2-propionyl-1H-pyrrol-3-yl)benzene sulfonamide; and
- 4-(5-(2,3-dihydrobenzo[b][1,4]dioxin-6-yl)-1,4-dimethyl-2-propionyl-1H-pyrrol-3-yl)benzene sulfonamide.

29. A pharmaceutical composition comprising a compound of claim 16, tautomer, stereoisomer, or pharmaceutically acceptable salt thereof, and a pharmaceutically acceptable carrier.

30. The compound of formula I, tautomer, stereoisomer, or pharmaceutically acceptable salt thereof, as claimed in claim 1, wherein Z is O.

31. The compound of formula I, tautomer, stereoisomer, or pharmaceutically acceptable salt thereof, as claimed in claim 30, wherein $R^2$ is selected from the group consisting of hydrogen and alkyl.

32. The compound of formula I, tautomer, stereoisomer, or pharmaceutically acceptable salt thereof, as claimed in claim 31, wherein $R^2$ is hydrogen.

33. The compound of formula I, tautomer, stereoisomer, or pharmaceutically acceptable salt thereof, as claimed in claim 30, wherein $R^3$ is selected from methoxy or ethoxy.

34. The compound of formula I, tautomer, stereoisomer, or pharmaceutically acceptable salt thereof, as claimed in claim 30, wherein $R^5$ and $R^6$ are selected independently from the group consisting of hydrogen and alkyl.

35. The compound of formula I, tautomer, stereoisomer, or pharmaceutically acceptable salt thereof, as claimed in claim 30, wherein m is 0, 1, or 2, and $R^4$ is or are selected from alkyl group or groups.

36. The compound of formula I, tautomer, stereoisomer, or pharmaceutically acceptable salt thereof, as claimed in claim 30, wherein:

$R^1$ is an optionally substituted phenyl;

$R^2$ is hydrogen or alkyl;

$R^3$ is methoxy or ethoxy;

$R^5$ and $R^6$ are hydrogen; m is 0, 1 or 2; and $R^4$ is or are selected from alkyl group or groups.

37. The compound of formula I, tautomer, stereoisomer, or pharmaceutically acceptable salt thereof, as claimed in claim 36, wherein:

$R^1$ is phenyl optionally substituted with 1 to 2 substituents selected from group consisting of halo, cyclopropyl, trifluoromethyl, methoxy, ethoxy, trifluoromethoxy, methyl, ethyl, dimethylamino, monomethylamino, tert-butyl and 4-methylpiperazinyl;

$R^2$ is selected from the group consisting of hydrogen and methyl;

$R^3$ is ethoxy;

$R^5$ and $R^6$ are selected independently from the group consisting of hydrogen;

m is 0, 1 or 2; and $R^4$ is methyl.

38. The compound of formula I, tautomer, stereoisomer, or pharmaceutically acceptable salt thereof, as claimed in claim 37, wherein the compound is ethyl 5-(4-chlorophenyl)-3-(4-sulfamoylphenyl)furan-2-carboxylate.

39. A pharmaceutical composition comprising a compound of claim 30, tautomer, stereoisomer, or pharmaceutically acceptable salt thereof, and a pharmaceutically acceptable carrier.

* * * * *

UNITED STATES PATENT AND TRADEMARK OFFICE
CERTIFICATE OF CORRECTION

Page 1 of 4

PATENT NO. : 9,072,731 B2
APPLICATION NO. : 14/000829
DATED : July 7, 2015
INVENTOR(S) : Sinha et al.

It is certified that error appears in the above-identified patent and that said Letters Patent is hereby corrected as shown below:

IN THE SPECIFICATION

Col. 7, lines 48, 57, and 66,
Col. 8, lines 8, 13, 47, and 54,
Col. 9, lines 12 and 24,
Col. 12, lines 6 and 63,
Col. 14, lines 34 and 45, and
Col. 23, line 11,
"hereroaryl" should read --heteroaryl--;

Col. 9, line 7, "alkyl" should read --alkyl,--;

Col. 11, line 5, "Ws" should read --$R^4$s--;

Col. 11, line 47, "yl," should read --pyridin-4-yl, pyridin-3-yl,--;

Col. 12, line 15, "alkynyl" should read --alkynyl,--;

Col. 12, line 42, "bicyclo[410]heptane," should read --bicyclo[4.1.0]heptane,--;

Col. 12, line 60, "cycloalkyl" should read --Cycloalkyl--;

Col. 13, line 5, "heterocyclyl" should read --heterocyclyl.--;

Col. 13, line 7, "aromatic." should read --aromatic--;

Col. 13, line 58, "heteroaryl" should read --Heteroaryl--;

Col. 14, line 18, "oxadiazolinyl." should read --oxadiazolinyl,--;

Signed and Sealed this
Eighth Day of March, 2016

Michelle K. Lee
*Director of the United States Patent and Trademark Office*

IN THE SPECIFICATION

Col. 14, line 20, "pyrazolidinyl." should read --pyrazolidinyl,--;

Col. 14, lines 22-23, "1,1-dioxidothiomorpholinyl (thiomorpholine sulfone)." should read --1,1-dioxidothiomorpholinyl (thiomorpholine sulfone),--;

Col. 14, line 63, "compound" should read --compound,--;

Col. 15, lines 54-55, "28. 4-(5-(1H-indol-5-yl)-4-methyl-2-propionylthiophen-3-yl)benzene sulfonamide." should read --28. 4-(5-(1*H*-indol-5-yl)-4-methyl-2-propionylthiophen-3-yl)benzene sulfonamide.--;

Col. 15, lines 56-57, "29. 4-(4-methyl-5-(1-methyl-1H-indol-5-yl)-2-propionylthiophen-3-yl)benzene sulfonamide." should read --29. 4-(4-methyl-5-(1-methyl-1*H*-indol-5-yl)-2-propionylthiophen-3-yl)benzene sulfonamide.--;

Col. 16, lines 31-32, "49. 4-(5-(4-chlorophenyl)-1,4-dimethyl-2-propionyl-1H-pyrrol-3-yl)benzene sulfonamide." should read --49. 4-(5-(4-chlorophenyl)-1,4-dimethyl-2-propionyl-1*H*-pyrrol-3-yl)benzene sulfonamide.--;

Col. 16, lines 33-34, "50. 5-(4-chlorophenyl)-N,N,1,4-tetramethyl-3-(4-sulfamoylphenyl)-1H-pyrrol-2-- carboxamide." should read --50. 5-(4-chlorophenyl)-N,N,1,4-tetramethyl-3-(4-sulfamoylphenyl)-1*H*-pyrrol-2--carboxamide.--;

Col. 16, lines 40-41, "53. 4-(5-(4-chlorophenyl)-4-methyl-2-propionyl-1H-pyrrol-3-yl)benzene sulfonamide." should read --53. 4-(5-(4-chlorophenyl)-4-methyl-2-propionyl-1*H*-pyrrol-3-yl)benzene sulfonamide.--;

Col. 16, lines 42-43, "54. 4-(5-(4-fluorophenyl)-1,4-dimethyl-2-propionyl-1H-pyrrol-3-yl)benzene sulfonamide." should read --54. 4-(5-(4-fluorophenyl)-1,4-dimethyl-2-propionyl-1*H*-pyrrol-3-yl)benzene sulfonamide.--;

Col. 16, lines 44-45, "55. 4-(5-(4-methoxyphenyl)-1,4-dimethyl-2-propionyl-1H-pyrrol-3-yl)benzene sulfonamide." should read --55. 4-(5-(4-methoxyphenyl)-1,4-dimethyl-2-propionyl-1*H*-pyrrol-3-yl)benzene sulfonamide.--;

Col. 16, lines 46-47, "56. 4-(2-butyryl-5-(4-chlorophenyl)-1,4-dimethyl-1H-pyrrol-3-yl)benzene sulfonamide." should read --56. 4-(2-butyryl-5-(4-chlorophenyl)-1,4-dimethyl-1*H*-pyrrol-3-yl)benzene sulfonamide.--;

Col. 16, lines 48-49, "57. 4-(5-(2,4-dichlorophenyl)-1,4-dimethyl-2-propionyl-1H-pyrrol-3-yl)benzene sulfonamide." should read --57. 4-(5-(2,4-dichlorophenyl)-1,4-dimethyl-2-propionyl-1*H*-pyrrol-3-yl)benzene sulfonamide.--;

CERTIFICATE OF CORRECTION (continued)
U.S. Pat. No. 9,072,731 B2

IN THE SPECIFICATION

Col. 16, lines 50-51, "58. 4-(5-(2,3-dihydrobenzo[b][1,4]dioxin-6-yl)-1,4-dimethyl-2-propionyl-1H-pyrrol-3-yl)benzene sulfonamide." should read --58. 4-(5-(2,3-dihydrobenzo[b][1,4]dioxin-6-yl)-1,4-dimethyl-2-propionyl-1$H$-pyrrol-3-yl)benzene sulfonamide.--;

Col. 23, line 64, "$R^4$" should read --$R^4$,--;

Col. 24, line 37,
Col. 25, line 58, and
Col. 33, lines 42 and 67,
"inventers" should read --inventors--;

Col. 29, lines 21 and 27, "W," should read --$R^1$,--;

Col. 34, line 37, "W" should read --$R^1$--;

Col. 39, line 6, "P.H. Einrich Stahland Camille G. wermuth," should read --P. Heinrich Stahl and Camille G. Wermuth,--;

Col. 43, line 50, "An" should read --A--;

Col. 49, line 42, "95-about" should read --95 to about--;

Col. 58, line 42, "(0.091 g, 43%)" should read --(0.091 g, 43%).--;

Col. 86, line 48, "1.07 (t, J=7.24 Hz, 3H)" should read --1.07 (t, J=7.24 Hz, 3H).--;

Col. 103, line 30, "prepared" should read --prepared.--;

Col. 104, line 32, "was purging" should read --purging--;

Col. 107, line 61, "(0.05 g, 18.1%)" should read --(0.05 g, 18.1%).--;

Col. 111, line 3, "θHOBT" should read --HOBT--;

Col. 111, line 6, and
Col. 113, line 52,
"the" should read --The--;

Col. 111, line 65, "(13.80 g, 7.93 ml, 118.00 mmol" should read --(13.80 g, 7.93 ml, 118.00 mmol)--;

CERTIFICATE OF CORRECTION (continued)
U.S. Pat. No. 9,072,731 B2

IN THE CLAIMS

Col. 120, line 29, "1H-indol-5-yl, 1-methyl-1H-indol-5-yl," should read --1*H*-indol-5-yl, 1-methyl-1*H*-indol-5-yl,--;

Col. 120, lines 33-34, "claim 11," should read --claim 12,--;

Col. 121, lines 24-25, "4-(5-(1H-indol-5-yl)-4-methyl-2-propionylthiophen-3-yl)benzene" should read --4-(5-(1*H*-indol-5-yl)-4-methyl-2-propionylthiophen-3-yl)benzene--;

Col. 121, lines 26-27, "4-(4-methyl-5-(1-methyl-1H-indol-5-yl)-2-propionylthiophen-3-yl)benzene" should read --4-(4-methyl-5-(1-methyl-1*H*-indol-5-yl)-2-propionylthiophen-3-yl)benzene--;

Col. 123, lines 14-15, "4-(5-(4-chlorophenyl)-1,4-dimethyl-2-propionyl-1H-pyrrol-3-yl)benzene" should read --4-(5-(4-chlorophenyl)-1,4-dimethyl-2-propionyl-1*H*-pyrrol-3-yl)benzene--;

Col. 123, lines 16-17, "5-(4-chlorophenyl)-N,N,1,4-tetramethyl-3-(4-sulfamoylphenyl)-1H-pyrrol-2-carboxamide" should read --5-(4-chlorophenyl)-N,N,1,4-tetramethyl-3-(4-sulfamoylphenyl)-1*H*-pyrrol-2-carboxamide--;

Col. 123, lines 18-19, "4-(5-(4-chlorophenyl)-1-ethyl-4-methyl-2-propionyl-1H-pyrrol-3-yl)benzene" should read --4-(5-(4-chlorophenyl)-1-ethyl-4-methyl-2-propionyl-1*H*-pyrrol-3-yl)benzene--;

Col. 123, lines 20-21, "4-(5-(4-chlorophenyl)-1-(cyclopropylmethyl)-4-methyl-2-propionyl-1H-pyrrol-3-yl)benzene" should read --4-(5-(4-chlorophenyl)-1-(cyclopropylmethyl)-4-methyl-2-propionyl-1*H*-pyrrol-3-yl)benzene--;

Col. 123, lines 22-23, "4-(5-(4-chlorophenyl)-4-methyl-2-propionyl-1H-pyrrol-3-yl)benzene" should read --4-(5-(4-chlorophenyl)-4-methyl-2-propionyl-1*H*-pyrrol-3-yl)benzene--;

Col. 123, lines 24-25, "4-(5-(4-fluorophenyl)-1,4-dimethyl-2-propionyl-1H-pyrrol-3-yl)benzene" should read --4-(5-(4-fluorophenyl)-1,4-dimethyl-2-propionyl-1*H*-pyrrol-3-yl)benzene--;

Col. 123, lines 26-27, "4-(5-(4-methoxyphenyl)-1,4-dimethyl-2-propionyl-1H-pyrrol-3-yl)benzene" should read --4-(5-(4-methoxyphenyl)-1,4-dimethyl-2-propionyl-1*H*-pyrrol-3-yl)benzene--;

Col. 123, lines 28-29, "4-(2-butyryl-5-(4-chlorophenyl)-1,4-dimethyl-1H-pyrrol-3-yl)benzene" should read --4-(2-butyryl-5-(4-chlorophenyl)-1,4-dimethyl-1*H*-pyrrol-3-yl)benzene--;

Col. 123, lines 30-31, "4-(5-(2,4-dichlorophenyl)-1,4-dimethyl-2-propionyl-1H-pyrrol-3-yl)benzene" should read --4-(5-(2,4-dichlorophenyl)-1,4-dimethyl-2-propionyl-1*H*-pyrrol-3-yl)benzene--;

Col. 123, lines 32-33, "4-(5-(2,3-dihydrobenzo[b][1,4]dioxin-6-yl)-1,4-dimethyl-2-propionyl-1H-pyrrol-3-yl)benzene" should read --4-(5-(2,3-dihydrobenzo[b][1,4]dioxin-6-yl)-1,4-dimethyl-2-propionyl-1*H*-pyrrol-3-yl)benzene--.